(12) United States Patent
Mahmood et al.

(10) Patent No.: US 8,747,810 B2
(45) Date of Patent: Jun. 10, 2014

(54) COMPOSITIONS AND METHODS FOR IMAGING TISSUES, ORGANS AND TUMORS

(75) Inventors: Ashfaq Mahmood, Newton Center, MA (US); Alun G. Jones, Newton Center, MA (US); Naengnoi Limpa-Amara, Cambridge, MA (US); Yijie Peng, Belmont, MA (US); Zeynep Akgun, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/325,051

(22) Filed: Dec. 13, 2011

(65) Prior Publication Data

US 2012/0269724 A1 Oct. 25, 2012

Related U.S. Application Data

(63) Continuation of application No. PCT/US2010/038443, filed on Jun. 13, 2010.

(60) Provisional application No. 61/186,839, filed on Jun. 13, 2009.

(51) Int. Cl.
*A61K 49/00* (2006.01)
*A61K 51/04* (2006.01)
*A61K 51/02* (2006.01)

(52) U.S. Cl.
CPC ............. *A61K 49/0002* (2013.01); *A61K 51/04* (2013.01); *A61K 51/02* (2013.01); *A61K 2123/00* (2013.01)
USPC ......... 424/9.1; 424/1.11; 424/1.65; 424/1.69; 424/1.73; 534/10; 534/14

(58) Field of Classification Search
CPC ............. A61K 51/088; A61K 51/0497; A61K 2123/00; A61K 51/0478; A61K 51/04; A61K 2121/00; A61K 38/00; A61K 49/0002; A61K 49/0004; A61K 49/001; A61K 51/00; A61K 51/02; C07F 13/005; C07C 19/041; C01B 23/0005
USPC ........ 424/1.11, 1.49, 1.65, 1.69, 9.1, 9.2, 9.3, 424/9.4, 9.5, 9.6, 9.7, 9.8, 1.73; 534/7, 534/10–16; 514/1, 1.1; 546/1, 152, 184, 546/249; 568/18, 300, 303; 564/1
See application file for complete search history.

(56) References Cited

U.S. PATENT DOCUMENTS

2006/0159617 A1  7/2006  Mahmood et al.

OTHER PUBLICATIONS

International Search Report and Written Opinion mailed Oct. 18, 2010, in corresponding PCT Patent Application No. PCT/US10/38443.

*Primary Examiner* — D L Jones
(74) *Attorney, Agent, or Firm* — Edwards Wildman Palmer LLP; Mark D. Russett

(57) ABSTRACT

The present invention relates to compounds and related technetium and rhenium complexes thereof which are suitable for imaging or therapeutic treatment of tissues, organs, or tumors. In another embodiment, the invention relates to methods of imaging tissues, organs, or tumors using radiolabeled metal complexes, particularly tissues, organs, or tumors which express certain receptors to which the compounds or complexes of the invention have an affinity. The present invention also relates to methods of treating cancer, particularly those cancer lines which express certain receptors to which the compounds or complexes of the invention have an affinity. In yet another embodiment, the present invention provides methods of imaging and/or inhibiting receptors or neuroreceptors using compounds or complexes of the invention which have an affinity for the receptor or neuroreceptor to be imaged and/or inhibited.

13 Claims, 12 Drawing Sheets

| Complex | n | R |
|---|---|---|
| Re-L3 | 6 | 4-phenylpiperidine |
| Re-L4 | 6 | 4-benzylpiperidine |
| Re-L5 | 6 | 1,2,3,4-tetrahydroisoquinoline |
| Re-L6 | 6 | isoindoline |
| Re-L11 | 6 | 2-methoxy-4-phenyl piperidin |
| Re-L12 | 6 | 6,7-dimethoxy-1,2,3,4- tetrahydroisoquinoline |
| Re-L13 | 6 | 5,6-dimethoxyisoindoline |
| Re-L20 | 3 | 4-phenylpiperidine |
| Re-L21 | 3 | 2-methoxy-4-phenyl piperidin |
| Re-L22 | 3 | 4-benzylpiperidine |

(i) a) thiophene methyl amine, EtOH, reflux, 4hr b) NaBH₄, MeOH, rt, overnight;
(ii) 1,3-chlorobromopropane, K₂CO₃, CH₃CN, rt
(iii) 4-(2-methoxyphenyl)piperidine, CH₃CN, K₂CO₃, rt
(iv) 50% TFA/CH₂Cl₂, 3 hr, rt (v) 2-(Aminomethyl)pyridine, CH₂Cl₂, K₂CO₃, rt, overnight.

ORTEP diagram of Re-L5

COMPOSITIONS AND METHODS FOR IMAGING TISSUES, ORGANS AND TUMORS

RELATED APPLICATIONS

This application is a continuation application of PCT Application No. PCT/US2010/038443, filed Jun. 13, 2010, which claims the benefit of and priority to U.S. Provisional Patent Application No. 61/186,839, filed Jun. 13, 2009. The contents of each of the foregoing applications are incorporated herein by reference in their entirety.

STATEMENT REGARDING FEDERALLY SPONSORED RESEARCH OR DEVELOPMENT

This invention was supported at least in part by National Institute of Health (NIH) Grant No. 5 R01 CA119334-30. The United States government has certain rights to the invention.

FIELD OF THE INVENTION

The present invention relates to small molecular radiometal diagnostic agents for imaging tissues, particularly tissues expressing or overexpressing one or more receptors for which the diagnostic agents of the invention have an affinity. More specifically, the present invention relates to small molecular diagnostic agents for imaging tissues, which include tumors, various brain tissues, and other organs and diseased states, bearing certain preferred receptors and corresponding therapeutic complexes for treating the same. Certain agents of the invention include technetium and rhenium complexes having a secondary or tertiary amine pharmacophore linked to a chelating ligand.

BACKGROUND OF THE INVENTION

Signal transduction in cells is defined as a biochemical communication from one part of the cell to another. Such communication between and within cells is carried out by, for example, binding of an extracellular ligand to a specific cell surface transmembranal receptor which are coupled to G-proteins in the cytoplasm or by regulation of ion channels such as $Ca^{2+}$, $Na^+$, $K^+$, $Cl^-$, or the like. Binding of the ligand to receptor induces a transmembranal signal which results in activation (or deactivation) of various cellular processes and functions. Small synthetic molecules that target these cellular receptors at the cell surface or intracellularly, with a high degree of specificity are highly desirable because of their rapid and increased tissue penetration, reduced immunogenicity and reduced metabolism when compared to monoclonal antibodies, their fragments or polypeptides.

The use of small molecules with gamma or positron emitting radiolabels also provides a means for non-invasive visualization and imaging of targeted receptors in both normal and diseased states. This has led to a search for small molecules labeled with positron emitting isotopes and single photon emitting isotopes that target various receptors and permit the non-invasive visualization of these receptors in the targeted tissues. See, for example, Nuclear Medicine Biology Vol 24, 485-498 1997. See also John (U.S. Pat. No. 5,919, 934), Nuclear Medicine Biology vol 28, 657-666 2001, and PCT international publications of Mach (WO/0180905 A2 and WO 00/71171 A2).

Serotonin, also known as 5-hydroxytryptamine (5-HT), is an important neurotransmitter molecule and various receptor subtypes have been identified, among these receptor subtypes $5HT_{1A}$ is one of the best characterized and studied as it is implicated in anxiety, depression, hallucinogenic behavior as well as in dementia such as Alzheimer's disease. See, for example, Neuropharmacology vol 38, 1083-1152 1999 and Euro.Journal of Nucl. Med. Vol 28, 113-129, 2001. A number of $^{99m}$Tc-complexes with 2-methoxyphenylpiperazines have been investigated for binding and visualization of the $5HT_{1A}$ receptor. See, also Nuclear Medicine Biology Vol 24, 485-498 1997; Technetium, rhenium and other metals in chemistry and nuclear medicine 5. Padova: Servizi Grafici Editoriali, 1999:393-9; and European Journal of Nuclear Medicine vol 29(2) 263-275, 2002.

In addition to its role as a neurotransmitter, 5HT can also function as a growth factor and is found in most neuroendocrine cells of the human prostate and in human prostate cancer cell lines. Several articles have reviewed 5HT's role in prostate cancer cell lines, for example, Anticancer Res 1987; 7:1-12; Cancer Res 1991; 51:2498-2505; and Cancer 1992; 70:254-68. A $5HT_{1A}$ receptor antagonist has also been shown to inhibit prostate tumor cell growth in vivo (Anticancer Res 1994; 14:1215-20).

Sigma-receptors are recognized to be intra-cellular cytoplasmatic sites, distinguished in at least σ-1 and σ-2 subtypes (with a σ-3 site also postuated). Both subtypes are widely distributed in CNS (central nervous system), liver, kidney, lung, and in endocrine, immune, and reproductive tissues, and are overexpressed in several tumor cell lines (Vilner et al Cancer Res. 1995, 55, 408-413.). A recent review recites several potential applications for compounds having affinity for sigma receptors. Moreover, preliminary studies indicate that certain sigma agonists or sigma antagonists may be suitable for imaging or treating various cancers. See, for example, Wayne Bowen and Fabian Moebius (Pharm. Acta Helv. 2000, 74, 211-218; Trends Pharmacol. Sci. 1997, 18, 67-70.).

Similar to the serotonin receptors, the sigma receptors (including sigma-1 and sigma-2) that are normally expressed in the brain are also over expressed in a number of tumors. Sigma receptors, originally thought be a subclass of opiate receptors, are nondopaminergic, nonopiate membrane proteins that possess high affinity for haloperidol and various other neuroleptics. Two subtypes, termed σ-1 and σ-2 have now been identified.

The (+)-benzomorphans ((+)-[$^3$H]-pentazocine) selectively label the σ-1 sites; the enantiomeric (−)-benzomorphans show lower affinity and no differentiation between the two sites. The σ-2 sites, however are identified with [$^3$H]-DTG a nonselective s-1/s-2 ligand in the presence of dextrallophan, which masks binding of the 6-1 sites (Pharmacological reviews vol 42(4), 355-402, 1990).

Several studies have now been reported on the overexpression of sigma receptors in human and murine tumors including human melanoma, small cell lung carcinoma, human breast carcinomas and both androgen-dependent and -independent prostate carcinomas (Cancer Research vol 55(2), 408-413, 1995; Bioconjugate Chem 1997; 8:304-9; and Nucl Med Biol 1998; 25:189-94). See also John (U.S. Pat. No. 5,919,934), Nuclear medicine Biology vol 28, 657-666 2001, and international publications to Mach (WO/0180905 A2 and WO 00/71171 A2).

Adrenoreceptors, including $α_1$ receptors, are another family of G-protein-coupled receptors expressed in the brain, and are expressed in prostatic diseases such as benign prostatic hyperplasia (BPH) and are used for the treatment of this disease (Journal of Andrology vol 12, 389-394, 1991 and Jour. Medicinal Chem. Vol 40, 1293-1315, 1997).

Malignant melanoma is one of the most highly invasive and metastatic tumors and causes 1 to 2 percent of all cancer deaths. Melanoma is an increasingly common malignancy as well, and its mortality rates have been rapidly increasing above those of any other cancer in recent years. Malignant melanoma ranks tenth in cancer incidence in 1998, and eighth in 2001 in the United States, there are 55,100 new cases for melanoma in the US 2004. As the early detection of the melanoma improves considerably the patient's prognosis, the search for in vivo diagnostic probes is of special interest.

2-[$^{18}$F]Fluoro-2-deoxy-D-glucose ([$^{18}$F]FDG) is widely used in positron emission tomographic (PET) imaging of various tumors including melanoma. Earlier attempts at imaging melanoma with radiolabeled peptides, such as $^{188}$Re- and $^{99m}$Tc-labeled melanotropin, have generated encouraging results for in vivo melanoma scintigraphy.

The wide spread availability of $^{99m}$Tc in most major hospitals and the routine use and practicality of SPECT imaging in nuclear medicine gives impetus to the development of such receptor-imaging agents labeled with technetium-99m. The use therapeutic rhenium-186 or rhenium-188 may permit the radiotherapy of diseases to which these small receptor-specific complexes bind.

The most widely used isotope in clinical nuclear medicine, technetium-99m, possesses ideal characteristics ($t_{1/2}$=6.02 h, 140 keV monoenergeric γ-emission) for nuclear medicine imaging and is available on demand from a $^{99}$Mo-$^{99m}$Tc generator system.

Thus, new and useful radiolabeled diagnostic agents, including $^{99m}$Tc and $^{186}$Re and $^{188}$Re labeled diagnostic agents, for imaging tissues, particularly tissues expressing or over expressing one or more of the receptors discussed supra, would be desirable. Moreover $^{99m}$Tc and $^{186}$Re and $^{188}$Re labeled diagnostic and therapeutic agents suitable for use in imaging or treating melanoma, prostate cancer, other tumor or diseased states, various portions of the brain or other tissues expressing or overexpressing one or more receptors discussed supra would be desirable.

SUMMARY OF THE INVENTION

The present invention provides new radiolabeled diagnostic and therapeutic agents which comprise a metal or radiometal center. Preferred radiometals include technetium, including 99m-technetium, and one or more radioactive and non-radioactive isotopes of rhenium. Preferred agents are useful for in-vivo and in-vitro imaging of tumors, such as neoplasms, carcinoma and melanoma, or tissues or organs expressing one or more proteins, receptors or neuroreceptors, such as serotonin receptors, α receptors, σ receptors, calcium channel receptors or emopamil binding proteins adrenergic receptors, adrenoceptors receptors, dopamine receptors, and any subclass of receptors or proteins thereof. Particularly preferred agents are useful for in-vivo and in-vitro imaging. Certain agents of the present invention comprise an oxotechnetium core (Tc=O) or an oxorhenium core (Re=O), or a technetium or rhenium tricarbonyl complex (e.g., Tc(CO)$_3$, Re(CO)$_3$), linked to a secondary or tertiary amine pharmacophore.

In one aspect, the invention provided a compound represented by the formula (Formula I):

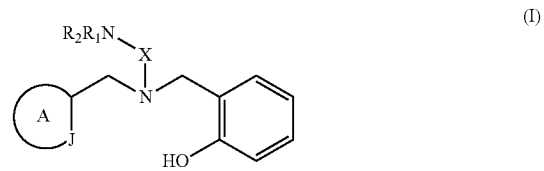

wherein:
J is N or S;
Ring A is a heteroaryl ring having 5 or 6 ring atoms;
X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl, wherein at least one of $R_1$ or $R_2$ is not hydrogen; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

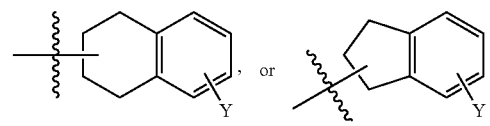

in which Y represents 0-4 substituents independently selected from halogen, alkyl, alkoxyl, or cyano; or $NR_1R_2$ is a moiety selected from:

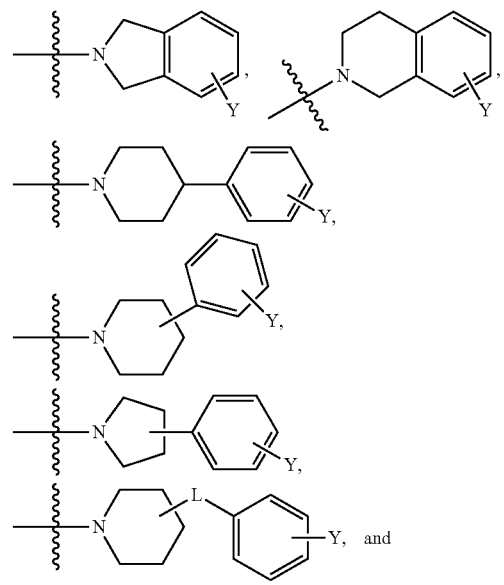

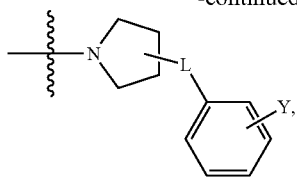

in which L represents a one or two atom linking group and Y represents 0-4 substituents independently selected from halogen, alkyl, alkoxyl, or cyano;

or a salt thereof.

In certain embodiments, the compound of Formula I is a compound of Formula X:

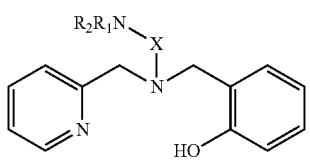

in which X, $R_1$ and $R_2$ are as defined for Formula I.

In another aspect, the invention provides a metal complex of a compound of Formula I. In certain embodiments, the complex is represented by the formula (Formula Ia):

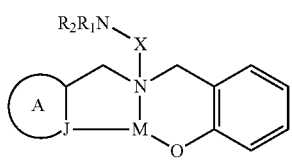

in which ring A, J, X, $R_1$ and $R_2$ are as defined in formula I, and

M is a metal or metal center selected from technetium, rhenium, yttrium, copper, gallium, indium, bismuth, platinum and rhodium, more preferably technetium and rhenium. It will be understood that M includes a metal atom, and can further include ligands for the metal (e.g., M can represent Tc(CO)$_3$, when the technetium atom has carbonyl ligands).

In certain embodiments, the complex is represented by the formula:

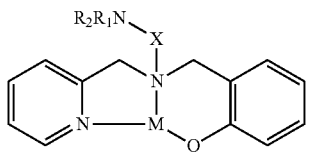

in which X, $R_1$ and $R_2$ are as defined for Formula X, and

M is a metal or metal center selected from technetium, rhenium, yttrium, copper, gallium, indium, bismuth, platinum and rhodium, more preferably technetium and rhenium. It will be understood that M includes a metal atom, and can further include ligands for the metal (e.g., M can represent Tc(CO)$_3$, when the technetium atom has carbonyl ligands).

In another aspect, the invention provides a compound represented by the formula (Formula II):

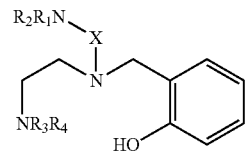

wherein:

X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl, wherein at least one of $R_1$ or $R_2$ is not hydrogen; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

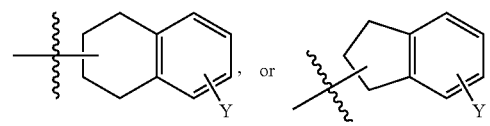

in which Y represents 0-4 substituents independently selected from halogen, alkyl, alkoxyl, or cyano; or $NR_1R_2$ is a moiety selected from:

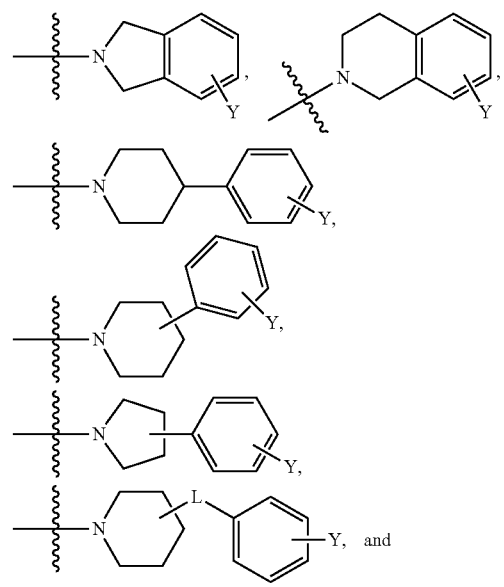

-continued

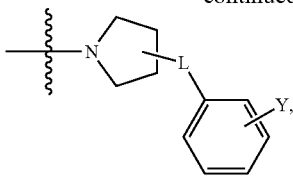

in which L represents a one or two atom linking group and Y represents 0-4 substituents independently selected from halogen, alkyl, alkoxyl, or cyano;

$R_3$ and $R_4$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl; or a salt thereof.

In another aspect, the invention provides a metal complex of a compound of Formula II. In certain embodiments, the complex is a complex represented by the formula (Formula IIa):

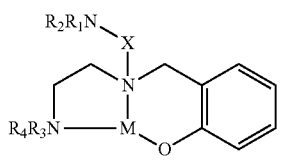

(IIa)

wherein:

X, $R_1$, $R_2$, $R_3$ and $R_4$ are as defined for Formula II; and M is a metal selected from technetium, rhenium, yttrium, copper, gallium, indium, bismuth, platinum and rhodium, more preferably technetium and rhenium. It will be understood that M includes a metal atom, and can further include ligands for the metal (e.g., M can represent $Tc(CO)_3$, when the technetium atom has carbonyl ligands or $Re(CO)_3$ rhenium when rhenium has carbonyl ligands). In certain embodiments, M is a metal such as Tc or Re.

In another aspect, the invention provides a compound represented by the formula (Formula III):

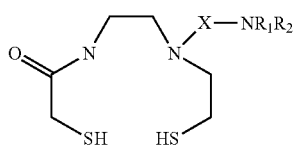

(III)

wherein:

X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl group having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl; or wherein $R_1$ and $R_2$ taken together with the nitrogen atom to which they are attached form an optionally substituted heterocyclic ring having from 3 to 8 atoms in the ring; or one of $R_1$ or $R_2$ is alkyl and the other is a moiety selected from:

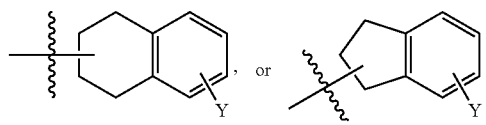

in which Y represents 0-4 substituents independently selected from halogen, alkyl, alkoxyl, or cyano;

or a salt thereof.

In certain embodiments, X is an optionally substituted $C_{2-8}$alkylene group, $R_1$ is a $C_{1-6}$alkyl group and $R_2$ is an optionally substituted (aryl)$C_{1-4}$alkyl or an optionally substituted (heteroaryl)$C_{1-4}$alkyl. In certain embodiments, $R_1$ and $R_2$ taken together with the nitrogen atom to which they are attached form an optionally substituted heterocyclic ring having from 3 to 8 atoms in the ring, more preferably 5 or 6 atoms in the ring. In certain embodiments, $R_1$ and $R_2$ taken together with the nitrogen atom to which they are attached form an optionally substituted piperidine or morpholine. In certain embodiments, $R_1$ and $R_2$ taken together with the nitrogen atom to which they are attached form a 4-phenylpiperidine group. In certain embodiments, $R_1$ and $R_2$ taken together with the nitrogen atom to which they are attached form a 4-benzylpiperidine group or a 4-((2-methoxyphenyl)methyl)piperidine group. In certain embodiments, $R_1$ and $R_2$ taken together with the nitrogen atom to which they are attached form a 6,7-dimethoxy-3,4-dihydroisoquinolinyl ring. In certain embodiments, $R_1$ and $R_2$ are independently lower alkyl (e.g., are both ethyl).

In certain embodiments, X is selected from the group consisting of —$(CH_2)_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5. In certain embodiments, X is $C_3$-$C_6$ alkylene.

In certain embodiments, $NR_1R_2$ is a moiety selected from:

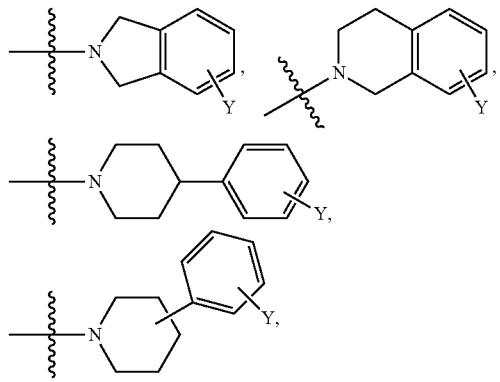

-continued

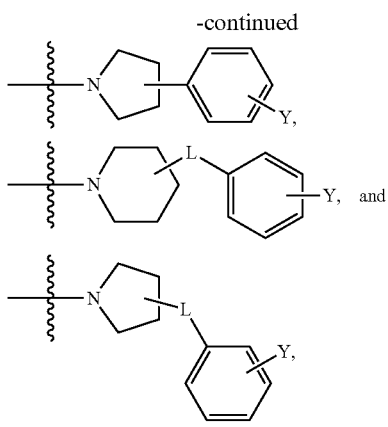

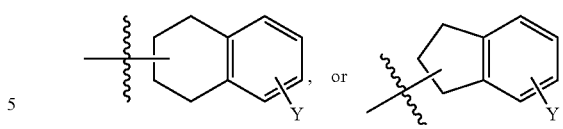

in which Y represents 0-4 substituents independently selected from halogen, alkyl, alkoxyl, or cyano; or $NR_1R_2$ is a moiety selected from:

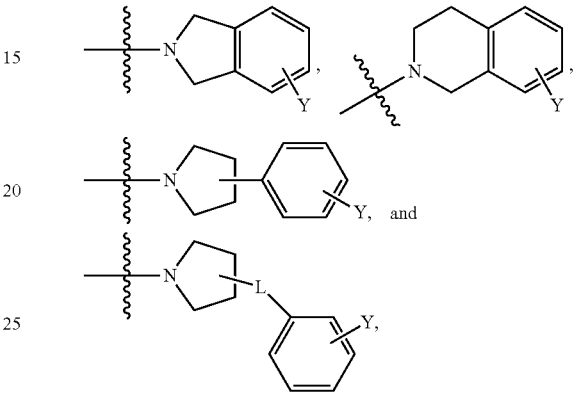

in which L represents a one or two atom linking group and Y represents 0-4 substituents independently selected from halogen, alkyl, alkoxyl, or cyano.

In another aspect, the invention provides a metal complex of a compound of Formula III. In certain embodiments, the complex is a complex represented by the formula (Formula IIIa):

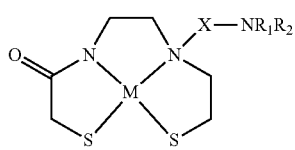

wherein:

X, $R_1$ and $R_2$ are as defined for Formula III; and

M is a metal selected from technetium, rhenium, yttrium, copper, gallium, indium, bismuth, platinum and rhodium, more preferably technetium and rhenium. M includes a metal atom, and can further include ligands such as halogens(s) (F, Cl, Br, I) for the metal, or oxygen.

In another aspect, the invention provides a compound represented by the formula (Formula IV):

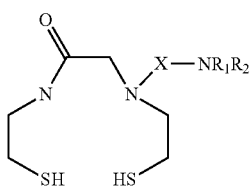

wherein:

X is a linking group comprising an aliphatic backbone chain having 1 to about 8 atoms, in which the aliphatic backbone chain can optionally include ester, amide, ether or thioether linkages in the aliphatic backbone chain; and one of $R_1$ or $R_2$ is alkyl and the other is a moiety selected from:

in which L represents a one or two atom linking group and Y represents 0-4 substituents independently selected from halogen, alkyl, alkoxyl, or cyano; or a salt thereof.

In certain embodiments, X is an optionally substituted $C_{2-8}$alkylene group, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, X is selected from the group consisting of —$(CH_2)_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5. In certain embodiments, L is —$CH_2$—, —$CH_2CH_2$—, O, or S.

In another aspect, the invention provides a metal complex of a compound of Formula IV. In certain embodiments, the complex is a complex represented by the formula (Formula IVa):

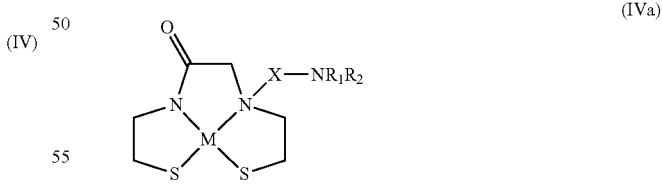

wherein:

X, $R_1$ and $R_2$ are as defined for Formula IV; and

M is a metal selected from technetium, rhenium, yttrium, copper, gallium, indium, bismuth, platinum and rhodium, more preferably technetium and rhenium. It will be understood that M includes a metal atom, and can further include ligands such as halogens(s) (F, Cl, Br, I) for the metal, or oxygen. For example, Formula IVa includes complexes according to Formula IVb:

In another aspect, the invention provides a compound represented by the formula (Formula V):

wherein

X is a linking group comprising an aliphatic backbone chain having 1 to about 8 atoms, wherein the aliphatic backbone chain can optionally include ester, amide, ether or thioether linkages in the aliphatic backbone chain;

Z is a chelating group capable of chelating to at least one metal ion; and one of $R_1$ or $R_2$ is alkyl and the other is a moiety selected from:

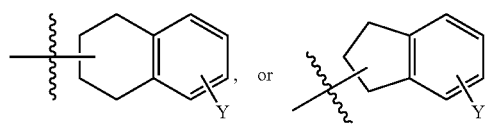

in which Y represents 0-4 substituents independently selected from halogen, alkyl, alkoxyl, or cyano; or $NR_1R_2$ is a moiety selected from:

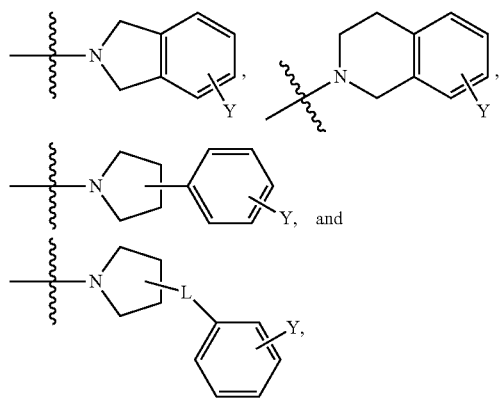

in which L represents a one or two atom linking group and Y represents 0-4 substituents independently selected from halogen, alkyl, alkoxyl, or cyano;

or a salt thereof.

In certain embodiments, Z is a tridentate, tetradentate, pentadentate, or hexadentate moiety capable of chelating a metal ion selected from the group consisting of technetium, rhenium, yttrium, copper, gallium, indium, bismuth, platinum and rhodium. In certain embodiments, Z is selected from:

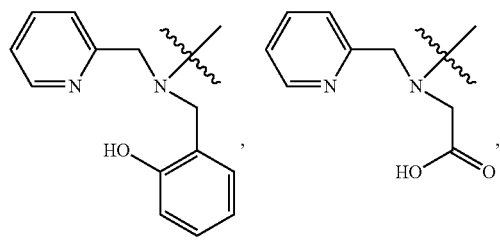

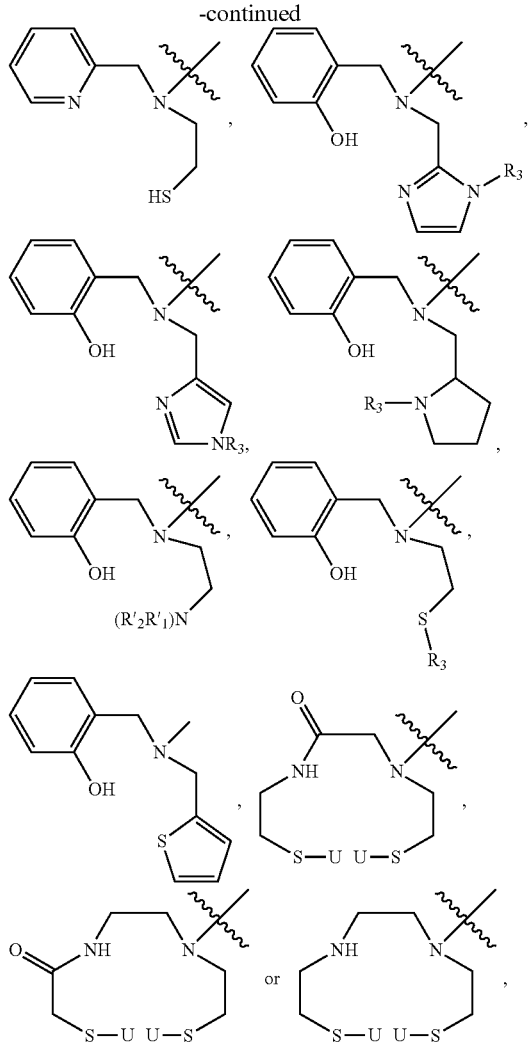

in which each $R'_1$ and $R'_2$ is independently hydrogen or alkyl, $R_3$ is independently hydrogen or alkyl, and U is independently H or a protecting or blocking group; or a salt thereof. In certain embodiments, Z is a chelating group capable of chelating to at least one metal to form a neutral metal complex.

In certain embodiments of Formula V, X is selected from the group consisting of —$(CH_2)_m$—C(O)NH— and α,ω-alkylene groups wherein the alkylene group has between about 1 and about 10 carbon atoms and between 0 and about 3 oxygen or sulfur atoms in the alkylene chain; and m is an integer of from about 1 to about 5. In certain embodiments, X is an optionally substituted $C_{2-8}$alkylene group; in certain embodiments, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, L is —$CH_2$—, —$CH_2CH_2$—, O, or S. In certain embodiments, the protecting group P is a trityl group.

In another aspect, the invention provides a complex comprising a compound of Formula V, and a metal ion selected from the group consisting of technetium, rhenium, yttrium, copper, gallium, indium, bismuth, platinum and rhodium. In certain embodiments, the metal, taken together with the moiety Z of formula V, is represented by any of the formulae selected from Formulae Vb:

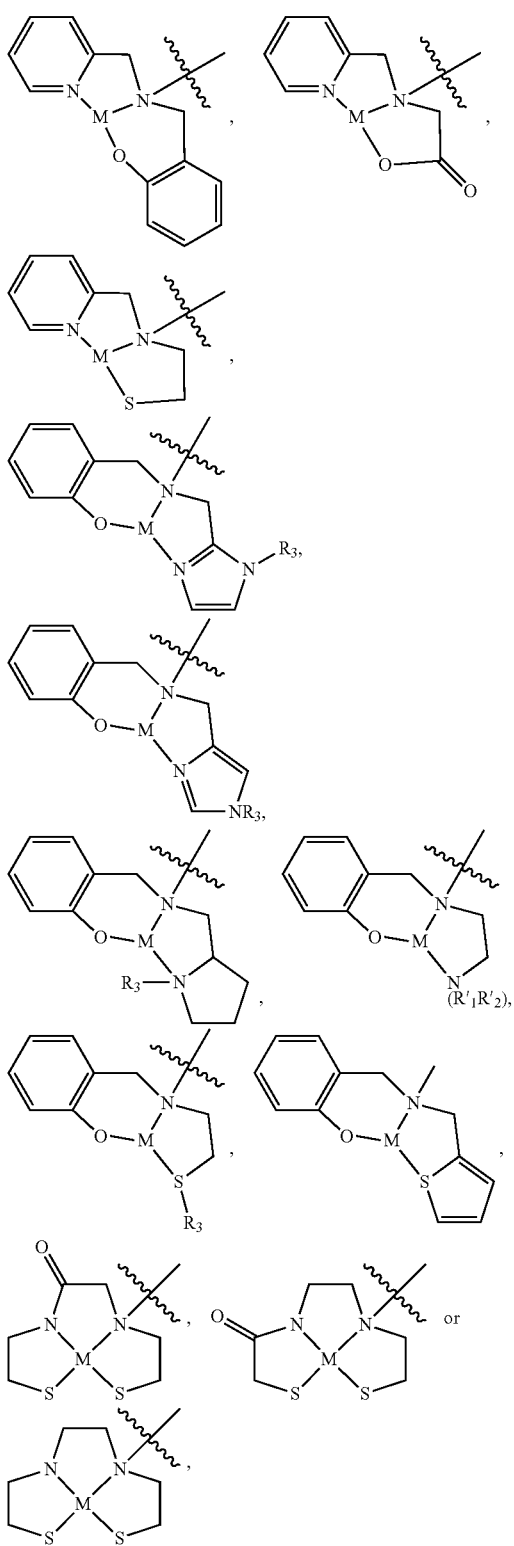

in which each $R'_1$ and $R'_2$ is independently hydrogen or alkyl, and $R_3$ is independently hydrogen or alkyl; and M is a metal selected from the group consisting of technetium, rhenium, yttrium, copper, gallium, indium, bismuth, platinum and rhodium. It will be understood that M includes a metal atom, and can further include ligands such as halogens (F, Cl, Br, I) for the metal or carbonyl ligands for the metal (e.g., M can represent $Tc(CO)_3$, when technetium or $Re(CO)_3$ when the rhenium atom has carbonyl ligands) or oxygen (e.g., M can be Tc=O or Re=O).

In another aspect, the invention provides a method for in-vivo or in-vitro imaging of at least one tumor comprising the steps of:

providing a complex of any one of Formulae Ia, Ib, Xa, Xb, IIa, IIb, IIIa, IIIb, IVa, IVb, Va;

contacting the tumor(s) with the radiolabeled metal complex; and making a radioagraphic image to visualize the tumor(s).

In another aspect, the invention provides a method for in-vivo or in-vitro imaging of at least one tissue expressing one or more proteins or receptors for which radiolabeled complexes have affinity, the method comprising the steps of:

providing a radiolabeled complex comprising a complex of any one of Formulae Ia, Ib, Xa, Xb, IIa, IIb, IIIa, IIIb, IVa, IVb, Va; contacting the tissue(s) expressing the receptors with the radiolabeled metal complex; and making a radiographic image to visualize the tissue(s).

In another aspect, the invention provides method for the treatment of cancer comprising the steps of: providing a complex of any one of Formulae Ia, Ib, Xa, Xb, IIa, IIb, IIIa, IIIb, IVa, IVb, Va; and contacting the tumor(s) with the metal complex.

In another aspect, the invention provides a complex of any one of Formulae Ia, Ib, Xa, Xb, IIa, IIb, IIIa, IIIb, IVa, IVb, Va, wherein the metal ion is radiolabelled or radioactive.

In another aspect, the invention provides a complex of any one of Formulae Ia, Ib, Xa, Xb, IIa, IIb, IIIa, IIIb, IVa, IVb, Va, wherein the metal ion is not radiolabelled or radioactive.

In another aspect, the invention provides a method of binding to or inhibiting a protein or receptor comprising the steps of: providing a metal complex according to any one of Formulae Ia, Ib, Xa, Xb, IIa, IIb, IIIa, IIIb, IVa, IVb, Va; and contacting the tumor(s) with the metal complex.

In certain embodiments, a cytotoxic metal complex comprises a complex according to any one of Formulae Ia, Ib, Xa, Xb, IIa, IIb, IIIa, IIIb, IVa, IVb, Va, wherein M is one or more isotopes of rhenium.

In certain embodiments, the metal ion is radiolabelled or radioactive.

In certain embodiments, the metal ion is not radiolabelled or radioactive.

In another aspect, the invention provides the use of any compound or complex disclosed herein for the manufacture of a composition (including a medicament) for the in-vivo or in-vitro imaging of at least one tissue expressing one or more proteins or receptors for which radiolabeled complexes have affinity; or for binding to or inhibiting a protein or receptor; or for the treatment of cancer; or in-vivo or in-vitro imaging of at least one tumor.

Certain linking groups, X, are lower alkyl groups having from 1 to about 8 atoms in the backbone such as, e.g., —$(CH_2)_n$—, ether groups having 1 to 8 atoms in the backbone such as, e.g., —$(CH_2)_n$—O—$(CH_2)_m$—, ester groups having 1 to 8 atoms in the backbone such as, e.g., —$(CH_2)_n$—CO—O—$(CH_2)_m$—, thioether groups having 1 to 8 atoms in the backbone such as, e.g., —$(CH_2)_n$—S—$(CH_2)_m$—, and amido groups having 3-8 atoms in the backbone such as, e.g., —$(CH_2)_n$CO—NH—$CH_2CH_2$— or —$(CH_2)_n$CO—NH—, where n and m are non-negative integers and the sum n+m is typically between about 1 and about 8. Particularly preferred linking groups X typically have between about 2 and about 5 atoms in the backbone.

Linking groups X may optionally have one or more substituents attached to the backbone chain including pendant aromatic groups. Preferred substituents include alkyl groups having from 1 to about 6 carbon atoms and from 0 to about 3 oxygen, sulfur, or oxidized sulfur atoms, hydroxyl, amino, carboxyl, alkoxy groups having from 1 to about 6 carbon atoms, aminoalkyl groups having from 1 to about 6 carbon atoms, dialkylaminoalkyl groups where each alkyl group has from about 1 to about 6 carbon atoms, halogen atoms including F, Cl, Br, and I, aromatic groups having about 5 to about 18 ring atoms which may include 0, 1, 2, or 3 N, O or S ring atoms.

The compounds of the invention can be complexed with a metal ion using methods well known in the art to provide metal complexes. Imaging applications typically comprise metal complexes which are radiolabelled and more typically comprise at least one radiolabelled metal ion (e.g., a radioactive metal ion). Therapeutic applications typically comprise metal complexes of the invention which are cytotoxic and may comprise cold (e.g., non-radioactive metal ions) or radiolabelled metal ions or a combination thereof. Typical radiolabeled complexes of the invention are cationic or neutral. Preferred radiometal ions include isotopes of metal ions that emit $\alpha$, $\beta^-$, $\beta^+$ or $\gamma$ radiation, including metal ions selected from the group consisting of technetium, rhenium, yttrium, copper, gallium, indium, bismuth, platinum and rhodium. Particularly preferred radiolabeled complexes of the invention comprise a technetium or rhenium metal ion.

Tissues suitable for use in the imaging methods of the present invention are not particularly limited. However, typically preferred tissues include those tissue which express or over-express one or more proteins, receptors or neuroreceptors, such as melanin, serotonin receptors, $\alpha$ receptors, $\sigma$ receptors, calcium channel receptors or emopamil binding proteins, adrenergic receptors, adrenoceptors receptors, dopamine receptors, and any subclass of receptors or proteins thereof. Tissues which can be imaged by the methods of the invention include brain tissue, organs, tumors and cells or tissues containing melanin or the like which express such proteins and/or receptors to which the molecules bind.

DEFINITIONS

Tr and Trt refer to trityl groups, e.g., triphenylmethyl groups.
DTG refers to ditolyl guanidine.
AADT refers to amino-amido-dithiolate ligands, preferred AADT ligands have a N-[2-(2-mercapto-ethylamino)-ethylamino]-ethanethiol structure.
DADT refers to diamino-dithiolate ligands, preferred DADT ligands have a 2-[2-(2-mercapto-ethylamino)-ethylamino]-ethanethiol structure.

The term "substituted", as used herein, means that any one or more hydrogens on the designated atom is replaced with a group selected from the defined list, provided that the designated atom's normal valence is not exceeded, and that the substitution results in a stable compound. When a substituent is keto (i.e., =O), then 2 hydrogens on the atom are replaced. Keto substituents are not directly attached to aromatic ring atoms.

When any variable occurs more than one time in any constituent or formula for a compound, its definition at each occurrence is independent of its definition at every other occurrence. Thus, for example, if a group is shown to be substituted with 0-2 R*, then said group may optionally be substituted with up to two R* groups and R* at each occurrence is selected independently from the definition of R*.

Also, combinations of substituents and/or variables are permissible provided that such combinations result in stable compounds.

As indicated herein, various substituents of the compounds of the present invention and various formulae set forth herein are "optionally substituted", including, e.g., a linker or carboxylate leaving group. When substituted, those substituents can be substituted at one or more of any of the available positions, typically 1, 2, 3, 4, or 5 positions, by one or more suitable groups such as those disclosed herein.

Suitable groups or "substituted" moieties for hydrogen atoms in compounds of the invention include, e.g., halogen such as fluoro, chloro, bromo or iodo; cyano; hydroxyl; nitro; azido; alkanoyl, such as a $C_{1-6}$ alkanoyl group such as acyl and the like; carboxamido; alkyl groups including those groups having 1 to about 12 carbon atoms, preferably 1-6 carbon atoms; alkenyl and alkynyl groups including groups having one or more unsaturated linkages and from 2 to about 12 carbon atoms, preferably 2-6 carbon atoms; alkoxy groups including those having one or more oxygen linkages and from 1 to about 12 carbon atoms, preferably 1-6 carbon atoms; aryloxy groups such as phenoxy and benzyloxy; alkylthio groups including those moieties having one or more thioether linkages and from 1 to about 12 carbon atoms, preferably 1-6 carbon atoms; alkylsulfinyl groups including those moieties having one or more sulfinyl linkages and from 1 to about 12 carbon atoms, preferably 1-6 carbon atoms; alkylsulfonyl groups including those moieties having one or more sulfonyl linkages and from 1 to about 12 carbon atoms, preferably 1-6 carbon atoms; aminoalkyl groups such as groups having one or more N atoms and from 1 to about 12 carbon atoms, preferably 1-6 carbon atoms; carbocyclic aryl groups having 6 or more carbons, particularly phenyl and benzyl (e.g., wherein an Ar group can be substituted or unsubstituted biphenyl moiety); arylalkyl having 1 to 3 separate or fused rings and from 6 to about 18 carbon ring atoms, with benzyl being a preferred group; arylalkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms.

As used herein, "alkyl" is intended to include both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are lower alkyl groups having from 1 to about 6 carbon atoms. The term $C_{1-6}$ alkyl as used herein means alkyl groups consisting of 1 to 6 carbon atoms.

"Cycloalkyl" is intended to include saturated ring groups, having a specified number of carbon atoms, such as cyclopropyl, cyclobutyl, cyclopentyl, or cyclohexyl and bridged or caged saturated ring groups such as norbornane or adamantane and the like. Preferred cycloalkyl groups are cycloalkyl groups having from 3 to about 8 ring atoms. The term $C_{3-8}$ cycloalkyl as used herein means cycloalkyl groups consisting of an aliphatic ring with 3 to 8 atoms in the ring.

"Alkenyl" is intended to include hydrocarbon chains of either a straight or branched configuration comprising one or more unsaturated carbon-carbon bonds, which may occur in any stable point along the chain such as, e.g., ethenyl and propenyl. Preferred alkenyl groups are lower alkenyl groups having from 2 to about 6 carbon atoms. The term $C_{2-6}$ alkenyl as used herein means alkenyl groups consisting of 2 to 6 carbon atoms.

"Alkynyl" is intended to include hydrocarbon chains of either a straight or branched configuration comprising one or more triple carbon-carbon bonds that may occur in any stable point along the chain such as, e.g., ethynyl and propynyl. Preferred alkynyl groups are lower alkynyl groups having from 2 to about 6 carbon atoms. The term $C_{2-6}$ alkynyl as used herein means alkynyl groups consisting of 2 to 6 carbon atoms.

As used herein, the term "heterocyclic group" is intended to include saturated, partially unsaturated, or unsaturated (aromatic) groups having 1 to 3 (preferably fused or spiro) rings with 3 to about 8 members per ring at least one ring containing an atom selected from N, O or S. The nitrogen and sulfur heteroatoms may optionally be oxidized. The term "heteroalicyclic" or "heterocycloalkyl" is used to refer to saturated or partially unsaturated heterocyclic groups.

As used herein, the term "aryl" includes groups that contain 1 to 3 separate or fused rings and from 6 to about 18 ring atoms, without hetero atoms as ring members. Specifically preferred carbocyclic aryl groups include phenyl, and naphthyl including 1-naphthyl and 2-naphthyl.

The term "heteroaryl" includes groups that contain 1 to 3 separate or fused rings and from 6 to about 18 ring atoms, with at least one hetero atom as a ring member. The term "heteroaryl ring having 5 or 6 ring atoms" refers to a heteroaryl group having 5 or 6 ring atoms of which 1-3 are heteroatoms such as O, N, or S. Examples of heteroaryl rings having 5 or 6 ring atoms include pyridinyl, thiophenyl, pyrrolyl, imidazolyl, and the like.

"Haloalkyl" is intended to include both branched and straight-chain saturated aliphatic hydrocarbon groups having the specified number of carbon atoms, substituted with 1 or more halogen (for example $-C_v(X^i)_{wi}(H_{2v+1-\Sigma(wi)})$ where v=1 to 6; $X^i$=F(i=1), Cl(i=2), Br(i=3), I(i=4) and $\Sigma w_i \leq 2v+1$). Examples of haloalkyl include, but are not limited to, trifluoromethyl, trichloromethyl, pentafluoroethyl, and pentachloroethyl. Preferred haloalkyl groups are lower haloalkyl groups having from 1 to about 6 carbon atoms. The term $C_{1-6}$ haloalkyl as used herein means haloalkyl groups consisting of 1 to 6 carbon atoms.

As used herein, the term "hydrocarbon group" is intended to include alkyl, cycloalkyl, alkenyl, alkynyl, and aryl groups or a group that comprises a combination of two or more alkyl, cycloalkyl, alkenyl, alkynyl or aryl group regions. Hydrocarbon groups may further comprise heteroatoms such as N, O, F, Si, S, Cl, Br and the like. Preferably, hydrocarbon groups have from 0 to about 3 heteroatoms. The term lower hydrocarbon group as used herein means a hydrocarbon group consisting of 1 to 6 carbon atoms which may include 1, 2, or 3 heteroatoms.

As used herein, the term "lipophilic group" refers to any hydrophobic group that is soluble in or miscible with lipids, hydrocarbons and other hydrophobic materials. Examples of lipophilic groups include, but are not limited to, long-chain $C_6-C_{32}$ alkyl groups that include linear alkyls, branched alkyls with one or more branch points or linear or branched alkyls which include one or more $C_3-C_8$ cycloalkane groups, long-chain $C_6-C_{32}$ alkenyl groups with one or more C—C double bonds that include linear alkenyls, branched alkenyls with one or more branch points or linear or branched alkenyls which include one or more $C_3-C_8$ cycloalkane or cycloalkene groups, long-chain $C_6-C_{32}$ alkynyl groups with one or more C—C triple bonds that include linear alkynyls, branched alkynyls with one or more branch points or linear or branched alkynyls which include one or more $C_3-C_8$ cycloalkane groups or long-chain $C_6-C_{32}$ alkyl, alkenyl or alkynyl groups that are optionally substituted with aryl, halogen, alkoxy, mono- or di($C_1-C_6$)amino, $C_1-C_6$-alkyl ester.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—CH$_2$-naphthyl), 1-phenethyl, 2-phenethyl, ω-phenyl-$C_{1-8}$alkyl, and other carbocyclic aralkyl groups, as discussed above.

"Alkoxy" means an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Preferred alkoxy groups are lower alkoxy groups having from 1 to about 6 carbon atoms, particularly methoxy.

The term "halogen" means fluorine, chlorine, bromine, iodine, or astatine.

As used herein, the term "metal ion" is intended to include any metal ion, including all natural and synthetic isotopes thereof, and further includes both radioactive and non-radioactive metal ions.

Unless otherwise stated or clear from context, it will be understood that a metal, metal ion or metal center can further include other ligands for the metal (e.g., halogens such as F, Cl, Br, or I) or a metal represented by M can include ligands, e.g., CO (e.g., forming Tc(CO)$_3$ (when the technetium atom has carbonyl ligands)) or oxygen (e.g., M can refer to an oxo-metal center such as an oxotechnetium or oxorhenium).

The term "radiolabelled" typically refers to compounds or complexes comprising at least one radioactive isotope. In preferred embodiments of the invention, radiolabelled typically comprises complexes and compounds having at least one metal ion which is present as one or more isotopes of which at least isotope is radioactive.

The term "protecting group" or "blocking group" refers to a group capable of protecting or blocking from reaction a reactive chemical moiety (such as an amine, a thiol, a hydroxyl group, a phenolic hydroxyl group, and the like). Exemplary protecting groups and methodologies (protection and deprotection) are known in the art and include, for example, those described in T. W. Greene and P. G. M. Wuts, *Protective Groups in Organic Synthesis*, 3$^{rd}$ Ed., John Wiley and Sons (1999). Examples of hydroxyl protecting groups include silyl ether groups (such as trimethylsilyl or t-butyldimethylsilyl), ethers (such as methyl, methoxymethyl, benzyl ether, or triphenylmethyl (trityl)), esters (such as acetate or benzoate), and the like. Protecting groups for amines include amides and carbamates (such as acetyl, tert-butoxycarbonyl, and benzyloxycarbonyl) and the like. A preferred protecting group for thiol and hydroxyl groups is a trityl group.

DETAILED DESCRIPTION OF THE INVENTION

Figure 1:
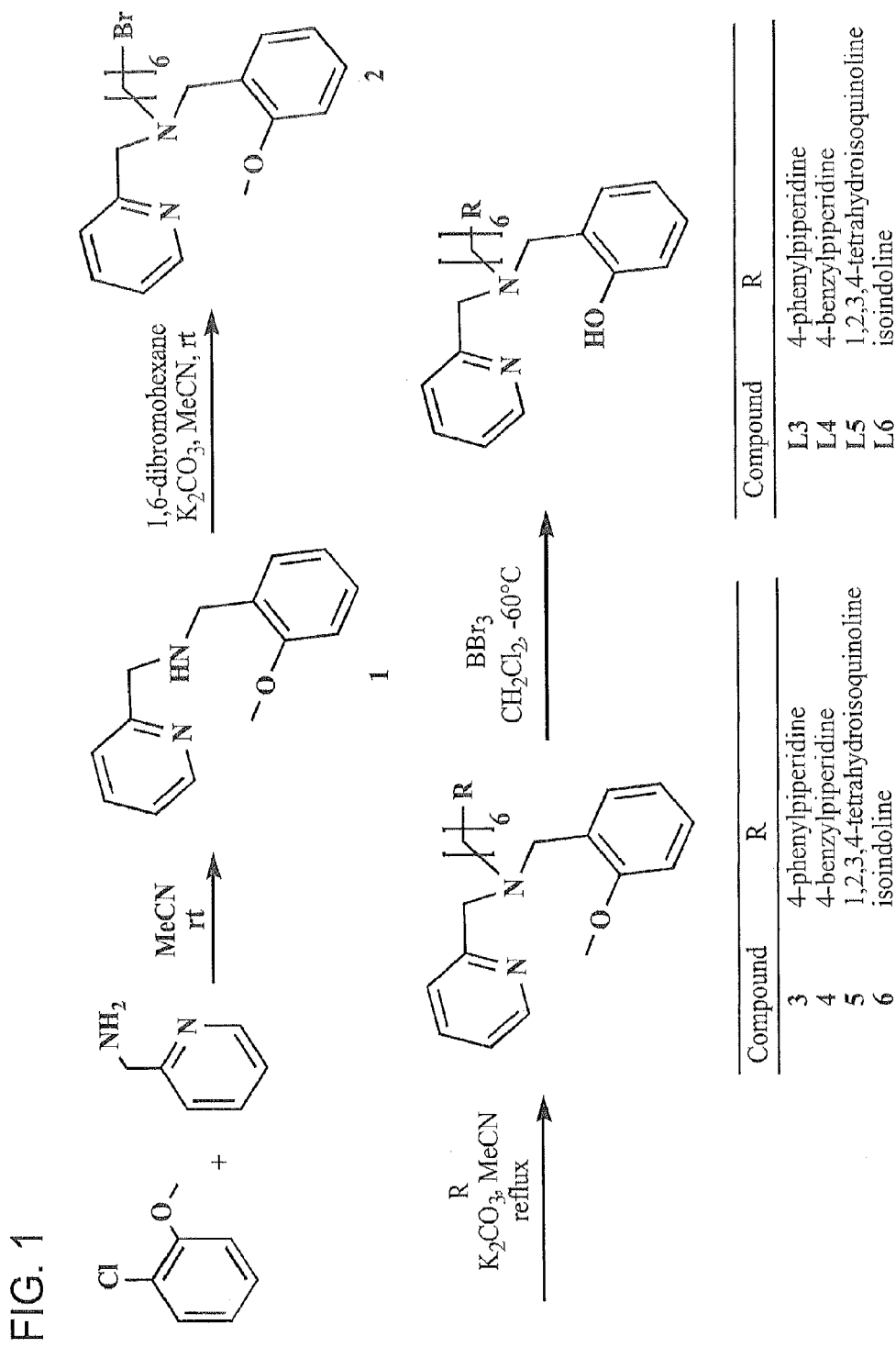
FIG. 1 is a scheme showing a synthesis of certain compounds and complexes of the invention.
Figure 1:
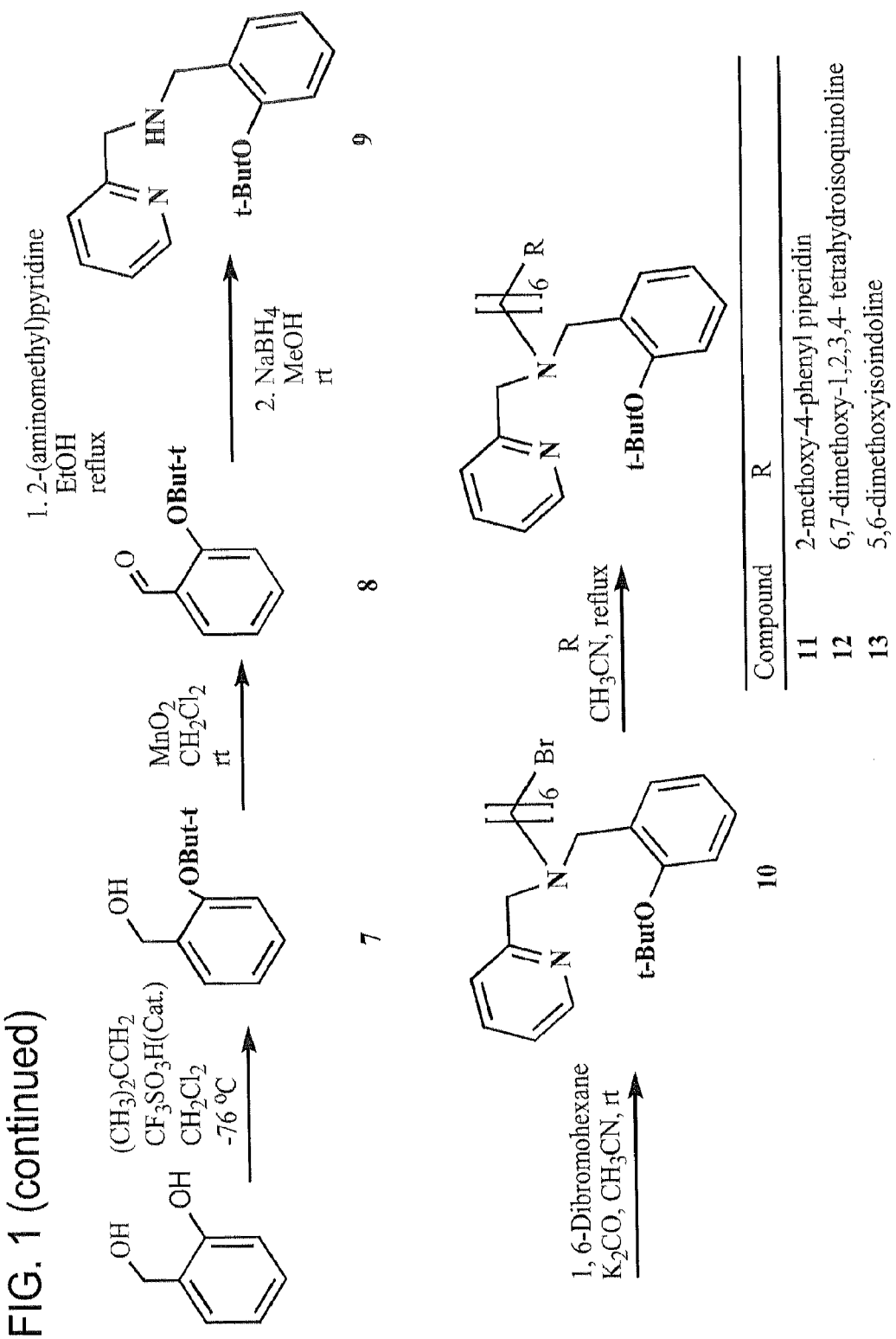
Figure 1:
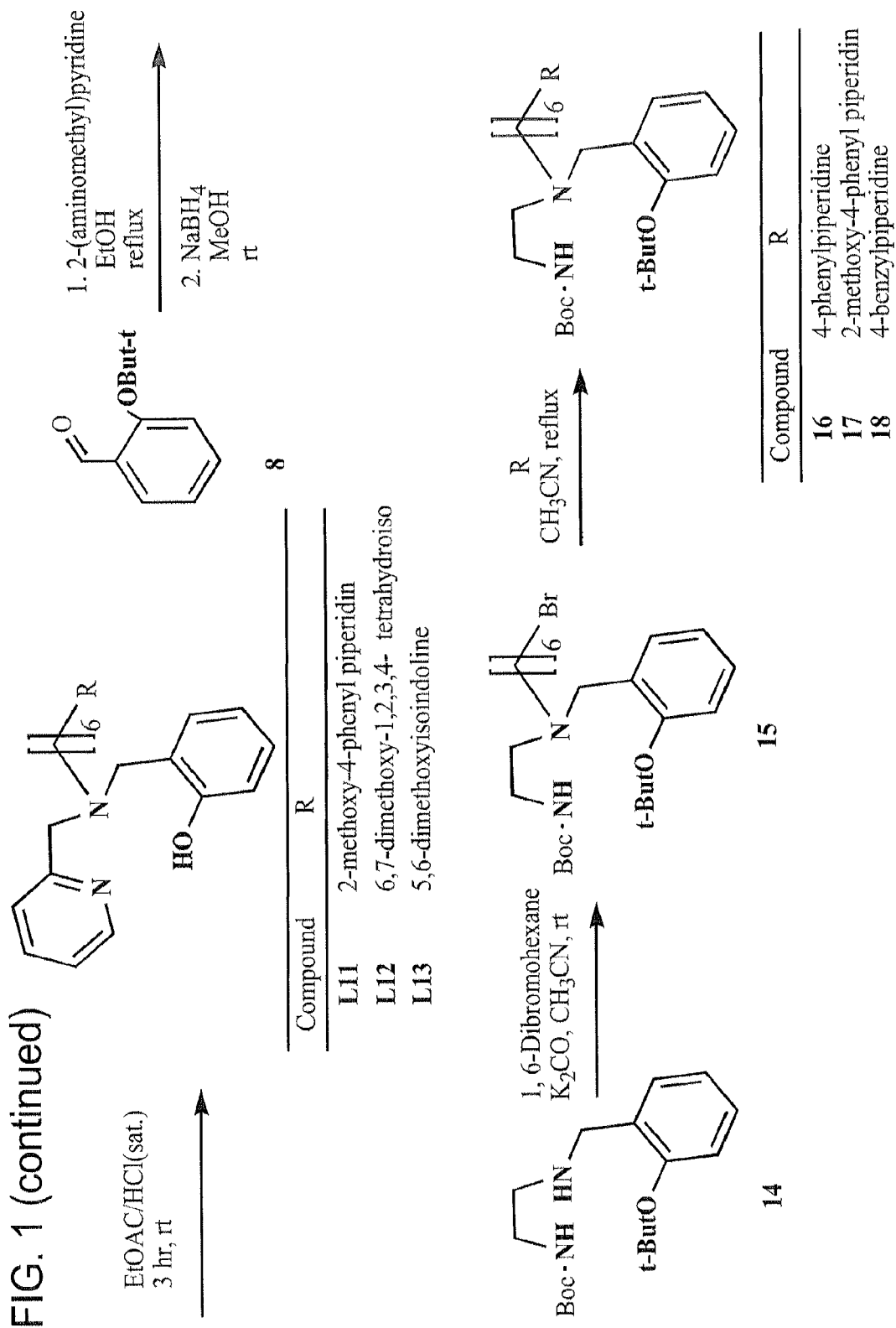
Figure 1:
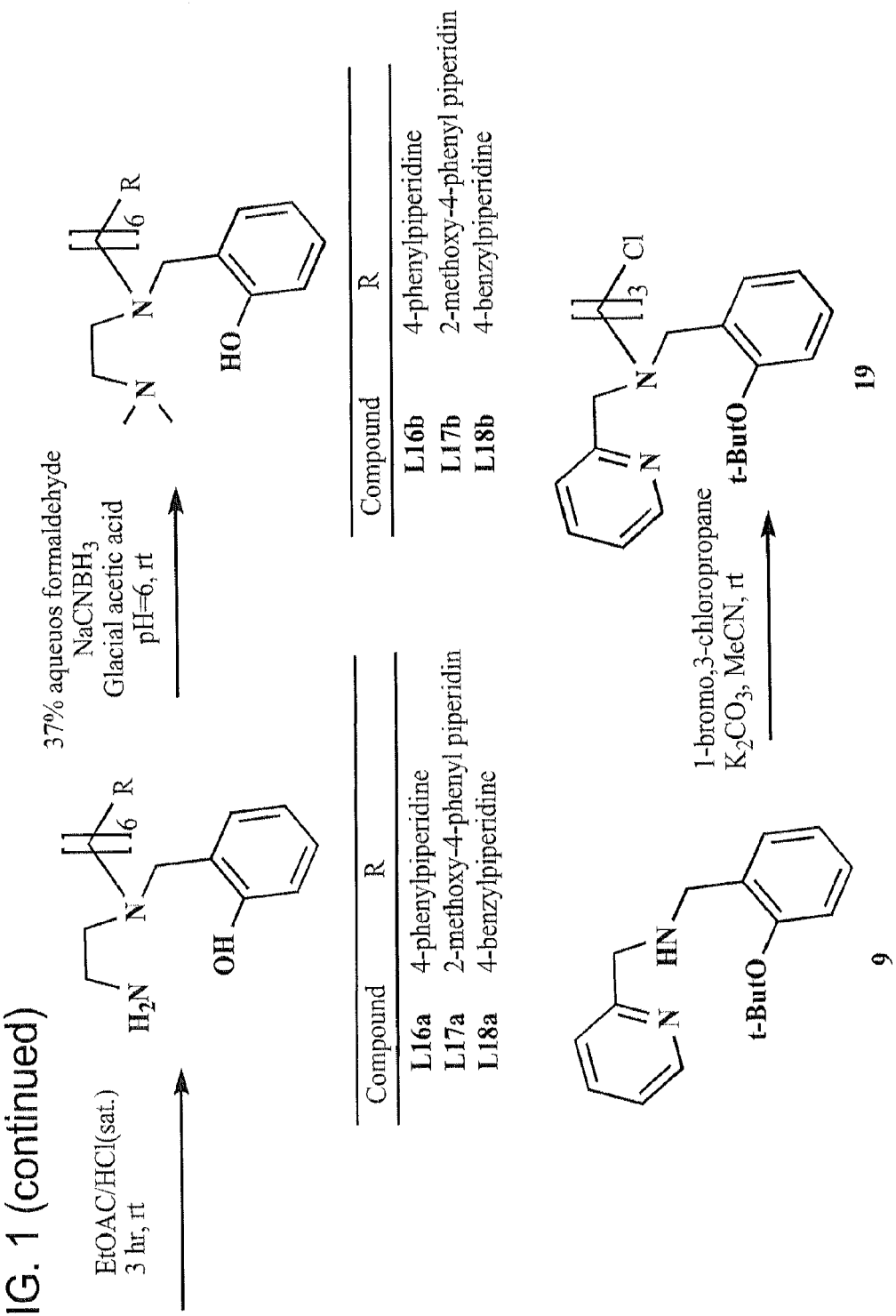
Figure 1:
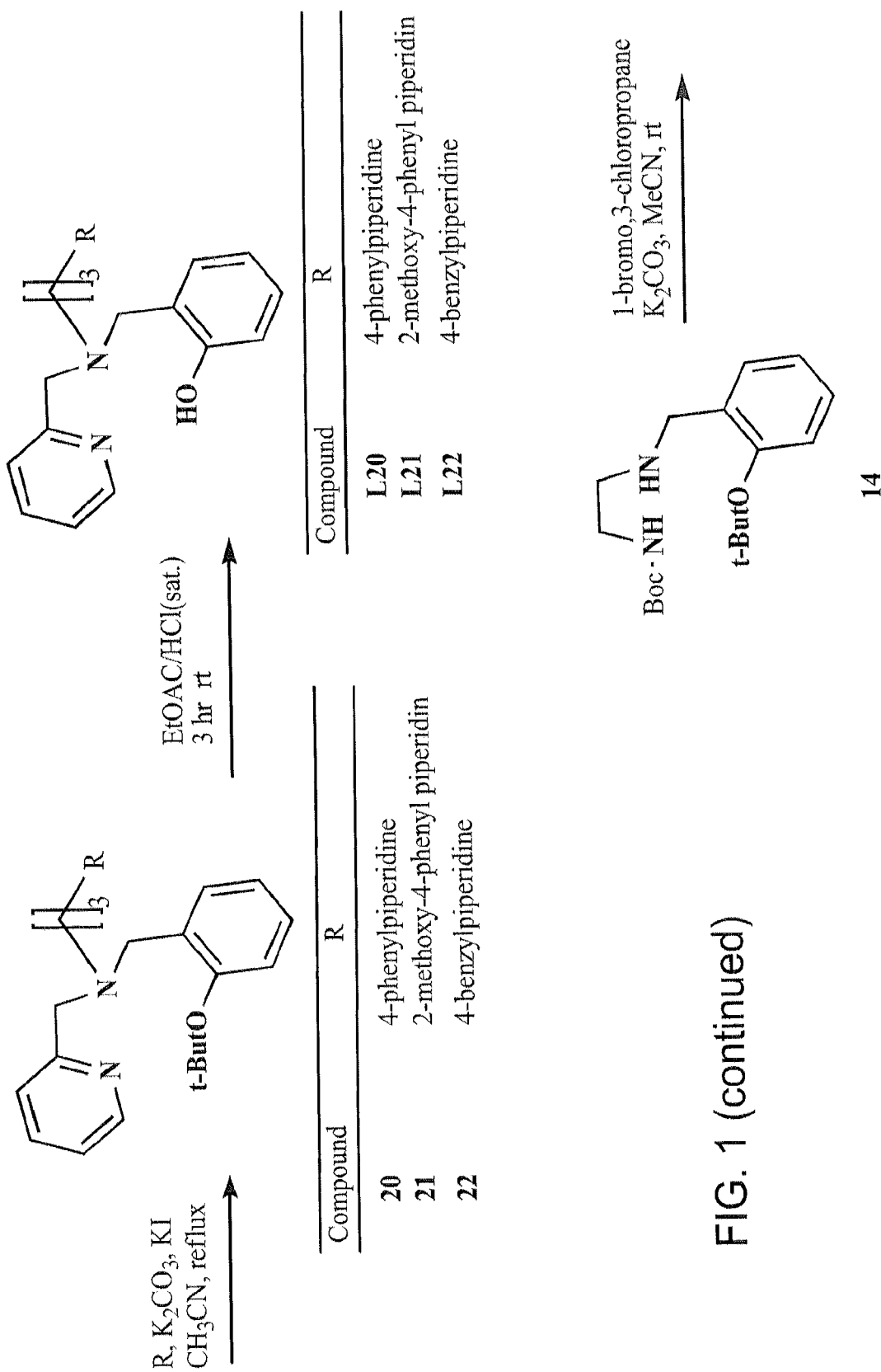
Figure 1:
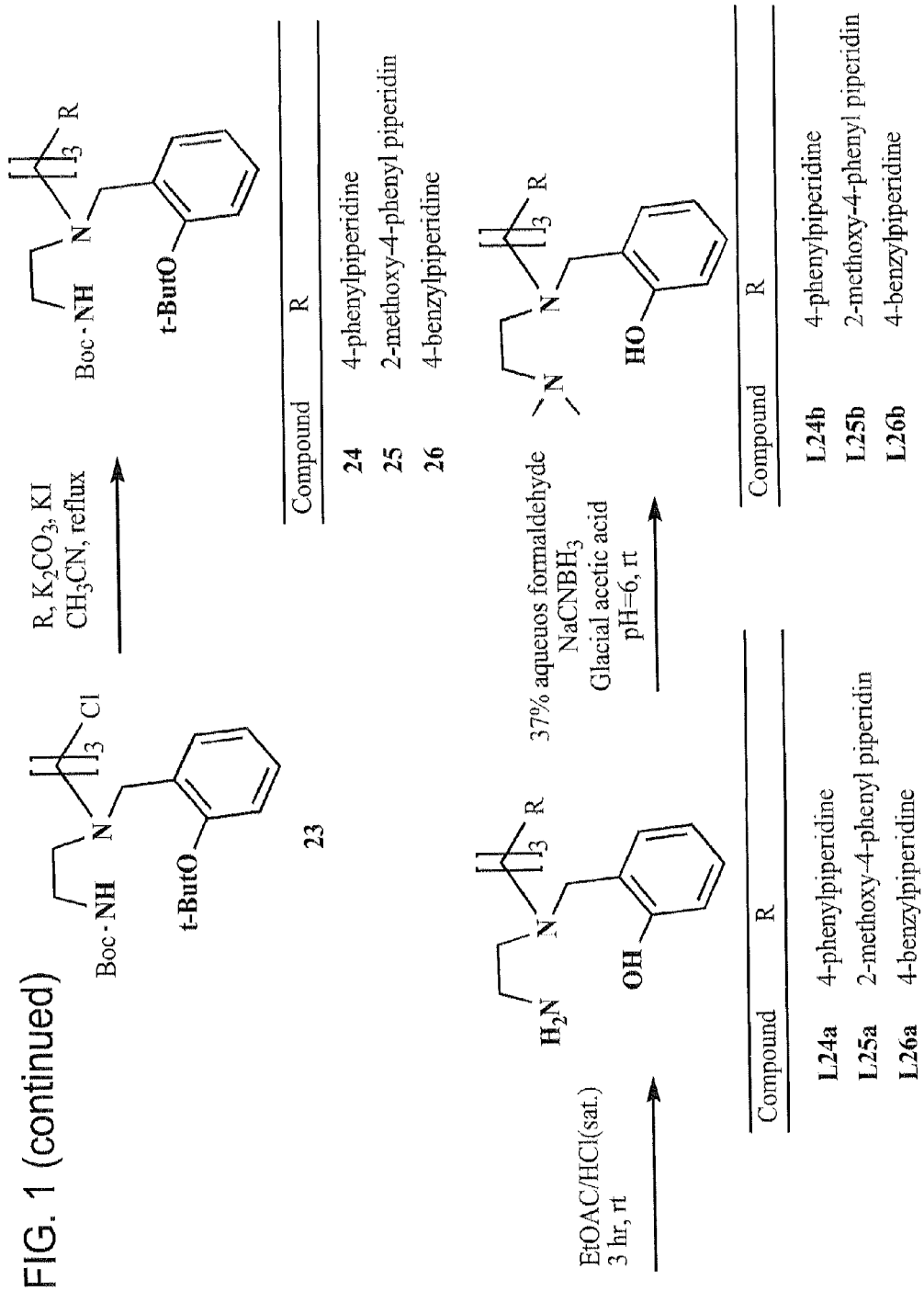
Figure 1:
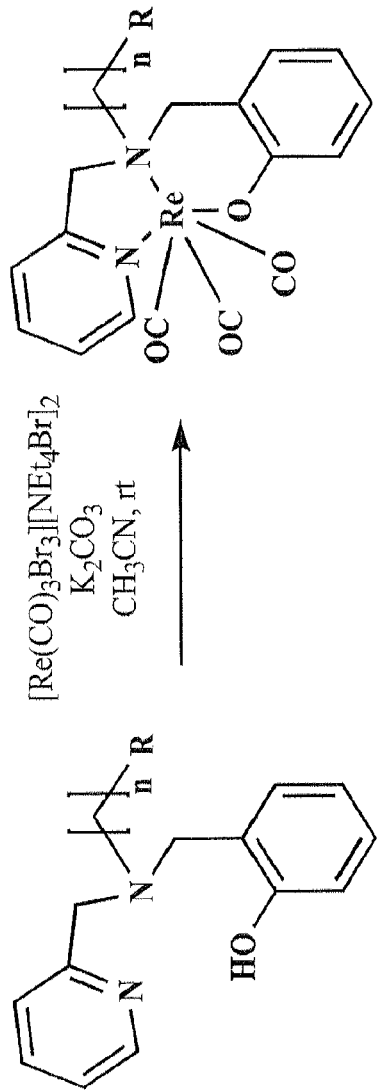
Figure 1:
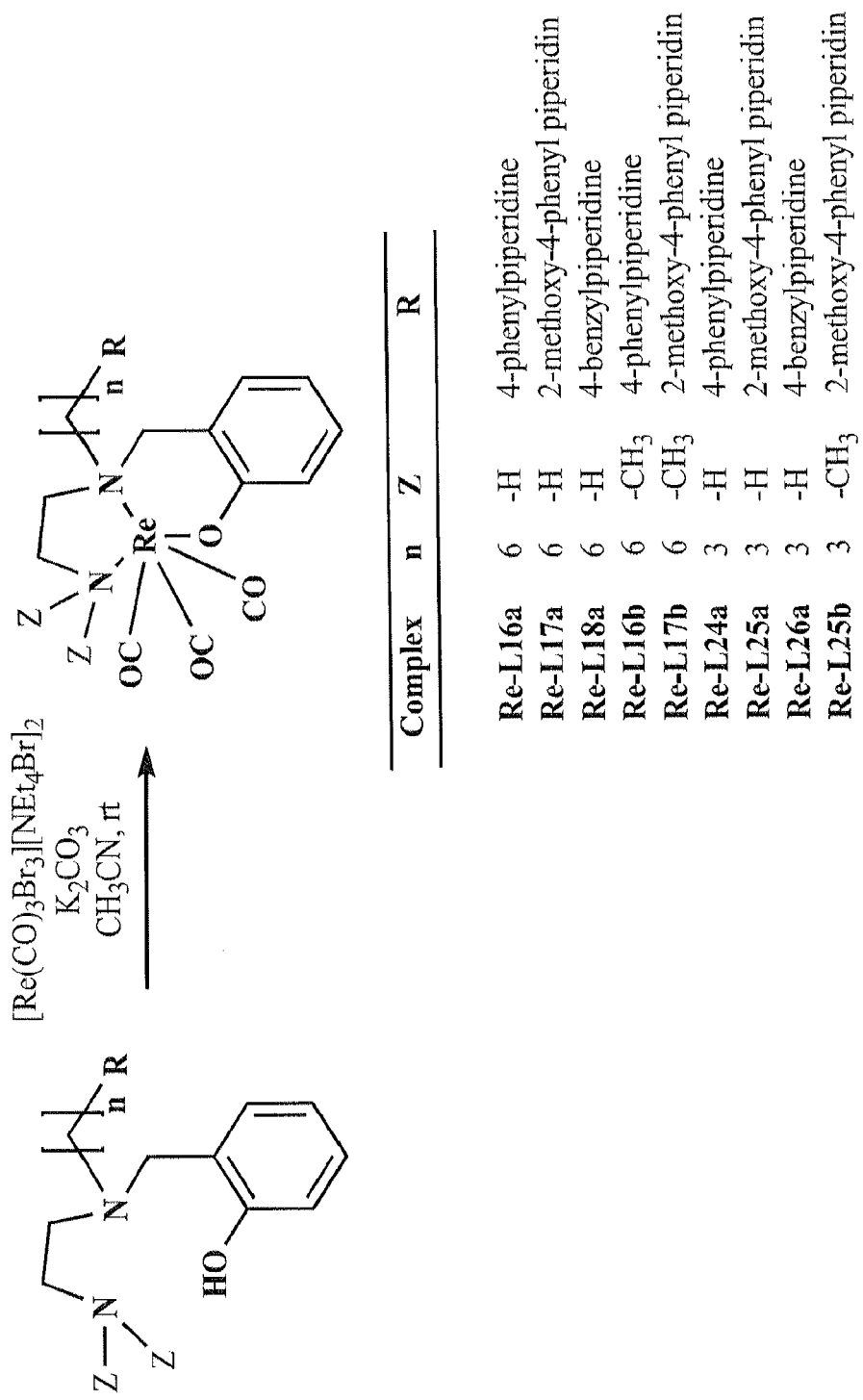

The present invention provides new radiolabeled diagnostic and therapeutic agents which comprise a metal center.

Preferred diagnostic agents comprise at least one radiometal, e.g., at least one radioactive isotope. Preferred therapeutic agents may comprise a radiolabelled or cold metal ions (e.g., isotopes of a metal which are not radioactive). Preferred radiometals include 99m-technetium and one or more radioactive isotopes of rhenium. Preferred agents of the present invention may comprise an oxotechnetium core (Tc=O) or an oxorhenium core (Re=O) chelated by at least one ligand group as described in Formulae I-V and X herein. Preferred radiolabeled metal complexes of the invention comprise a neutral or cationic metal complex, e.g., a metal ion and the inner coordination sphere of ligands taken together are neutral or cationic. Preferably, the overall charge of the radiolabeled complex is either neutral or cationic.

The present invention provides small-molecule metal-complexes and methods of using such small molecule metal complexes as diagnostic and therapeutic probes for the non-invasive imaging and localization of proteins or receptors expressed (or over expressed) in normal tissues and organs as well as identification of said receptors over expressed in certain diseases or tumors.

Particular proteins, receptors and neuroreceptors, such as serotonin receptors, including 5HT receptors, adrenoreceptors, including $\alpha_1$ receptors, sigma receptors including $\sigma_1$ and $\sigma_2$ receptors, calcium channel receptors, emopamil binding proteins, adrenergic receptors, dopamine receptors, are implicated in various neurological disorders and are also over expressed in a variety of tumors or pathological conditions. The $^{99m}$Tc-complexes and the corresponding rhenium complexes are linked via a linker to a secondary or tertiary amine, or the like, and possess affinity for $5HT_{1A}$, sigma-1, sigma-2, $Ca^{2+}$ channel receptors, EBP, or alpha-1 receptors expressed or over expressed on the cell surface or within the cell of neuronal cells or tumor cells.

In one aspect, the invention provided a compound represented by the formula (Formula I):

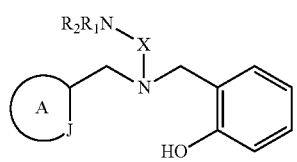

(I)

wherein:
  J is N or S;
  Ring A is a heteroaryl ring having 5 or 6 ring atoms;
  X is a linking group comprising an aliphatic backbone chain having 1 to about 8 atoms, in which the aliphatic backbone chain can optionally include ester, amide, ether or thioether linkages in the aliphatic backbone chain; and
  $R_1$ and $R_2$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl, wherein at least one of $R_1$ or $R_2$ is not hydrogen; or wherein $R_1$ and $R_2$ taken together with the nitrogen atom to which they are attached form a heterocyclic ring having from 3 to 8 atoms in the ring; or
  one of $R_1$ or $R_2$ is alkyl and the other is a moiety selected from:

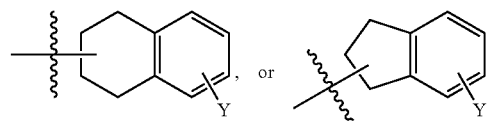

in which Y represents 0-4 substituents independently selected from halogen, alkyl, alkoxyl, or cyano; or
  $NR_1R_2$ is a moiety selected from:

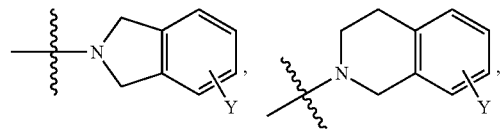

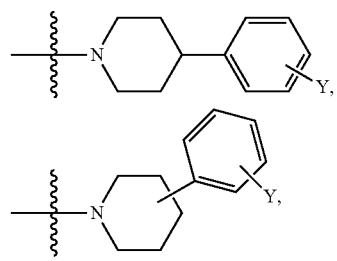

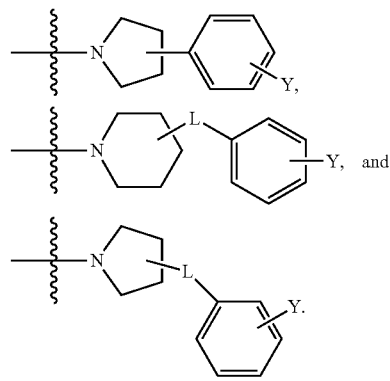

in which L represents a one or two atom linking group and Y represents 0-4 substituents independently selected from halogen, alkyl, alkoxyl, or cyano;
  or a salt thereof.

In certain embodiments, X is selected from the group consisting of $-(CH_2)_m-C(O)NH-$ and an $\alpha,\omega$-alkylene group, wherein the alkylene group has between about 1 and about 10 carbon atoms and between 0 and about 3 oxygen or sulfur atoms in the alkylene chain; and m is an integer of from about 1 to about 5. In certain embodiments, X is an optionally substituted $C_{2-8}$alkylene group, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, J in N. In certain embodiments, J is S and ring A is a thiophenyl (e.g., thiophen-2-yl) ring. In certain embodiments, the compound is 2-(((3-(4-(2-methoxyphenyl)piperidin-1-1)propyl)(thiophen-2-ylmethyl)amino)methyl)phenol.

In one aspect, the invention provided a compound represented by the formula (Formula Ic):

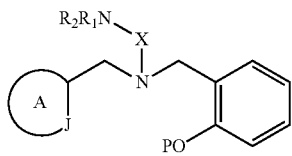

wherein:
ring A, J, X, $R_1$ and $R_2$ are as defined in formula I; and P is a protecting group.

In another aspect, the invention provides a metal complex of Formula I. In certain embodiments, the complex is represented by the formula (Formula Ia):

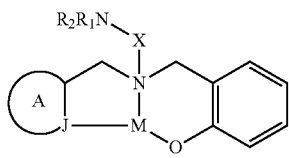

in which ring A, J, X, $R_1$ and $R_2$ are as defined in formula I, and

M is a metal or metal center selected from technetium, rhenium, yttrium, copper, gallium, indium, bismuth, platinum and rhodium, more preferably technetium and rhenium. It will be understood that M includes a metal atom, and can further include ligands for the metal (e.g., M can represent Tc(CO)$_3$, when the technetium atom has carbonyl ligands).

In certain embodiments of Formula Ia, the complex is represented by the formula:

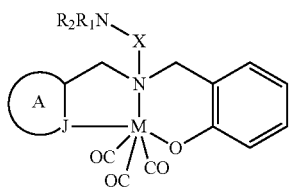

in which Ring A, J, M, X, $R_1$ and $R_2$ are as defined for Formula Ia. M is preferably technetium or rhenium.

In one aspect, the invention provided a compound represented by the formula (Formula X):

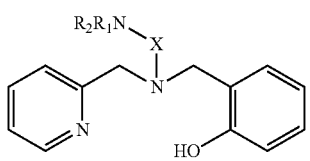

wherein:
X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl, wherein at least one of $R_1$ or $R_2$ is not hydrogen; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

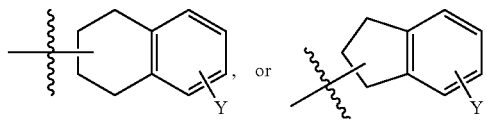

in which Y represents 0-4 substituents independently selected from halogen, alkyl, alkoxyl, or cyano; or $NR_1R_2$ is a moiety selected from:

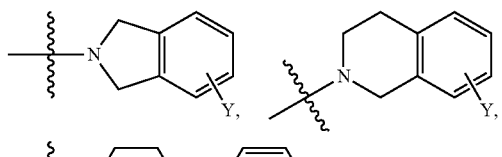

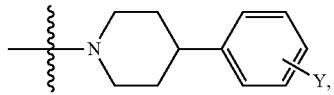

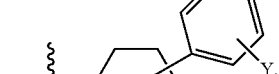

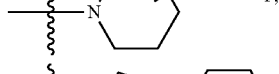

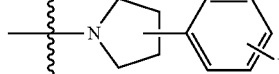

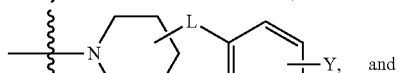

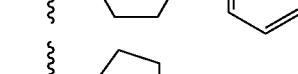, and

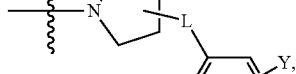

in which L represents a one or two atom linking group and Y represents 0-4 substituents independently selected from halogen, alkyl, alkoxyl, or cyano;
or a salt thereof.

In certain embodiments, X is an optionally substituted $C_{2-8}$alkylene group, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, X is selected from the group consisting of —(CH$_2$)$_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5.

In certain embodiments, $NR_1R_2$ is 4-phenylpiperidin-1-yl; 4-benzylpiperidin-1-yl; 3,4-dihydroisoquinolin-2(1H)-yl; isoindolin-2-yl; 4-(2-methoxyphenyl)cyclohexyl; 6,7-dimethoxy-3,4-dihydroisoquinolin-2(1H)-yl; 5,6-dimethoxyisoindolin-2-yl; 2-methoxyphenyl)piperidin-1-yl; or 4-(2-methoxyphenyl)piperidin-1-yl.

In certain embodiments, the compound is:
N-(2-methoxybenzyl)-6-(4-phenylpiperidin-1-yl)-N-(pyridin-2-ylmethyl)hexan-1-amine;
6-(4-benzylpiperidin-1-yl)-N-(2-methoxybenzyl)-N-(pyridin-2-ylmethyl)hexan-1-amine;
6-(3,4-dihydroisoquinolin-2(1H)-yl)-N-(2-methoxybenzyl)-N-(pyridin-2-ylmethyl)hexan-1-amine;
6-(isoindolin-2-yl)-N-(2-methoxybenzyl)-N-(pyridin-2-ylmethyl)hexan-1-amine;
2-(((6-(4-phenylpiperidin-1-yl)hexyl)(pyridin-2-ylmethyl)amino)methyl)phenol;
2-(((6-(4-benzylpiperidin-1-yl)hexyl)(pyridin-2-ylmethyl)amino)methyl)phenol;
2-(((6-(3,4-dihydroisoquinolin-2(1H)-yl)hexyl)(pyridin-2-ylmethyl)amino)methyl)-phenol;
2-(((6-(isoindolin-2-yl)hexyl)(pyridin-2-ylmethyl)amino)methyl)phenol;
N-(2-tert-butoxybenzyl)-6-(4-(2-methoxyphenyl)cyclohexyl)-N-(pyridin-2-ylmethyl)hexan-1-amine;
N-(2-tert-butoxybenzyl)-6-(6,7-dimethoxy-3,4-dihydroisoquinolin-2(1H)-yl)-N-(pyridin-2-ylmethyl)hexan-1-amine;
N-(2-tert-butoxybenzyl)-6-(5,6-dimethoxyisoindolin-2-yl)-N-(pyridin-2-ylmethyl)hexan-1-amine;
2-(((6-(4-(2-methoxyphenyl)piperidin-1-yl)hexyl)(pyridin-2-ylmethyl)amino)methyl)phenol;
2-(((6-(6,7-dimethoxy-3,4-dihydroisoquinolin-2(1H)-yl)hexyl)(pyridin-2-ylmethyl)amino)methyl)phenol;
2-(((6-(5,6-dimethoxyisoindolin-2-yl)hexyl)(pyridin-2ylmethyl)amino)methyl)phenol;
2-(((3-(4-phenylpiperidin-1-yl)propyl)(pyridin-2-ylmethyl)amino)methyl)phenol;
2-(((3-(4-(2-methoxyphenyl)piperidin-1-yl)propyl)(pyridin-2-ylmethyl)amino)methyl)phenol;
2-(((3-(4-benzylpiperidin-1-yl)propyl)(pyridin-2-ylmethyl)amino)methyl)phenol;
or a salt thereof.

In one aspect, the invention provided a compound represented by the formula (Formula Xc):

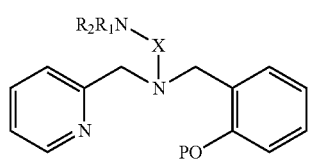

(Xc)

in which X, $R_1$ and $R_2$ are as defined in formula X, and P is a protecting group.

In another aspect, the invention provides a metal complex of a compound of Formula X. In certain embodiments, the complex is a complex represented by the formula (Formula Xa):

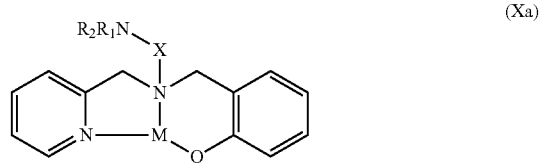

(Xa)

wherein:

X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl, wherein at least one of $R_1$ or $R_2$ is not hydrogen; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

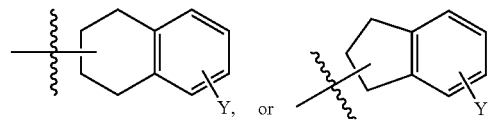

in which Y represents 0-4 substituents independently selected from halogen, alkyl, alkoxyl, or cyano; or $NR_1R_2$ is a moiety selected from:

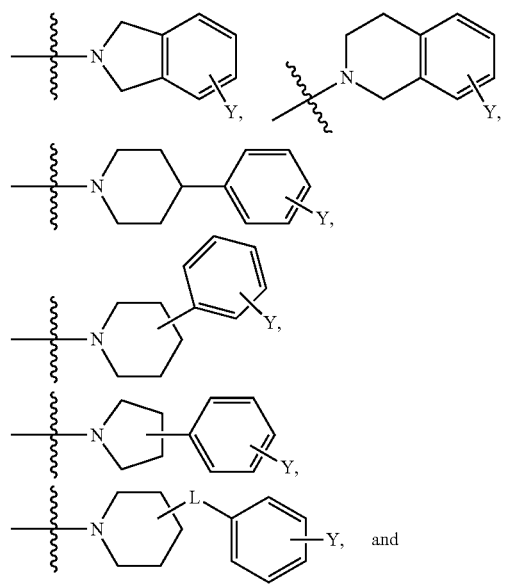

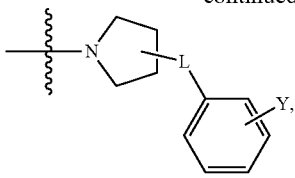

in which L represents a one or two atom linking group and Y represents 0-4 substituents independently selected from halogen, alkyl, alkoxyl, or cyano;

and

M is a metal or metal center selected from technetium, rhenium, yttrium, copper, gallium, indium, bismuth, platinum and rhodium, more preferably technetium and rhenium. It will be understood that M includes a metal atom, and can further include ligands for the metal (e.g., M can represent Tc(CO)$_3$, when the technetium atom has carbonyl ligands). For example, Formula Xa includes complexes according to Formula Xb:

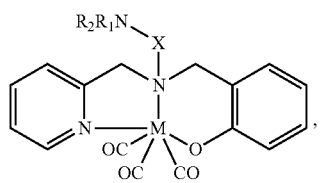

(Xb)

where M is a metal, preferably a metal such as Tc or Re.

In another aspect, the invention provides a compound represented by the formula (Formula II):

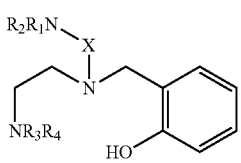

(II)

wherein:

X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl, wherein at least one of $R_1$ or $R_2$ is not hydrogen; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

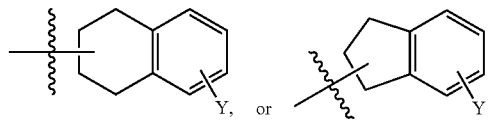

in which Y represents 0-4 substituents independently selected from halogen, alkyl, alkoxyl, or cyano; or
$NR_1R_2$ is a moiety selected from:

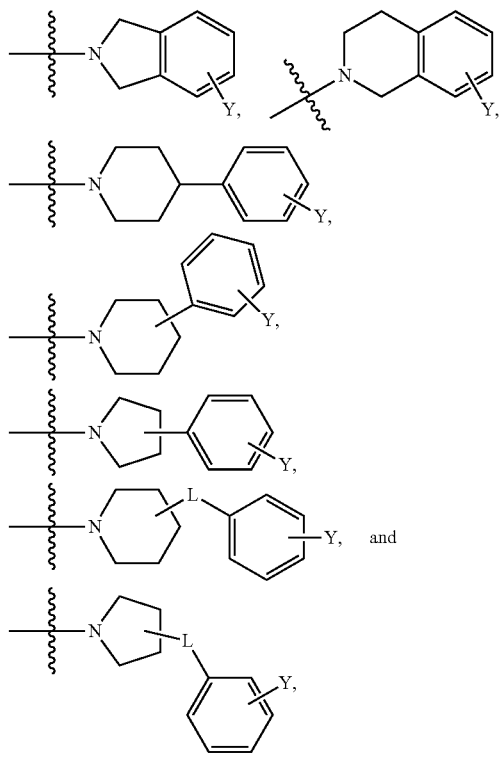

in which L represents a one or two atom linking group and Y represents 0-4 substituents independently selected from halogen, alkyl, alkoxyl, or cyano;

$R_3$ and $R_4$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl; or a salt thereof.

In certain embodiments, X is an optionally substituted $C_{2-8}$alkylene group, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, X is selected from the group consisting of —(CH$_2$)$_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5.

In certain embodiments, $NR_1R_2$ is 4-phenylpiperidin-1-yl; 4-benzylpiperidin-1-yl; 3,4-dihydroisoquinolin-2(1H)-yl; isoindolin-2-yl; 4-(2-methoxyphenyl)cyclohexyl; 6,7-dimethoxy-3,4-dihydroisoquinolin-2(1H)-yl; 5,6- dimethoxyisoindolin-2-yl; 2-methoxyphenyl)piperidin-1-yl; or 4-(2-methoxyphenyl)piperidin-1-yl.

In certain embodiments, wherein the compound is:
2-(((2-aminoethyl)(6-(4-phenylpiperidin-1-yl)hexyl)amino)methyl)phenol;
2-(((2-aminoethyl)(6-(4-(2-methoxyphenyl)piperidin-1-yl)hexyl)amino)methyl)phenol;
2-(((2-aminoethyl)(6-(4-benzylpiperidin-1-yl)hexyl)amino)methyl)phenol;
2-(((2-(dimethylamino)ethyl)(6-(4-phenylpiperidin-1-yl)hexyl)amino)methyl)phenol;
2-(((2-(dimethylamino)ethyl)(6-(4-(2-methoxyphenyl)piperidin-1-yl)hexyl)amino)methyl)phenol;
2-(((6-(4-benzylpiperidin-1-yl)hexyl)(2-(dimethylamino)ethyl)amino)methyl)phenol;
2-(((2-aminoethyl)(3-(4-phenylpiperidin-1-yl)propyl)amino)methyl)phenol;
2-(((2-aminoethyl)(3-(4-(2-methoxyphenyl)piperidin-1-yl)propyl)amino)methyl)phenol;
2-(((2-aminoethyl)(3-(4-benzylpiperidin-1-yl)propyl)amino)methyl)phenol;
2-(((2-(dimethylamino)ethyl)(3-(4-(2-methoxyphenyl)piperidin-1-yl)propyl)amino)methyl)phenol; or
2-(((3-(4-benzylpiperidin-1-yl)propyl)(2-(dimethylamino)ethyl)amino)methyl)phenol; or a salt thereof.

In another aspect, the invention provides a compound represented by the formula (Formula II):

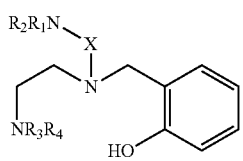

(IIc)

wherein:
X, $R_1$ and $R_2$ are as defined in formula II, and P is a protecting group.

In another aspect, the invention provides a metal complex of a compound of Formula II. In certain embodiments, the complex is a complex represented by the formula (Formula IIa):

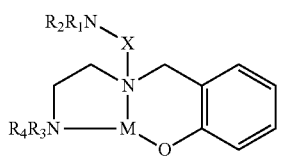

(IIa)

wherein:
X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl, wherein at least one of $R_1$ or $R_2$ is not hydrogen; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

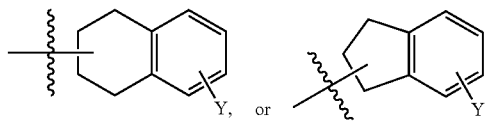

in which Y represents 0-4 substituents independently selected from halogen, alkyl, alkoxyl, or cyano; or $NR_1R_2$ is a moiety selected from:

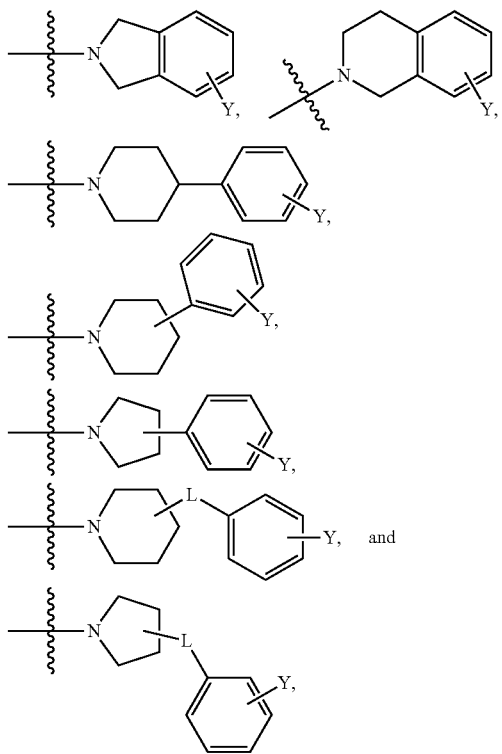

in which L represents a one or two atom linking group and Y represents 0-4 substituents independently selected from halogen, alkyl, alkoxyl, or cyano;

$R_3$ and $R_4$ each are independently selected from the group consisting of hydrogen, unsubstituted alkyl groups having from 1 to about 8 carbon atoms, alkoxyalkyl groups having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl; and M is a metal selected from technetium, rhenium, yttrium, copper, gallium, indium, bismuth, platinum and rhodium, more preferably technetium and rhenium. It will be understood that M includes a metal atom, and can further include ligands for the metal (e.g., M can represent $Tc(CO)_3$, when the technetium atom has carbonyl ligands). For example, Formula IIa includes complexes according to Formula IIb:

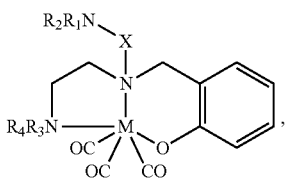

(IIb)

where M is a metal, preferably a metal such as Tc or Re.

In another aspect, the invention provides a compound represented by the formula (Formula III):

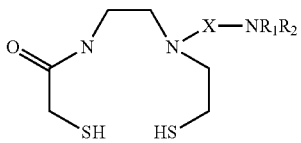

(III)

wherein:

X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl group having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl; or wherein $R_1$ and $R_2$ taken together with the nitrogen atom to which they are attached form an optionally substituted heterocyclic ring having from 3 to 8 atoms in the ring; or one of $R_1$ or $R_2$ is alkyl and the other is a moiety selected from:

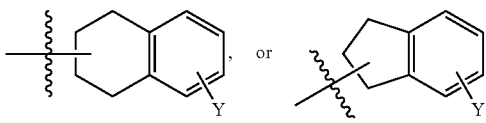

in which Y represents 0-4 substituents independently selected from halogen, alkyl, alkoxyl, or cyano;

or a salt thereof.

In certain embodiments, X is an optionally substituted $C_{2-8}$alkylene group, $R_1$ is a $C_{1-6}$alkyl group and $R_2$ is an optionally substituted (aryl)$C_{1-4}$alkyl or an optionally substituted (heteroaryl)$C_{1-4}$alkyl. In certain embodiments, $R_1$ and $R_2$ taken together with the nitrogen atom to which they are attached form an optionally substituted heterocyclic ring having from 3 to 8 atoms in the ring, more preferably 5 or 6 atoms in the ring. In certain embodiments, $R_1$ and $R_2$ taken together with the nitrogen atom to which they are attached form an optionally substituted piperidine or morpholine. In certain embodiments, $R_1$ and $R_2$ taken together with the nitrogen atom to which they are attached form a 4-phenylpiperidine group. In certain embodiments, $R_1$ and $R_2$ taken together with the nitrogen atom to which they are attached form a 4-benzylpiperidine group or a 4-((2-methoxyphenyl)methyl)piperidine group. In certain embodiments, $R_1$ and $R_2$ taken together with the nitrogen atom to which they are attached form a 6,7-dimethoxy-3,4-dihydroisoquinolinyl ring. In certain embodiments, $R_1$ and $R_2$ are independently lower alkyl (e.g., are both ethyl).

In certain embodiments, X is selected from the group consisting of —$(CH_2)_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5. In certain embodiments, X is $C_3$-$C_6$ alkylene.

In certain embodiments, $NR_1R_2$ is a moiety selected from:

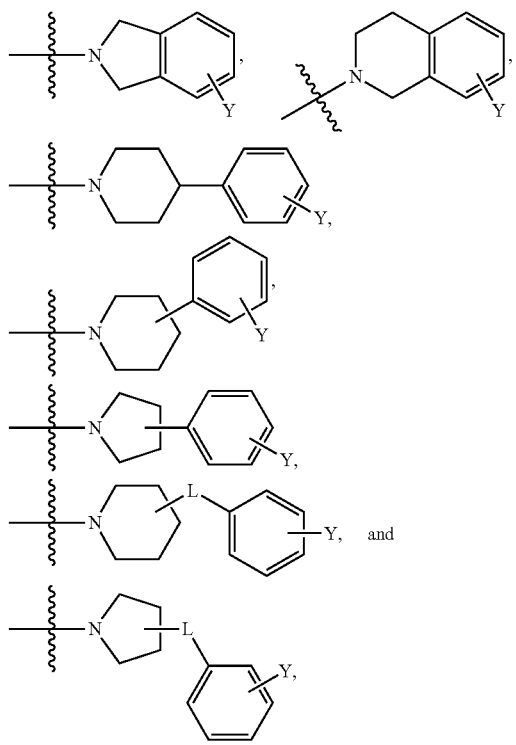

in which L represents a one or two atom linking group and Y represents 0-4 substituents independently selected from halogen, alkyl, alkoxyl, or cyano.

In another aspect, the invention provides a metal complex of a compound of Formula III. In certain embodiments, the complex is a complex represented by the formula (Formula IIIa):

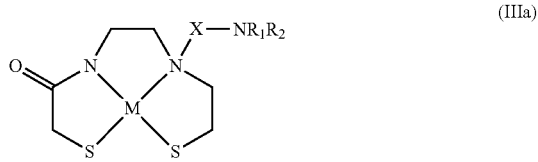

(IIIa)

wherein:

X is a linking group comprising an aliphatic backbone chain having 1 to about 8 atoms, in which the aliphatic backbone chain can optionally include ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl group having from 2 to about 8 carbon atoms, substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

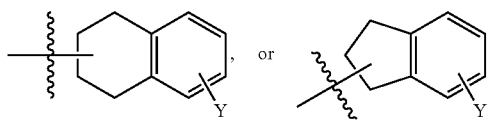

in which Y represents 0-4 substituents independently selected from halogen, alkyl, alkoxyl, or cyano; and M is a metal selected from technetium, rhenium, yttrium, copper, gallium, indium, bismuth, platinum and rhodium, more preferably technetium and rhenium. It will be understood that M includes a metal atom, and can further include ligands such as halogens(s) (F, Cl, Br, I) for the metal, or oxygen. For example, Formula IIIa includes complexes according to Formula IIIb:

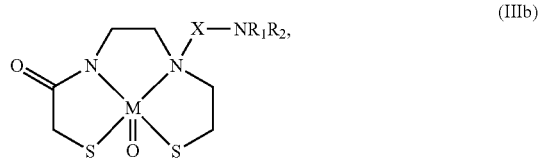

where M is a metal such as Tc or Re.

In certain embodiments, $NR_1R_2$ is a moiety selected from:

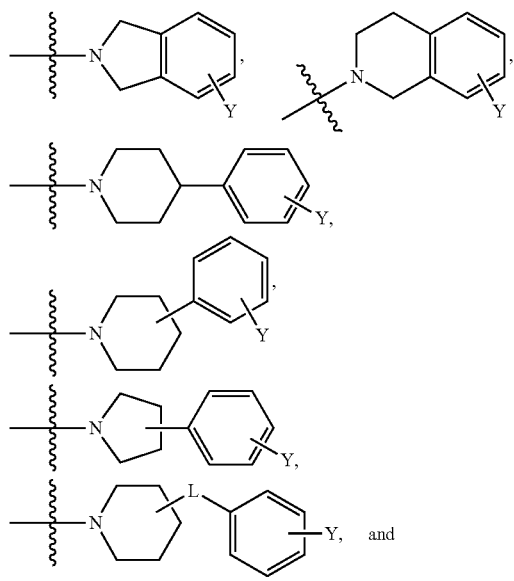

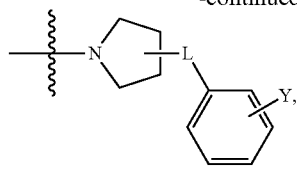

in which L represents a one or two atom linking group and Y represents 0-4 substituents independently selected from halogen, alkyl, alkoxyl, or cyano.

In another aspect, the invention provides a compound represented by the formula (Formula IIIc):

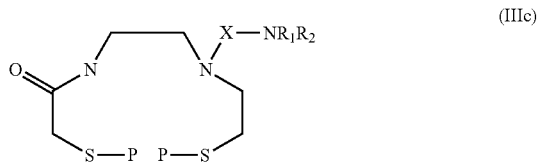

wherein:

X is a linking group comprising an aliphatic backbone chain having 1 to about 8 atoms, in which the aliphatic backbone chain can optionally include ester, amide, ether or thioether linkages in the aliphatic backbone chain;

$R_1$ and $R_2$ each are independently selected from the group consisting of hydrogen, unsubstituted alkyl groups having from 1 to about 8 carbon atoms, alkoxyalkyl group having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

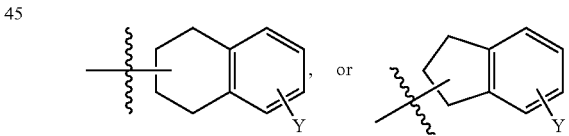

in which Y represents 0-4 substituents independently selected from halogen, alkyl, alkoxyl, or cyano; and P is, independently for each occurrence, a protecting or blocking group;

or a salt thereof.

In certain embodiments, X is an optionally substituted $C_{2-8}$alkylene group, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, X is selected from the group consisting of —(CH$_2$)$_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5. In certain embodiments, the protecting group P is a trityl group.

In certain embodiments, $NR_1R_2$ is a moiety selected from:

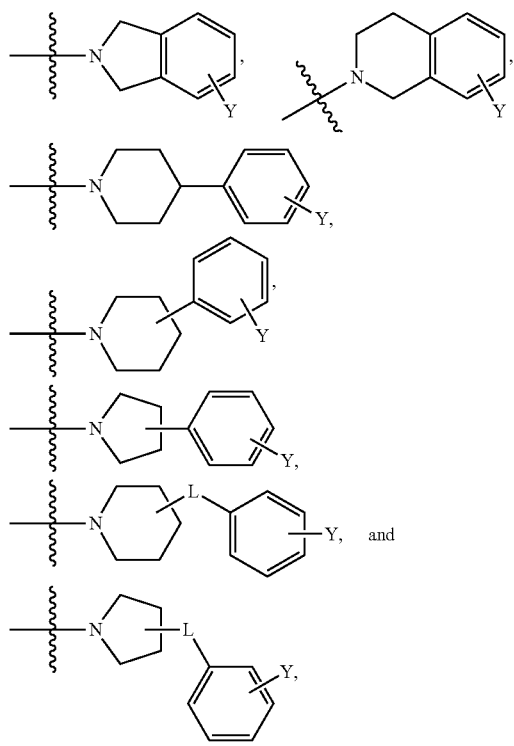

in which L represents a one or two atom linking group and Y represents 0-4 substituents independently selected from halogen, alkyl, alkoxyl, or cyano.

In another aspect, the invention provides a compound represented by the formula (Formula IV):

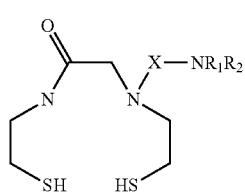

(IV)

wherein:

X is a linking group comprising an aliphatic backbone chain having 1 to about 8 atoms, in which the aliphatic backbone chain can optionally include ester, amide, ether or thioether linkages in the aliphatic backbone chain; and one of $R_1$ or $R_2$ is alkyl and the other is a moiety selected from:

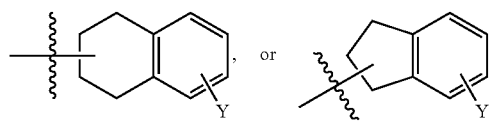

in which Y represents 0-4 substituents independently selected from halogen, alkyl, alkoxyl, or cyano; or $NR_1R_2$ is a moiety selected from:

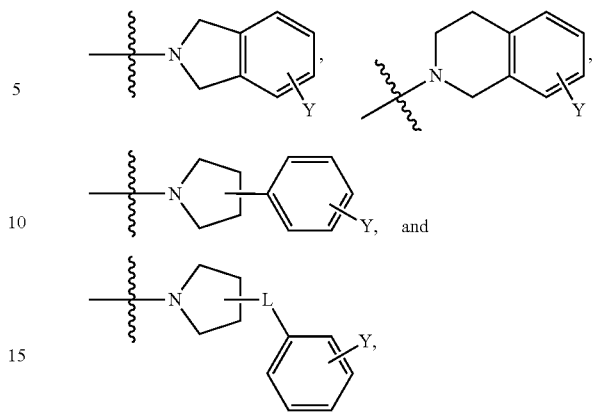

in which L represents a one or two atom linking group and Y represents 0-4 substituents independently selected from halogen, alkyl, alkoxyl, or cyano; or a salt thereof.

In certain embodiments, X is an optionally substituted $C_{2-8}$alkylene group, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, X is selected from the group consisting of —$(CH_2)_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5. In certain embodiments, L is —$CH_2$—, —$CH_2CH_2$—, O, or S.

In another aspect, the invention provides a metal complex of a compound of Formula IV. In certain embodiments, the complex is a complex represented by the formula (Formula IVa):

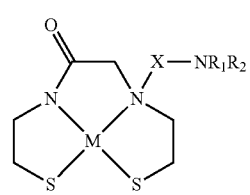

(IVa)

wherein:

X is a linking group comprising an aliphatic backbone chain having 1 to about 8 atoms, in which the aliphatic backbone chain can optionally include ester, amide, ether or thioether linkages in the aliphatic backbone chain; and one of $R_1$ or $R_2$ is alkyl and the other is a moiety selected from:

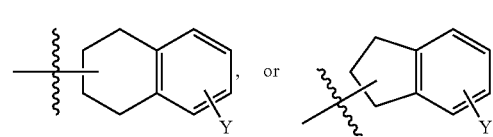

in which Y represents 0-4 substituents independently selected from halogen, alkyl, alkoxyl, or cyano; or NR₁R₂ is a moiety selected from:

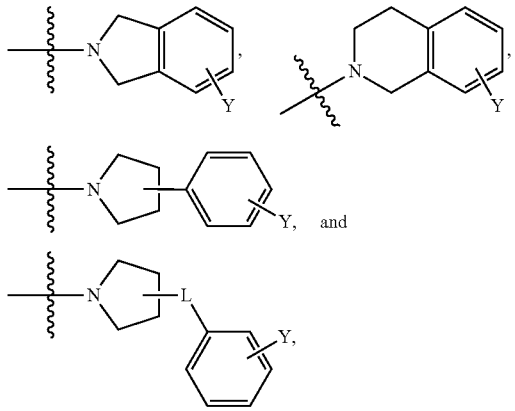

in which L represents a one or two atom linking group and Y represents 0-4 substituents independently selected from halogen, alkyl, alkoxyl, or cyano; and M is a metal selected from technetium, rhenium, yttrium, copper, gallium, indium, bismuth, platinum and rhodium, more preferably technetium and rhenium. It will be understood that M includes a metal atom, and can further include ligands such as halogens(s) (F, Cl, Br, I) for the metal, or oxygen. For example, Formula IVa includes complexes according to Formula IVb:

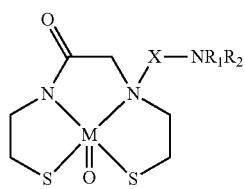

(IVb)

where M is a metal such as Tc or Re.

In another aspect, the invention provides a compound represented by the formula (Formula IVb):

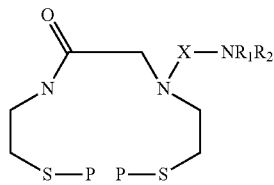

(IVc)

wherein:

X is a linking group comprising an aliphatic backbone chain having 1 to about 8 atoms, in which the aliphatic backbone chain can optionally include ester, amide, ether or thioether linkages in the aliphatic backbone chain;

one of R₁ or R₂ is alkyl and the other is a moiety selected from:

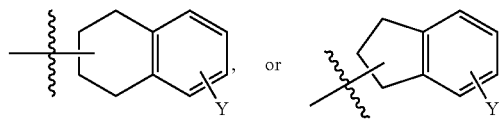

in which Y represents 0-4 substituents independently selected from halogen, alkyl, alkoxyl, or cyano; or NR₁R₂ is a moiety selected from:

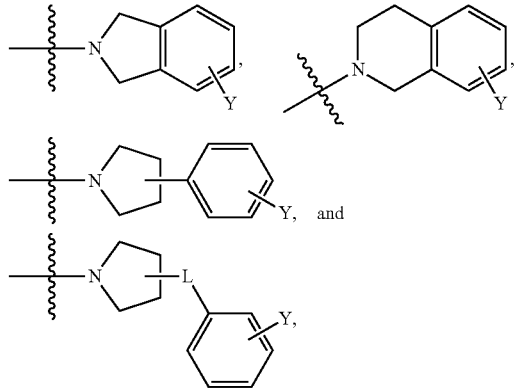

in which L represents a one or two atom linking group and Y represents 0-4 substituents independently selected from halogen, alkyl, alkoxyl, or cyano; and P is, independently for each occurrence, a protecting or blocking group;

or a salt thereof.

In certain embodiments, X is an optionally substituted $C_{2-8}$alkylene group, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, X is selected from the group consisting of —(CH₂)$_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5. In certain embodiments, L is —CH₂—, —CH₂CH₂—, O, or S. In certain embodiments, the protecting group P is a trityl group.

In another aspect, the invention provides a compound represented by the formula (Formula V):

Z—X—NR₁R₂        (V)

wherein

X is a linking group comprising an aliphatic backbone chain having 1 to about 8 atoms, wherein the aliphatic backbone chain can optionally include ester, amide, ether or thioether linkages in the aliphatic backbone chain;

Z is a chelating group capable of chelating to at least one metal ion; and one of R₁ or R₂ is alkyl and the other is a moiety selected from:

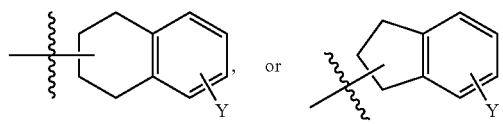

in which Y represents 0-4 substituents independently selected from halogen, alkyl, alkoxyl, or cyano; or
NR₁R₂ is a moiety selected from:

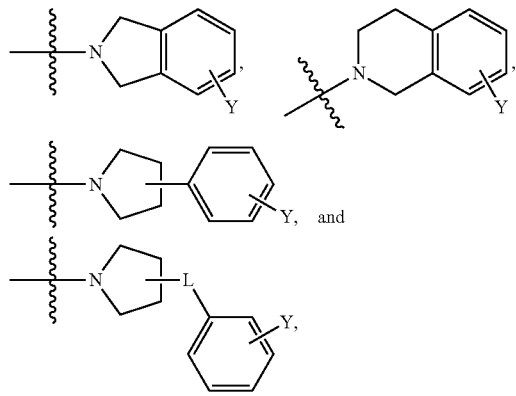

in which L represents a one or two atom linking group and Y represents 0-4 substituents independently selected from halogen, alkyl, alkoxyl, or cyano;
or a salt thereof.

In certain embodiments, Z is a tridentate, tetradentate, pentadentate, or hexadentate moiety capable of chelating a metal ion selected from the group consisting of technetium, rhenium, yttrium, copper, gallium, indium, bismuth, platinum and rhodium. In certain embodiments, Z is selected from:

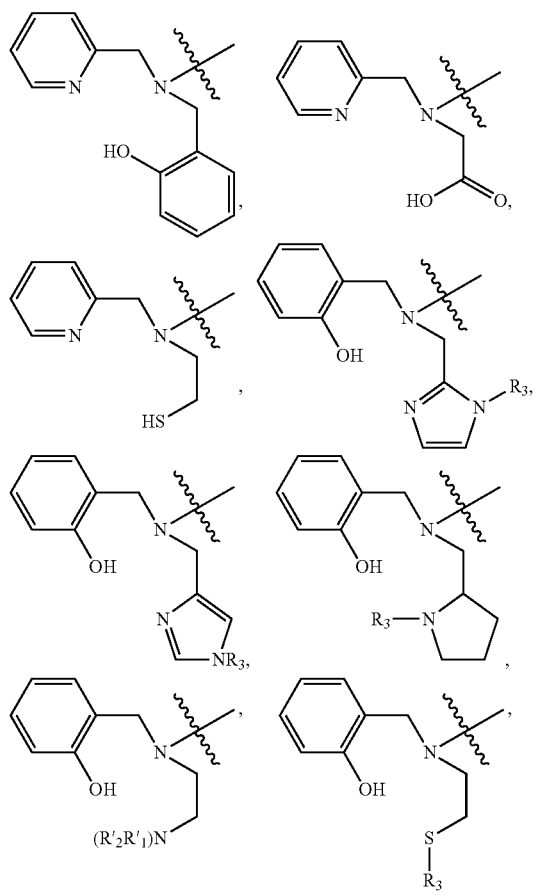

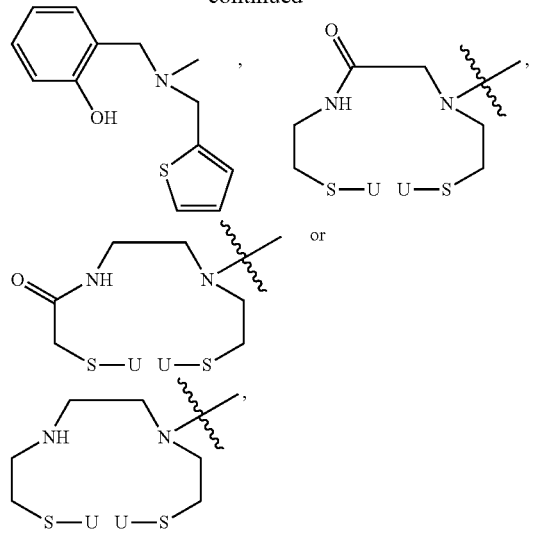

in which each $R'_1$ and $R'_2$ is independently hydrogen or alkyl, $R_3$ is independently hydrogen or alkyl, and U is independently H or a protecting or blocking group; or a salt thereof. In certain embodiments, Z is a chelating group capable of chelating to at least one metal to form a neutral metal complex.

In certain embodiments of Formula V, X is selected from the group consisting of $-(CH_2)_m-C(O)NH-$ and α,ω-alkylene groups wherein the alkylene group has between about 1 and about 10 carbon atoms and between 0 and about 3 oxygen or sulfur atoms in the alkylene chain; and m is an integer of from about 1 to about 5. In certain embodiments, X is an optionally substituted $C_{2-8}$alkylene group; in certain embodiments, $R_1$ is $C_{1-6}$alkyl group and $R_2$ is an optionally substituted (aryl)$C_{1-4}$alkyl or an optionally substituted (heteroaryl)$C_{1-4}$alkyl. In certain embodiments, L is $-CH_2-$, $-CH_2CH_2-$, O, or S. In certain embodiments, the protecting group P is a trityl group.

In another aspect, the invention provides a complex comprising a compound of Formula V, and a metal ion selected from the group consisting of technetium, rhenium, yttrium, copper, gallium, indium, bismuth, platinum and rhodium. In certain embodiments, the metal, taken together with the moiety Z of formula V, is represented by any of the formulae selected from Formulae Vb:

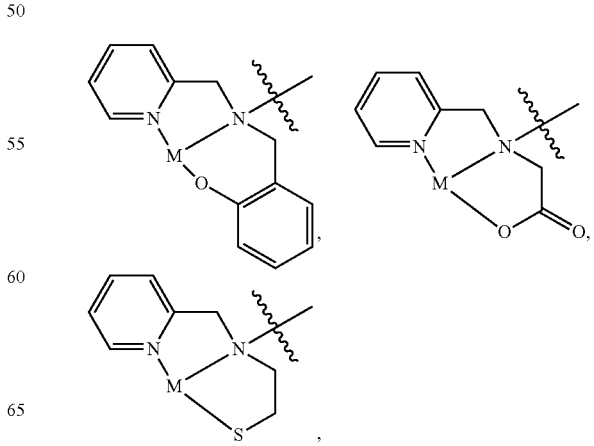

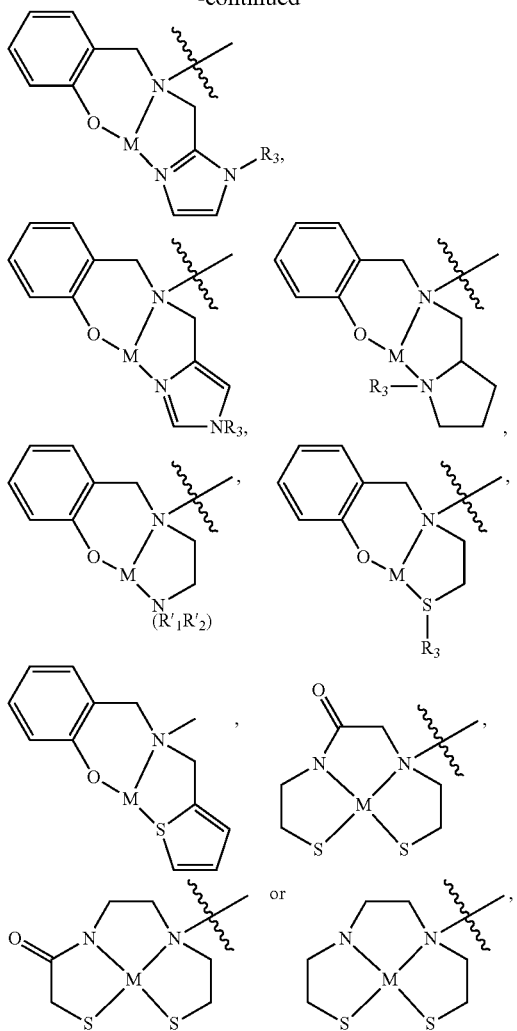

in which each $R'_1$ and $R'_2$ is independently hydrogen or alkyl, and $R_3$ is independently hydrogen or alkyl; and M is a metal selected from the group consisting of technetium, rhenium, yttrium, copper, gallium, indium, bismuth, platinum and rhodium. It will be understood that M includes a metal atom, and can further include ligands such as halogens (F, Cl, Br, I) for the metal or carbonyl ligands for the metal (e.g., M can represent $Tc(CO)_3$, when technetium or $Re(CO)_3$ when the rhenium atom has carbonyl ligands) or oxygen (e.g., M can be Tc=O or Re=O).

In another aspect, the invention provides a method for in-vivo or in-vitro imaging of at least one tumor comprising the steps of:
providing a complex of any one of Formulae Ia, Ib, Xa, Xb, IIa, IIb, IIIa, IIIb, IVa, IVb, Va;
contacting the tumor(s) with the radiolabeled metal complex; and
making a radioagraphic image to visualize the tumor(s).

In certain embodiments, the metal ion M is one or more isotopes of a metal selected from the group consisting of technetium, rhenium, yttrium, copper, gallium, indium, bismuth, platinum and rhodium. In certain embodiments, the metal is technetium-99m or one or more isotopes of rhenium.

In certain embodiments, the tumor(s) are neoplasm(s). In certain embodiments, the tumor(s) are carcinoma(s). In certain embodiments, the tumor(s) are melanoma(s). In certain embodiments, the tumor(s) are prostate carcinoma, breast carcinoma, lung carcinoma, renal carcinoma, colon carcinoma, glioblastoma, neuroblastoma, sarcoma, or a combination thereof.

In certain embodiments, the radiolabeled metal complex is capable of binding to, or has affinity for, one or more proteins or receptors selected from melanin, serotonin receptors, adrenergic receptors, adrenoceptors receptors, dopamine receptors, sigma receptors, emopamil binding proteins, calcium channel receptors, or any subtype or subclass thereof. In certain embodiments, the protein or receptor(s) are selected from $5HT_{1A}$, $\sigma_1$, $\sigma_2$, $\alpha_1$, $Ca^{+2}$ channel receptors, EBP or a combination thereof.

In another aspect, the invention provides a method for in-vivo or in-vitro imaging of at least one tissue expressing one or more proteins or receptors for which radiolabeled complexes have affinity, the method comprising the steps of:
providing a radiolabeled complex comprising a complex of any one of Formulae Ia, Ib, Xa, Xb, IIa, IIb, IIIa, IIIb, IVa, IVb, Va;
contacting the tissue(s) expressing the receptors with the radiolabeled metal complex; and
making a radiographic image to visualize the tissue(s).

In certain embodiments, the proteins or receptors are selected from melanin, serotonin receptors, adrenergic receptors, adrenoceptors receptors, dopamine receptors, sigma receptors, emopamil binding proteins, calcium channel receptors, or any subtype or subclass thereof. In certain embodiments, the protein or receptor expressed by the tissue to be imaged are selected from $5HT_{1A}$, $\sigma_1$, $\sigma_2$, $\alpha_1$, Ca+2 channel receptors, EBP or a combination thereof.

In certain embodiments, the tissue is part of the central nervous system or nervous system. In certain embodiments, the tissue is brain tissue expressing the protein or receptors. In certain embodiments, the tissue is a tumor. In certain embodiments, the tumor(s) are neoplasm(s), carcinoma(s), melanoma(s), or a combination thereof. In certain embodiments, the tumor(s) are melanoma, prostate carcinoma, breast carcinoma, lung carcinoma, renal carcinoma, colon carcinoma, glioblastoma, neuroblastoma, sarcoma, or a combination thereof.

In another aspect, the invention provides a method for the treatment of cancer comprising the steps of:
providing a complex of any one of Formulae Ia, Ib, Xa, Xb, IIa, IIb, IIIa, IIb, IVa, IVb, Va; and
contacting the tumor(s) with the metal complex.

In certain embodiments, M is one or more isotopes of rhenium. In certain embodiments, the tumor cells express one or more proteins or receptors selected from melanin, serotonin receptors, adrenergic receptors, adrenoceptors receptors, dopamine receptors, sigma receptors, emopamil binding proteins, calcium channel receptors, or any subtype or subclass thereof. In certain embodiments, the proteins or receptor are selected from $5HT_{1A}$, $\sigma_1$, $\sigma_2$, $\alpha_1$, $Ca^{2+}$ channel receptors, EBP, or a combination thereof.

In certain embodiments, the metal ion is one or more isotopes of a metal selected from the group consisting of technetium, rhenium, yttrium, copper, gallium, indium, bismuth, platinum, rhodium or a combination thereof.

In certain embodiments, the tumor(s) are neoplasm(s), carcinoma(s), melanoma(s), or a combination thereof. In certain embodiments, the tumor(s) are melanoma, prostate carcinoma, breast carcinoma, lung carcinoma, renal carcinoma, colon carcinoma, glioblastoma, neuroblastoma, sarcoma, or a combination thereof.

In another aspect, the invention provides a complex of any one of Formulae Ia, Ib, Xa, Xb, IIa, IIb, IIIa, IIIb, IVa, IVb, Va, wherein the metal ion is radiolabelled or radioactive.

In another aspect, the invention provides a complex of any one of Formulae Ia, Ib, Xa, Xb, IIa, IIb, IIIa, IIIb, IVa, IVb, Va, wherein the metal ion is not radiolabelled or radioactive.

In another aspect, the invention provides a method of inhibiting a protein or receptor comprising the steps of:
providing a metal complex according to any one of Formulae Ia, Ib, Xa, Xb, IIa, IIb, IIIa, IIIb, IVa, IVb, Va; and
contacting the tumor(s) with the metal complex.

In certain embodiments, the protein or receptor are selected from melanin, serotonin receptors, adrenergic receptors, adrenoceptors receptors, dopamine receptors, sigma receptors, emopamil binding proteins, calcium channel receptors, or any subtype or subclass thereof.

In certain embodiments, the neuroreceptor(s) are selected from $5HT_{1A}$, $\sigma_1$, $\sigma_2$, $\alpha_1$, $Ca^{2+}$ channel receptors, EBP or a combination thereof.

In certain embodiments, a cytotoxic metal complex comprises a complex according to any one of Formulae Ia, Ib, Xa, Xb, IIa, IIb, IIIa, IIIb, IVa, IVb, Va, wherein M is one or more isotopes of rhenium.

In certain embodiments, the metal ion is radiolabelled or radioactive.

In certain embodiments, the metal ion is not radiolabelled or radioactive.

Radiolabeled complexes of the present invention can be isomerically pure or can comprise a mixture of isomers including mixtures of two or more isomers selected from enantiomers, diastereomers, complexation isomers, rotational isomers, geometric isomers, tautomers and like isomers. For example, isomeric complexes which result from the relative orientation of metal ligand group and a substitutents on the metal chelate group, Z, such as are typically referred to as syn/anti isomers or alternatively as cis/trans isomers where the syn isomer has the oxo ligand and the ligand substituent oriented in generally the same direction and the anti isomer has the oxo ligand and the ligand substituent oriented in generally opposite directions.

Preferred metal ions for use in radiolabeled complexes of the invention are sources capable of emitting one or more discrete forms of radiation. Preferred radiation emissions include alpha, beta and gamma radiation emissions. Additionally preferred are metal ions that emit alpha, beta(+), beta(-) or gamma radiation with sufficient energy to be detected by standard radiography techniques or have sufficient alpha, beta or gamma energy for radiotherapeutic applications. Particularly preferred metal ions include one or more isotopes of metals selected from technetium, rhenium, yttrium, copper, gallium, indium, bismuth, platinum and rhodium. Technetium-99m and radioactive isotopes of rhenium are exemplary metal ion for use in the present invention. Metal ions suitable for use in radiolabeled complexes of the invention may include additional ligands coordinated to the metal atom. Preferred ligands include oxo, nitride, fluoride, chloride, bromide, iodide, carbonyl, isonitrile, nitrile, nitrosyl, alkoxide groups with 1 to about 6 carbon atoms, amine groups with 1 to about 12 carbon atoms, water, ether groups with 2 to about 8 carbon atoms, thioether groups with 2 to about 8 carbon atoms including thiophene, phosphines and phosphates with 1 to about 20 carbon atoms and other common ligands for technetium and rhenium chemistry. Particularly preferred technetium and rhenium metal ions comprise an oxo ligand, e.g., a Tc=O or Re=O, or ligands such as carbonyl (as in technetium tricarbonyl complexes).

Compounds and complexes of the invention have a chelating ligand moiety that is able to bind to a metal ion through a plurality of donor atoms. Each donor atom is typically C, N, O, S, or P but other donor atoms are also acceptable for certain applications. Preferred donor atoms are N, O and S. The plurality of donor atoms can be present in a single compound or can be present in two or more compounds such that the two compounds bind to the metal to form the chelating ligand-metal complex. In certain embodiments, one compound will comprise three or four donor atoms. Alternatively, two compounds, which can be the same or different, each of which can independently comprise two or more donor atoms can bind to a metal center to form a bis-ligand metal complex.

Particularly preferred compounds and radiolabeled metal complexes comprise a tetradentate ligand system wherein the tetradentate ligand is contained in a single compound that includes four donor atoms. In certain preferred compounds and radiolabeled metal complexes, the tetradentate chelating ligand is a "3+1" ligand system wherein three donor atoms of the tetradentate chelating ligand moiety are contained in one compound and the fourth donor atom is present in another compound. Other chelating ligands, including bidentate, pentadentate, and ligands capable of chelating to two or more metal ions, are also contemplated for use in the compounds and metal complexes provided by the present invention.

Preferred linking groups, X, are lower alkyl groups having from 1 to about 8 atoms in the backbone such as, e.g., —$(CH_2)_n$— (in which n is 1 to 8), ether groups having 3 to 8 atoms in the backbone such as, e.g., —$(CH_2)_n$—O—$(CH_2)_m$—, ester groups having 4 to 8 atoms in the backbone such as, e.g., —$(CH_2)_n$—CO—O—$(CH_2)_m$—, thioether groups having 3 to 8 atoms in the backbone such as, e.g., —$(CH_2)_n$—S—$(CH_2)_m$—, and amido groups having 4-8 atoms in the backbone such as, e.g., —$(CH_2)_n$CO—NH—$(CH_2)_m$— where n and m are non-negative integers and the sum n+m is typically between about 2 and about 8. Particularly preferred linking groups X have between about 2 and about 5 atoms in the backbone.

Linking groups X may optionally have one or more substituents attached to the backbone chain including pendant aromatic groups. Preferred substituents include alkyl groups having from 1 to about 6 carbon atoms and from 0 to about 3 N, O or S atoms, hydroxyl, amino, carboxyl, alkoxy groups having from 1 to about 6 carbon atoms, aminoalkyl groups having from 1 to about 6 carbon atoms, dialkylaminoalkyl groups where each alkyl group has from about 1 to about 6 carbon atoms, halogen atoms including F, Cl, Br, and I, aromatic groups having about 5 to about 18 ring atoms which may include 0, 1, 2, or 3 N, O or S ring atoms.

Radiolabeled complexes of the invention include neutral or cationic metal centers where the metal center refers to the metal ion and the inner sphere of ligands directly bound to the metal ion. Preferred radiolabeled complexes of the invention contain a metal center that is neutral or cationic. Moreover, the radiolabeled complex comprising a metal ion and a compound of the formula Z—X—$NR_1R_2$ taken in its entirety is neutral or cationic.

In another embodiment, the present invention provides complexes wherein the metal complex is neutral or cationic that include a compound according to any one of Formula Ia, Ib, Xa, Xb, IIa, IIb, IIIa, IIIb, IVa, IVb, Va, or any subformula thereof and a metal ion. Additional preferred complexes comprise a metal ion and a compound of any of Formulas Ia, Ib, Xa, Xb, IIa, IIb, IIIa, IIIb, IVa, IVb, Va, or any subformula thereof wherein the metal ion may comprise one or more radiolabeled isotopes or non-radiolabeled isotopes of the metal ion of the complex.

Preferred metal ions for use in radiolabeled complexes of the invention are sources of capable of emitting one or more discrete forms of radiation. Preferred radiation emissions include alpha, beta(+), beta(−), and gamma radiation emissions. Additionally preferred are metal ions that emit alpha, beta(+), beta(−), or gamma radiation with sufficient energy to be detected by standard radiography techniques or have sufficient alpha, beta(+), beta(−), or gamma energy for radiotherapeutic applications. Particularly preferred metal ions include one or more isotopes of metals selected from technetium, rhenium, yttrium, copper, gallium, indium, bismuth, platinum and rhodium. Technetium-99m and radioactive isotopes of rhenium, e.g., $^{186}$Re and/or $^{188}$Re, are exemplary radiolabeled metal ions for use in the radiolabeled complexes and imaging methods using same provided by the present invention.

The present invention additionally provides complexes comprising a compound according to Formula I and a metal ion. Preferred complexes include complexes comprising a compound according to Formulae I-V or X and a metal ion which may be radiolabeled or non-radiolabeled. Preferred radiolabeled complexes include those complexes according to any one of Formulae Ia, Ib, Xa, Xb, IIa, IIb, IIIa, IIIb, IVa, IVb, Va.

Tumors suitable for imaging by the method of the present invention include neoplasms, carcinomas and other cancerous tumors. Preferred tumors for imaging include neoplasms of breast, prostate, lung, pancreas, liver, colon, lymphomas, gliomas, melanomas, and other neoplasms. Tumors, especially neoplasm and melanoma tumors, can be imaged in-vivo or in-vitro in any tissue. Preferably the tumor to be imaged is in a mammalian tissue, more preferably the tumor is in a human tissue. Preferred tissues and organs include skin, heart, brain, lung, spleen, colon, liver, kidney, muscle, lymph nodes, and other internal organs.

In theory, any tissue, organ, tumor, growth of cells, bone, or other biomaterial may be imaged using the compounds, complexes or methods of the present invention provided that the radiolabeled metal complex used in the imaging methods is selectively taken up in the target tissue such that there is sufficient contrast between the tissue, organ, tumor, growth of cells, bone, or other biomaterial to be imaged and the background. Preferred tissue, organ, tumor, growth of cells, bone, or other biomaterial which are suitable for imaging using the compounds, metal complexes and imaging methods of the present invention express or overexpress one or more receptors for which the compound or metal complex has an affinity.

Tissues suitable for imaging using the compounds and metal complexes or the methods of the invention are not particularly limited. Preferred tissues are capable of binding or taking up compounds of the present invention or are capable of retaining the compounds of the present invention to a greater extent than other tissues in the general vicinity of the tissue to be imaged. Thus, the emission of the radiolabeled complex retained in the tissue to be imaged has sufficient contrast against the other proximate tissues to allow for imaging of the tissue. Typically preferred tissues have one or more proteins and/or receptors to which the compounds of the present invention bind include one or more proteins, receptors or neuroreceptors, such as melanin, serotonin receptors, including 5HT receptors, adrenoreceptors, including $\alpha_1$ receptors, sigma receptors including $\sigma_1$ and $\sigma_2$ receptors, calcium channel receptors, emopamil binding proteins, adrenergic receptors, dopamine receptors subtypes and subclasses thereof and the like. More preferably, tissues comprise one or more receptors chosen from 5HT, including 5HT$_{1A}$, $\sigma_1$, $\sigma_2$, $\alpha_1$, EBP, Ca$^{2+}$ channel receptors, and the like.

The present invention provides preferred methods of imaging tumors in-vivo or in-vitro, the method comprising the steps of:

providing a radiolabeled complex of any one of Formula Ia, Ib, Xa, Xb, IIa, IIb, IIIa, IIIb, IVa, IVb, Va or any subformula thereof;

contacting the tumor(s) with the radiolabeled metal complex; and making a radiographic image to image the tumor(s).

The present invention also provides preferred methods of imaging tissues or organs, particularly imaging of at least one tissue or organ expressing one or more receptors for which radiolabeled complexes have affinity, in-vivo or in-vitro, the method comprising the steps of:

providing a radiolabeled complex comprising a compound of any one of Formula Ia, Ib, Xa, Xb, IIa, IIb, IIIa, IIIb, IVa, IVb, Va or any subformula thereof;

contacting the tissue(s) or organ(s) expressing or overexpressing receptors with the radiolabeled metal complex; and making a radiographic image to image the tissue(s).

In preferred embodiments, proteins and receptors are selected from melanin, serotonin receptors, α receptors, σ receptors, calcium channel receptors or emopamil binding proteins adrenergic receptors, adrenoceptors receptors, dopamine receptors, sigma receptors and any subclass of receptors or proteins thereof, more preferably the receptors are selected from 5HT$_{1A}$, $\sigma_1$, $\sigma_2$, $\alpha_1$, EBP, Ca$^{2+}$ channel receptors, and the like.

In other preferred embodiments of the invention, the tissue to be imaged is part of the central nervous system, particularly the brain or the spinal cord of a patient, or a tumor or organ which expresses one or more proteins or receptors to which one of the radiolabeled metal complexes of the invention have a binding affinity. Particularly preferred tissues include brain tissue which expresses one or more of proteins, receptors or neuroreceptors, particularly brain tissue expressing one or more of 5HT$_{1A}$, $\sigma_1$, $\sigma_2$, or $\alpha_1$, EBP, Ca$^{2+}$ channel receptors, and the like.

The present invention further provides methods for the treatment of cancer, the method comprising the steps of:

providing a cytotoxic metal complex comprising a complex of any one of Formula Ia, Ib, Xa, Xb, IIa, IIb, IIIa, IIIb, IVa, IVb, Va or any subformula thereof; and contacting the tumor(s) with the cytotoxic metal complex.

Preferred methods of treatment of the invention contemplate the use of both cold metal complexes, e.g., non-radiolabeled metal complexes, and radiolabeled complexes for certain cancer therapies.

The present invention further provides methods of inhibiting a protein, receptor or neuroreceptor comprising the steps of providing a metal complex according to any one of Formula Ia, Ib, Xa, Xb, IIa, IIb, IIIa, IIIb, IVa, IVb, Va or any subformula thereof; and contacting the protein, receptor or neuroreceptor with the metal complex.

Preferred receptors or neuroreceptors which are suitable for inhibition by metal complexes of the invention include melanin, serotonin receptors, α receptors, σ receptors, calcium channel receptors or emopamil binding proteins adrenergic receptors, adrenoceptors receptors, dopamine receptors, and any subclass of receptors or proteins thereof, or more preferably include 5HT$_{1A}$, $\sigma_1$, $\sigma_2$, $\alpha_1$, EBP, Ca$^{2+}$ channel receptors, and the like.

The imaging and therapeutic methods of the invention generally comprise administration of an effective amount of one or more compounds of the invention to a subject including a mammal, such as a primate, especially a human, in need of such imaging or treatment. For imaging applications, typically a sufficient amount of a radiolabeled complex is administered to the tissue, organ, tumor, or the like to be imaged to provide for selective uptake of the radiolabeled complex into the tissue, organ or tumor to be imaged. Preferably the amount of radiolabeled complex taken up in the tissue, organ or tumor is sufficient to be imaged and/or quantified by standard radiographic techniques.

The treatment methods of the invention also will be useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Compounds of the invention may be administered singularly (i.e. sole therapeutic agent of a regime) or in combination with other agents for diagnostic or therapeutic purposes which may or may not be radiolabeled to treat or prevent diseases and conditions such as undesired cell proliferation as disclosed herein. For combined diagnostic or therapeutic applications, additional agents are preferably chemotherapy agents or neuroleptic agents.

Pharmaceutical compositions of the invention include a compound of the invention packaged together with instructions (written) for therapeutic use of the compound, particularly to treat a subject suffering from or susceptible to tumors, e.g., cancers, such as melanoma, prostate cancer or the like. Pharmaceutical compositions of the invention may also be packaged together with instructions (written) for therapeutic use of the compound, particularly to image tissues or tumors within a subject to diagnose, identify or locate one or more tissues or tumors within the subject.

EXAMPLES

Certain compounds were prepared as shown in FIG. 1 and/or as described hereinbelow.

Example 1

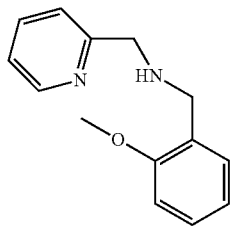 [SMILES: COc1ccccc1CNCc1ccccn1]

N-(2-methoxybenzyl)-1-(pyridin-2-yl)methanamine [1]

2-methoxybenzyl chloride (1.50 g, 9.5 mmol) and 2-(Aminomethyl)pyridine (5.18 g, 47 mmol) were dissolved in 800 mL CH$_3$CN. To this solution was added potassium carbonate (1.324 g, 9.5 mmol) and the mixture was stirred at room temperature for three days. The solvent was evaporated, and the residual oil was dissolved in CH$_2$Cl$_2$ (75 mL) and extracted with water (75 mL×3). The combined CH$_2$Cl$_2$ layers were reduced in volume, and the resulting yellow-orange oil was purified by silica gel chromatography eluting with CH$_2$Cl$_2$, followed by a 3% (NH$_3$)MeOH/97% CH$_2$Cl$_2$ solution (62%). $^1$H NMR (CDCl$_3$) δ 8.520 (dd, 1H, Ar), 7.600 (m, 1H, Ar), 7.335 (d, 1H, Ar), 7.27 (d, 1H, Ar), 7.211 (t, 1H, Ar), 7.113 (m, 1H, Ar), 6.895 (t, 1H, Ar), 6.832 (d, 1H, Ar), 3.921 (s, 2H, —CH$_2$—), 3.864 (s, 2H, —CH$_2$—), 3.800 (s, 3H, —OCH$_3$), 3.043 (s(br), 1H, —CH—). Mass Spec.=229.13 (M+H)$^+$.

Example 2

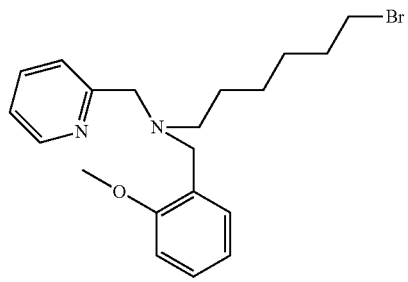 [SMILES: COc1ccccc1CN(CCCCCCBr)Cc1ccccn1]

6-bromo-N-(2-methoxybenzyl)-N-(pyridin-2-ylmethyl)hexan-1-amine [2]

Compound 1 (0.3 g, 1.3 mmol) was dissolved in 10 mL CH$_3$CN and 1,6-dibromohexane (4.85 g, 19 mmol), and potassium carbonate (0.37 g, 2.6 mmol) was added. The reaction mixture stirred overnight at room temperature. The solvent was evaporated to a minimum volume and purified by silica gel chromatography eluting with 100% CH$_2$Cl$_2$ twice and several times with 0.5% methanolic NH$_3$ (7 M NH$_3$ in methanol)/99.5% CH. The organic layers were combined and rotovaped (61.5%). $^1$H NMR (CDCl$_3$) δ 8.480 (d, 1H, Ar), 7.612 (t, 1H, Ar), 7.553 (d, 1H, Ar), 7.474 (d, 1H, Ar), 7.192 (t, 1H, Ar), 7.097 (t, 1H, Ar), 6.923 (t, 1H, Ar), 6.824 (d, 1H, Ar), 3.776 (overlapped s, 5H, —CH$_2$—, —OCH$_3$), 3.671 (s, 2H, —CH$_2$—), 3.328 (m, 2H, —CH$_2$—), 2.488 (ddd, 2H, —CH$_2$—), 1.783 (p, 2H, —CH$_2$—), 1.531 (m, 2H, —CH$_2$—), 1.331 (p, 2H, —CH$_2$—), 1.271 (p, 2H, —CH$_2$—). Mass Spect=391.14 (M+H)$^+$.

Example 3

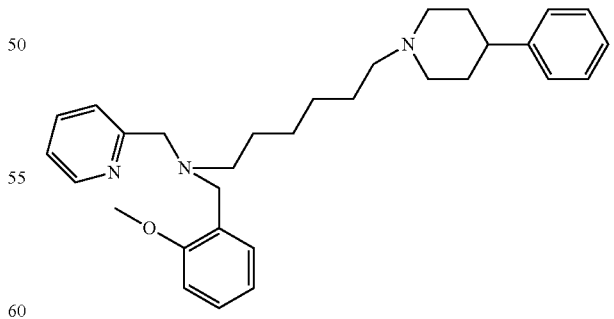

N-(2-methoxybenzyl)-6-(4-phenylpiperidin-1-yl)-N-(pyridin-2-ylmethyl)hexan-1-amine [3]

The compound 2 (0.31 g, 0.8 mmol), 4-phenylpiperidine (0.2 g, 1.2 mmol) and K$_2$CO$_3$ (0.166 g, 1.2 mmol) were added to 50 mL CH₃CN, and the solution was refluxed under argon atmosphere for 16 h. After cooling to room temperature, the solvent was evaporated to dryness. Purification was carried out on a silica gel TLC plate that was developed in 4% methanolic NH₃ (7 M NH₃ in methanol)/96% CH₂Cl₂. The product was obtained as pale yellow oil (60.75%). ¹H NMR (CDCl₃) δ 8.489 (dd, 1H, Ar), 7.624 (ddd, 1H, Ar), 7.572 (d, 1H, Ar), 7.497 (dd, 1H, Ar), 7.290 (t, 2H, Ar), 7.203 (m, 4H, Ar), 7.106 (m, 1H, Ar), 6.936 (ddd, 1H, Ar), 6.836 (d, 1H, Ar), 3.792 (s, 3H, —OCH₃), 3.763 (s, 2H, —CH₂—), 3.667 (s, 2H, —CH₂—), 3.063 (m, 2H, —CH₂—), 2.486 (t, 3H, —CH—CH₂—), 2.336 (s(br), 2H, —CH₂—), 2.041 (s(br), 2H, —CH₂—), 1.836 (s(br), 4H, —CH₂—CH₂—), 1.543 (m, 4H, —CH₂—CH₂—), 1.300 (m, 2H, —CH₂—), 1.238 (m, 2H, —CH₂—). Mass Spect.=471.68 (M+H)⁺.

Example 4

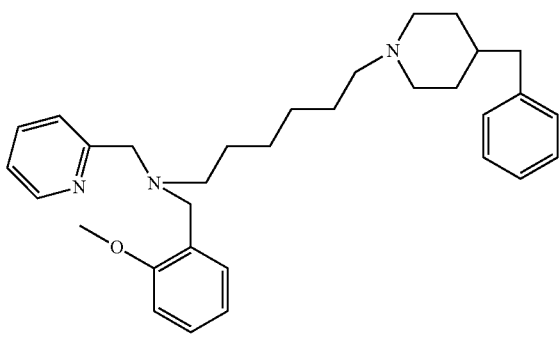

6-(4-benzylpiperidin-1-yl)-N-(2-methoxybenzyl)-N-(pyridin-2-ylmethyl)hexan-1-amine [4]

The procedure similar to that described for 3 was used with 4-benzylpiperidine (1.24 g, 7.67 mmol) as the amine source. The product was obtained as yellow oil with a 98% yield. ¹H NMR (CDCl₃) δ 8.485 (dd, 1H, Ar), 7.614 (ddd, 1H, Ar), 7.564 (d, 1H, Ar), 7.490 (d, 1H, Ar), 7.265 (m, 2H, Ar), 7.186 (m, 2H, Ar), 7.134 (d, 2H, Ar), 7.099 (t, 1H, Ar), 6.930 (t, 1H, Ar), 6.830 (d, 1H, Ar), 3.786 (s, 3H, —OCH₃), 3.753 (s, 2H, —CH₂—), 3.657 (s, 2H, —CH₂—), 2.874 (d, 2H, —CH₂—), 2.52 (d, 2H, —CH₂—), 2.469 (t, 2H, —CH₂—), 2.228 (t, 2H, —CH₂—), 1.812 (t, 2H, —CH₂—), 1.617 (d, 2H, —CH₂—), 1.511 (m, 3H, —CH—CH₂—), 1.437 (m, 2H, —CH₂—), 1.280 (m, 2H, —CH₂—), 1.197 (m, 2H, —CH₂—). Mass Spec.=486.35 (M+H)⁺.

Example 5

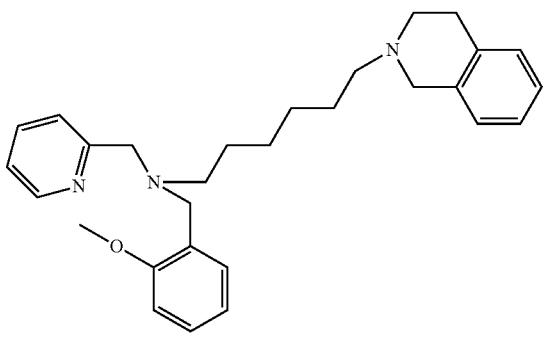

6-(3,4-dihydroisoquinolin-2(1H)-yl)-N-(2-methoxybenzyl)-N-(pyridin-2-ylmethyl)hexan-1-amine [5]

The compound 2 (0.44 g, 1.13 mmol), 1,2,3,4-tetrahydroisoquinoline (0.22 g, 1.69 mmol) and triethylamine (0.218 g, 1.69 mmol) were added to 300 mL CH₃CN, and the solution was stirred for two days. Purification was carried out on a silica gel TLC plate that was developed in 4% methanolic NH₃ (7 M NH₃ in methanol)/96% CH₂Cl₂. The product was obtained as pale yellow oil (73%). ¹H NMR (CDCl₃) δ 8.488 (dd, 1H, Ar), 7.616 (ddd, 1H, Ar), 7.573 (dd, 1H, Ar), 7.497 (dd, 1H, Ar), 7.219 (ddd, 1H, Ar), 7.090 (m, 4H, Ar), 7.004 (d, 1H, Ar), 6.933 (ddd, 1H, Ar), 6.833 (d, 1H, Ar), 3.789 (s, 3H, —OCH₃), 3.766 (s, 2H, —CH₂—), 3.671 (s, 2H, —CH₂—), 3.608 (s, 2H, —CH₂—), 2.895 (t, 2H, —CH₂—), 2.712 (t, 2H, —CH₂—), 2.491 (t, 2H, —CH₂—), 2.455 (t, 2H, —CH₂—), 1.554 (m, 4H, —CH₂—CH₂—), 1.298 (m, 4H, —CH₂—CH₂—). Mass Spec.=443.62 (M+H)⁺.

Example 6

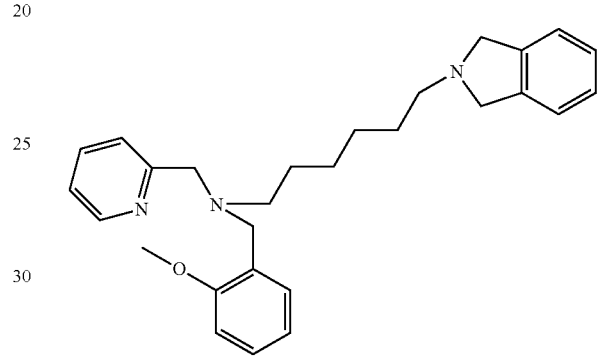

6-(isoindolin-2-yl)-N-(2-methoxybenzyl)-N-(pyridin-2-ylmethyl)hexan-1-amine [6]

The procedure similar to that described for 3 was used with isoindoline (0.365 g, 3.0 mmol) as the amine source. Purification was carried out on a silica gel TLC plate that was developed in with a 3.5% methanolic NH₃ (7 M NH₃ in methanol/96.5% CH₂Cl₂. The product was obtained as yellow oil with a 74% yield. ¹H NMR (CDCl₃) δ 8.495 (dd, 1H, Ar), 7.624 (ddd, 1H, Ar), 7.584 (d, 1H, Ar), 7.509 (d, 1H, Ar), 7.184 (m, 5H, Ar), 7.107 (t, 1H, Ar), 6.942 (t, 1H, Ar), 6.84 (d, 1H, Ar), 3.904 (s, 4H, —CH₂—CH₂—), 3.795 (s, 3H, —OCH₃), 3.775 (s, 2H, —CH₂—), 3.679, (s, 2H, —CH₂—), 2.667 (t, 2H, —CH₂—), 2.503 (t, 2H, —CH₂—), 1.552 (m, 4H, —CH₂—CH₂—), 1.324 (m, 4H, —CH₂—CH₂—). Mass Spec.=430.28 (M+H)⁺.

Example 7

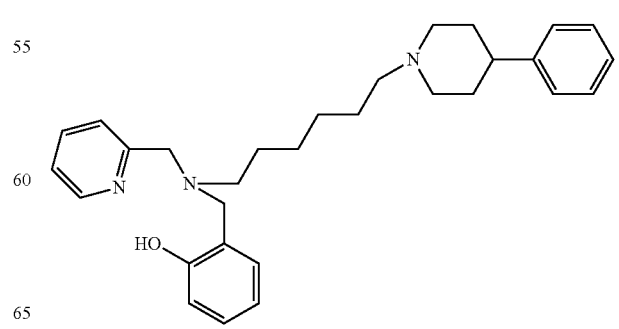

2-(((6-(4-phenylpiperidin-1-yl)hexyl)(pyridin-2-ylmethyl)amino)methyl)phenol [L3]

Compound 3 (0.23 g, 0.4 mmol) was dissolved in 25 mL of CH$_2$Cl$_2$. The solution was cooled at −78° C. in a dry ice CH$_2$Cl$_2$ bath under argon atmosphere for 1 h. After the solution cooled, 1.0 M boron tribromide (3.28 g, 0.013 mol) dissolved in 25 mL of CH$_2$Cl$_2$ was added dropwise. The reaction mixture was allowed to reach room temperature and was stirred overnight. The solvent was removed and quenched with methanol (30 mL×3). After the methanol was removed, hydrochloric saturated methanol (5 mL) was stirred for 1 h at room temperature. The solution was rotovaped and washed with methanol (30 mL×3) before being extracted in CH$_2$Cl$_2$ with water (50 mL×3). The combined organic layers were evaporated and a dissolved in a minimum volume and purified by silica gel TLC plate that was developed in 3% methanolic NH$_3$ (7 M NH$_3$ in methanol)/97% CH$_2$Cl$_2$. The product was obtained as pale yellow oil (68.31%). $^1$H NMR (CDCl$_3$) δ 8.562 (d, 1H, Ar), 7.652 (ddd, 1H, Ar), 7.280 (m, 3H, Ar), 7.220 (d, 2H, Ar), 7.161 (m, 3H, Ar), 6.980 (d, 1H, Ar), 6.823 (d, 1H, Ar), 6.755 (ddd, 1H, Ar), 3.790 (s, 2H, —CH$_2$—), 3.757 (s, 2H, —CH$_2$—), 3.168 (d, 2H, —CH$_2$—), 2.544 (m, 3H, —CH—CH$_2$—), 2.458 (t, 2H, —CH$_2$—), 2.225 (t, 2H, —CH$_2$—), 2.016 (m, 2H, —CH$_2$—), 1.858 (d, 2H, —CH$_2$—), 1.569 (m, 4H, —CH$_2$—CH$_2$—), 1.236 (m, 4H, —CH$_2$—CH$_2$—). Mass Spec.=458.32 (M+H)$^+$.

Example 8

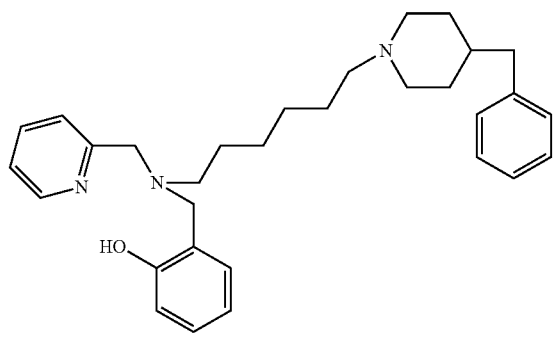 [SMILES: Oc1ccccc1CN(CCCCCCN1CCC(Cc2ccccc2)CC1)Cc1ccccn1]

2-(((6-(4-benzylpiperidin-1-yl)hexyl)(pyridin-2-ylmethyl)amino)methyl)phenol [L4]

The same procedure as described for compound L3 was applied to 4 (0.689 g, 1.4 mmol). Purification was carried out on a silica gel TLC plate that was developed in with a 4% methanolic NH$_3$ (7 M NH$_3$ in methanol/96% CH$_2$Cl$_2$. The product was isolated as pale yellow oil (68%). $^1$H NMR (CDCl$_3$) δ 8.572 (dd, 1H, Ar), 7.669 (ddd, 1H, Ar), 7.313 (d, 1H, Ar), 7.266 (m, 2H, Ar), 7.192 (m, 5H, Ar), 7.987 (dd, 1H, Ar), 6.825 (dd, 1H, Ar), 6.765 (ddd, 1H, Ar), 3.794 (s, 2H, —CH$_2$—), 3.768 (s, 2H, —CH$_2$—), 2.999 (s, 2H, —CH$_2$—), 2.541 (m, 4H, —CH$_2$—CH$_2$—), 2.350 (s(br), 2H, —CH$_2$—), 1.976 (s(br), 2H, —CH$_2$—), 1.662 (d(br), 2H, —CH$_2$—), 1.552 (m, 7H), 1.212 (m, 4H, —CH$_2$—CH$_2$—). Mass Spec.=472.33 (M+H)$^+$.

Example 9

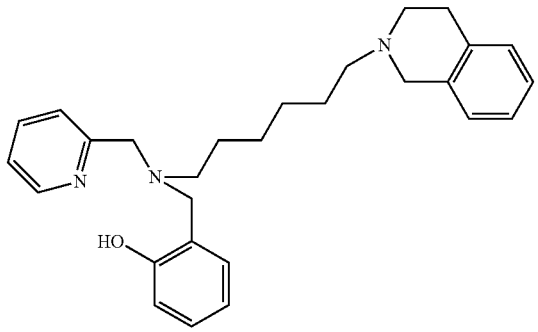 [SMILES: Oc1ccccc1CN(CCCCCCN1CCc2ccccc2C1)Cc1ccccn1]

2-(((6-(3,4-dihydroisoquinolin-2(1H)-yl)hexyl)(pyridin-2-ylmethyl)amino)methyl)-phenol [L5]

The same procedure as described for compound L3 was applied to 5 (0.3 g, 0.6 mmol). Purification was carried out on a silica gel TLC plate that was developed in with a 2% methanolic NH$_3$ (7 M NH$_3$ in methanol/98% CH$_2$Cl$_2$. The product was isolated as pale yellow oil (30%). $^1$H NMR (CDCl$_3$) δ 8.575 (dd, 1H, Ar), 7.664 (ddd, 1H, Ar), 7.324 (d, 1H, Ar), 7.159 (m, 2H, Ar), 7.095 (m, 3H, Ar), 7.003 (m, 2H, Ar), 6.845 (d, 1H, Ar), 6.804 (t, 1H, Ar), 3.805 (s, 2H, —CH$_2$—), 3.784 (s, 2H, —CH$_2$—), 3.625 (s, 2H, —CH$_2$—), 2.904 (t, 2H, —CH$_2$—), 2.729 (t, 2H, —CH$_2$—), 2.559 (t, 2H, —CH$_2$—), 2.463 (t, 2H, —CH$_2$—), 1.570 (m, 4H, —CH$_2$—CH$_2$—), 1.271 (m, 4H, —CH$_2$—CH$_2$—). Mass Spec.=430.28 (M+H)$^+$.

Example 10

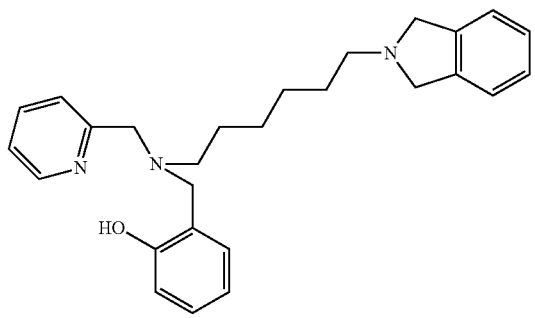 [SMILES: Oc1ccccc1CN(CCCCCCN1Cc2ccccc2C1)Cc1ccccn1]

2-(((6-(isoindolin-2-yl)hexyl)(pyridin-2-ylmethyl)amino)methyl)phenol [L6]

The same procedure as described for compound L3 was applied to 6 (0.27 g, 0.6 mmol). Purification was carried out on a silica gel TLC plate that was developed in with a 2% methanolic NH$_3$ (7 M NH$_3$ in methanol/98% CH$_2$Cl$_2$. The product was isolated as pale yellow oil (22%). $^1$H NMR (CDCl$_3$) δ 8.572 (dd, 1H, Ar), 7.653 (ddd, 1H, Ar), 7.317 (d, 1H, Ar), 7.176 (m, 6H, Ar), 6.993 (dd, 1H, Ar), 6.844 (dd, 1H, Ar), 6.768 (ddd, 1H, Ar), 3.934 (s, 4H, —CH$_2$—CH$_2$—), 3.804 (s, 2H, —CH$_2$—), 3.779 (s, 2H, —CH$_2$—), 2.679, (t, 2H, —CH$_2$—), 2.561 (t, 2H, —CH$_2$—), 1.569 (m, 4H, —CH$_2$—CH$_2$—), 1.29 (m, 4H, —CH$_2$—CH$_2$—). Mass Spec.=416.27 (M+H)$^+$.

Example 11

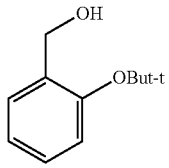

(2-tert-butoxyphenyl)methanol [7]

The procedure was adopted from the previously published literature (J. Org. Chem. 1986, 51, 113-114). To a flame-dried flask, 2-hydroxy benzyl alcohol (10 g, 80 mg) and 400 mL CH$_2$Cl$_2$ was added. The reaction mixture was cooled to −78° C. by use of a dry ice/acetone bath. Following the addition of liquefied 2-methylpropene (40 mL), trifluoromethanesulfonic acid (2 mL, 22 mmol) was added. The reaction mixture was stirred for 5 hr while maintaining the temperature at −78° C. The reaction was quenched with triethylamine and then allowed to warm to room temperature. The solvent was removed by distillation under reduced pressure and the oily product was triturated with 500 mL petroleum ether several times. Petroleum ether was then evaporated and the crude product was purified by silica gel column with the following eluents: 20% EtOAc/80% Hexane. The product was isolated as pale yellow oil (30% yield). $^1$H NMR (CDCl$_3$) δ 7.286 (dd, 1H, Ar), 7.195 (ddd, 1H, Ar), 7.063 (d, 1H, Ar), 7.003 (ddd, 1H, Ar), 4.669 (s, 2H, —CH$_2$—), 1.447 (s, 9H, —C(CH$_3$)$_3$—). Mass Spec.=180.24 (M+H)$^+$.

Example 12

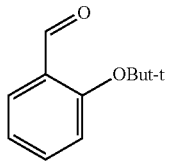

2-tert-butoxybenzaldehyde [8]

To a stirred solution of 7 (3.8 g, 21 mmol) in 250 mL CH$_2$Cl$_2$, MnO$_2$ (11 g, 126 mmol) was added. The reaction mixture was stirred overnight, filtered on Celite® and the solvent was distilled under reduced pressure. The crude product was purified by a silica gel column with 17% EtOAc/83% Hexane as eluents. The product was isolated as pale yellow oil (70% yield). $^1$H NMR (CDCl$_3$) δ 7.286 (dd, 1H, Ar), 7.195 (ddd, 1H, Ar), 7.063 (d, 1H, Ar), 7.003 (ddd, 1H, Ar), 4.669 (s, 2H, —CH$_2$—), 1.447 (s, 9H, —C(CH$_3$)$_3$). Mass Spec.=203.09 (M+H)$^+$+Na$^+$.

Example 13

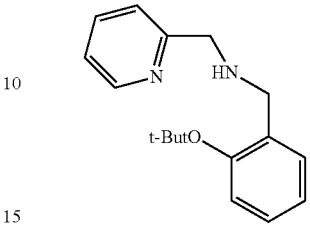

N-(2-tert-butoxybenzyl)-1-(pyridin-2-yl)methanamine [9]

2-(Aminomethyl)pyridine (0.849 g, 7.85 mmol) and 8 (1.4 g, 7.8 mmol) were added to 150 mL of CH$_3$CN and the reaction mixture was refluxed under argon for 4 hr. After cooling down to room temperature, the solvent was removed and the residue was redissolved in MeOH. The solvent was then evaporated and NaBH$_4$ (1.485 g, 39 mmol) was added and stirred overnight. The solvent was evaporated, followed by extraction with CH$_2$Cl$_2$. The CH$_2$Cl$_2$ extract was concentrated and purified by a silica gel column using 3% methanolic NH$_3$ (7 M NH$_3$ in methanol/97% CH$_2$Cl$_2$ as eluent to yield the desired product as a pale yellow oil (58%). $^1$H NMR (CDCl$_3$) δ 8.530 (m, 1H, Ar), 7.604 (ddd, 1H, Ar), 7.330 (m, 2H, Ar), 7.128 (m, 2H, Ar), 7.027 (d, 2H, Ar), 6.969 (ddd, 1H, Ar), 3.892 (s, 2H, —CH$_2$—), 3.837 (s, 2H, —CH$_2$—), 2.523 (s, 1H, —CH—), 1.373 (s, 9H, —C(CH$_3$)$_3$). Mass Spec.=271.18 (M+H)$^+$.

Example 14

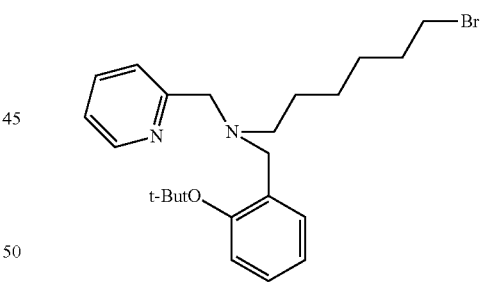

6-bromo-N-(2-tert-butoxybenzyl)-N-(pyridin-2-ylmethyl)hexan-1-amine [10]

Compound 10 was synthesized with 9 (2 g, 8.84 mmol), using 1,6-dibromohexane (30 g, 130 mmol) and K$_2$CO$_3$ (1.22 g, 8.84 mmol) following a procedure analogous to that described for 2. Purification was carried out on a silica gel TLC plate that was developed in with a 1% methanolic NH$_3$ (7 M NH$_3$ in methanol/99% CH$_2$Cl$_2$. The product was isolated as pale yellow oil (73%). $^1$H NMR (CDCl$_3$) δ 8.491 (dd, 1H, Ar), 7.630 (t, 1H, Ar), 7.565 (t, 2H, Ar), 7.120 (t, 2H, Ar), 7.020 (t, 2H, Ar), 3.740 (s, 2H, —CH$_2$—), 3.660 (s, 2H, —CH$_2$—), 3.334 (t, 2H, —CH$_2$—), 2.452 (s, 2H, —CH$_2$—), 1.787 (p, 2H, —CH₂—), 1.516 (m, 2H, —CH₂—), 1.354 (s, 9H, —C(CH₃)₃), 1.269 (m, 4H). Mass Spec.=435.18 (M+H)⁺.

Example 15

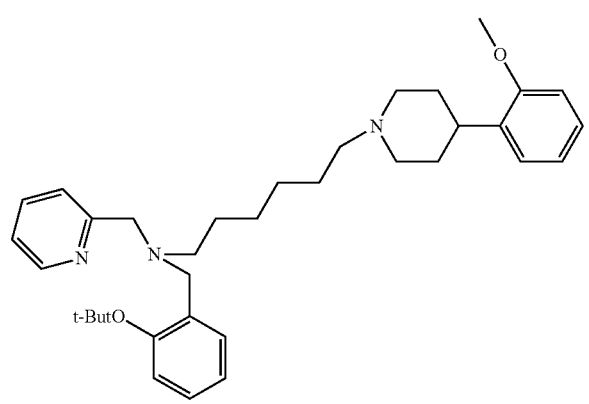

N-(2-tert-butoxybenzyl)-6-(4-(2-methoxyphenyl)cyclohexyl)-N-(pyridin-2-ylmethyl)hexan-1-amine [11]

The compound 10 (0.377 g, 0.85 mmol), 2-methoxy-4-phenylpiperidine (0.262 g, 1.54 mmol) and $K_2CO_3$ (0.118 g, 0.85 mmol) were added to 50 mL $CH_3CN$, and the solution was refluxed under argon atmosphere for 6 h and stirred overnight. Then the solvent was evaporated to dryness. Purification was carried out on a silica gel TLC plate that was developed in 4% methanolic $NH_3$ (7 M $NH_3$ in methanol)/96% $CH_2Cl_2$. The product was obtained as pale yellow oil (58%). $^1H$ NMR (CDCl₃) δ 8.491 (d, 1H, Ar), 7.262 (m, 1H, Ar), 7.583 (m, 2H, Ar), 7.216 (d, 1H, Ar), 7.160 (m, 1H, Ar), 7.112 (m, 2H, Ar), 7.024 (m, 2H, Ar), 6.917 (t, 1H, Ar), 6.839 (d, 1H, Ar), 3.806 (s, 3H, —OCH₃), 3.744 (s, 2H, —CH₂—), 3.667 (s, 2H, —CH₂—), 3.043 (d, 2H, —CH₂—), 2.958 (m, 1H, —CH—), 2.459 (t, 2H, —CH₂—), 2.326 (m, 2H, —CH₂—), 2.061 (m, 2H, —CH₂—), 1.790 (m, 4H, —CH₂—CH₂—), 1.531 (m, 4H, —CH₂—CH₂—), 1.360 (s, 9H, —C(CH₃)₃—), 1.298 (m, 2H, —CH₂—), 1.228 (m, 2H, —CH₂—). Mass Spec.=543.78 (M+H)⁺.

Example 16

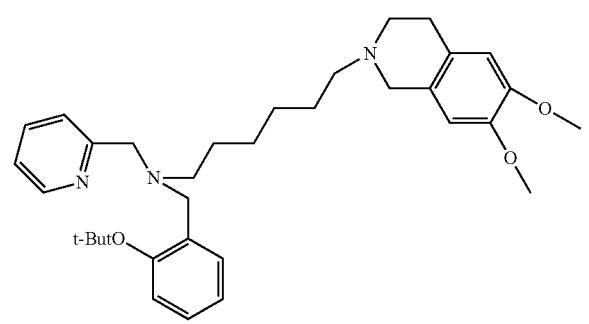

N-(2-tert-butoxybenzyl)-6-(6,7-dimethoxy-3,4-dihydroisoquinolin-2(1H)-yl)-N-(pyridin-2-ylmethyl)hexan-1-amine [12]

The same procedure as described for compound 11 was applied to starting material 10 (0.4 g, 0.92 mmol) and 6,7-dimethoxy-1,2,3,4-tetrahydroisoquinoline (0.267 g, 1.38 mmol). Purification was carried out on a silica gel TLC plate that was developed in with a 4.5% methanolic $NH_3$ (7 M $NH_3$ in methanol/94.5% $CH_2Cl_2$. The product was isolated as pale yellow oil (99%). $^1H$ NMR (CDCl₃) δ 8.463 (dt, 1H, Ar), 7.574 (m, 3H, Ar), 7.082 (m, 2H, Ar), 6.996 (m, 2H, Ar), 6.552 (s, 1H, Ar), 6.486 (s, 1H, Ar), 3.797 (s, 3H, —OCH₃), 3.792 (s, 3H, —OCH₃), 3.723 (s, 2H, —CH₂—), 3.646, (s, 2H, —CH₂—), 3.504 (s, 2H, —CH₂—), 2.784 (t, 2H, —CH₂—), 2.655 (t, 2H, —CH₂—), 2.430 (m, 4H, —CH₂—CH₂—), 1.521 (m, 4H, —CH₂—CH₂—), 1.333 (s, 9H, —C(CH₃)₃—), 1.264 (m, 4H, —CH₂—CH₂—). Mass Spec=546.37 (M+H)⁺.

Example 17

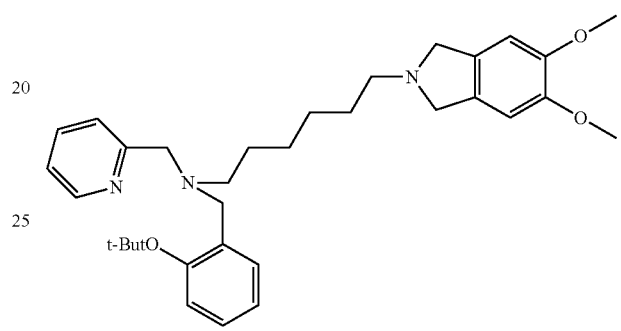

N-(2-tert-butoxybenzyl)-6-(5,6-dimethoxyisoindolin-2-yl)-N-(pyridin-2-ylmethyl)hexan-1-amine [13]

The same procedure as described for compound 11 was applied to starting material 10 (0.428 g, 0.988 mmol) and 5,6-dimethoxyisoindoline (0.175 g, 0.975 mmol). Purification was carried out on a silica gel TLC plate that was developed in with a 5% methanolic $NH_3$ (7 M $NH_3$ in methanol/95% $CH_2Cl_2$. The product was isolated as pale yellow oil (60%). $^1H$ NMR (CDCl₃) δ 8.446 (dd, 1H, Ar), 7.72 (m, 3H, Ar), 7.062 (m, 2H, Ar), 6.981 (ddd, 2H, Ar), 6.888 (s, 2H, Ar), 3.816 (s, 4H, —CH₂—CH₂—), 3.792 (s, 6H, —OCH₃—), 3.714 (s, 2H, —CH₂—), 3.637 (s, 2H, —CH₂—), 2.611 (t, 2H, —CH₂—), 2.436 (t, 2H, —CH₂—), 1.503 (m, 4H, —CH₂—CH₂—), 1.319 (s, 9H, —C(CH₃)₃), 1.275 (m, 4H, —CH₂—CH₂—). Mass Spec.=531.73 (M+H)⁺.

Example 18

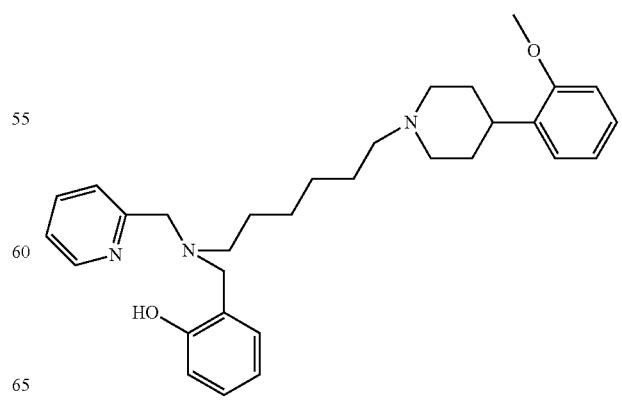

2-(((6-(4-(2-methoxyphenyl)piperidin-1-yl)hexyl)(pyridin-2-ylmethyl)amino)methyl)phenol [L11]

Compound 11 (0.2 g, 0.36 mmol) was dissolved in 25 mL EtOAc saturated with HCl and stirred for 3 hr. The filtrate was evaporated to dryness. The residue was purified on a silica gel TLC plate that was developed in 5% methanolic $NH_3$ (7 M $NH_3$ in methanol/95% $CH_2Cl_2$. The product was obtained as white solid (36%). $^1H$ NMR ($CDCl_3$) δ 8.566 (dd, 1H, Ar), 7.659 (ddd, 1H, Ar), 7.313 (d, 1H, Ar), 7.207 (dd, 1H, Ar), 7.156 (m, 3H, Ar), 6.983 (d, 1H, Ar), 6.908 (t, 1H. Ar), 6.833 (d, 2H, Ar), 6.760 (ddd, 1H, Ar), 3.803 (s, 3H, —$OCH_3$), 3.793 (s, 2H, —$CH_2$—), 3.771 (s, 2H, —$CH_2$—), 3.066, (d, 2H, —$CH_2$—), 2.960 (m, 1H, —CH—), 2.542 (t, 2H, —$CH_2$—), 2.352 (t, 2H), 2.113 (m, 2H, —$CH_2$—), 1.807 (m, 4H, —$CH_2$—$CH_2$—), 1.566 (p, 2H, —$CH_2$—), 1.506 (p, 2H, —$CH_2$—), 1.238 (m, 4H, —$CH_2$—$CH_2$—). Mass Spec.=487.68 $(M+H)^+$.

Example 19

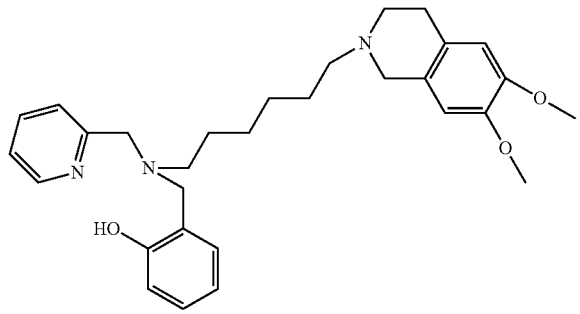 [SMILES: COc1cc2c(cc1OC)CN(CCCCCCN(Cc1ccccn1)Cc1ccccc1O)CC2]

2-(((6-(6,7-dimethoxy-3,4-dihydroisoquinolin-2(1H)-yl)hexyl)(pyridin-2-ylmethyl)amino)methyl)phenol [L12]

The same procedure as described for compound L11 was applied to compound 12 (0.13 g, 0.24 mmol). Purification was carried out on a silica gel TLC plate that was developed in with a 2.5% methanolic $NH_3$ (7 M $NH_3$ in methanol/97.5% $CH_2Cl_2$. The product was isolated as pale yellow oil (53%). $^1H$ NMR ($CDCl_3$) δ 8.560 (dd, 1H, Ar), 7.651 (ddd, 1H, Ar), 7.306 (d, 1H, Ar), 7.159 (m, 2H, Ar), 6.981 (dd, 1H, Ar), 6.824 (d, 1H, Ar), 6.756 (ddd, 1H, Ar), 6.572 (s, 1H, Ar), 6.502 (s, 1H, Ar), 3.820 (s, 3H, —$OCH_3$), 3.814 (s, 3H, —$OCH_3$), 3.790 (s, 2H, —$CH_2$—), 3.766, (s, 2H, —$CH_2$—), 3.565 (s, 2H, —$CH_2$—), 2.822 (t, 2H, —$CH_2$—), 2.722 (t, 2H, —$CH_2$—), 2.543 (ddd, 2H, —$CH_2$—), 2.466 (ddd, 2H, —$CH_2$—), 1.563 (m, 4H, —$CH_2$—$CH_2$—), 1.257 (m, 4H, —$CH_2$—$CH_2$—).

Example 20

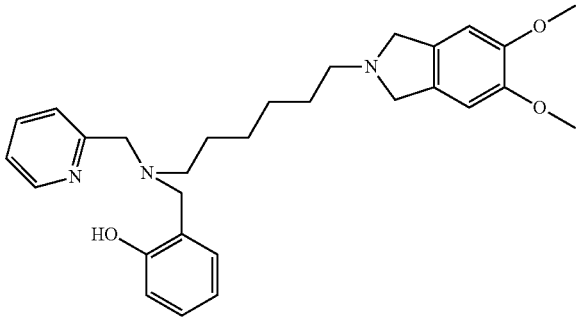 [SMILES: COc1cc2c(cc1OC)CN(CCCCCCN(Cc1ccccn1)Cc1ccccc1O)C2]

2-(((6-(5,6-dimethoxyisoindolin-2-yl)hexyl)(pyridin-2ylmethyl)amino)methyl)phenol [L13]

The same procedure as described for compound L11 was applied to compound 13 (0.30 g, 0.56 mmol). Purification was carried out on a silica gel TLC plate that was developed in with a 5% methanolic $NH_3$ (7 M $NH_3$ in methanol/95% $CH_2Cl_2$. The product was isolated as pale yellow oil (69%). $^1H$ NMR ($CDCl_3$) δ 8.570 (m, 1H, Ar), 7.665 (ddd, 1H, Ar), 7.321 (d, 1H, Ar), 7.183 (m, 1H, Ar), 7.154 (m, 1H, Ar), 6.989 (dd, 1H, Ar), 6.833 (dd, 1H, Ar), 6.765 (ddd, 1H, Ar), 6.727 (s, 2H, Ar), 3.846 (overlapped s, 4H, —$CH_2$—), 3.841 (overlapped s, 6H, —$OCH_3$), 3.801 (s, 2H, —$CH_2$—), 3.781, (s, 2H, —$CH_2$—), 2.639 (t, 2H, —$CH_2$—), 2.557 (t, 2H, —$CH_2$—), 1.584 (p, 2H, —$CH_2$—), 1.513 (p, 2H, —$CH_2$—), 1.283 (m, 4H, —$CH_2$—$CH_2$—). Mass Spec=476.29 $(M+H)^+$.

Example 21

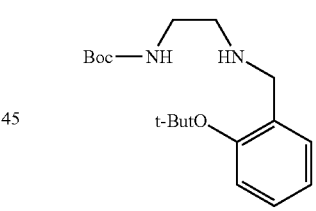

tert-butyl 2-(2-tert-butoxybenzylamino)ethylcarbamate [14]

N-Boc-ethylenediamine (2.6 g, 16 mmol) and 8 (2.9 g, 16 mmol) were added to 250 mL of $CH_3CN$ and the reaction mixture was refluxed under argon for 4 hr. After cooling down to room temperature, the solvent was removed and the residue was redissolved in MeOH. The solvent was then evaporated and $NaBH_4$ (3 g, 16 mmol) was added and stirred overnight. The solvent was evaporated, followed by extraction with $CH_2Cl_2$. The $CH_2Cl_2$ extract was concentrated and purified by a silica gel column using 2% methanolic $NH_3$ (7 M $NH_3$ in methanol/98% $CH_2Cl_2$ as eluent to yield the desired product as a pale yellow oil (97%). $^1H$ NMR ($CDCl_3$) δ 7.204 (dd, 1H, Ar), 7.115 (ddd, 1H, Ar), 7.007 (dd, 1H, Ar), 6.930 (ddd, 1H, Ar), 3.718 (s, 2H, —$CH_2$—), 3.175 (d, 2H, —$CH_2$—), 2.638

(t, 2H, —CH$_2$—), 1.402 (s, 9H, —C(CH$_3$)$_3$), 1.382 (s, 9H, —C(CH$_3$)$_3$). Mass Spect.=323.23 (M+H)$^+$.

Example 22

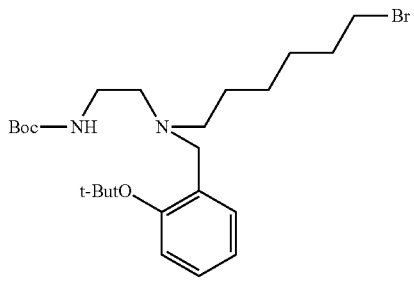

tert-butyl 2-((6-bromohexyl)(2-tert-butoxybenzyl)amino)ethylcarbamate [15]

Compound 14 (3.56 g, 14.6 mmol), 1,6-dibromohexane (35.3 g, 146 mmol) and K$_2$CO$_3$ (2 g, 14.6 mmol) were added to 50 mL CH$_3$CN, and the solution was stirred for 48 h. The solvent was evaporated to dryness and the residue was dissolved in a minimum amount of CH$_2$Cl$_2$ followed by purification via silica gel chromatographed, eluting with a 2% methanolic NH$_3$ (7 M NH$_3$ in methanol/98% CH$_2$Cl$_2$ yield the desired product as a pale yellow oil (64%). $^1$H NMR (CDCl$_3$) δ 7.354 (dd, 1H, Ar), 7.121 (ddd, 1H, Ar), 7.013 (d, 1H, Ar), 6.986 (t, 1H, Ar), 3.569 (s, 2H, —CH$_2$), 3.351 (t, 2H, —CH$_2$—), 3.145 (d, 2H, —CH$_2$—), 2.507 (t, 2H, —CH$_2$—), 2.399 (t, 2H, —CH$_2$—), 1.805 (p, 2H, —CH$_2$—),1.447 (p, 2H, —CH$_2$—), 1.409 (s, 9H, —C(CH$_3$)$_3$), 1.372 (s, 9H, —C(CH$_3$)$_3$), 1.362 (p, 2H, —CH$_2$—), 1.254 (p, 2H, —CH$_2$—). Mass Spec.=485.48 (M+H)$^+$.

Example 23

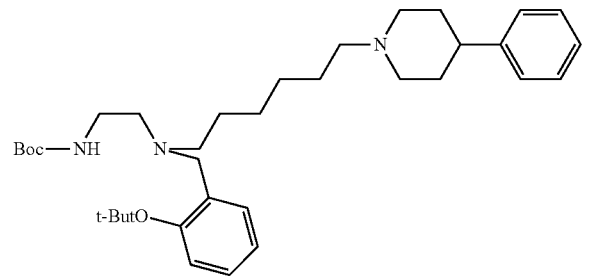

tert-butyl 2-((2-tert-butoxybenzyl)(6-(4-phenylpiperidin-1-yl)hexyl)amino)ethylcarbamate, [16]

The compound 15 (1.9 g, 4.46 mmol), 4-phenylpiperidine (1.128 g, 6.99 mmol) and K$_2$CO$_3$ (0.64 g, 4.66 mmol) were added to 50 mL CH$_3$CN, and the solution was refluxed under argon atmosphere for 16 h. After cooling to room temperature, the solvent was evaporated to dryness. Purification was carried out on a silica gel TLC plate that was developed in 3% methanolic NH$_3$ (7 M NH$_3$ in methanol)/97% CH$_2$Cl$_2$. The product was obtained as pale yellow oil (73%). $^1$H NMR (CDCl$_3$) δ 7.382 (d, 1H, Ar), 7.289 (m, 2H, Ar), 7.229 (m, 2H, Ar), 7.186 (m, 1H, Ar), 7.136 (m, 1H, Ar), 7.013 (m, 2H, Ar), 3.587 (s, 2H, —CH$_2$—), 3.160 (m, 2H, —CH$_2$—), 3.071 (d, 2H, —CH$_2$—), 2.519 (overlapping m, 2H, —CH$_2$—), 2.496 (overlapping m, 1H, —CH—), 2.419 (t, 2H, —CH$_2$—), 2.355 (m, 2H, —CH$_2$—), 2.045 (m, 2H, —CH$_2$—), 1.837 (m, 4H, —CH$_2$—CH$_2$—), 1.525 (m, 2H, —CH$_2$—), 1.472 (m, 2H, —CH$_2$—), 1.437 (s, 9H, —C(CH$_3$)$_3$), 1.426 (s, 9H, —C(CH$_3$)$_3$), 1.280 (m, 4H, —CH$_2$—CH$_2$—). Mass Spec=566.43 (M+H)$^+$.

Example 24

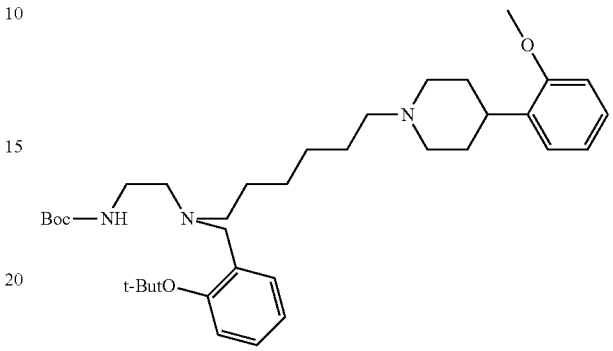

tert-butyl-2-((2-tert-butoxybenzyl)(6-(4-(2-methoxyphenyl)piperidin-1-yl)hexyl)amino)ethylcarbamate [17]

The same procedure as described for compound 16 was applied to starting material 15 (1.9 g, 4.66 mmol), 2-methoxy-4-phenylpiperidin (1.338 g, 6.99 mmol) and K$_2$CO$_3$ (0.644 g, 4.66 mmol). Purification was carried out on a silica gel TLC plate that was developed in with a 3% methanolic NH$_3$ (7 M NH$_3$ in methanol/97% CH$_2$Cl$_2$. The product was isolated as pale yellow oil (63.4%). Mass Spec.=596.44 (M+H)$^+$.

Example 25

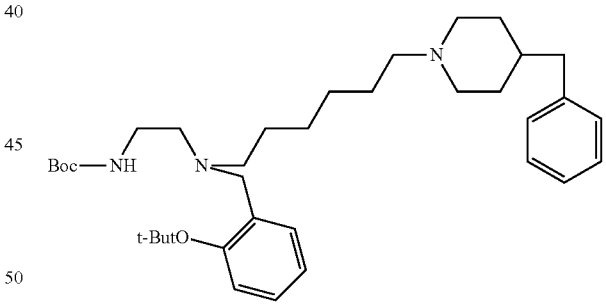

tert-butyl-2-((6-(4-benzylpiperidin-1-yl)hexyl)(2-tert-butoxybenzyl)amino)ethylcarbamate [18]

The same procedure as described for compound 16 was applied to starting material 15 (2.4 g, 5.89 mmol), 4-benzylpiperidine (2.06 g, 11.78 mmol) and K$_2$CO$_3$ (0.814 g, 5.89 mmol). Purification was carried out on a silica gel TLC plate that was developed in with a 3% methanolic NH$_3$ (7 M NH$_3$ in methanol/97% CH$_2$Cl$_2$. The product was isolated as pale yellow oil (58%). $^1$H NMR (CDCl$_3$) δ 7.328 (dd, 1H, Ar), 7.211 (t, 2H, Ar), 7.132 (t, 1H, Ar), 7.077 (m, 3H, Ar), 6.951 (m, 2H, Ar), 3.576 (s, 2H, —CH$_2$—), 3.302 (d, 2H, —CH$_2$—), 3.112 (m, 2H, —CH$_2$—), 2.729 (m, 2H, —CH$_2$—), 2.525 (m, 6H), 2.395 (m, 2H, —CH$_2$—), 1.819

(m, 2H, —CH₂—), 1.724 (m, 5H), 1.424 (m, 2H, —CH₂—), 1.356 (s, 9H, —C(CH₃)₃), 1.325 (s, 9H, —C(CH₃)₃), 1.224 (s(br), 4H, —CH₂—CH₂—). Mass Spec.=579.86 (M+H)⁺.

Example 25

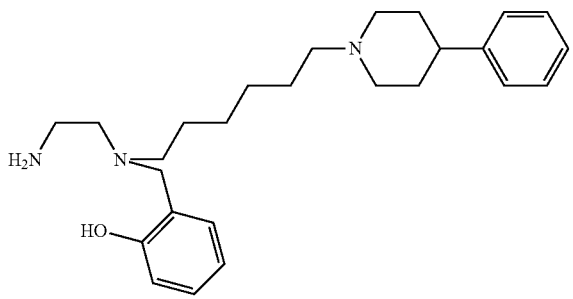 [SMILES: NCCN(CCCCCCN1CCC(c2ccccc2)CC1)Cc1ccccc1O]

2-(((2-aminoethyl)(6-(4-phenylpiperidin-1-yl)hexyl)amino)methyl)phenol [L16a]

Compound L16a (0.97 g, 1.71 mmol) was dissolved in 25 mL EtOAc saturated with HCl and stirred for 3 hr. The pH of the reaction mixture was adjusted to 8-9 with methanolic NH₃. Then the inorganic salts were filtered, and the filtrate was evaporated to dryness. The residue was purified on a silica gel TLC plate that was developed in 5% methanolic NH₃ (7 M NH₃ in methanol/95% CH₂Cl₂. The product was obtained as white solid (62%). ¹H NMR (CDCl₃) δ 7.268 (m, 2H, Ar), 7.210 (d, 2H, Ar), 7.151 (m, 2H, Ar), 6.945 (d, 2H, Ar), 6.800 (d, 1H, Ar), 6.750 (ddd, 1H, Ar), 3.723 (s, 2H, —CH₂—), 3.031 (d, 2H, —CH₂—), 2.852 (t, 2H, —CH₂—), 2.558 (t, 2H, —CH₂—), 2.504 (t, 2H, —CH₂—), 2.478 (overlapping m, 1H, —CH—), 2.322 (ddd, 2H, —CH₂—), 2.009 (ddd, 2H, —CH₂—), 1.805 (m, 4H, —CH₂—CH₂—), 1.515 (m, 4H, —CH₂—CH₂—), 1.282 (m, 4H, —CH₂—CH₂—). Mass Spec.=596.44 (M+H)⁺.

Example 26

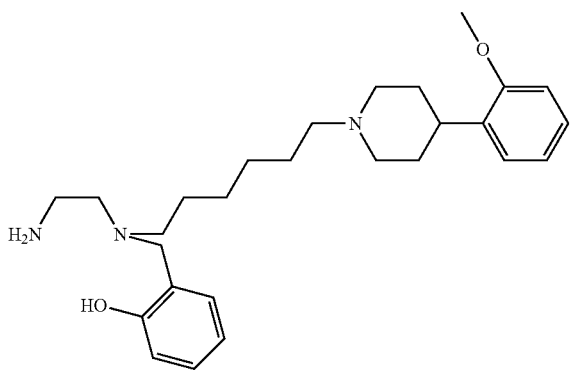 [SMILES: COc1ccccc1C1CCN(CCCCCCN(CCN)Cc2ccccc2O)CC1]

2-(((2-aminoethyl)(6-(4-(2-methoxyphenyl)piperidin-1-yl)hexyl)amino)methyl)phenol [L17a]

The same procedure as described for compound L16a was applied to 17 (0.88 g, 1.47 mmol). Purification was carried out on a silica gel TLC plate that was developed in with a 5% methanolic NH₃ (7 M NH₃ in methanol/95% CH₂Cl₂. The product was isolated as pale yellow oil (86%). ¹H NMR (CDCl₃) δ 7.192 (dd, 1H, Ar), 7.130 (m, 2H, Ar), 6.936 (d, 1H, Ar), 6.890 (ddd, 1H, Ar), 6.801 (dd, 2H, Ar), 6.41 (ddd, 1H, Ar), 3.774 (s, 3H, —OCH₃—), 3.714 (s, 2H, —CH₂—), 3.015 (d, 2H, —CH₂—), 2.940 (m, 1H, —CH—), 2.838 (t, 2H, —CH₂—), 2.545 (t, 2H, —CH₂—), 2.494 (t, 2H, —CH₂—), 2.316 (t, 2H, —CH₂—), 2.039 (ddd, 2H, —CH₂—), 1.760 (m, 4H, —CH₂—CH₂—), 1.514 (m, 4H, —CH₂—CH₂—), 1.273 (m, 4H, —CH₂—CH₂—). Mass Spec.=440.33 (M+H)⁺.

Example 27

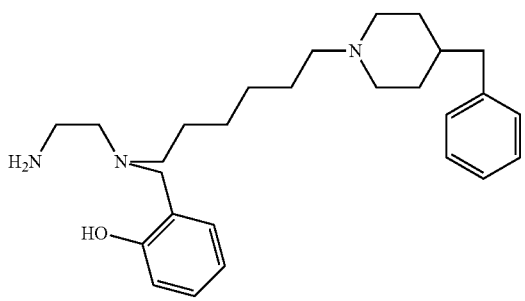 [SMILES: NCCN(CCCCCCN1CCC(Cc2ccccc2)CC1)Cc1ccccc1O]

2-(((2-aminoethyl)(6-(4-benzylpiperidin-1-yl)hexyl)amino)methyl)phenol [L18a]

The same procedure as described for compound L16a was applied to 18 (1.5 g, 2.58 mmol). Purification was carried out on a silica gel TLC plate that was developed in with a 10% methanolic NH₃ (7 M NH₃ in methanol/90% CH₂Cl₂. The product was isolated as pale yellow oil (94%). ¹H NMR (CDCl₃) δ 7.218 (t, 2H, Ar), 7.128 (m, 1H, Ar), 7.096 (m, 3H, Ar), 6.915 (dd, 1H, Ar), 6.769 (dd, 1H, Ar), 6.720 (ddd, 1H, Ar), 3.684 (s, 2H, —CH₂—), 2.852 (d, 2H, —CH₂—), 2.807 (t, 2H, —CH₂—), 2.487 (m, 6H), 2.226 (t, 2H, —CH₂—), 1.803 (ddd, 2H, —CH₂—), 1.588 (d, 2H, —CH₂—), 1.455 (overlapped m, 5H), 1.283 (m, 2H, —CH₂—), 1.237 (m, 4H, —CH₂—CH₂—). Mass Spec.=423.63 (M+H)⁺.

Example 28

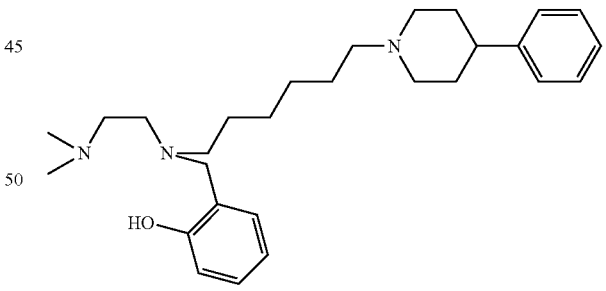

2-(((2-(dimethylamino)ethyl)(6-(4-phenylpiperidin-1-yl)hexyl)amino)methyl)phenol [L16b]

Synthesis of the L16b was carried out according to the following procedure. Compound L16a (0.15 g, 0.3 mmol), 37% aqueous formaldehyde (0.24 g, 3.0 mmol) and NaCNBH₃ (0.09 g, 1.5 mmol) were added to 50 mL CH₃CN, and the solution was stirred at room temperature for 30 min. Then the pH was adjusted to ~6 by dropwise addition of glacial acid and stirring was continued for 12 h. Then the solvent was evaporated and the residue was redissolved in CH₂Cl₂ and extract with 2 N NaOH. The organic layer was dried over $Na_2SO_4$ and filtered to afforded crude product. Purification was carried out on a silica gel TLC plate that was developed in 5% methanolic $NH_3$ (7 M $NH_3$ in methanol/95% $CH_2Cl_2$. The product was obtained as pale yellow oil (37%). $^1H$ NMR ($CDCl_3$) δ 7.278 (q, 2H, Ar), 7.223 (d, 2H, Ar), 7.178 (m, 2H, Ar), 6.982 (d, 1H, Ar), 6.797 (m, 2H, Ar), 3.791 (s, 2H, —$CH_2$—), 3.157 (d, 2H, —$CH_2$—), 2.998 (m, 2H, —$CH_2$—), 2.882 (m, 2H, —$CH_2$—), 2.580 (s overlapping multiplet, 8H, —$CH_2$— and —$C(CH_3)_2$), 2.534 (overlapping m, 1H, —$CH_2$—), 2.468 (m, 2H, —$CH_2$—), 2.180 (m, 2H, —$CH_2$—), 1.940 (m, 2H, —$CH_2$—), 1.858 (d, 2H, —$CH_2$—), 1.603 (m, 4H, —$CH_2$—$CH_2$—), 1.343 (m, 4H, —$CH_2$—$CH_2$—). Mass Spec.=437.66 $(M+H)^+$.

Example 29

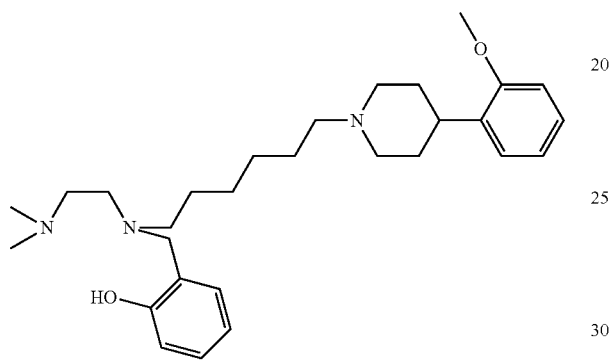

2-(((2-(dimethylamino)ethyl)(6-(4-(2-methoxyphenyl)piperidin-1-yl)hexyl)amino)methyl)phenol [L17b]

The same procedure as described for compound L16b was applied to 17a (0.388 g, 0.885 mmol). Purification was carried out on a silica gel TLC plate that was developed in with a 5% methanolic $NH_3$ (7 M $NH_3$ in methanol/95% $CH_2Cl_2$. The product was isolated as pale yellow oil (41%). $^1H$ NMR ($CDCl_3$) δ 7.208 (dd, 1H, Ar), 7.147 (m, 2H, Ar), 6.957 (dd, 1H, Ar), 6.909 (ddd, 1H, Ar), 6.823 (m, 2H, Ar), 6.740 (ddd, 1H, Ar), 3.799 (s, 3H, —$OCH_3$—), 3.648 (s, 2H, —$CH_2$—), 3.045 (d, 2H, —$CH_2$—), 2.959 (m, 1H, —CH—), 2.613 (t, 2H, —$CH_2$—), 2.475 (m, 4H, —$CH_2$—$CH_2$—), 2.328 (m, 2H, —$CH_2$—), 2.235 (s, 6H, —$N(CH_3)_2$), 2.079 (m, 2H, —$CH_2$—), 1.789 (m, 4H, —$CH_2$—$CH_2$—), 1.482 (m, 4H, —$CH_2$—$CH_2$—), 1.229 (m, 4H, —$CH_2$—$CH_2$—). Mass Spec.=468.36 $(M+H)^+$.

Example 30

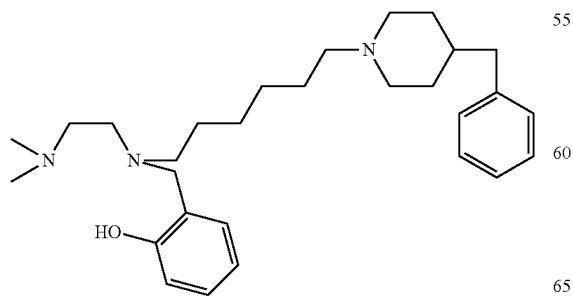

2-(((6-(4-benzylpiperidin-1-yl)hexyl)(2-(dimethylamino)ethyl)amino)methyl)phenol [L18b]

The same procedure as described for compound L16b was applied to 18a (0.5 g, 1.22 mmol). Purification was carried out on a silica gel TLC plate that was developed in with a 6% methanolic $NH_3$ (7 M $NH_3$ in methanol/94% $CH_2Cl_2$. The product was isolated as pale yellow oil (74%). $^1H$ NMR ($CDCl_3$) δ 7.247 (t, 2H, Ar), 7.158 (t, 2H, Ar), 7.114 (d, 2H, Ar), 6.969 (d, 1H, Ar), 6.783 (t, 2H, Ar), 3.768 (s, 2H, —$CH_2$—), 2.975 (m, 2H, —$CH_2$—), 2.923 (m, 2H, —$CH_2$—), 2.858 (m, 2H, —$CH_2$—), 2.559 (overlapped s and m, 8H), 2.516 (d, 2H, —$CH_2$—), 2.309 (t, 2H, —$CH_2$—), 1.896 (t, 2H, —$CH_2$—), 1.627 (d, 2H, —$CH_2$—), 1.530 (overlapped m, 5H), 1.356 (m, 2H, —$CH_2$—), 1.292 (m, 4H, —$CH_2$—$CH_2$—). Mass Spec.=451.69 $(M+H)^+$.

Example 31

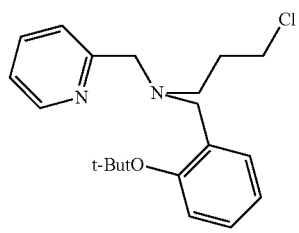

N-(2-tert-butoxybenzyl)-3-chloro-N-(pyridin-2-ylmethyl)propan-1-amine [19]

Compound 19 was synthesized with 9 (0.9 g, 3.32 mmol), using 1-bromo-3-chloropropane (10.5 g, 66 mmol) and $K_2CO_3$ (0.46 g, 3.32 mmol) following a procedure analogous to that described above for 10. Purification was carried out on a silica-gel column with the following eluents: First with 100% $CH_2Cl_2$ and then 2% methanolic $NH_3$ (7 M $NH_3$ in methanol/98% $CH_2Cl_2$. The product was isolated as pale yellow oil (65%). $^1H$ NMR ($CDCl_3$) δ 8.491 (m, 1H, Ar), 7.624 (m, 1H, Ar), 7.512 (t, 1H, Ar), 7.111 (m, 2H, Ar), 7.010 (m, 2H, Ar), 3.750 (s, 2H, —$CH_2$—), 3.690 (s, 2H, —$CH_2$—), 3.513 (ddd, 2H, —$CH_2$—), 2.616 (t, 2H, —$CH_2$—), 1.946 (m, 2H, —$CH_2$—), 1.354 (s, 9H, $C(CH_3)_3$). Mass Spec.=346.89 $(M+H)^+$.

Example 32

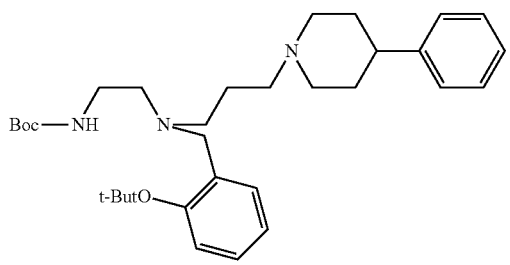

N-(2-tert-butoxybenzyl)-3-(4-phenylpiperidin-1-yl)-N-(pyridin-2-ylmethyl)propan-1-amine [20]

4-phenyl piperidin (0.21 g, 1.2 mmol), compound 19 (0.3 g, 0.86 mmol), KI (0.43 g, 2.59 mmol) and $K_2CO_3$ (0.59 g, 4.3 mmol) were added to 50 mL $CH_3CN$, and the solution was refluxed under argon atmosphere for 12 h. After cooling to room temperature, the inorganic salts were filtered, and the filtrate was evaporated to dryness. The residue was redissolved in CH$_2$Cl$_2$ and chromatographed on a silica gel TLC plate that was developed with the following eluents: 5% methanolic NH$_3$ (7 M NH$_3$ in methanol/95% CH$_2$Cl$_2$. The product was isolated as yellow oil (36% yield). $^1$H NMR (CDCl$_3$) δ 8.492 (dd, 1H, Ar), 7.619 (ddd, 1H, Ar), 7.571 (t, 2H, Ar), 7.272 (t, 2H, Ar), 7.203 (d, 2H, Ar), 7.167 (t, 1H, Ar), 7.107 (m, 2H, Ar), 7.024 (t, 2H, Ar), 3.770 (s, 2H, —CH$_2$—), 3.695, (s, 2H, —CH$_2$—), 3.003 (d, 2H, —CH$_2$—), 2.524 (t, 2H, —CH$_2$—), 2.459 (m, 1H, —CH—), 2.367 (t, 2H, —CH$_2$—), 2.01 (ddd, 2H, —CH$_2$—), 1.783 (m, 6H), 1.359 (s, 9H, —C(CH$_3$)$_3$). Mass Spec.=472.34 (M+H)$^+$.

Example 33

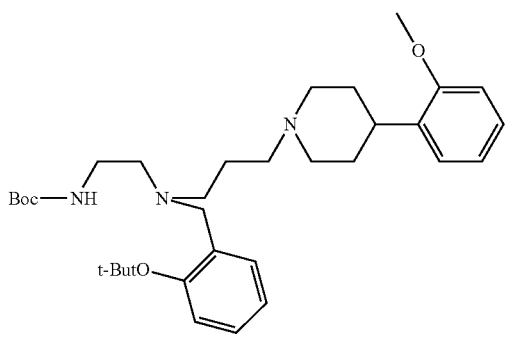

N-(2-tert-butoxybenzyl)-3-(4-(2-methoxyphenyl) piperidin-1-yl)-N-(pyridin-2-ylmethyl)propan-1-amine [21]

The same procedure as described for compound 20 was applied to 2-methoxy-2-phenylpiperidin (0.33 g, 1.73 mmol), compound 19 (0.4 g, 1.15 mmol), KI (0.57 g, 3.45 mmol) and K$_2$CO$_3$ (0.79 g, 5.75 mmol). Purification was carried out on a silica gel TLC plate that was developed in with a 5% methanolic NH$_3$ (7 M NH$_3$ in methanol/95% CH$_2$Cl$_2$. The product was isolated as pale yellow oil (59%). $^1$H NMR (CDCl$_3$) δ 8.486 (m, 1H, Ar), 7.591 (m, 3H, Ar), 7.22 (dd, 1H, Ar), 7.135 (m, 3H, Ar), 7.017 (dd, 2H, Ar), 6.901 (dd, 1H, Ar), 6.819 (d, 1H, Ar), 3.781 (s, 3H, —OCH$_3$), 3.764, (s, 2H, —CH$_2$—), 3.691 (s, 2H, —CH$_2$—), 3.002 (d, 2H, —CH$_2$—), 2.939 (m, 1H, —CH—), 2.521 (t, 2H, —CH$_2$—), 2.373 (t, 2H, —CH$_2$—), 2.053 (m, 3H, —CH—CH$_2$—), 1.769 (m, 6H), 1.354 (s, 9H, —C(CH$_3$)$_3$). Mass Spec.=502.34 (M+H)$^+$.

Example 34

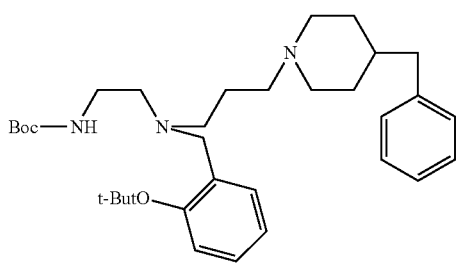

3-(4-benzylpiperidin-1-yl)-N-(2-tert-butoxybenzyl)-N-(pyridin-2-ylmethyl)propan-1-amine [22]

The same procedure as described for compound 20 was applied to 4-benzyl piperidin (0.30 g, 1.73 mmol), compound 19 (0.4 g, 1.15 mmol), KI (0.57 g, 3.45 mmol) and K$_2$CO$_3$ (0.79 g, 5.75 mmol). The residue was redissolved in CH$_2$Cl$_2$ and chromatographed on a silica-gel column with the following eluents: 5% methanolic NH$_3$ (7 M NH$_3$ in methanol/95% CH$_2$Cl$_2$. The product was isolated as yellow oil (64% yield). $^1$H NMR (CDCl$_3$) δ 8.453 (dd, 1H, Ar), 7.576 (ddd, 1H, Ar), 7.516 (m, 2H, Ar), 7.224 (m, 2H, Ar), 7.135 (m, 1H, Ar), 7.075 (m, 4H, Ar), 6.982 (m, 2H, Ar), 3.730 (s, 2H, —CH$_2$—), 3.655 (s, 2H, —CH$_2$—), 2.864 (d, 2H, —CH$_2$—), 2.482 (t, 4H, —CH$_2$—CH$_2$—), 2.324 (t, 2H, —CH$_2$—), 1.888 (t, 2H, —CH$_2$—), 1.728 (p, 2H, —CH$_2$—), 1.586 (d, 2H, —CH$_2$—), 1.502 (m, 1H, —CH—), 1.324 (s, 9H, —C(CH$_3$)$_3$), 1.288 (overlapped m, 2H, —CH$_2$—). Mass Spec.=486.35 (M+H)$^+$.

Example 35

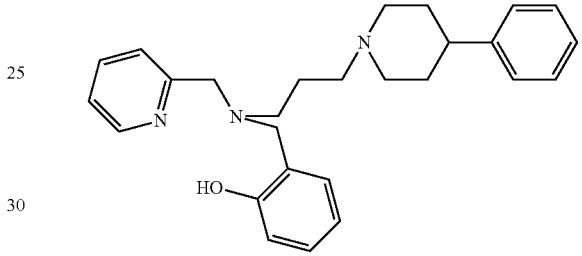

2-(((3-(4-phenylpiperidin-1-yl)propyl)(pyridin-2-ylmethyl)amino)methyl)phenol [L20]

Compound 20 (0.15 g, 0.31 mmol) was dissolved in 25 mL EtOAc saturated with HCl and stirred for 3 hr. The solvent was evaporated to dryness. The residue was purified on a silica gel TLC plate that was developed in 8% methanolic NH$_3$ (7 M NH$_3$ in methanol/92% CH$_2$Cl$_2$. The product was obtained as white solid (92%). $^1$H NMR (CDCl$_3$) δ 8.589 (dd, 1H, Ar), 7.675 (ddd, 1H, Ar), 7.332 (d, 1H, Ar), 7.289 (ddd, 3H, Ar), 7.189 (m, 5H, Ar), 7.009 (dd, 1H, Ar), 6.854 (dd, 1H, Ar), 6.780 (ddd, 1H, Ar), 3.843 (s, 2H, —CH$_2$—), 3.798, (s, 2H, —CH$_2$—), 2.974 (d, 2H, —CH$_2$—), 2.633 (t, 2H, —CH$_2$—), 2.458 (m, 1H, —CH—), 2.333 (m, 2H, —CH$_2$—), 2.000 (m, 2H, —CH$_2$—), 1.782 (m (br), 6H). Mass Spec.=416.27 (M+H)$^+$.

Example 36

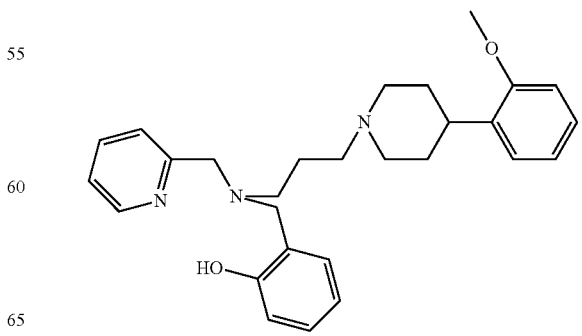

2-(((3-(4-(2-methoxyphenyl)piperidin-1-yl)propyl)(pyridin-2-ylmethyl)amino)methyl)phenol [L21]

The same procedure as described for compound L20 was applied to compound 21 (0.3 g, 10.59 mmol). Purification was carried out on a silica gel TLC plate that was developed in with a 8% methanolic NH$_3$ (7 M NH$_3$ in methanol/92% CH$_2$Cl$_2$. The product was isolated as pale yellow oil (64%). $^1$H NMR (CDCl$_3$) δ 8.577 (m, 1H, Ar), 7.652 (dd, 1H, Ar), 7.313 (d, 1H, Ar), 7.164 (m, 4H, Ar), 7.001 (dd, 1H, Ar), 6.910 (ddd, 1H, Ar), 6.849 (m, 2H, Ar), 3.835 (s, 2H, —CH$_2$—), 3.790 (s, 3H, —OCH$_3$), 3.777, (s, 2H, —CH$_2$—), 3.00 (d, 2H, —CH$_2$—), 2.939 (m, 1H, —CH—), 2.612 (t, 2H, —CH$_2$—), 2.390 (t, 2H, —CH$_2$—), 2.080 (m, 2H, —CH$_2$—), 1.815 (m, 2H, —CH$_2$—), 1.774 (m, 6H). Mass Spec.=458.7 (M+H)$^+$.

Example 37

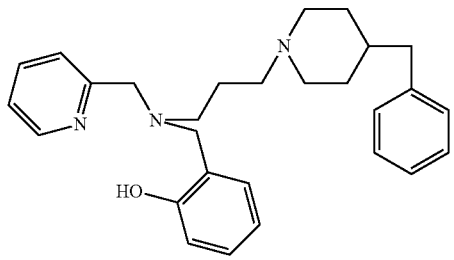 [SMILES: Oc1ccccc1CN(CCCN1CCC(Cc2ccccc2)CC1)Cc1ccccn1]

2-(((3-(4-benzylpiperidin-1-yl)propyl)(pyridin-2-ylmethyl)amino)methyl)phenol [L22]

The same procedure as described for compound L20 was applied to compound 22 (0.36 g, 7.41 mmol). Purification was carried out on a silica gel TLC plate that was developed in with a 8% methanolic NH$_3$ (7 M NH$_3$ in methanol/92% CH$_2$Cl$_2$. The product was isolated as pale yellow oil (74%). $^1$H NMR (CDCl$_3$) δ 8.563 (dd, 1H, Ar), 7.642 (ddd, 1H, Ar), 7.298 (d, 1H, Ar), 7.256 (m, 2H, Ar), 7.158 (m, 3H, Ar), 7.110 (d, 2H, Ar), 6.984 (dd, 1H, Ar), 6.835 (dd, 1H, Ar), 6.758 (ddd, 1H, Ar), 3.813 (s, 2H, —CH$_2$—), 3.753, (s, 2H, —CH$_2$—), 2.864 (d, 2H, —CH$_2$—), 2.581 (t, 2H, —CH$_2$—), 2.502 (d, 2H, —CH$_2$—), 2.302 (m, 2H, —CH$_2$—), 1.865 (m, 2H, —CH$_2$—), 1.786 (p, 2H,), 1.583 (d, 2H, —CH$_2$—), 1.493 (m, 1H, —CH—), 1.304 (m, 2H, —CH$_2$—). Mass Spec.=430.28 (M+H)$^+$.

Example 38

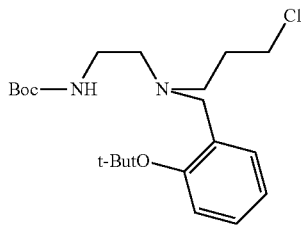

N-(2-((2-tert-butoxybenzyl)(3-chloropropyl)amino)ethyl)pivalamide [23]

Compound 14 (1 g, 4.1 mmol), 1-bromo-3-chloropropane (9.7 g, 60 mmol) and K$_2$CO$_3$ (0.56 g, 4.09 mmol) were added to 50 mL CH$_3$CN, and the solution was stirred for 48 h. The solvent was evaporated to dryness and the residue was purified on a silica gel TLC plate that was developed in 2% methanolic NH$_3$ (7 M NH$_3$ in methanol/98% CH$_2$Cl$_2$ yield the desired product as a pale yellow oil (55%). $^1$H NMR (CDCl$_3$) δ 7.341 (d, 1H, Ar), 7.139 (dd, 1H, Ar), 7.029 (m, 1H, Ar), 6.995 (m, 1H, Ar), 3.592 (s, 2H, —CH$_2$—), 3.539 (t, 2H, —CH$_2$—), 3.167 (m, 2H, —CH$_2$—), 2.583 (ddd, 2H, —CH$_2$—), 2.519 (ddd, 2H, —CH$_2$—), 1.900 (p, 2H, —CH$_2$—), 1.425 (s, 9H, —C(CH$_3$)$_3$), 1.385 (s, 9H, —C(CH$_3$)$_3$). Mass Spec.=399.96 (M+H)$^+$.

Example 39

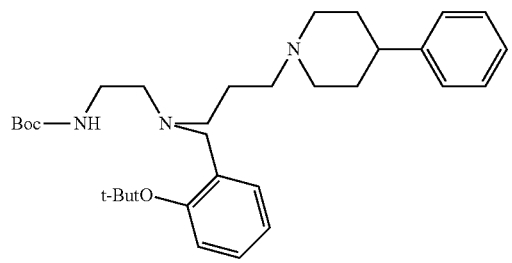

tert-butyl 2-((2-tert-butoxybenzyl)(3-(4-phenylpiperidin-1-yl)propyl)amino)ethylcarbamate [24]

4-phenyl piperidin (0.48 g, 3.0 mmol), compound 23 (0.8 g, 2.0 mmol), KI (0.99 g, 6.0 mmol) and K$_2$CO$_3$ (1.38 g, 10 mmol) were added to 50 mL CH$_3$CN, and the solution was refluxed under argon atmosphere for 12 h. After cooling to room temperature, the inorganic salts were filtered, and the filtrate was evaporated to dryness. The residue was purified on a silica gel TLC plate that was developed in 5% methanolic NH$_3$ (7 M NH$_3$ in methanol/95% CH$_2$Cl$_2$. The product was isolated as yellow oil (97% yield). $^1$H NMR (CDCl$_3$) δ 7.4045 (dd, 1H, Ar), 7.287 (m, 2H, Ar), 7.226 (m, 2H, Ar), 7.183 (m, 1H, Ar), 7.133 (m, 1H, Ar), 7.015 (m, 2H, Ar), 3.608 (s, 2H, —CH$_2$), 3.20, (m, 2H, —CH$_2$—), 3.036 (d, 2H, —CH$_2$—), 2.532 (t, 2H, —CH$_2$—), 2.490 (t, 3H), 2.381 (t, 2H, —CH$_2$—), 2.037 (m, 2H, —CH$_2$—), 1.826 (m, 4H, —CH$_2$—CH$_2$—), 1.718 (p, 2H, —CH$_2$—), 1.436 (s, 9H, —C(CH$_3$)$_3$, 1.392 (s, 9H, —C(CH$_3$)$_3$). Mass Spec.=524.38 (M+H)$^+$.

Example 40

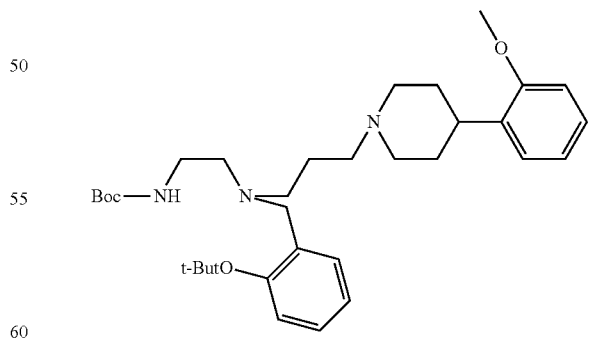

N-(2-((2-tert-butoxybenzyl)(3-(4-(2-methoxyphenyl)piperidin-1-yl)propyl)amino)ethyl)pivalamide [25]

The same procedure as described for compound 20 was applied to 2-methoxy-4-phenyl piperidin (0.5 g, 2.63 mmol), compound 23 (0.7 g, 1.75 mmol), KI (0.87 g, 5.25 mmol) and K$_2$CO$_3$ (1.21 g, 8.75 mmol). The residue was purified on a silica gel TLC plate that was developed in 5% methanolic NH$_3$ (7 M NH$_3$ in methanol/95% CH$_2$Cl$_2$. The product was isolated as yellow oil (65% yield). $^1$H NMR (CDCl$_3$) δ 7.3965 (m, 1H, Ar), 7.2067 (dd, 1H, Ar), 7.1655 (m, 1H, Ar), 7.1315 (m, 1H, Ar), 7.0245 (dd, 1H, Ar), 7.001 (s, 1H, Ar), 6.9195 (ddd, 1H, Ar), 6.8465 (s, 1H, Ar), 3.814 (s, 3H, —OCH$_3$), 3.599, (s, 2H, —CH$_2$—), 3.1885 (m, 2H, —CH$_2$—), 3.041 (m, 2H, —CH$_2$—), 2.951 (m, 1H, —CH—), 2.525 (t, 2H, —CH$_2$—), 2.475 (t, 2H, —CH$_2$—), 2.367 (t, 2H, —CH$_2$—), 2.066 (m, 2H, —CH$_2$—), 1.7455 (m, 6H), 1.430 (s, 9H, —C(CH$_3$)$_3$, 1.386 (s, 9H, —C(CH$_3$)$_3$. Mass Spec.=554.40 (M+H)$^+$.

Example 41

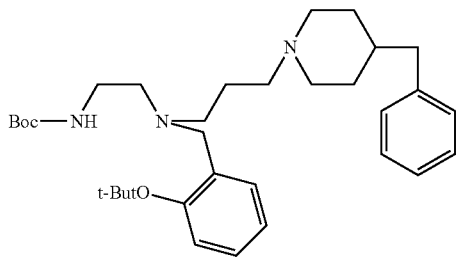

tert-butyl 2-((3-(4-benzylpiperidin-1-yl)propyl)(2-tert-butoxybenzyl)amino)ethylcarbamate [26]

The same procedure as described for compound 20 was applied to 4-benzylpiperidine (0.46 g, 2.63 mmol), compound 23 (0.7 g, 1.75 mmol), KI (0.87 g, 5.25 mmol) and K$_2$CO$_3$ (1.21 g, 8.75 mmol). The residue was purified on a silica gel TLC plate that was developed in 5% methanolic NH$_3$ (7 M NH$_3$ in methanol/95% CH$_2$Cl$_2$. The product was isolated as yellow oil (80% yield). $^1$H NMR (CDCl$_3$) δ 7.373 (d, 1H, Ar), 7.264 (m, 2H, Ar), 7.176 (t, 1H, Ar), 7.137 (d, 2H, Ar), 7.137 (d, 2H, Ar), 7.108 (d, 1H, Ar), 7.021 (dd, 1H, Ar), 6.985 (t, 1H, Ar), 3.577 (s, 2H, —CH$_2$—), 3.167 (d, 2H, —CH$_2$—), 2.892 (d, 2H, —CH$_2$—), 2.524 (d, 2H, —CH$_2$—), 2.498 (t, 2H, —CH$_2$—), 2.453 (t, 2H, —CH$_2$—), 2.290 (t, 2H, —CH$_2$—), 1.839 (t, 2H, —CH$_2$—), 1.657 (m, 2H, —CH$_2$—), 1.618 (d, 2H, —CH$_2$—), 1.517 (m, 1H, —CH—), 1.426 (s, 9H, —C(CH$_3$)$_3$, 1.376 (s, 9H, —C(CH$_3$)$_3$, 1.329 (overlapped m, 4H). Mass Spec.=538.77 (M+H)$^+$.

Example 42

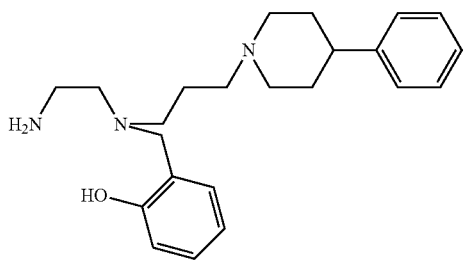 [SMILES: NCCN(CCCN1CCC(c2ccccc2)CC1)Cc1ccccc1O]

2-(((2-aminoethyl)(3-(4-phenylpiperidin-1-yl)propyl)amino)methyl)phenol [L24a]

Compound 24 (0.8 g, 1.52 mmol) was dissolved in 25 mL EtOAc saturated with HCl and stirred for 3 hr. The solvent was evaporated to dryness. The residue was purified on a silica gel TLC plate that was developed in 8% methanolic NH$_3$ (7 M NH$_3$ in methanol/92% CH$_2$Cl$_2$. The product was obtained as white solid (61%). $^1$H NMR (CDCl$_3$) δ 7.276 (m, 2H, Ar), 7.208 (m, 2H, Ar), 7.165 (m, 2H, Ar), 6.972 (dd, 1H, Ar), 6.822 (dd, 1H, Ar), 6.769 (ddd, 1H, Ar), 3.744 (s, 2H, —CH$_2$), 3.013, (d, 2H, —CH$_2$—), 2.902 (t, 2H, —CH$_2$—), 2.596 (m, 4H, —CH$_2$—CH$_2$), 2.473 (m, 1H, —CH—), 2.356 (t, 2H, —CH$_2$—), 2.023 (ddd, 2H, —CH$_2$—), 1.784 (m, 6H). Mass Spec.=368.27 (M+H)$^+$.

Example 43

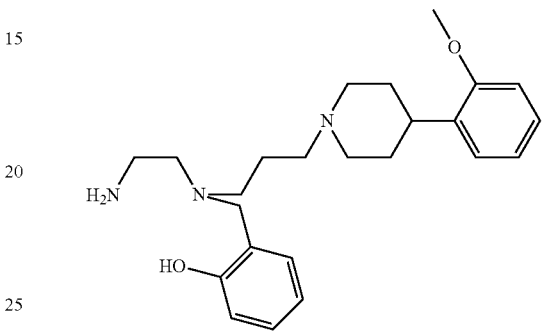

2-(((2-aminoethyl)(3-(4-(2-methoxyphenyl)piperidin-1-yl)propyl)amino)methyl)phenol [L25a]

The same procedure as described for compound L24 was applied to compound 25 (1.1 g, 2.04 mmol). Purification was carried out on a silica gel TLC plate that was developed in with a 8% methanolic NH$_3$ (7 M NH$_3$ in methanol/92% CH$_2$Cl$_2$. The product was isolated as white solid (87%). $^1$H NMR (CDCl$_3$) δ 7.1605 (m, 3H, Ar), 6.961 (dd, 1H, Ar), 6.904 (m, 1H, Ar), 6.816 (m, 2H, Ar), 6.764 (dd, 1H, Ar), 3.784 (s, 3H, —OCH$_3$), 3.744, (s, 2H, —CH$_2$—), 3.000 (d, 2H, —CH$_2$—), 2.914 (m, 3H, —CH—, —CH$_2$—), 2.584 (m, 4H, —CH$_2$—CH$_2$—), 2.339 (t, 2H, —CH$_2$—), 2.06 (ddd, 2H, —CH$_2$—), 1.773 (m, 4H, —CH$_2$—CH$_2$—), 1.719 (m, 2H, —CH$_2$—). Mass Spec. 398.28 (M+H)$^+$.

Example 44

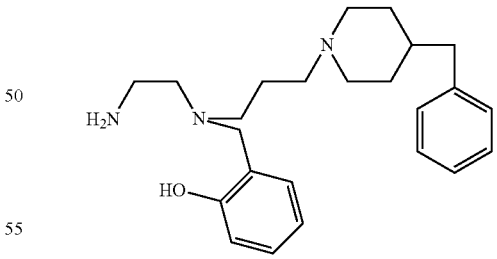

2-(((2-aminoethyl)(3-(4-benzylpiperidin-1-yl)propyl)amino)methyl)phenol [L26a]

The same procedure as described for compound L24a was applied to compound 26 (0.7 g, 1.3 mmol) Purification was carried out on a silica gel TLC plate that was developed in with a 6% methanolic NH$_3$ (7 M NH$_3$ in methanol/94% CH$_2$Cl$_2$. The product was isolated as pale yellow oil (60%). $^1$H NMR (CDCl$_3$) δ 7.257 (t, 2H, Ar), 7.163 (m, 2H, Ar), 7.118 (d, 2H, Ar), 6.952 (d, 1H, Ar), 6.801 (d, 1H, Ar), 6.757 (t, 1H, Ar), 3.724 (s, 2H, —CH₂—), 2.867 (q, 4H, —CH₂—CH—), 2.553 (m, 4H, —CH₂—CH₂—), 2.511 (d, 2H, —CH₂—), 2.278 (t, 2H, —CH₂—), 1.837 (ddd, 2H, —CH₂—), 1.725 (p, 2H, —CH₂—), 1.608 (d, 2H, —CH₂—), 1.500 (m, 1H, —CH—), 1.275 (m, 2H, —CH₂—). Mass Spec.=382.29 (M+H)⁺.

Example 45

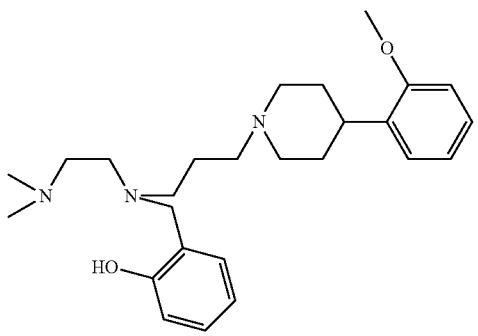 [SMILES: COc1ccccc1C1CCN(CCCN(CCN(C)C)Cc2ccccc2O)CC1]

2-(((2-(dimethylamino)ethyl)(3-(4-(2-methoxyphenyl)piperidin-1-yl)propyl)amino)methyl)phenol [L25b]

The same procedure as described for compound L16b was applied to compound L25a (0.3 g, 0.78 mmol). Purification was carried out on a silica gel TLC plate that was developed in with a 5% methanolic NH₃ (7 M NH₃ in methanol/95% CH₂Cl₂. The product was isolated as pale yellow oil (24%). ¹H NMR (CDCl₃) δ 7.179 (m, 3H, Ar), 6.994 (dd, 1H, Ar), 6.915 (m, 1H, Ar), 6.821 (m, 3H, Ar), 3.810 (s, 3H, —OCH₃), 3.806 (s, 2H, —CH₂—), 3.035 (m, 4H, —CH₂—CH₂—), 2.668 (m, 4H, —CH—CH₂—), 2.589 (s, 6H, —N(CH₃)₂), 2.426 (t, 2H, —CH₂—), 2.128 (m, 2H, —CH₂—), 1.788 (m, 7H). Mass Spec.=426.31 (M+H)⁺.

Example 46

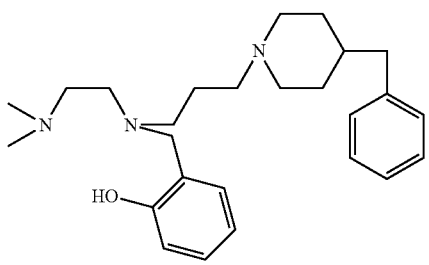 [SMILES: CN(C)CCN(CCCN1CCC(Cc2ccccc2)CC1)Cc1ccccc1O]

2-(((3-(4-benzylpiperidin-1-yl)propyl)(2-(dimethylamino)ethyl)amino)methyl)phenol [L26b]

The same procedure as described for compound L16b was applied to compound L26a (0.3 g, 0.78 mmol). Purification was carried out on a silica gel TLC plate that was developed in with a 5% methanolic NH₃ (7 M NH₃ in methanol/95% CH₂Cl₂. The product was isolated as pale yellow oil (53%). ¹H NMR (CDCl₃) δ 7.255 (m, 2H, Ar), 7.166 (m, 2H, Ar), 7.118 (d, 2H, Ar), 6.978 (d, 1H, Ar), 6.797 (d, 2H, Ar), 3.778 (s, 2H, —CH₂—), 3.001 (m, 2H, —CH₂—), 2.860 (m, 4H, —CH₂—CH₂—), 2.618 (t, 2H, —CH₂—), 2.558 (s, 6H, —N(CH₃)₂), 2.517 (d, 2H, —CH₂—), 2.319 (t, 2H, —CH₂—), 1.871 (t, 2H, —CH₂—), 1.759 (p, 2H, —CH₂—), 1.621 (d, 2H, —CH₂—), 1.516 (m, 1H, —CH—), 1.275 (m, 2H, —CH₂—). Mass Spec.=410.60 (M+H)⁺.

Example 47

General Procedure for Rhenium Complexation

Ligand (0.15 mmol), [Re(CO)₃Br₃][NEt₄Br]₂ (0.15 mmol) and K₂CO₃ (0.15 mmol) was stirred in 15 mL of CH₃CN at room temperature for 12 h. Purification was carried out on a silica gel TLC plate that was developed with 5% methanolic NH₃ (7 M NH₃ in methanol)/95% CH₂Cl₂.

[Re-L3]

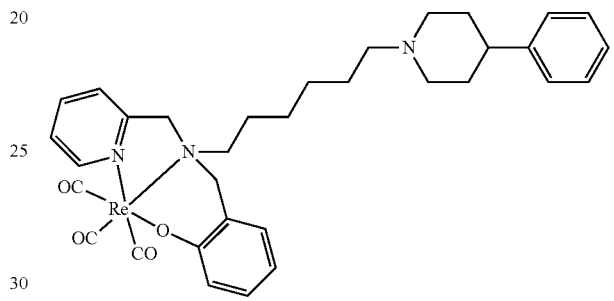

yield 88.6%; ¹H NMR (CDCl₃) δ 8.770 (s(br), 1H, Ar), 7.674 (s(br), 1H, Ar), 7.291 (m, 2H, Ar), 7.239 (m, 2H, Ar), 7.188 (m, 2H, Ar), 6.975 (s(br), 1H, Ar), 6.806 (s(br), 1H, Ar), 6.547 (s(br), 1H, Ar), 6.402 (s(br), 1H, Ar), 4.30 (m(br), 2H, —CH₂—), 3.702 (s, 3H, —CH—, —CH₂—), 3.453 (m(br), 2H, —CH₂—), 2.948 (t, 2H, —CH₂—), 2.812 (t, 2H, —CH₂—), 2.590 (t, 2H, —CH₂—), 2.014 (m, 1H, —CH—), 1.808 (m, 1H, —CH—), 1.704 (p, 2H, —CH₂—), 1.483 (m, 4H). Mass Spec.=728.26 (M+H)⁺.

[Re-L4]

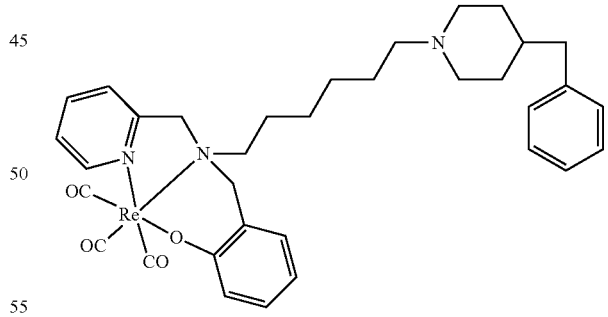

yield 94.3%; ¹H NMR (CDCl₃) δ 8.744 (s(br), 1H, Ar), 7.656 (s(br), 1H, Ar), 7.264 (m, 3H, Ar), 7.158 (overlapped m, 5H, Ar), 6.965 (s(br), 1H, Ar), 6.793 (s(br), 1H, Ar), 6.515 (s(br), 1H, Ar), 6.394 (s(br), 1H, Ar), 4.255 (m(br), 2H, —CH₂—), 3.696 (s, 1H, —CH—), 3.425 (m(br), 3H, —CH—, —CH₂—), 2.918 (d, 2H, —CH₂—), 2.531 (d, 2H, —CH₂—), 2.316 (t, 2H, —CH₂—), 1.197 (s(br), 1H, —CH—), 1.871 (t, 2H, —CH₂—), 1.754 (m, 1H, —CH—), 1.628 (d, 2H, —CH₂—), 1.550 (m, 4H, —CH₂—CH₂—), 1.337 (m, 7H). Mass Spec.=742.26 (M+H)⁺.

[Re-L5]

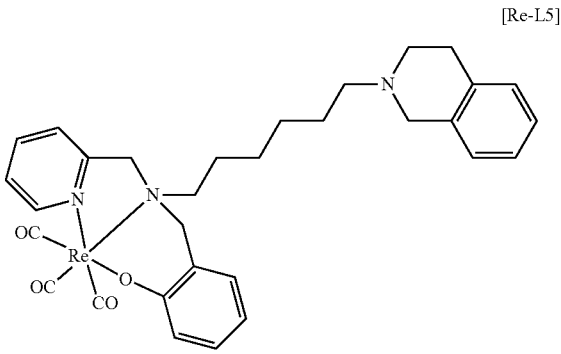

yield 90%; $^1$H NMR (CDCl$_3$) δ 8.791 (s(br), 1H, Ar), 7.686 (s(br), 1H, Ar), 7.171 (overlapped m, 4H, Ar), 7.015 (overlapped m, 2H, Ar), 6.808 (s(br), 1H, Ar), 6.407 (s(br), 1H, Ar), 4.30 (m(br), 2H, —CH$_2$—), 3.702 (s, 3H, —CH—, —CH$_2$—), 3.453 (m(br), 2H, —CH$_2$—), 2.948 (t, 2H, —CH$_2$—), 2.812 (t, 2H, —CH$_2$—), 2.590 (t, 2H, —CH$_2$—), 2.014 (m, 1H, —CH—), 1.808 (m, 1H, —CH—), 1.704 (p, 2H, —CH$_2$—), 1.483 (m, 4H, —CH$_2$—CH$_2$—). Mass Spec.=700.22 (M+H)$^+$.

[Re-L6]

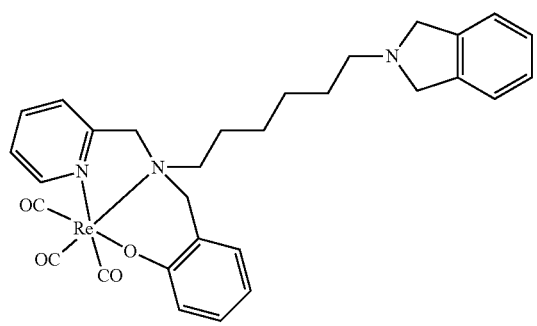

yield 75%; $^1$H NMR (CDCl$_3$) δ 8.705 (s(br), 1H, Ar), 7.605 (s(br), 1H, Ar), 7.139 (m, 6H, Ar), 6.908 (s(br), 1H, Ar), 6.734 (s(br), 1H, Ar), 6.329 (s(br), 2H, Ar), (dd, 1H, Ar), 4.195 (m(br), 2H, —CH$_2$—), 3.901 (s, 4H), 3.450 (m(br), 2H, —CH$_2$—), 2.707 (t, 2H, —CH$_2$—), 1.949 (m, 1H, —CH—), 1.741 (m, 1H, —CH—), 1.608 (m, 2H, —CH$_2$—), 1.46 (m, 2H, —CH$_2$—), 1.378 (m, 2H, —CH$_2$—). Mass Spec.=686.20 (M+H)$^+$.

[Re-L11]

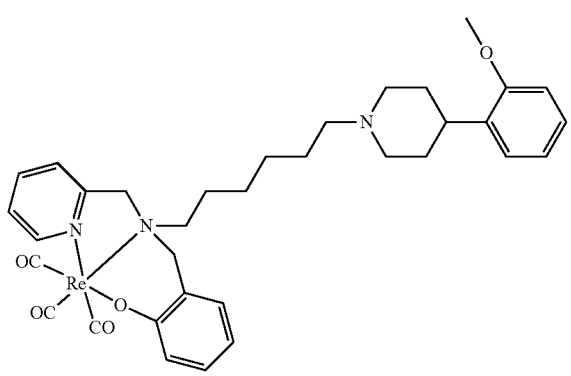

yield 88.5%; $^1$H NMR (CDCl$_3$) δ 8.788 (s(br), 1H, Ar), 7.688 ((s(br), 1H, Ar), 7.200 (m, 4H, Ar), 6.979 (s(br), 1H, Ar), 6.929 (t, 1H, Ar), 6.857 (d, 1H, Ar), 6.813 (s(br), 1H, Ar), 6.520 (s(br), 1H, Ar), 6.407 (s(br), 1H, Ar), 4.316 (m(br), 2H, —CH$_2$—), 3.826 (s, 3H, —OCH$_3$), 3.423 (m(br), 3H), 3.153 (s(br), 2H, —CH$_2$—), 3.006 (m, 1H, —CH—), 2.488 (m(br), 2H, —CH$_2$—), 2.202 (m(br), 2H, —CH$_2$—), 2.022 (m(br), 1H, —CH—), 1.856 (m(br), 6H), 1.679 (s(br), 2H, —CH$_2$—), 1.453 (s(br), 5H). Mass Spec.=758.26 (M+H)$^+$.

[Re-L12]

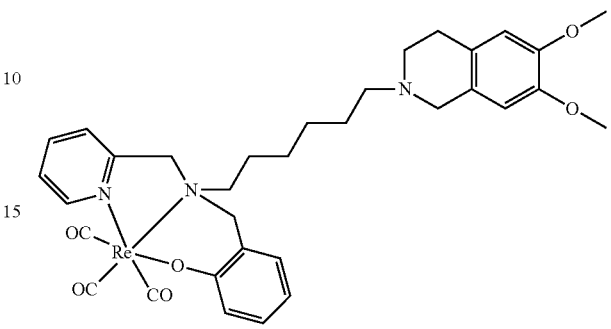

yield 85%; $^1$H NMR (CDCl$_3$) δ 8.752 (s(br), 1H, Ar), 7.670 ((s(br), 1H, Ar), 7.183 ((s(br), 2H, Ar), 6.959 (s(br), 1H, Ar), 6.798 ((s(br), 1H, Ar), 6.582 (s, 1H, Ar), 6.517 (s, 2H, Ar), 6.390 (s(br), 1H, Ar), 4.326-4.258 (m(br), 2H, —CH$_2$—), 3.817 (s, 6H, —OCH$_3$), 3.652 (s, 2H, —CH$_2$—), 3.536-3.364 (m, 4H), 2.865 (m, 2H, —CH$_2$—), 2.815 (m, 2H, —CH$_2$—), 2.601 (t, 2H, —CH$_2$—), 1.992 (s(br), 1H, —CH—), 1.822 (m, 1H, —CH—), 1.709 (p, 2H, —CH$_2$—), 1.480 (m, 2H, —CH$_2$—), (1.444, m, 3H). Mass Spec.=759.87 (M+H)$^+$.

[Re-L13]

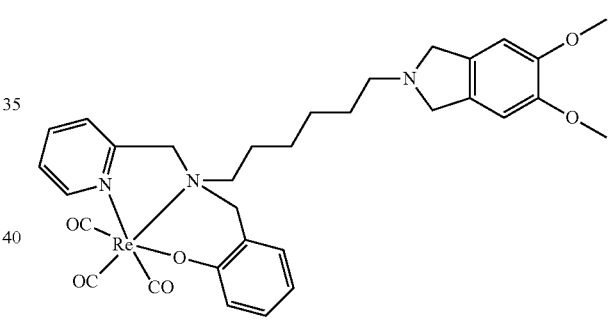

yield 58%; $^1$H NMR (CDCl$_3$) δ 8.785 (s(br), 1H, Ar), 7.685 ((s(br), 1H, Ar), 7.211 (s(br), 2H, Ar), 6.978 (s(br), 1H, Ar), 6.808 (s(br), 1H, Ar), 6.535 (s(br), 1H, Ar), 6.403 (s(br), 1H, Ar), 4.322 (m(br), 2H, —CH$_2$—), 4.028 (s, 4H), 3.855 (s, 6H, —OCH$_3$), 3.454 (m(br), 4H, —CH$_2$—CH$_2$—), 2.843 (t, 2H, —CH$_2$—), 2.030 (m, 1H, —CH—), 1.833 (m, 1H, —CH—), 1.730 (p, 2H, —CH$_2$—), 1.538 (p, 2H, —CH$_2$—), 1.457 (p, 2H, —CH$_2$—). Mass Spec.=746.25 (M+H)$^+$.

[Re-L16a]

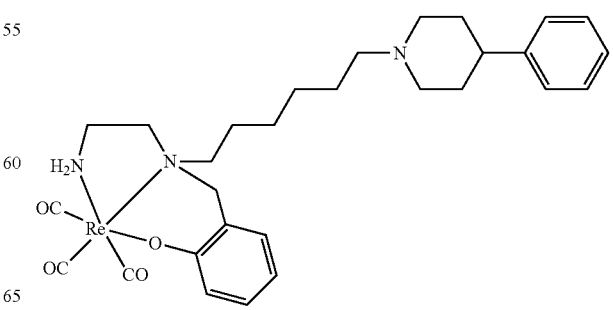

[Re-L16b]

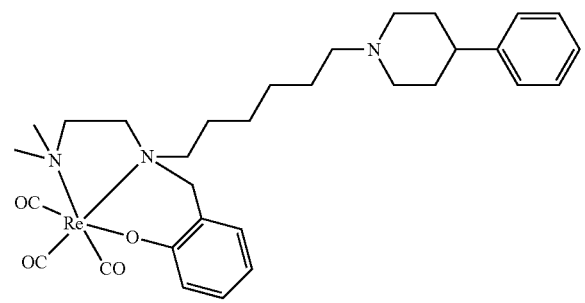

yield 45%; ¹H NMR (CDCl₃) δ 7.300 (m, 2H, Ar), 7.239 (m, 2H, Ar), 7.172 (m, 2H, Ar), 6.929 (dd, 1H, Ar), 6.698 (d, 1H, Ar), 6.602 (ddd, 1H, Ar), 4.318 (m, 1H, —CH—), 4.044 (d, 1H, —CH—), 3.738 (m, 1H, —CH—), 3.612 (d, 1H, —CH—), 3.344 (m, 2H, —CH₂—), 3.272 (m, 1H, —CH—), 3.173-3.101 (broad m, 3H, —CH—, —CH₂—), 3.038 (ddd, 1H, —CH—), 2.960 (m, 1H, —CH), 2.667 (m, 1H, —CH—), 2.524 (m, 1H, —CH—), 2.420 (m, 1H, —CH—), 2.107 (m, 2H, —CH₂—), 1.974 (m, 1H, —CH—), 1.866 (m, 4H, —CH₂—CH₂—), 1.786 (m, 1H, —CH—), 1.613 (m, 2H, —CH₂—), 1.416 (m, 4H, —CH₂—CH₂—). Mass Spec.=680.25 (M+H)⁺.

yield 25%; ¹H NMR (CDCl₃) δ 7.343 (t, 2H, Ar), 7.247 (d, 2H, Ar), 7.174 (m, 2H, Ar), 6.868 (dd, 1H, Ar), 6.731 (d, 1H, Ar), 6.524 (ddd, 1H, Ar), 4.389 (dd, 1H, —CH—), 3.544 (dd, 1H, —CH—), 3.447 (ddd, 1H, —CH—), 3.119 (m, 7H), 2.700 (s, 6H, —C(CH₃)₂), 2.520 (m, 1H, —CH—), 2.450 (ddd, 2H, —CH₂—), 2.100 (m, 3H, —CH—, —CH₂—), 1.89 (m, 4H), 1.78 (m, 1H, —CH—), 1.65 (m, 2H, —CH₂—), 1.45 (m, 4H, —CH₂—CH₂—). Mass Spec.=708.29=(M+H)⁺.

[Re-L17a]

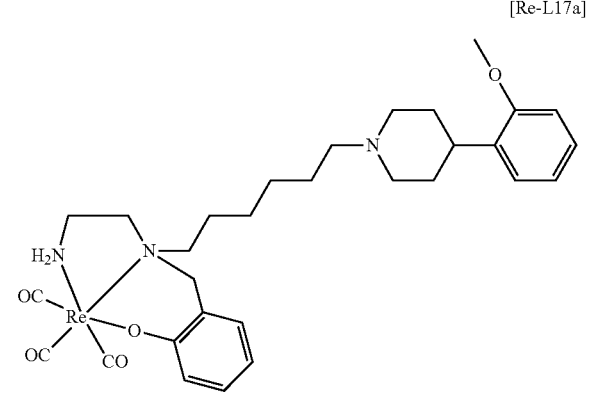

yield 49%; ¹H NMR (CDCl₃) δ 7.219 (dd, 1H, Ar), 7.166 (m, 2H, Ar), 6.922 (m, 2H, Ar), 6.855 (d, 1H, Ar), 6.711 (d, 1H, Ar), 6.596 (t, 1H, Ar), 4.147 (d, 1H, —CH—), 4.035 (m, 1H, —CH—), 3.852 (overlapped m, 1H, —CH—), 3.820 (s, 3H, —OCH₃—), 3.580 (d, 1H, —CH—), 3.292 (m, 2H, —CH₂—), 3.113 (m, 3H, —CH—, —CH₂—), 2.989 (m, 2H, —CH₂—), 2.619 (m, 1H, —CH), 2.427 (t, 2H, —CH₂—), 2.113 (ddd, 2H, —CH₂—), 1.995 (m, 1H, —CH—), 1.818 (m, 5H), 1.611 (m, 2H, —CH₂—), 1.411 (m, 4H, —CH₂—CH₂—). Mass Spect.=710.26 (M+H)⁺.

[Re-L17b]

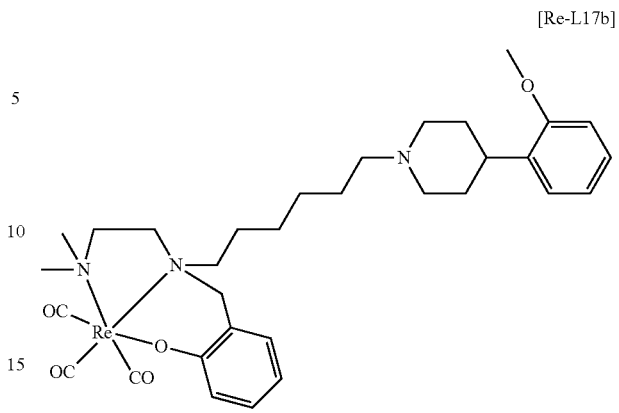

yield 30%; ¹H NMR (CDCl₃) δ 7.221 (dd, 1H, Ar), 7.171 (m, 2H, Ar), 6.922 (ddd, 1H, Ar), 6.850 (d, 2H, Ar), 6.717 (dd, 1H, Ar), 6.514 (ddd, 1H, Ar), 4.359 (d, 1H, —CH—), 3.819 (s, 3H, —OCH₃—), 3.549 (d, 1H, —CH—), 3.442 (ddd, 1H, —CH—), 3.103 (overlapped m and s, 8H,), 2.688 (s, 6H, overlapped m and s), 2.484 (t, 2H, —CH₂—), 2.198 (t, 2H, —CH₂—), 2.080 (m, 1H, —CH—), 1.848 (m, 4H, —CH₂—CH₂—), 1.662 (m, 2H, —CH₂—), 1.443 (m, 4H, —CH₂—CH₂—). Mass Spec.=738.29 (M+H)⁺.

[Re-L18a]

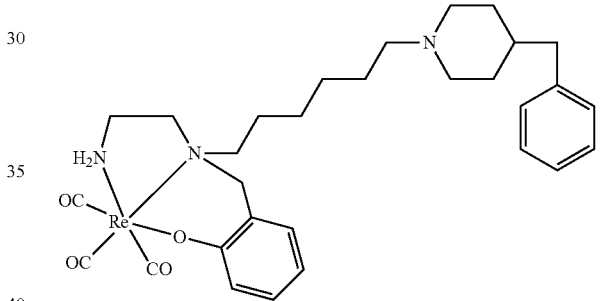

yield 59%; ¹H NMR (CDCl₃) δ 7.275 (m, 2H, Ar), 7.199 (m, 1H, Ar), 7.142 (m, 3H, Ar), 6.910 (d, 1H, Ar), 6.688 (d, 1H, Ar), 6.584 (t, 1H, Ar), 4.075 (m, 2H, —CH₂—), 3.945 (m, 1H, —CH—), 3.575 (d, 1H, —CH—), 3.254 (m, 2H, —CH₂—), 3.123 (m, 3H, —CH—, —CH₂—), 2.991 (m, 1H, —CH—), 2.931 (m, 1H, —CH—), 2.626 (m, 1H, —CH—), 2.549 (m, 5H), 2.110 (t, 2H, —CH₂—), 1.957 (m, 1H, —CH—), 1.705 (d, 2H, —CH₂—), 1.593 (m, 2H, —CH₂—), 1.480 (m, 2H, —CH₂—), 1.389 (m, 4H, —CH₂—CH₂—). Mass Spect.=696.88 (M+H)⁺.

Re-[L20]

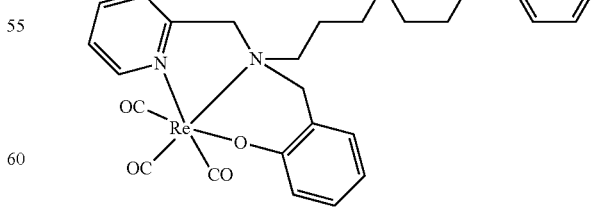

yield 68.5%; ¹H NMR (CDCl₃) δ 8.766 (s(br), 1H, Ar), 7.684 (m(br), 1H, Ar), 7.308 (m, 3H, Ar), 7.234 (m(br), 4H, Ar), 6.978 (s(br), 1H, Ar), 6.830 (s(br), 1H, Ar), 6.520 (s(br), 1H, Ar), 6.407 (s(br), 1H, Ar), 4.374 (m(br), 1H, —CH—), 4.297 (m(br), 1H, —CH—), 3.544 (m(br), 2H, —CH₂—), 3.413 (d, 1H, —CH—), 3.189 (d, 2H, —CH₂—), 2.557 (m, 3H, —CH—CH₂—), 2.267 (m, 3H, —CH—CH₂—), 2.12 (m, 1H, —CH—), 1.916 (m, 5H). Mass Spec.=685.80 (M+H)$^+$.

Re-[L21]

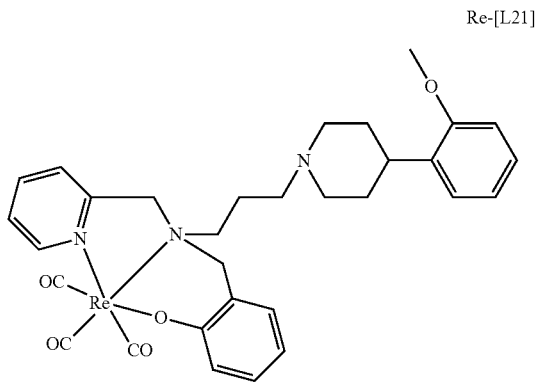

yield 69%; $^1$H NMR (CDCl₃) δ 8.765 (s(br), 1H, Ar), 7.673 (m(br), 1H, Ar), 7.198 (m, 4H, Ar), 6.975 (m(br), 1H, Ar), 6.933 (m, 1H, Ar), 6.869 (m, 1H, Ar), 6.822 (s(br), 1H, Ar), 6.520 (s(br), 1H, Ar), 6.406 (s(br), 1H, Ar), 4.364 (m(br), 1H, —CH—), 4.281 (m(br), 1H, —CH—), 3.826 (s, 3H, —OCH₃—), 3.536 (m(br), 2H, —CH₂—), 3.397 (m, 1H, —CH—), 3.117 (d, 2H, —CH₂—), 3.001 (m, 1H, —CH—), 2.493 (dd, 2H, —CH₂—), 2.216 (m, 3H, —CH—, —CH₂—), 2.045 (m, 1H, —CH—), 1.817 (m, 4H, —CH₂—CH₂—). Mass Spec.=715.83 (M+H)$^+$.

Re-[L22]

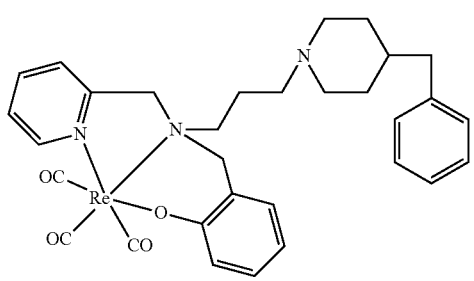

yield 80%; $^1$H NMR (CDCl₃) δ 8.753 (s(br), 1H, Ar), 7.660 (m(br), 1H, Ar), 7.271 (m, 2H, Ar), 7.169 (m, 4H, Ar), 6.985 (m(br), 1H, Ar), 6.798 (m(br), 1H, Ar), 6.510 (s(br), 1H, Ar), 6.394 (s(br), 1H, Ar), 4.331 (s(br), 1H, —CH—), 4.274 (d, 1H, —CH—), 3.732 (s(br), 1H, —CH—), 3.517 (m(br), 2H, —CH₂—), 3.374 (d, 1H, —CH—), 2.956 (d, 2H, —CH₂—), 2.546 (d, 2H, —CH₂—), 2.402 (t, 2H, —CH₂—), 2.195 (m, 1H, —CH—), 1.977 (t, 3H, —CH—, —CH₂—), 1.676 (d, 2H, —CH₂—), 1.561 (m, 1H, —CH—), 1.356 (m, 2H, —CH₂—). Mass Spec.=699.82 (M+H)$^+$.

Re-[L24a]

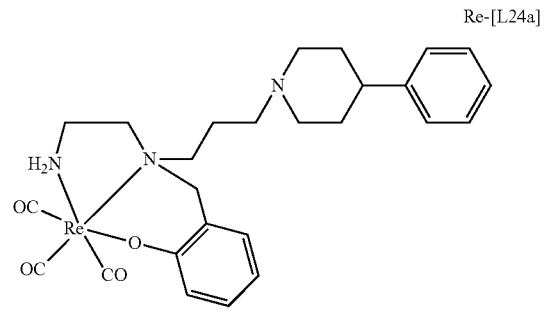

yield 48%; $^1$H NMR (CDCl₃) δ 7.317-7.171 (m(br), 6H, Ar), 6.932 (d(br), 1H, Ar), 6.715 (d(br), 1H, Ar), 6.601 (d(br), 1H, Ar), 4.217 (d(br), 1H, —CH—), 4.006 (s(br), 1H, —CH—), 3.711, (s, (br), 1H, —CH—), 3.614 (d(br), 2H, —CH₂—), 3.362 (s(br), 2H, —CH₂—), 3.193-3.133 (m(br), 4H), 3.020 (m(br), 1H, —CH—), 2.667-2.562 (overlapped m(br) and s(br), 4H), 2.267-2.121 (overlapped m(br) and s(br), 4H), 1.906 (s, 4H). Mass Spec.=639.8 (M+H)$^+$.

Re-[L25a]

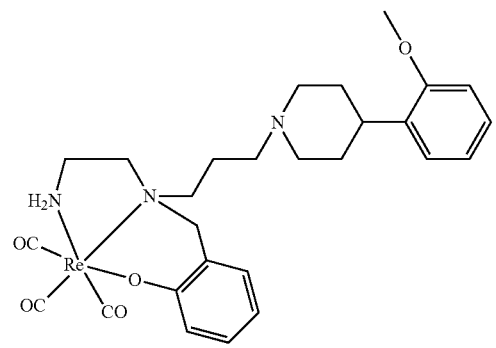

yield 44%; $^1$H NMR (CDCl₃) δ 7.224 (m, 2H, Ar), 7.163 (m, 1H, Ar), 6.904 (m, 3H, Ar), 6.730 (m, 1H, Ar), 6.593 (m, 1H, Ar), 4.383 (d, 1H, —CH—), 3.842 (s, 3H, —OCH₃), 3.719, (s, 1H, —CH—), 3.568 (m, 2H, —CH₂—), 3.389-3.149 (m(br), 6H), 3.058 (m, 2H, —CH₂—), 2.621 (m, 3H, —CH—, —CH₂—), 2.399 (m(br), 4H, —CH₂—CH₂—), 1.937 (m, 4H, —CH₂—CH₂—). Mass Spec.=670.80 (M+H)$^+$.

Re-[L26a]

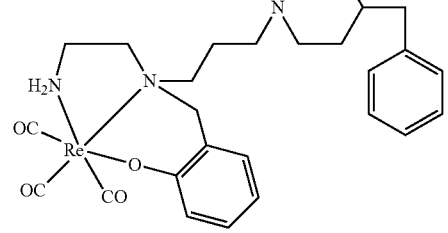

yield 70%; $^1$H NMR (CDCl₃) δ 7.280 (s(br), 2H, Ar), 7.151 (m(br), 4H, Ar), 6.923 (m(br), 1H, Ar), 6.689 (m(br), 1H, Ar), 6.593 (s(br), 1H, Ar), 4.337 (s(br), 1H, —CH—), 4.0565 (d(br), 1H, —CH—), 3.681, (s(br), 1H, —CH—), 3.603 (s(br), 1H, —CH—), 3.313 (m(br), 2H, —CH₂—), 3.167 (s(br), 1H, —CH—), 3.082 (s(br), 1H, —CH—), 2.957 (s(br), 3H, —CH—, —CH₂—), 2.664 (s(br), 1H, —CH—), 2.549 (m(br), 2H, —CH₂—), 2.406 (s(br), 2H, —CH₂—), 2.175

(s(br), 1H, —CH—), 1.983 (m(br), 3H, —CH—, —CH$_2$—), 1.673 (s(br), 2H, —CH$_2$—), 1.556 (s(br), 1H, —CH—), 1.343 (s(br), 2H, —CH$_2$—). Mass Spec.=654.80 (M+H)$^+$.

Re-[L25b]

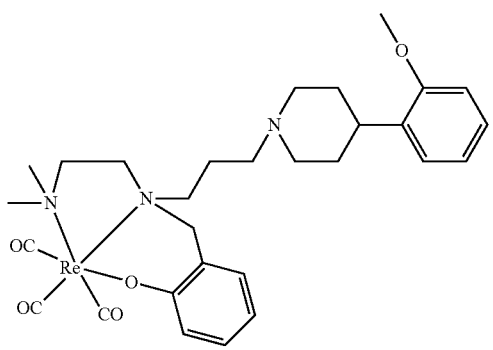

yield 31%; $^1$H NMR (CDCl$_3$) δ 7.179 (m, 3H, Ar), 6.994 (dd, 1H, Ar), 6.924 (m, 1H, Ar), 6.828 (m, 3H, Ar), 3.823 (s, 3H, —OCH$_3$), 3.814 (s, 2H, —CH$_2$—), 3.115 (m, 3H, —CH—, —CH$_2$—), 3.064 (m, 2H, —CH$_2$—), 3.002 (s, 3H, —CH—, —CH$_2$—), 2.930 (m, 2H, —CH$_2$—), 2.697 (m, 2H, —CH$_2$—), 2.613 (s, 6H, —N(CH$_3$)$_2$, 2.514 (m, 2H, —CH$_2$—), 2.236 (m, 2H, —CH$_2$—), 1.89 (m, 7H). Mass Spec.=698.85 (M+H)$^+$.

Example 48

Figure 2:
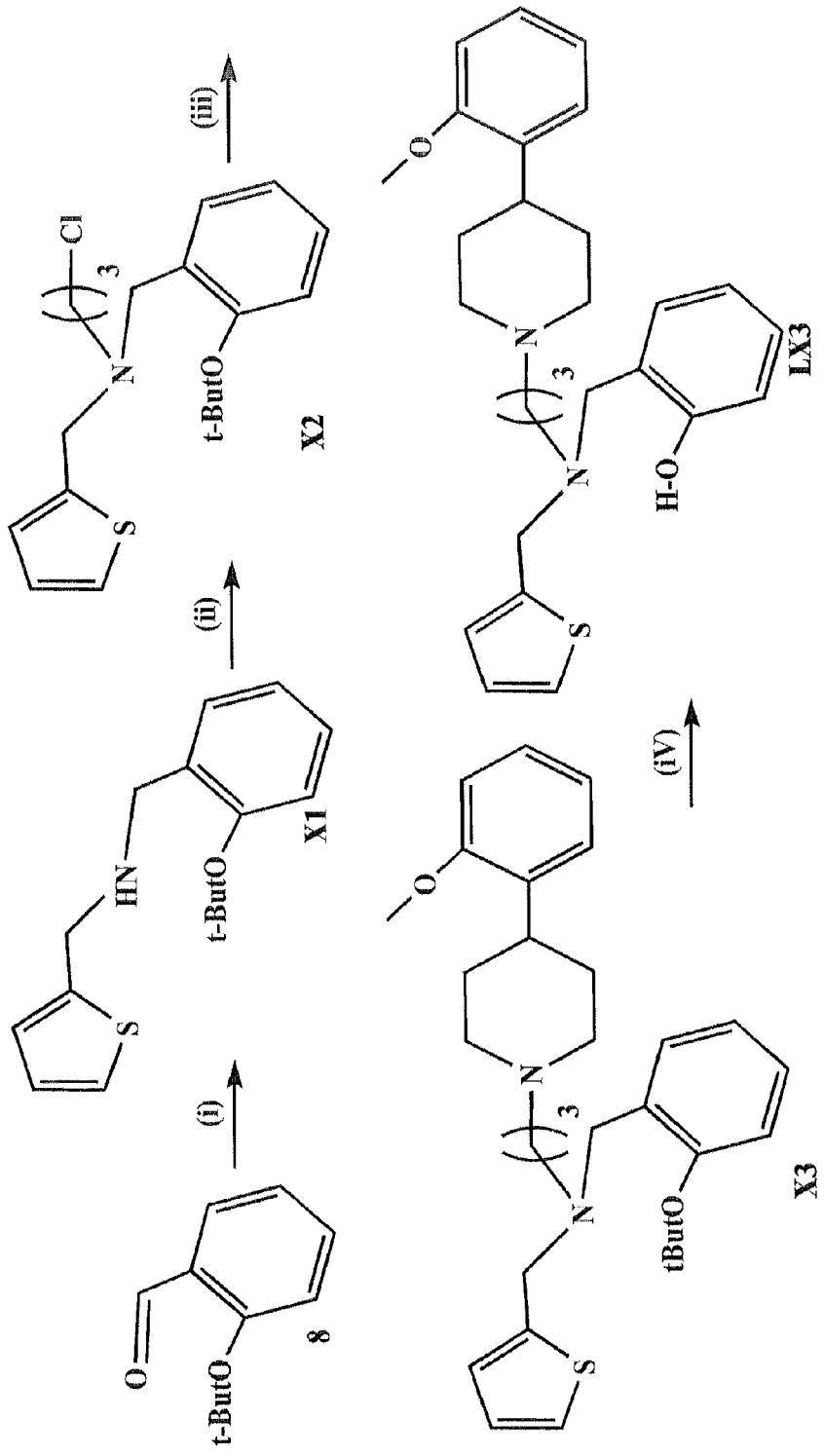
FIG. 2 is a scheme showing a synthesis of certain compounds and complexes of the invention.
Figure 2:
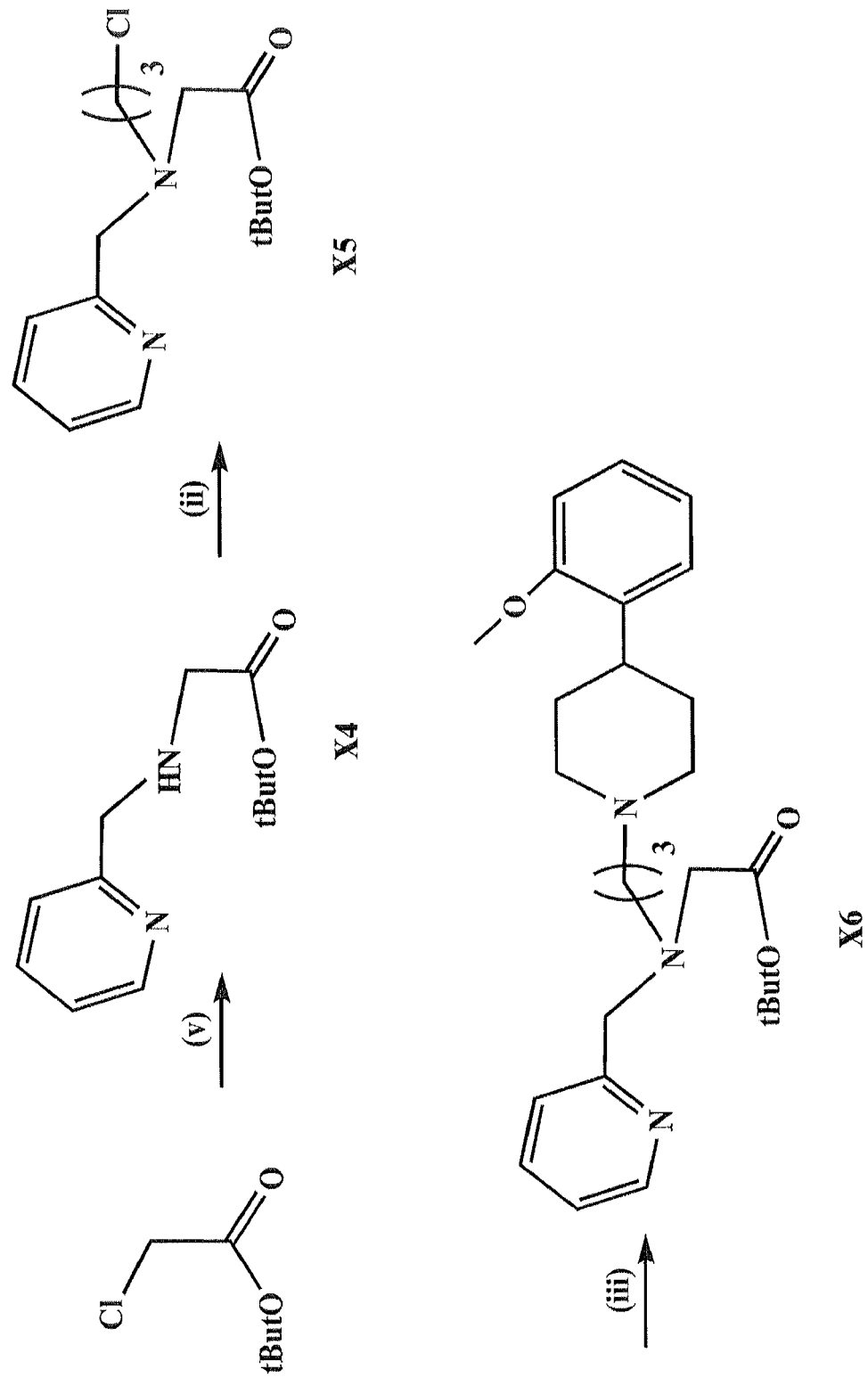
Figure 2:
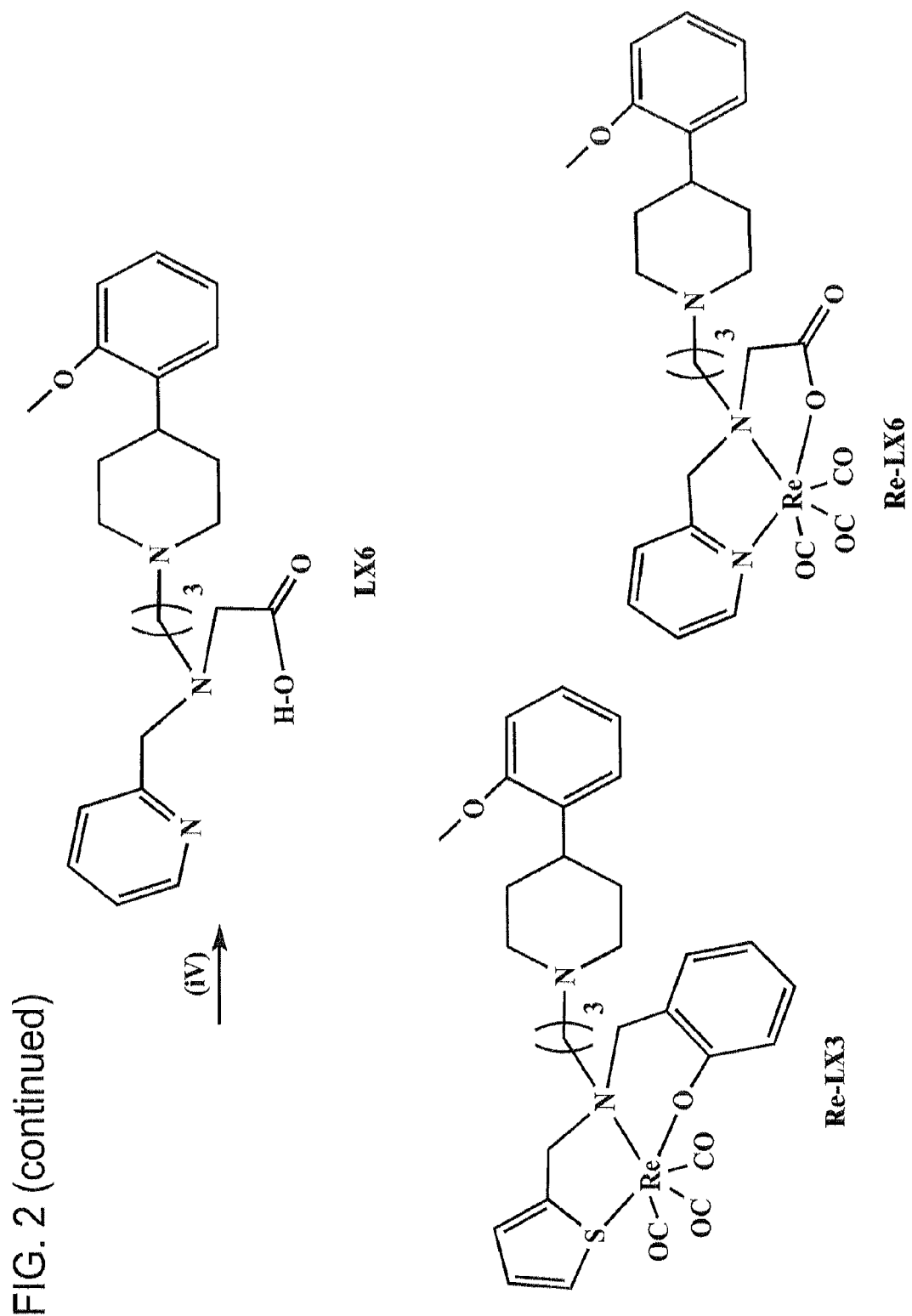

Additional compounds were prepared as described below (see also FIG. 2).

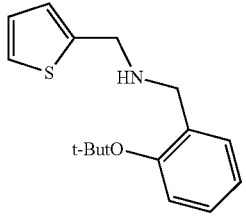

N-(2-(tert-butoxy)benzyl)-1-(thiophen-2-yl)methanamine [X1]

Compound [X1] was synthesized using procedures similar to that described for compound 9 using the starting material 8 (0.5 g, 2.8 mmol) and 2-(Aminomethyl)pyridine (0.5 g, 4.41 mmol). Purification was carried out on a silica gel preparative plate that was developed in with a 3% methanolic NH$_3$ (7 M NH$_3$ in methanol)/97% CH$_2$Cl$_2$. The product was isolated as pale yellow oil (68%). $^1$H NMR (CDCl$_3$) δ 7.303 (d, 1H, Ar), 7.212 (dd, 1H, Ar), 7.188 (t, 1H, Ar), 7.079 (d, 1H, Ar), 7.007 (t, 1H, Ar), 6.959 (m, 1H, Ar), 6.942 (m, 1H, Ar), 3.953 (s, 2H, —CH$_2$—), 3.858 (s, 2H, —CH$_2$—), 2.5 (s, 1H, —CH—), 1.423 (s, 9H, —C(CH$_3$)$_3$). Mass Spect. observed 276.14 (M+H)$^+$.

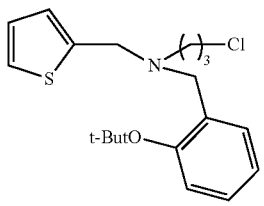

N-(2-(tert-butoxy)benzyl)-3-chloro-N-(thiophen-2-ylmethyl)propan-1-amine [X2]

Compound [X2] was synthesized using [X1] (0.53 g, 1.91 mmol), 1-bromo-3-chloropropane (9 g, 57 mmol) and K$_2$CO$_3$ (0.26 g, 1.91 mmol) following a procedure analogous to that described for 19. Purification was carried out on a silica gel preparative plate that was developed with 100% CH$_2$Cl$_2$. The product was isolated as pale yellow oil (97%). $^1$H NMR (CDCl$_3$) δ 7.683 (dd, 1H, Ar), 7.278 (m, 1H, Ar), 7.235 (ddd, 1H, Ar), 7.139 (m, 2H, Ar), 7.009 (m, 2H, Ar), 3.877 (s, 2H, —CH$_2$—), 3.788 (s, 2H, —CH$_2$—), 3.643 (m, 2H, —CH$_2$—), 2.693 (t, 2H, —CH$_2$—), 2.035 (p, 2H, —CH$_2$—), 1.477 (s, 9H, —C(CH$_3$)$_3$). Mass Spect. observed 352.15 (M+H)$^+$.

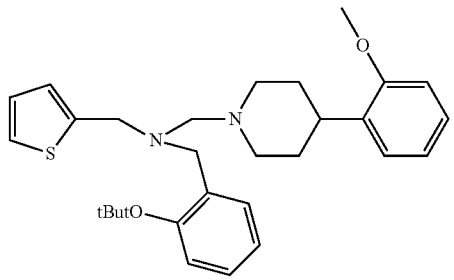

N-(2-(tert-butoxy)benzyl)-3-(4-(2-methoxyphenyl)piperidin-1-yl)-N-(thiophen-2-ylmethyl)propan-1-amine [X3]

Compound [X3] was synthesized using procedures similar to that described for compound 21, using 2-methoxy-4-phenylpiperidin (0.32 g, 1.67 mmol), compound [X2] (0.58 g, 1.64 mmol), KI (0.87 g, 5 mmol) and K$_2$CO$_3$ (1.15 g, 8.35 mmol). Purification was carried out on a silica gel preparative plate that was developed in with a 1% methanolic NH$_3$ (7 M NH$_3$ in methanol/99% CH$_2$Cl$_2$. The product was isolated as pale yellow oil (69%). $^1$H NMR (CDCl$_3$) δ 7.632 (dd, 1H, Ar), 7.210 (ddd, 2H, Ar), 7.177 (m, 1H, Ar), 7.136 (m, 1H, Ar), 7.056 (t, 1H, Ar), 7.024 (d, 1H, Ar), 6.927 (m. 3H, Ar), 6.854 (d, 1H, Ar), 3.821 (s, 3H, —OCH$_3$), 3.792 (s, 2H, —CH$_2$—), 3.678 (m, 2H, —CH$_2$—), 3.042 (d, 2H, —CH$_2$—), 2.957 (m, 1H, —CH—), 2.503 (t, 2H, —CH$_2$—), 2.414 (t, 2H, —CH$_2$—), 2.088 (t, 2H, —CH$_2$—), 1.791 (m, 6H), 1.377, (s, 9H, —C(CH$_3$)$_3$). Mass Spect. observed 507.31 (M+H)$^+$.

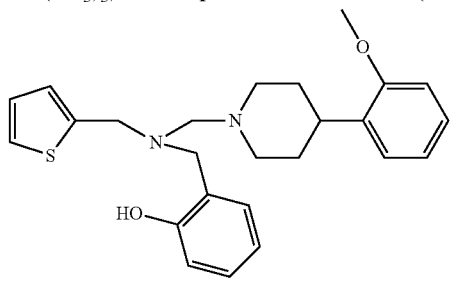

2-(((3-(4-(2-methoxyphenyl)piperidin-1-1)propyl)(thiophen-2-ylmethyl)amino)methyl)phenol [LX3]

Compound [LX3] was synthesized using procedures similar to that described for compound L21 using compound [X3] (0.29 g, 0.57 mmol). Purification was carried out on a silica gel preparative plate that was developed in with a 2% methanolic NH₃ (7 M NH₃ in methanol/98% CH₂Cl₂. The product was isolated as pale yellow oil (70%). ¹H NMR (CDCl₃) δ 7.277 (dd, 1H, Ar), 7.220 (dd, 1H, Ar), 7.192 (m, 2H, Ar), 7.015 (d, 1H, Ar), 6.991 (m, 1H, Ar), 6.961 (m, 1H, Ar), 6.936 (m. 1H, Ar), 6.868 (t, 2H, Ar), 6.813 (ddd, 1H, Ar), 3.917 (s, 2H, —CH₂—), 3.825 (s, 3H, —OCH₃), 3.816 (s, 2H, —CH₂—), 3.052 (d, 2H, —CH₂—), 2.978 (m, 1H, —CH—), 2.630 (t, 2H, —CH₂—), 2.417 (t, 2H, —CH₂—), 2.126 (t, 2H, —CH₂—), 1.892 (p, 2H, —CH₂—), 1.805 (m, 4H). Mass Spect. observed 449.22 (M–H)⁻.

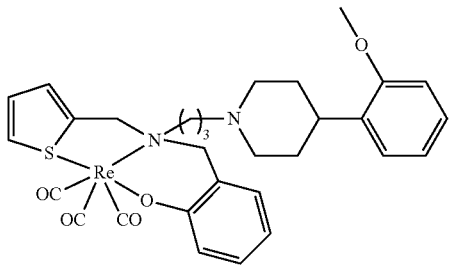

Re-LX3

The rhenium-tricarbonyl complex of LX3 was synthesized using the general procedure for the synthesis of Re(CO)₃ complexes.

Yield 26%. ¹H NMR (CDCl₃) δ 7.449 (m, 1H, Ar), 7.257-7.151 (m, 5H, Ar), 7.117 (m, 1H, Ar), 6.940 (m, 1H, Ar), 6.886 (m, 2H, Ar), 6.667 (m, 1H, Ar), 4.561 (m, 2H, —CH₂—), 3.934-3.814 (m, 5H), 3.730-3.557 (m, 4H), 3.284 (m, 1H), 3.170 (m, 2H), 3.110 (m, 1H, —CH₂—), 2.129 (m, 2H), 1.981 (m, 3H), 1.612 (m, 2H). Mass Spect. observed 721.18 (M+H)⁺.

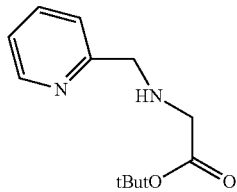

tert-butyl 2-((pyridin-2-ylmethyl)amino)acetate [X4]

tert-butyl 2-chloroacetate (0.83 g, 5.55 mmol) and 2-(Aminomethyl)pyridine (1.5 g, 8.32 mmol) were dissolved in 400 mL CH₃CN. To this solution was added potassium carbonate (0.76 g, 5.55 mmol) and the mixture was stirred at room temperature for two days. The crude product was obtained as an oil after removal of the solvent and was purified on a silica gel preparative plate that was developed in with a 2% methanolic NH₃ (7 M NH₃ in methanol/98% CH₂Cl₂. The product was isolated as pale yellow oil (57%). ¹H NMR (CDCl₃) δ 8.414 (dd, 1H, Ar), 7.499 (dd, 1H, Ar), 7.200 (d, 1H, Ar), 7.013 (m, 1H, Ar), 3.806 (s, 2H, —CH₂—), 3.242 (s, 2H, —CH₂—), 2.458 (s, 1H, —CH—), 1.333 (s, 9H, —C(CH₃)₃).

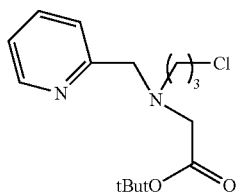

tert-butyl 2-((3-chloropropyl)(pyridin-2-ylmethyl) amino)acetate [X5]

Compound [X5] was synthesized using [X4] (0.9 g, 3.05 mmol), 1-bromo-3-chloropropane (14.4 g, 90 mmol) and K₂CO₃ (0.42 g, 3.06 mmol) following a procedure analogous to that described for 19. Purification was carried out on a silica gel preparative plate that was developed with 100% CH₂Cl₂ twice and several times with 1% methanolic NH₃ (7 M NH₃ in methanol)/99% CH. The product was isolated as pale yellow oil (52%). ¹H NMR (CDCl₃) δ 8.419 (dd, 1H, Ar), 7.553 (ddd, 1H, Ar), 7.400 (d, 1H, Ar), 7.049 (m, 1H, Ar), 3.829 (s, 2H, —CH₂—), 3.480 (t, 2H, —CH₂—), 3.202 (s, 2H, —CH₂—), 2.725 (t, 2H, —CH₂—), 1.808 (p, 2H, —CH₂—), 1.363 (s, 9H, —C(CH₃)₃).

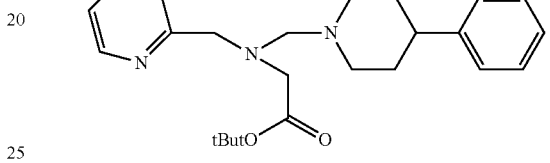

tert-butyl 2-((3-(4-(2-methoxyphenyl)piperidin-1-yl) propyl)(pyridin-2-ylmethyl)amino)acetate [X6]

Using procedures similar to that used for compound 21, [×6] was synthesized with 2-methoxy-4-phenylpiperidin (0.36 g, 1.90 mmol), compound [X5] (0.38 g, 1.27 mmol), KI (0.63 g, 3.8 mmol) and K₂CO₃ (0.876 g, 6.35 mmol). Purification was carried out on a silica gel preparative plate that was developed in with a 1% methanolic NH₃ (7 M NH₃ in methanol/99% CH₂Cl₂. The product was isolated as pale yellow oil (66%). ¹H NMR (CDCl₃) δ 8.521 (dd, 1H, Ar), 7.643 (ddd, 1H, Ar), 7.528 (d, 1H, Ar), 7.193-7.126 (m, 3H, Ar), 6.910 (t, 1H, Ar), 6.860 (d, 1H, Ar), 3.921 (s, 2H, —CH₂—), 3.906 (s, 3H, —OCH₃), 3.309 (s, 2H, —CH₂—), 3.039 (s(br), 2H, —CH₂—), 2.943 (m, 1H, —CH—), 2.696 (t, 2H, —CH₂—), 2.416 (s(br), 2H, —CH₂—), 2.088 (s(br), 2H, —CH₂—), 1.775 (m(br), 6H), 1.459 (s, 9H, —C(CH₃)₃).

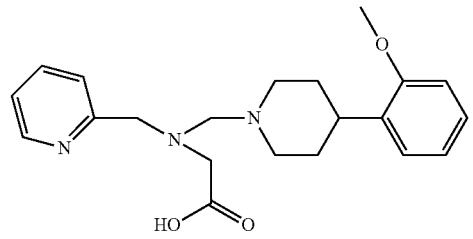 [SMILES: COc1ccccc1C1CCN(CN(CC(=O)O)Cc2ccccn2)CC1]

2-((3-(4-(2-methoxyphenyl)piperidin-1-yl)propyl) (pyridin-2-ylmethyl)amino)acetic acid [LX6]

The procedure similar to that used for compound L21 was applied to compound [X6] (0.114 g, 0.25 mmol). Purification was carried out on a silica gel TLC plate that was developed in with a 2% methanolic NH₃ (7 M NH₃ in methanol/98% CH₂Cl₂. The product was isolated as dark yellow oil (80%). ¹H NMR (CDCl₃) δ 8.397 (d, 1H, Ar), 7.524 (t, 1H, Ar), 7.198 (d, 1H, Ar), 7.105 (m, 2H, Ar), 7.048 (m, 1H, Ar), 6.823 (t, 1H, Ar), 6.766 (d, 1H, Ar), 3.775 (s, 2H, —CH₂—), 3.728 (s, 3H, —OCH₃), 3.603 (s, 2H, —CH₂—), 3.040-3.073 (overlapped m, 3H), 3.023 (t, 2H, —CH$_2$—), 2.687 (t, 2H, —CH$_2$—), 2.598 (t, 2H, —CH$_2$—), 2.106 (q, 2H, —CH$_2$—), 1.862 (s(br), 2H), 1.797 (d, 2H, —CH$_2$—).

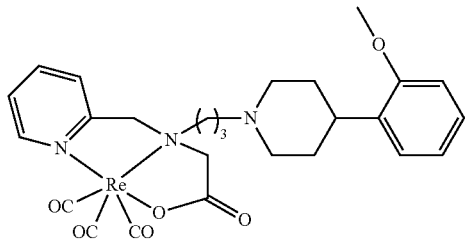

Re-LX6

The rhenium-tricarbonyl complex of LX6 was synthesized using the general procedure for the synthesis of Re(CO)$_3$ complexes.

Yield 60%. $^1$H NMR (CDCl$_3$) δ 8.774 (d, 1H, Ar), 7.901 (ddd, 1H, Ar), 7.519 (d, 1H, Ar), 7.372 (t, 1H, Ar), 7.195-7.155 (m, 2H, Ar), 6.916 (t, 1H, Ar), 6.845 (d, 1H, Ar), 4.508 (d, 1H, —CH—), 4.357 (d, 1H, —CH—), 3.808 (s, 3H, —OCH$_3$), 3.670 (d, 1H, —CH—), 3.574 (m, 2H, —CH$_2$—), 3.402 (d, 1H, —CH—), 3.064 (d, 2H, —CH$_2$—), 2.972 (m, 1H, —CH—), 2.220 (m, 2H, —CH$_2$—), 2.079-1.974 (overlapped m, 2H), 1.836-1.743 (overlapped m, 4H).

Example 49

Iso-[$^{99m}$TcOAADT]-(CH$_2$)$_2$-NEt$_2$) was synthesized, and tested in vivo for melanoma. Structurally analogous nonradioactive oxorhenium(V) complex was also synthesized and characterized. In vivo evaluation of the complex in the C57B1/B16 mouse melanoma model demonstrated significant tumor localization. The complex displayed an in vivo tumor uptake of 9.61% ID/g at 1 h after administration, 8.19 ID/g at 3 h after administration, and 7.37 ID/g at 6 h after administration. This tumor uptake and retention is superior to that observed for [$^{99m}$TcOAADT]-(CH$_2$)$_2$—N(Et$_2$), in which there is significant washout from the tumor over time. With the Iso-[$^{99m}$TcOAADT]-(CH$_2$)$_2$-NEt$_2$) faster washout is observed from the non-target organs such as liver, lungs, spleen relative to the tumor and hence better contrast rations (tumor/non-tumor) is observed over time.

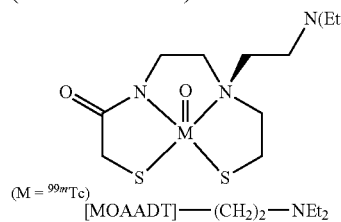

(M = $^{99m}$Tc)
[MOAADT]—(CH$_2$)$_2$—NEt$_2$

Experimental Section

General. All Chemicals and reagents were purchased from commercial sources. and were used as received. $^1$H NMR spectra were collected on a Bruker spectrometer. Mass spectra were obtained on MicroMass LCZ electrospray LC-MS instrument. The high-performance liquid chromatography (HPLC) method used a Water Millennium Chromatography System equipped with a 996 UV-Vis diode-array detector attached in series to a γ-detector consisting of a shielded photomultiplier powered by a Canberra voltage amplifier and connected to a ratemeter. A reverse-phase C8 column equipped with a C18 guard was eluted with methanol (solvent A) and 2 mmol/L PBS, pH 7.4 (solvent B, Gibco Life Technologies) using a 60-minute linear gradient from 15:85 (A/B) to 95:5 (A/B) at a 1.0 mL/min flow rate.

Experimental Procedures:

Synthesis of Iso-AADT ([2-(tritylthio)-N-(2-(2-(tritylthio)ethylamino)ethyl)acetamide]) (Compound 26)

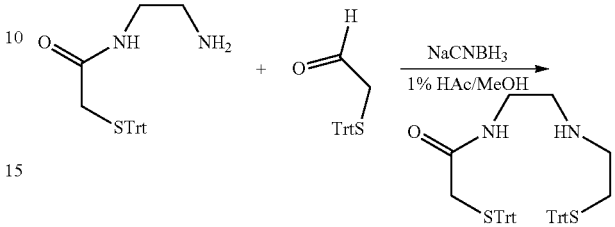

To the solution of 2-(tritylthio)acetaldehyde[8] (4.0 g, 12.5 mmol) and N-(2-aminoethyl)-2-(S-tritylmercapto)acetamide[9] (4.5 g, 12.5 mmol) in 1% HAc/MeOH (200 mL) was slowly added NaCNBH$_3$ (2.25 g, 36 mmol). The mixture was stirred overnight at rt. Solvent was then removed under reduced pressure to give crude product which was purified by flash chromatography (ammonia/methanol (7 M):methylene chloride=2.5:100) as an off-white solid (2.0 g, 23%): $^1$H NMR (CDCl$_3$) δ 2.34 (t, 2H, J=6.6 Hz), 2.40 (t, 2H, J=6.6 Hz), 2.43 (t, 2H, J=6.6 Hz), 2.96 (q, 2H, J=6.0 Hz), 3.07 (s, 2H), 6.33 (t, 1H, J=4.8 Hz), 7.14-7.22 (m, 6H), 7.23-7.30 (m, 12H), 7.36-7.42 (m, 12H). MS, m/z (M+H)$^+$=679.28

Synthesis of Iso-AADT-(CH$_2$)$_2$-NEt$_2$ ([N-(2-((2-(diethylamino)ethyl)(2-(tritylthio)ethyl)amino)ethyl)-2-(tritylthio)acetamide]) (compound 27)

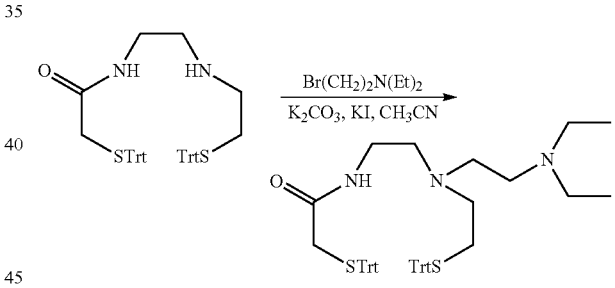

Iso-AADT (26) (200 mg, 0.29 mmol), 2-bromo-N,N-diethylethylamine hydrobromide (75 mg, 0.29 mmol), K$_2$CO$_3$ (135 mg, 0.98 mmol) were mixed in CH$_3$CN (100 mL). The mixture was refluxing overnight. The solvent was evaporated, and the residue was purified on Silica gel column (2.5% NH$_3$.MeOH/CH$_2$Cl$_2$) to yield desired product as a white solid (146 mg, 65% yield): $^1$H NMR (CDCl$_3$) δ 0.94 (t, 6H, J=7.2 Hz), 2.25 (t, 2H, J=6.6 Hz), 2.29 (t, 2H, J=6.6 Hz), 2.33-2.46 (m, 10H), 2.97 (s, 2H), 2.99 (q, 2H, J=6.0 Hz), 6.83 (t, 1H, J=4.8 Hz), 7.14-7.23 (m, 6H), 7.23-7.30 (m, 12H), 7.36-7.43 (m, 12H). MS, m/z (M+H)$^+$=778.38.

Procedure for Rhenium Complexation Compound (Re-27)

Iso-AADT-(CH$_2$)$_2$-NEt$_2$ (Compound 27) (0.13 mmol) was mixed with TFA (15 mL), the resulting yellow solution was stirred for 5 min, and then titrated with triethylsilyl hydride until colorless. The solution was evaporated and the residue was placed under high vacuum until completely dry.

The deprotected compound was dissolved in argon-saturated EtOH (10 mL), Salicylic acid, sodium salt (SA) in H$_2$O (2 mL) and NaReO$_4$ in H$_2$O (2 mL) were added into the solution, and then additional EtOH (30 mL) was added into the mixture. SnCl$_2$ (50.3 mg, 0.266 mmol) was added into the solution with stirring. The solution began to turn brownish purple. The pH of the reaction was adjusted to 4.5-5.0, and the mixture was heated at 75° C. (water bath) for 4 h. The solution was allowed to cooled to rt, and stirred overnight. Solvent was evaporated. The residue was purified by silica gel column (4% NH$_3$.MeOH/CH$_2$Cl$_2$) as purple solid (77%): $^1$H NMR (CDCl$_3$) δ 1.09 (t, 6H, J=7.2 Hz), 2.23 (dt, 1H, J=5.4 and 12.0 Hz), 2.60-2.70 (m, 5H), 2.97 (s, 2H), 3.36-3.44 (m, 1H), 3.46-3.54 (m, 1H), 3.56-3.62 (m, 1H), 3.84-3.96 (m, 3H), 3.93 (X of AX, 1H, J=16.8 Hz), 4.00-4.05 (m, 1H), 4.24-4.30 (m, 1H), 4.66 (A of AX, 1H, J=16.8 Hz). MS, m/z (M+H)$^+$= 494.09.

Procedure for $^{99m}$Tc Labeling.

Iso-AADT-(CH$_2$)$_2$-NEt$_2$ (Compound 27) (5.0 mg) was mixed with TFA (10 mL), the resulting yellow solution was stirred for 5 min, and then titrated with triethylsilylhydride until colorless. The solution was evaporated and the residue was placed under high vacuum until completely dry. The dry residue was later redissolved in argon-saturated methanol and distributed into 10 vials that were dried and kept under vacuum for later preparation of the technetium-99m-labeled compound. 100 μL solution from 10 mg SA in 1 mL of argon-saturated water was mixed with $^{99m}$Tc activity (25-30 mCi). To the solution was added 20 μL of 1 mg SnAc$_2$ in 1 mL of argon-saturated water, and after sitting at water bath (75° C.) for 1 min, the solution was added into one vial which contained 0.5 mg of the above thiol-deprotected ligand, and the reaction was heated at 75° C. for 30 min.

Results and Discussion

Chemistry

Synthesis of Iso-AADT-(CH$_2$)$_2$NEt$_2$ (27) Reductive alkylation reaction of 2-(tritylthio)acetaldehyde with N-(2-aminoethyl)-2-(S-tritylmercapto)acetamide in 1% HAc/MeOH solution afforded the desired product in 59% yield as outlined in Scheme 1. 2-(tritylthio)acetaldehyde was carried out as published method, via a hydroxamate intermediate (8). N-(2-aminoethyl)-2-(S-tritylmercapto)acetamide was synthesized as described in literature (9).

Scheme 1: Synthesis of Rhenium and $^{99m}$Technetium Iso-AADT-(CH$_2$)$_2$—N(Et)$_2$ complexes

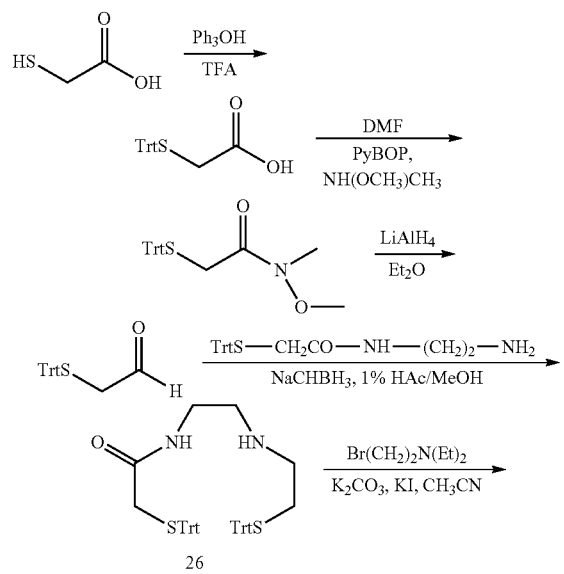

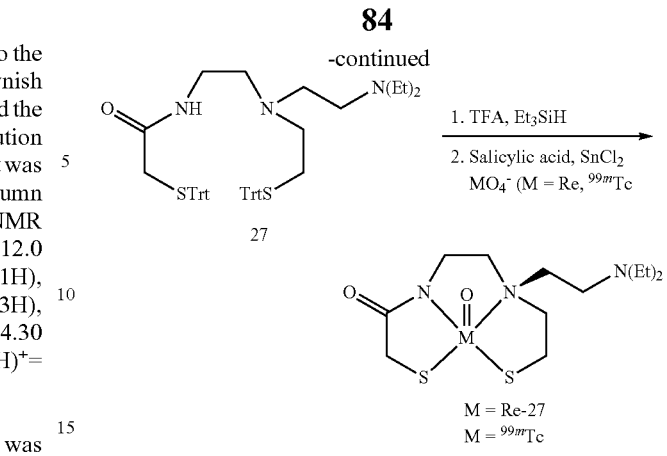

In Vivo Tumor Uptake

To study the tumor uptake of Iso-[$^{99m}$TcOAADT]-(CH$_2$)$_2$-NEt$_2$) ($^{99m}$Tc-27), in vivo, biodistribution experiments at 1 and 6 hours after their administration were carried out in C57B16 mice with B16 melanoma nodules. The biodistribution data including melanoma/nontumor (M/NT) ratios for selected organs, summarized in Table 1 as percentage injected dose per gram (% ID/g)

Complex $^{99m}$Tc-27 displays tumor uptake (9.61% ID/g) and melanoma/blood (14.71), melanoma/spleen (3.65), melanoma/lung (1.43) and melanoma/liver (0.75) ratios at 1 hour after administration, and tumor uptake (7.05% ID/g) and melanoma/blood (47.25), melanoma/spleen (13.99), melanoma/lung (5.87) and melanoma/liver (2.00) ratios at 6 hour after administration (Table 1).

TABLE 1

Biodistribution and Tumor/Nontumor Ratios of Complexes [TcOAADT]-C$_2$—N(Et)$_2$ and [TcO(isoAADT)]-C$_2$—N(Et)$_2$ at 1 and 6 h Postinjection

| organ | [TcOAADT]-C2—N(Et)2 | | [TcO(isoAADT)]-C2—N(Et)2 ($^{99m}$Tc-27) | |
|---|---|---|---|---|
| | 1 h | 6 h | 1 h | 6 h |
| eyes | | | 15.42 ± 2.07 | 11.09 ± 0.84 |
| blood | 1.00 ± 0.46 | 0.32 ± 0.19 | 1.05 ± 0.19 | 0.25 ± 0.02 |
| heart | 0.82 ± 0.37 | 0.11 ± 0.02 | 1.34 ± 0.18 | 0.18 ± 0.02 |
| lung | 1.40 ± 0.49 | 0.47 ± 0.21 | 6.75 ± 0.57 | 1.39 ± 0.41 |
| spleen | 1.83 ± 0.55 | 0.34 ± 0.10 | 3.00 ± 1.45 | 0.78 ± 0.85 |
| liver | 12.7 ± 1.54 | 4.08 ± 0.92 | 12.62 ± 1.80 | 3.69 ± 0.48 |
| kidney | 5.53 ± 0.81 | 1.98 ± 0.21 | 5.33 ± 1.10 | 1.11 ± 0.13 |
| muscle | 0.35 ± 0.21 | 0.08 ± 0.01 | 0.94 ± 0.14 | 0.07 ± 0.01 |
| brain | 0.30 ± 0.10 | 0.05 ± 0.02 | 0.24 ± 0.04 | 0.05 ± 0.01 |
| melanoma | 7.62 ± 0.62 | 3.45 ± 1.2 | 9.61 ± 1.02 | 7.05 ± 1.23 |
| mel/blood | 7.6 ± 0.54 | 10.8 ± 1.00 | 14.71 ± 2.40 | 47.25 ± 7.32 |
| mel/spleen | 4.2 ± 0.58 | 10.1 ± 1.11 | 3.65 ± 1.19 | 13.99 ± 5.17 |
| mel/lung | 5.4 ± 0.60 | 7.3 ± 0.98 | 1.43 ± 0.15 | 5.87 ± 1.79 |
| mel/liver | 0.6 ± 0.09 | 0.9 ± 0.35 | 0.75 ± 0.11 | 2.00 ± 0.23 |

REFERENCES (1) Goldstein, B. G.; Goldstein, A. O. Diagnosis and Management of Malignat Melanoma. American Family Physician 2001, 63(7), 1359-1369.

(2) American Cancer Society, Cancer Facts & Figures 2004

(3) Giblin, M. F.; Jurisson, S. S.; Quinn, T. P. Synthesis and Characterization of Rhenium-complexed α-Melanotropin Analogs. Bioconjugate Chem. 1997, 8, 347-353.

(4) Chem, J. Q.; Cheng, Z.; Hoffman, T. J.; Jurisson, S. S.; Quinn, T. P. Melanoma-Targeting Properties of $^{99m}$Technetium-Labeled Cyclic α-Melanocyte-Stimulationg Hormone Peptide Analogues. Cancer Res. 2000, 60, 5649-5658.

(5) Rigel, D. S.; Carucci, J. A. Malignant Melanoma: Prevention, Early Detection, and Treatment in 21st Century. Ca Cancer J. Clin. 2000, 50, 215-236.

(6) Friebe, M.; Mahmood, A.; Bolzati, C.; Drews, A.; Johannsen, B.; Eisenhut, M.; Kraemer, D.; Davison, A.; Jones, A. G. [99mTc]Oxotechnetium(V) Complexes of Amine-Amide-Dithiol Chelates with Dialkyaminoalkyl substituents as Potential Diagnostic Probes for Malignant Melanoma. J. Med. Chem. 2001, 44, 3132-3140.

(7) Cheng, Z.; Mahmood, A.; Li, H.; Davison, A.; Jones, A. G. [99mTcOAADT]-(CH$_2$)$_2$-NEt$_2$: A potential Small-Molecule Single-Photon Emission Computed Tomography Probe for Imaging Metastatic Melanoma. Cancer Res 2005, 65, 4979-4986.

(8) Qvit, Nir; Reuveni, Hadas; Gazal, Sharon; Zundelevich, Adi; Blum, Galia; Niv, Masha Y.; Feldstein, Alexandra; Meushar, Sharon; Shalev, Deborah E.; Friedler, Assaf; Gilon, Chaim. J. Combinatorial Chem. 2008, 10(2), 256-266.

(9) Lipowska, Malgorzata; Hansen, Lory; Xu, Xiaolong; Marzilli, Patricia A.; Taylor, Andrew, Jr.; Marzilli, Luigi G. Inorg. Chem. 2002, 41 (11), 3032-3041.

Example 50

Diagnostic Probes for σ1, σ2, 5-HT$_{1A}$ and D$_2$ Receptors

Introduction

Sigma receptor was first discovered in 1976, there are overexpression of sigma receptors in human tumors such as melanoma, breast cancer, small lung carcinoma and prostate cancer. The number of sigma receptors in tumors ranges between 200,000 and a million receptors per cell. So sigma receptors are appropriate targets for developing tumor imaging agents.

Serotomin1A (5-HT$_{1A}$) and dopamine D2 receptors belong to a large family of GPCR receptors and have been implicated in the various neuro-pathophysiologies of mood and anxiety disorders, depression, sexual dysfunction, eating disorders, neurodegenerative diseases. The receptors have high concentration in the brain and are an attractive target for quantification imaging in vivo using PET or SPECT.

We have synthesized and characterized various iso-AADT-(CH$_2$)$_n$—NR$_1$R$_2$ ligands and their Rhenium Complexes and have determined their affinity towards sigma receptors, 5-HT$_{1A}$ receptors and D2 receptors.

Scheme 2. Synthesis of Re complexes of iso-AADT-(CH$_2$)$_n$—NR$_1$R$_2$

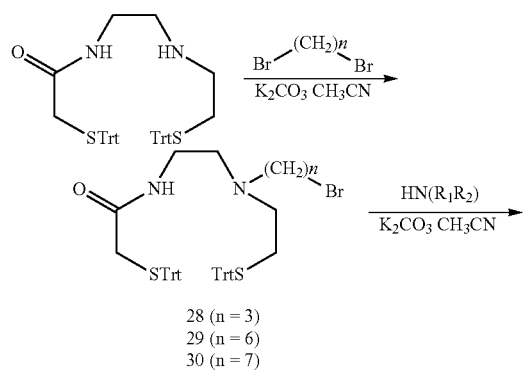

28 (n = 3)
29 (n = 6)
30 (n = 7)

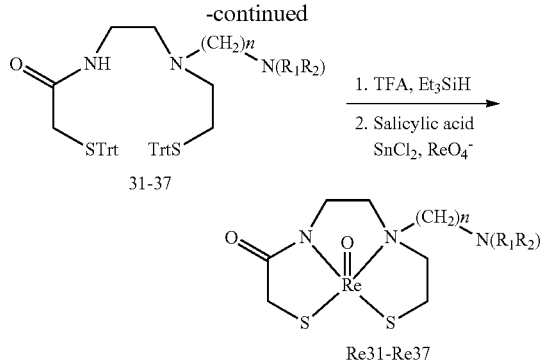

Re31-Re37

General Procedure for 31-37.

To a solution of compound 28, 29 or 30 (0.25 mmol), and K$_2$CO$_3$ (0.30 mmol) in CH$_3$CN (20 mL) was added a secondary amine (0.25 mmol). The mixture was refluxing overnight. The solvent was evaporated, and the residue was purified on Silica gel column to yield desired product.

Compound 31:

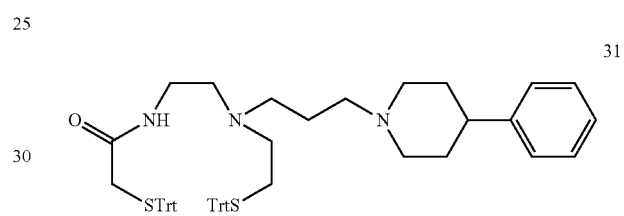

yield 70%: $^1$H NMR (CDCl$_3$) δ 1.61-1.71 (m, 2H), 1.73-1.81 (m, 2H), 1.86-1.96 (m, 2H), 2.00-2.13 (m, 2H), 2.20-2.38 (m, 8H), 2.40-2.53 (m, 3H), 2.92-3.00 (m, 2H), 3.03 (s, 2H), 3.00-3.15 (m, 2H), 6.46 (t, 1H, J=4.8 Hz), 7.15-7.35 (m, 23H), 7.36-7.46 (m, 12H). MS, m/z (M+H)$^+$=880.43

Compound 32:

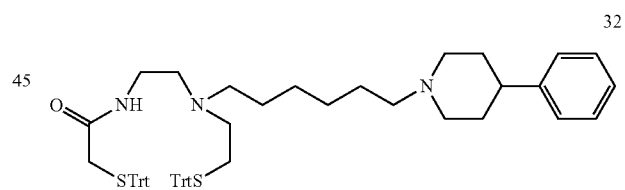

yield 66%: $^1$H NMR (CDCl$_3$) δ 1.19-1.33 (m, 6H), 1.56-1.68 (m, 2H), 1.84-1.91 (m, 2H), 2.18-2.30 (m, 8H), 2.31-2.36 (m, 2H), 2.48-2.60 (m, 3H), 2.93-2.98 (m, 2H), 2.99 (s, 2H), 3.14-3.28 (m, 2H), 6.46 (t, 1H, J=4.8 Hz), 7.36-7.47 (m, 23H), 7.37-7.47 (m, 12H). MS, m/z (M+H)$^+$=921.47

Compound 33:

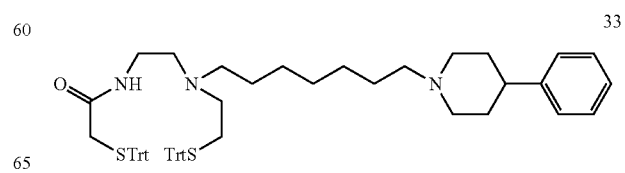

yield 70%: ¹H NMR (CDCl₃) δ 1.16-1.31 (m, 8H), 1.65-1.75 (m, 2H), 1.88-1.95 (m, 2H), 2.16-2.26 (m, 8H), 2.28-2.33 (m, 2H), 2.32-2.45 (m, 2H), 2.56-2.65 (m, 3H), 2.90-2.96 (m, 2H), 2.98 (s, 2H), 3.25-3.35 (m, 2H), 6.46 (t, 1H, J=4.8 Hz), 7.15-7.33 (m, 23H), 7.34-7.42 (m, 12H). MS, m/z (M+H)⁺=935.48.

Compound 34:

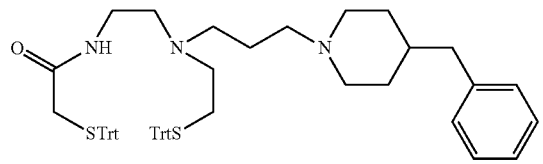

34 yield 66%: ¹H NMR (CDCl₃) δ 1.45-1.51 (m, 1H), 1.50-1.57 (m, 2H), 1.57-1.73 (m, 2H), 1.73-1.86 (m, 2H), 2.20-2.33 (m, 8H), 2.54 (d, 2H, J=7.2 Hz)), 2.62-2.74 (m, 1H), 2.90-2.96 (m, 2H), 3.03 (s, 2H), 3.08-3.20 (m, 2H), 6.40 (s, 2H, J=5.4 Hz), 7.12-7.30 (m, 23H), 7.30-7.40 (m, 12H). MS, m/z (M+H)⁺=894.44.

Compound 35:

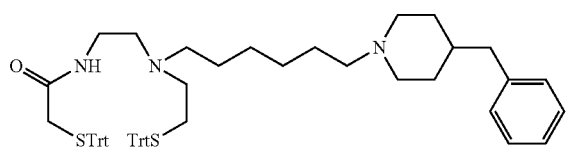

35 yield 68%: ¹H NMR (CDCl₃) δ 1.19-1.30 (m, 6H), 1.50-1.66 (m, 5H), 1.64-1.70 (m, 2H), 1.96-2.10 (m, 2H), 2.15-2.25 (m, 6H), 2.28-2.33 (m, 2H), 3.37-3.46 (m, 2H), 2.54-2.58 (m, 2H), 2.90-2.95 (m, 2H), 2.98 (s, 2H), 2.98-3.08 (m, 2H), 6.46 (t, 1H, J=4.8 Hz), 7.12-7.31 (m, 23H), 7.32-7.41 (m, 12H). MS, m/z (M+H)⁺=935.48.

Compound 36:

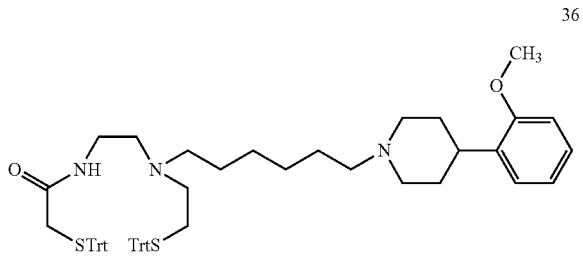

36 yield 69%: ¹H NMR (CDCl₃) δ 1.23-1.33 (m, 5H), 1.53-1.57 (m, 1H), 1.57-1.64 (m, 3H), 1.81-1.87 (m, 2H), 2.01-2.08 (m, 2H), 2.17-2.37 (m, 8H), 2.49-2.57 (m, 2H), 2.57-2.63 (m, 1H), 2.90-2.97 (m, 2H), 2.99 (s, 2H), 2.99-3.10 (m, 1H), 3.11-3.22 (m, 1H), 3.22 (d, 2H, J=10.8 Hz), 3.81 (s, 3H), 6.49 (t, 1H, J=4.8 Hz), 6.86 (d, 1H, J=7.8 Hz), 6.93 (t, 1H, J=7.8 Hz), 7.16-7.7.30 (m, 20H), 7.31-7.43 (m, 12H). MS, m/z (M+H)⁺=951.48.

Compound 37:

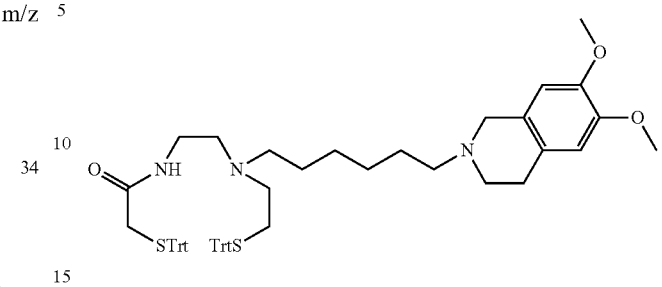

37 yield 75%: ¹H NMR (CDCl₃) δ 1.20-1.31 (m, 6H), 1.60-1.68 (m, 2H), 2.10-2.28 (m, 6H), 2.28-2.33 (m, 2H), 2.57-2.63 (m, 2H), 2.82-2.98 (m, 6H), 2.98 (s, 2H), 3.64-3.71 (m, 2H), 3.80 (s, 3H), 3.83 (s, 3H), 6.45-6.48 (m, 1H), 6.49 (s, 1H), 6.59 (s, 1H), 7.14-7.34 (m, 19H), 7.35-7.42 (m, 12H). MS, m/z (M+H)⁺=953.46.

Synthesis of 28

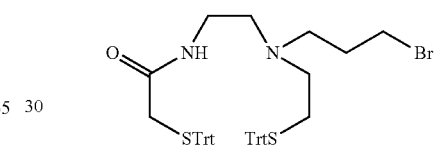

28

To a solution of iso-AADT (197 mg, 0.29 mmol), and K₂CO₃ (42 mg, 0.30 mmol) in CH₃CN (20 mL) was added 1,3-dibromopropane (1.8 g, 9.0 mmol). The mixture was stirred for two days at rt. The solvent was evaporated, and the residue was purified on Silica gel column (2.0% NH₃.MeOH/CH₂Cl₂) to yield desired product as a white solid (151 mg, 65% yield): ¹H NMR (CDCl₃) δ 1.76-1.80 (m, 2H), 2.26 (t, 2H, J=6.0 Hz), 2.30 (s, 4H), 2.38 (t, 2H, J=6.0 Hz), 2.97-3.02 (m, 2H), 3.04 (s, 2H), 3.67 (t, 2H, J=6.0 Hz), 6.49-6.51 (m, 1H), 7.17-7.30 (m, 18H), 7.36-7.45 (m, 12H). MS, m/z (M+H)⁺=799.23.

Synthesis of 29

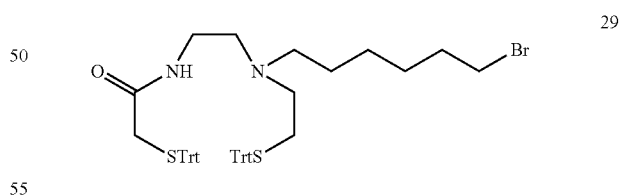

29

To a solution of iso-AADT (300 mg, 0.44 mmol), and K₂CO₃ (69 mg, 0.50 mmol) in CH₃CN (30 mL) was added 1,6-dibromohexane (3.23 g, 13.2 mmol). The mixture was stirred for two days at rt. The solvent was evaporated, and the residue was purified on Silica gel column (2.0% NH₃.MeOH/CH₂Cl₂) to yield desired product as a white solid (260 mg, 70% yield): ¹H NMR (CDCl₃) δ 1.20-1.27 (m, 2H), 1.27-1.34 (m, 2H), 1.34-1.40 (m, 2H), 1.75-1.84 (m, 2H), 2.19-2.30 (m, 6H), 2.34-2.37 (m, 2H), 2.93-3.00 (m, 2H), 3.03 (s, 2H), 3.36 (t, 2H, J=6.6 Hz), 6.52 (bs, 1H), 7.18-7.31 (m, 18H), 7.39-7.45 (m, 12H). MS, m/z (M+H)⁺=841.28.

Synthesis of 30

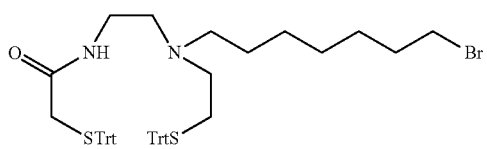

To a solution of iso-AADT (250 mg, 0.37 mmol), and K$_2$CO$_3$ (55 mg, 0.40 mmol) in CH$_3$CN (20 mL) was added 1,3-dibromoheptane (2.8 g, 11.0 mmol). The mixture was stirred for two days at rt. The solvent was evaporated, and the residue was purified on Silica gel column (2.0% NH$_3$.MeOH/CH$_2$Cl$_2$) to yield desired product as a white solid (164 mg, 52% yield): $^1$H NMR (CDCl$_3$) δ 1.15-1.26 (m, 4H), 1.26-1.42 (m, 2H), 1.42-1.50 (m, 2H), 1.54-1.60 (m, 2H), 2.26-2.33 (m, 4H), 2.92-3.01 (m, 2H), 6.50 (bs, 1H), 7.15-7.30 (m, 18H), 7.36-7.43 (m, 12H). MS, m/z (M+H)$^+$=855.30.

General Procedure for Rhenium Complexation.

Re-31-Re-37 (0.10 mmol) was mixed with TFA (15 mL), the resulting yellow solution was stirred for 5 min, and then titrated with triethylsilyl hydride until colorless. The solution was evaporated and the residue was placed under high vacuum until completely dry. The deprotected compound was dissolved in argon-saturated EtOH (10 mL), Salicylic acid, sodium salt (SA) in H$_2$O (2 mL) and NaReO$_4$ in H$_2$O (2 mL) were added into the solution, and then additional EtOH (30 mL) was added into the mixture. SnCl$_2$ (50.3 mg, 0.266 mmol) was added into the solution with stirring. The solution began to turn brownish purple. The pH of the reaction was adjusted to 4.5-5.0, and the mixture was heated at 75° C. (water bath) for 4 h. The solution was allowed to cooled to rt, and stirred overnight. Solvent was evaporated. The residue was purified by silica gel column (3% NH$_3$.MeOH/CH$_2$Cl$_2$) to yield desired product.

Re-31:

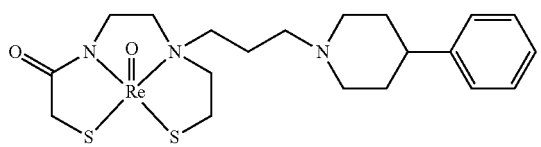

yield 50%: $^1$H NMR (CDCl$_3$) δ 1.93-1.99 (m, 2H), 2.01-2.14 (m, 2H), 2.18-2.27 (m, 1H), 2.28-2.42 (m, 2H), 2.42-2.58 (m, 2H), 2.62-2.70 (m, 2H), 2.71-2.82 (m, 2H), 3.28-3.38 (m, 2H), 3.36-3.43 (m, 2H), 3.51-3.58 (m, 1H), 3.64-3.71 (m, 1H), 3.80-3.93 (m, 2H), 3.93 (X of AX, 1H, J=16.8 Hz), 4.02-4.10 (m, 1H), 4.23-4.29 (m, 1H), 4.66 (A of AX, 1H, J=16.8 Hz), 7.18-7.35 (m, 5H). MS, m/z (M+H)$^+$= 595.13.

Re-32:

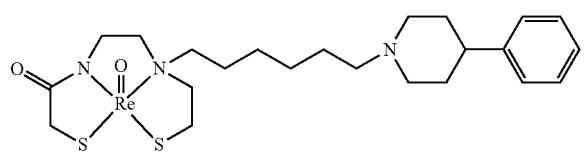

yield 70%: $^1$H NMR (CDCl$_3$) δ 1.40-1.52 (m, 4H), 1.86-2.03 (m, 6H), 2.15-2.22 (m, 1H), 2.30-2.49 (m, 2H), 2.62-2.78 (m, 4H), 2.84-2.92 (m, 2H), 3.49-3.53 (m, 2H), 3.53-3.58 (m, 3H), 3.67-3.76 (m, 3H), 3.91 (X of AX, 1H, J=16.8 Hz), 3.95-4.05 (m, 1H), 4.20-4.27 (m, 1H), 4.64 (A of AX, 1H, J=16.8 Hz), 7.20-7.33 (m, 5H). MS, m/z (M+H)$^+$= 638.18.

Re-33:

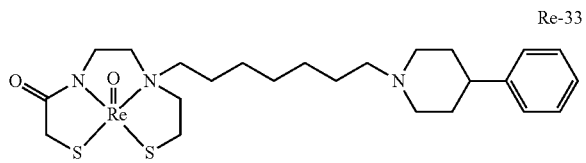

yield 77%: $^1$H NMR (CDCl$_3$) δ 1.32-1.46 (m, 6H), 1.62-1.70 (m, 2H), 1.86-1.84 (m, 4H), 1.84-2.04 (m, 2H), 2.14-2.28 (m, 3H), 2.51-2.61 (m, 3H), 2.61-2.68 (m, 1H), 3.20-3.23 (m, 2H), 3.32-3.42 (m, 2H), 3.43-3.50 (m, 1H), 3.61-3.66 (m, 1H), 3.67-3.78 (m, 2H), 3.94 (X of AX, 1H, J=16.8 Hz), 3.99-4.05 (m, 1H), 4.21-4.27 (m, 1H), 4.66 (A of AX, 1H, J=16.8 Hz), 7.18-7.30 (m, 5H). MS, m/z (M+H)$^+$= 652.20.

Re-34:

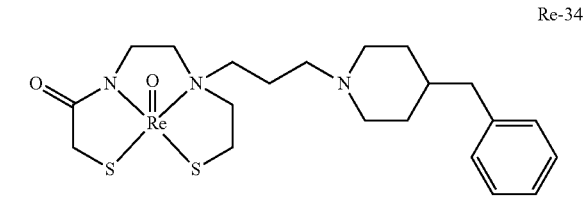

yield 73%: $^1$H NMR (CDCl$_3$) δ 1.53-1.76 (m, 3H), 1.76-1.81 (m, 2H), 2.17-2.25 (m, 1H), 2.25-2.45 (m, 4H), 2.58 (d, 2H, J=6.0 Hz), 2.60-2.68 (m, 1H), 2.68-2.80 (m, 2H), 3.14-3.30 (m, 2H), 3.35-3.42 (m, 2H), 3.49-3.56 (m, 1H), 3.63-3.69 (m, 1H), 3.77-3.89 (m, 2H), 3.91 (X of AX, 1H, J=16.8 Hz), 4.00-4.08 (m, 1H), 4.22-4.28 (m, 1H), 4.65 (A of AX, 1H, J=16.8 Hz), 7.12 (d, 2H, J=7.2 Hz), 7.20 (t, 1H, J=7.2 Hz), 7.27 (dd, 2H, J=7.2, 6.0 Hz). MS, m/z (M+H)$^+$=652.20.

Re-35:

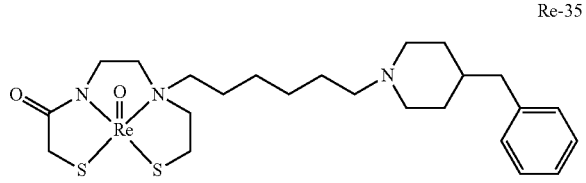

yield 69%: $^1$H NMR (CDCl$_3$) δ 1.33-1.44 (m, 6H), 1.53-1.58 (m, 2H), 1.64-1.69(m, 2H), 1.84-1.91 (m, 2H), 1.92-1.99 (m, 2H), 2.13-2.20 (m, 1H), 2.34-2.40 (m, 2H), 2.54 (d, 2H, J=7.2 Hz), 2.60-2.66 (m, 2H), 2.95-3.00 (m, 2H), 3.30-3.35 (m, 1H), 3.35-3.38 (m, 1H),3.42-3.48 (m, 1H), 3.58-3.64 (m, 1H), 3.70-3.75 (m, 2H), 3.94 (X of AX, 1H, J=16.8 Hz), 3.98-4.04 (m, 1H), 4.20-4.25 (m, 1H), 4.66 (A of AX, 1H, J=16.8 Hz), 7.11-7.14 (m, 2H), 7.16-7.20 (m, 1H), 7.22-7.28 (m, 2H). MS, m/z (M+H)$^+$=636.20.

Re-36:

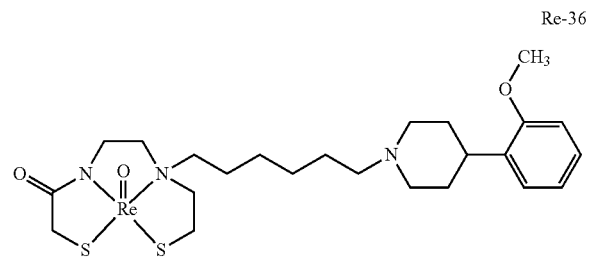

yield 63%: $^1$H NMR (CDCl$_3$) δ 1.43-1.57 (m, 4H), 1.95-2.06 (m, 6H), 2.17-2.23 (m, 1H), 2.40-2.55 (m, 2H), 2.62-2.70 (m, 1H), 2.73-2.90 (m, 2H), 2.93-3.03 (m, 2H), 3.17-3.24 (m, 1H), 3.38-3.56 (m, 3H), 3.57-3.81 (m, 5H), 3.82 (s, 3H), 3.92 (X of AX, 1H, J=16.8 Hz), 4.00-4.07 (m, 1H), 4.22-4.28 (m, 1H), 4.65 (A of AX, 1H, J=16.8 Hz), 6.85 (d, 1H, J=6.8 Hz), 6.93 (t, 1H, J=7.2 Hz), 7.2-7.26 (m, 2H). MS, m/z (M+H)$^+$=668.19.

Re-37:

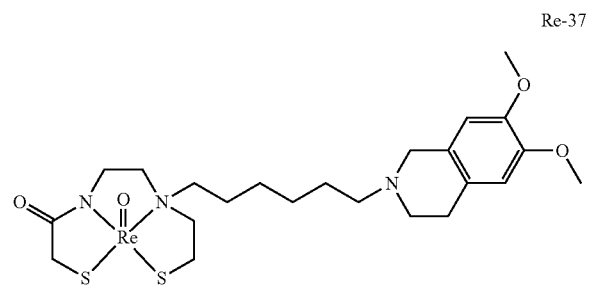

yield 62%: $^1$H NMR (CDCl$_3$) δ 1.43-1.56 (m, 4H), 1.90-2.00 (m, 4H), 2.17-2.22 (m, 1H), 2.60-2.68 (m, 1H), 2.90-2.99 (m, 2H), 3.01-3.13 (m, 2H), 3.21-3.31 (m, 2H), 3.38-3.42 (m, 2H), 3.45-3.55 (m, 1H), 3.63-3.80 (m, 3H), 3.84 (s, 3H), 3.85 (s, 3H), 3.92 (X of AX, 1H, J=16.8 Hz), 3.99-4.13 (m, 3H), 4.22-4.25 (m, 1H), 4.65 (A of AX, 1H, J=16.8 Hz), 6.55 (s, 1H), 6.62 (s, 1H). MS, m/z (M+H)$^+$=670.17.

Results and Discussion

Chemistry

Synthesis of Chelators (31-37). The reaction of iso-AADT with large excess of dibromo alkanes in CH$_3$CN solution afforded mono-bromo substitution on the secondary nitrogen of the chelate in good yield, which was then allowed to react with a secondary amine (NHR$_1$R$_2$) in the basic condition to yield the chelator 31-37 in good yield as outlined in Scheme 2.

The mono-oxorhenium(V) complexes (Re-31-Re-37) were obtained by reduction of perrhenate(VII) with stannous chloride in the presence of salicylic acid, sodium salt and the deprotected N$_2$S$_2$-Chelating ligands which were obtained from the reaction of 31-37 with TFA and Et$_3$SiH, heating the reaction mixture at 80° C. for 4 hours afforded brownish-purple solids of the rhenium complexes in good yield.

Example 51

Additional isoAADT-(CH$_2$)$_n$—NR$_1$R$_2$ ligands and their rhenium complexes have been synthesized and tested as described below.

Experimental

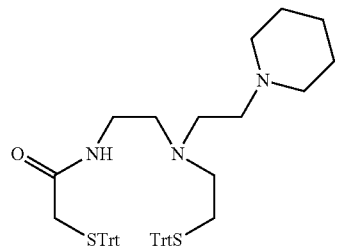

Synthesis of Z2.

Compound 26 (380 mg, 0.56 mmol), 1-(2-chloroethyl) piperidine (103 mg, 0.56 mmol), K$_2$CO$_3$ (463 mg, 3.36 mmol) and KI (282 mg 1.68 mmol) were mixed in CH$_3$CN (100 mL). The mixture was refluxing overnight. The solvent was evaporated, and the residue was purified on Silica gel column (4.0% NH$_3$.MeOH/CH$_2$Cl$_2$) to yield desired product as a white solid (146 mg, 65% yield): $^1$H NMR (CDCl$_3$) δ 1.37-1.43 (m 2H) 1.55 (t 4H, J=3.6 Hz) 2.20-2.40 (m, 12H), 2.44 (t 2H, J=6.0 Hz), 2.96 (q, 2H J=5.4 Hz), 2.99 (s, 2H), 6.62 (t 1H J=4.8 Hz), 7.17-7.27 (m, 18H) 7.28-7.42 (m, 12H). MS, m/z (M+H)$^+$ theoretical mass for C$_{51}$H$_{55}$N$_3$OS$_2$: 790.40. Found: 790.39.

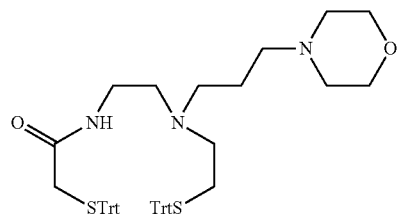

Synthesis of Z3.

Compound 28 (230 mg, 0.29 mmol), morpholine (38 mg, 0.43 mmol), K$_2$CO$_3$ (60 mg, 0.43 mmol) were mixed in CH$_3$CN (20 mL). The mixture was refluxing overnight. The solvent was evaporated, and the residue was purified on Silica gel column (3.5% NH$_3$.MeOH/CH$_2$Cl$_2$) to yield desired product as a white solid (146 mg, 65% yield): $^1$H NMR (CDCl$_3$) δ 1.48-1.56 (m 2H) 2.38-2.50 (m, 14H), 2.95 (q, 2H J=6.0 Hz), 3.01 (s, 2H), 6.46 (t 1H J=4.8 Hz), 7.14-7.32 (m, 18H) 7.33-7.42 (m, 12H). MS, m/z (M+H)$^+$ theoretical mass for C$_{51}$H$_{55}$N$_3$O$_2$S$_2$: 806.38. Found: 806.40.

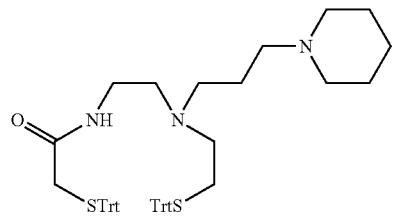

Synthesis of Z4.

Compound 28 (80 mg, 0.10 mmol), piperidine (20 mg, 0.20 mmol), $K_2CO_3$ (30 mg, 0.20 mmol) were mixed in $CH_3CN$ (10 mL). The mixture was refluxing overnight. The solvent was evaporated, and the residue was purified on Silica gel column (3.5% $NH_3$.MeOH/$CH_2Cl_2$) to yield desired product as a white solid (146 mg, 65% yield): $^1$H NMR (CDCl$_3$) δ 1.40-1.56 (m 2H) 1.60-2.00 (m, 6H) 2.20-2.33 (m, 8H), 2.60-2.90 (m, 6H), 2.95 (q, 2H J=6.0 Hz), 3.05 (s, 2H), 6.39 (t, 1H J=4.8 Hz), 7.17-7.33 (m, 18H) 7.33-7.44 (m, 12H). MS, m/z (M+H)$^+$ theoretical mass for $C_{52}H_{57}N_3OS_2$: 804.39. Found: 804.39.

General Procedure for Rhenium Complexation.

(0.13 mmol) of the trityl protected ligand was mixed with TFA (15 mL), the resulting yellow solution was stirred for 5 min, and then titrated with triethylsilyl hydride until colorless. The solution was evaporated and the residue was placed under high vacuum until completely dry.

The deprotected compound was dissolved in argon-saturated MeOH (10 mL), Salicylic acid, sodium salt (SA) (0.26 mmol) in $H_2O$ (2 mL) and NaReO$_4$ (0.26 mmol) in $H_2O$ (2 mL) were added into the solution, with additional methanol (30 mL) added into the mixture and gently stirred for 1-3 min at 75° C. Solid SnCl$_2$ (0.26 mmol) was added to the reaction mixture with stiffing. The solution begins to turn brownish purple. The pH of the reaction was adjusted to 4.5-5.0, and the mixture was heated at 75° C. (water bath) for 4 h. The solution was allowed to cooled to room temp and stirred overnight. Solvent was evaporated to dryness. The residue dissolved in $CH_2CL_2$ purified by silica gel column (5% $NH_3$.MeOH/$CH_2Cl_2$) to yield desired rhenium complex as a pale purple product.

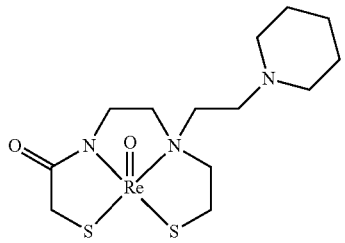

Re-Z2

Re-Z2: yield 62%: $^1$H NMR (CDCl$_3$) δ 1.40-1.50 (m 2H), 1.58 (p, 4, J=6.0 Hz), 2.20 (td, 1H, J=12.0, 4.8 Hz), 2.38-2.53 (m, 4H), 2.63-2.68 (m, 1H), 2.73-2.80 (m, 2H), 3.35-3.38 (m, 1H), 3.46-3.52 (m, 1H), 3.57 (dt, 1H, J=12.6, 3.6 Hz), 3.80-3.92 (m, 3H), 3.92 (X of AX, 1H, J=16.8 Hz), 3.98-4.05 (m, 1H), 4.25 (dt, 1H, J=14.4, 4.8 Hz), 4.64 (A of AX, 1H, J=16.2 Hz). MS, m/z (M+H)$^+$ theoretical mass for $C_{13}H_{24}N_3O_2ReS_2$: 506.09. Found: 506.08.

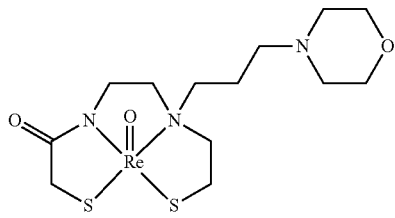

Re-Z3

Re-Z3: Yield 77%: $^1$H NMR (CDCl$_3$) δ 2.03-2.14 (m, 2H), 2.21 (dt, 1H, J=12.0, 5.4 Hz), 2.43-2.56 (m, 6H), 2.60-2.68 (m, 1H), 3.28-3.33 (m, 1H), 3.38-3.44 (m, 1H), 3.44-3.50 (m, 1H), 3.59 (dt, 1H, J=12.6, 4.2 Hz), 3.74 (t, 4H, J=4.2 Hz), 3.76-3.88 (m, 2H), 3.95 (X of AX, 1H, J=16.8 Hz), 3.98-4.05 (m, 1H), 4.26-4.33 (m, 1H), 4.67 (A of AX, 1H, J=16.8 Hz). MS, m/z (M+H)$^+$ theoretical mass for $C_{13}H_{24}N_3O_3ReS_2$: 522.08. Found: 522.08.

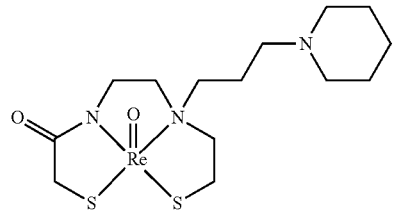

Re-Z4

Re-Z4: yield 62%: $^1$H NMR (CDCl$_3$) δ 1.40-1.50 (m 2H), 1.85-2.01 (m, 2H), 2.18-2.31 (m, 3H), 2.60-2.80 (m, 5H), 3.09 (t, 2H, J=7.8 Hz), 3.42-3.48 (m, 2H), 3.55-3.70 (m, 3H), 3.70-3.77 (m, 1H), 3.77-3.82 (m, 1H), 3.84-3.90 (m, 1H), 3.93 (X of AX, 1H, J=16.8 Hz), 4.03-4.18 (m, 1H), 4.23-4.28 (m, 1H), 4.69 (A of AX, 1H, J=16.2 Hz). MS, m/z (M+H)$^+$ theoretical mass for $C_{14}H_{26}N_3O_2ReS_2$: 520.10. Found: 520.10.

Procedure for $^{99m}$Tc Labeling.

The tetradentate $N_2S_2$-chelated ligand (5.0 mg) was mixed with TFA (10 mL) in a clean round bottom flask, the resulting yellow solution was stirred for 5 min, and then titrated with triethylsilylhydride until colorless. The solution was then evaporated and the residue was placed under high vacuum till complete dryness. The dry residue was later redissolved in argon-saturated methanol and distributed into 10 vials that were dried and kept under vacuum for later preparation of the technetium-99m-labeled compound.

100 μL solution of a (10 mg/ml) sodium salt of Salicylic acid solution made in argon-saturated water was mixed with generator eluted $^{99m}$TcO4$^-$ (25-30 mCi) in a glass test tube or vial. To this solution was added 20 μL of a SnCl$_2$ solution (1-2 mg/ml) freshly made in argon-saturated water, after gently stirring in a water bath (75° C.) for 1-2 min, this prereduced $^{99m}$Tc-Salicyclic acid solution was added into one vial which contained 0.5 mg of the above thiol-deprotected ligand, and the reaction was heated at 75° C. for 30 min.

Results and Discussion

Chemistry.

26 was mixed with 1-(2-chloroethyl)piperidine to yield desired product Z2 (Scheme 3). Z3 and Z4 were obtained by reacting 28 with morpholine or piperidine in good yield. (Scheme 4)

$^{99m}$Tc-labeled complexes were synthesized by transmetalation of technetium-99m from a pre-reduced [$^{99m}$Tc-salicylic acid] precursor upon heating the reaction mixture at 80° C., ligand exchange of the $N_2S_2$-chelated ligand and the $^{99m}$Tc(V)-SA precursor yielded complexes $^{99m}$Tc-Z2-$^{99m}$Tc-Z4 in nearly quantitative yield within 30 min. Using a method similar to that for $^{99m}$Tc complexes, the non-radioactive mono-oxorhenium(V) complexes (Re-Z2-Re-Z4) were obtained by reduction of perrhenate(VII) with stannous acetate in the presence of salicylic acid and the deprotected $N_2S_2$-chelating ligand, heating the reaction mixture at 80° C. for 4 hours afforded brownish-purple solution which was evaporated to dryness and purified on silica gel preparative plates using (3-5% $NH_3$.MeOH (7M $NH_3$ in methanol)/$CH_2Cl_2$). The purified pale-purple rhenium complexes were isolated in 40-70% yield and characterized with $^1$H NMR, and high resolution mass spectrometry (MS)

Scheme 3. Synthesis of M-Z2

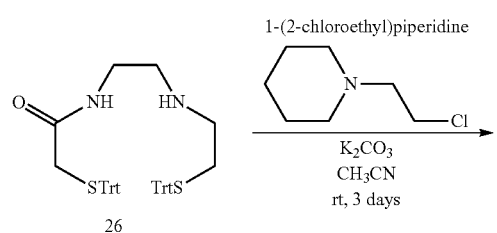

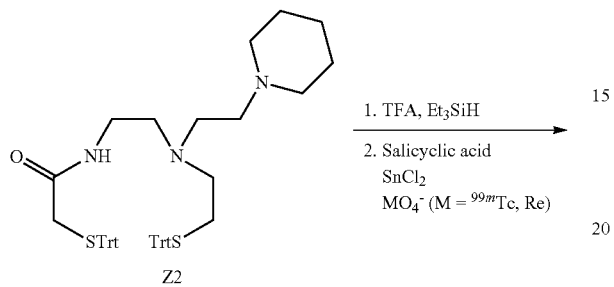

Scheme 4. Synthesis of M-Z3 and M-Z4

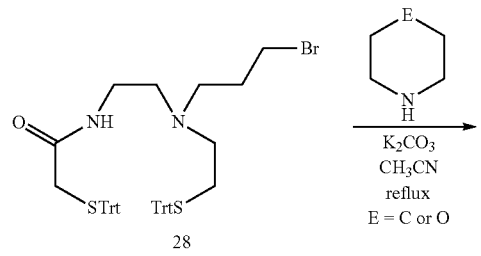

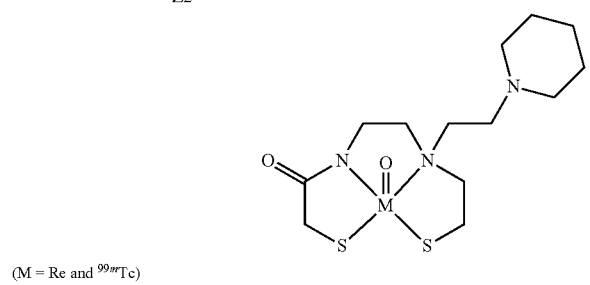

In Vivo Tumor Uptake

To study the tumor uptake of $^{99m}$Tc complexes, $^{99m}$Tc-Z2-$^{99m}$Tc-Z4, in vivo biodistribution experiment at 1, 3, 6 hours post intra-venous injection of the $^{99m}$Tc-complex were carried out in C57B16 mice bearing B16F10 melanoma tumors. The biodistribution data including melanoma/nontumor (M/NT) ratios for selected organs are summarized in Table 2 as percentage injected dose per gram (% ID/g) (Table 2). Complex $^{99m}$Tc-Z2 displays the second highest tumor uptake of the set with 8.52% ID/g at 1 h, 7.56% ID/g at 3 h and 3.71% ID/g at 6 h after administration. The tumor/liver ratio was able to reach the highest (2.29 at 3 h) among test set and displays high tumor to background (mel/blood, mel/spleen, mel/lung) ratios in other organs as well. This is due to washout from no-tumor organs and increased retention in the tumor.

The $^{99m}$Tc-complexes of the isoAADT ligands Z1 and Z2 display significant improvement in vivo melanoma uptake and retention compared to those of AADT chelate system described earlier. The improved in-vivo distribution characteristics of both $^{99m}$Tc-Z1 and $^{99m}$Tc-Z2 may be attributable to significant tumor retention which results in higher melanoma/nontumor ratios over time and indicates that these complexes may be useful in the early detection and diagnosis of melanoma and its metastasis with widely available SPECT and SPECT/CT.

TABLE 2

Biodistribution and Tumor/Nontumor Ratios of Complexes Tc-Z2, Tc-Z3 and Tc-Z4 at 1, 3 and 6 h Postinjection

| organ | Tc-Z2 | | | Tc-Z3 | | Tc-Z4 | | |
|---|---|---|---|---|---|---|---|---|
| | 1 h | 3 h | 6 h | 1 h | 3 h | 1 h | 3 h | 6 h |
| Eyes | 13.57 ± 2.1 | 13.55 ± 2.49 | 8.89 ± 1.55 | 4.85 ± 0.63 | 4.72 ± 0.62 | 6.72 ± 0.77 | 7.19 ± 1.40 | 7.01 ± 0.41 |
| blood | 0.41 ± 0.08 | 0.22 ± 0.02 | 0.12 ± 0.02 | 0.35 ± 0.11 | 0.10 ± 0.02 | 0.33 ± 0.03 | 0.34 ± 0.09 | 0.14 ± 0.03 |
| heart | 0.62 ± 0.10 | 0.22 ± 0.02 | 0.10 ± 0.02 | 0.49 ± 0.11 | 0.14 ± 0.02 | 0.59 ± 0.07 | 0.63 ± 0.07 | 0.25 ± 0.06 |
| lung | 1.29 ± 0.36 | 0.49 ± 0.03 | 0.31 ± 0.03 | 2.08 ± 0.60 | 0.87 ± 0.35 | 2.37 ± 0.17 | 2.36 ± 0.54 | 0.91 ± 0.24 |
| spleen | 0.90 ± 0.22 | 0.93 ± 0.78 | 1.19 ± 0.6 | 3.19 ± 1.05 | 3.16 ± 0.46 | 1.37 ± 0.19 | 1.22 ± 0.42 | 0.58 ± 0.20 |
| liver | 10.28 ± 2.9 | 3.32 ± 0.67 | 3.10 ± 0.31 | 17.75 ± 2.56 | 12.58 ± 1.4 | 20.32 ± 1.0 | 16.67 ± 3.8 | 12.9 ± 1.72 |
| kidney | 3.50 ± 0.95 | 1.64 ± 0.15 | 0.84 ± 0.08 | 2.62 ± 1.50 | 1.02 ± 0.13 | 2.50 ± 0.32 | 2.73 ± 0.76 | 1.07 ± 0.17 |
| muscle | 0.36 ± 0.06 | 0.11 ± 0.01 | 0.04 ± 0.01 | 0.38 ± 0.11 | 0.09 ± 0.02 | 0.63 ± 0.17 | 0.70 ± 0.52 | 0.09 ± 0.02 |
| brain | 0.13 ± 0.03 | 0.06 ± 0.01 | 0.03 ± 0.01 | 0.08 ± 0.02 | 0.01 ± 0.00 | 0.16 ± 0.01 | 0.18 ± 0.04 | 0.02 ± 0.01 |
| melanoma | 8.52 ± 0.08 | 7.56 ± 1.69 | 5.39 ± 0.36 | 2.36 ± 0.25 | 2.74 ± 0.24 | 3.43 ± 0.70 | 3.59 ± 1.76 | 3.52 ± 0.88 |
| mel/blood | 16.49 ± 6.7 | 34.80 ± 10.2 | 43.14 ± 4.9 | 7.49 ± 2.79 | 26.65 ± 4.9 | 10.50 ± 1.9 | 9.22 ± 4.93 | 24.95 ± 4.6 |
| mel/spleen | 7.94 ± 2.79 | 17.28 ± 10.2 | 5.10 ± 2.59 | 0.85 ± 0.44 | 0.87 ± 0.17 | 2.49 ± 0.24 | 2.57 ± 1.21 | 6.44 ± 2.12 |

TABLE 2-continued

Biodistribution and Tumor/Nontumor Ratios of Complexes Tc-Z2, Tc-Z3 and Tc-Z4 at 1, 3 and 6 h Postinjection

| organ | Tc-Z2 | | | Tc-Z3 | | | Tc-Z4 | | |
|---|---|---|---|---|---|---|---|---|---|
| | 1 h | 3 h | 6 h | 1 h | 3 h | 6 h | 1 h | 3 h | 6 h |
| mel/lung | 4.93 ± 1.13 | 15.48 ± 3.91 | 16.9 ± 1.41 | 1.26 ± 0.57 | 3.24 ± 1.79 | 1.45 ± 0.30 | 1.30 ± 0.67 | 3.99 ± 1.10 |
| mel/liver | 0.64 ± 0.21 | 2.29 ± 0.30 | 1.71 ± 0.13 | 0.14 ± 0.03 | 0.22 ± 0.03 | 0.17 ± 0.03 | 0.15 ± 0.09 | 0.28 ± 0.08 |

Example 52

Synthesis of AADT Ligands and Complexes

General Procedure for the Synthesis of Compounds 38-47

The AADT chelate, N-(2-(tritylthio)ethyl)-2-(2-(tritylthio)ethylamino)acetamide was synthesized using procedures described earlier (Friebe M, Mahmood A, Bolzati C, Drews A, Johannsen B, Eisenhut M, Kraemer D, Davison A, Jones AG. [$^{99m}$Tc]oxotechnetium(V) complexes of amine-amide-dithiol chelates with dialkylaminoalkyl substituents as potential diagnostic probes for malignant melanoma. J Med Chem 2001; 44:3132-40). Compounds 38-47 were synthesized using a procedure similar to that described for compound 29 and 30.

Scheme 5: Synthesis of AADT compounds 40-47

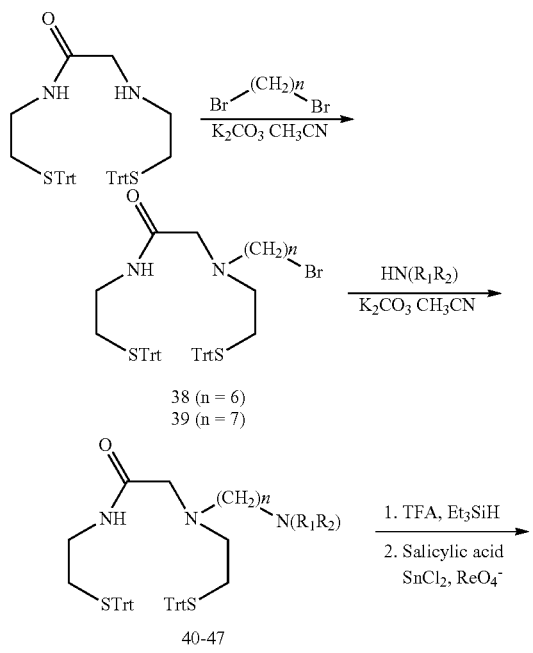

Compound 38:

2-((6-bromohexyl)(2-(tritylthio)ethyl)amino)-N-(2-(tritylthio)ethyl)acetamide

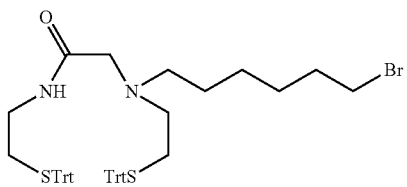

38

$^1$H NMR (CDCl$_3$) δ 1.18-1.25 (m, 2H), 1.29-1.38 (m, 4H), 1.73-1.80 (m, 2H), 2.22-2.30 (m, 4H), 2.34-2.43 (m, 4H), 2.83 (s, 2H), 3.02 (q, 2H, J=6 Hz), 3.32 (t, 2H, J=6.6 Hz), 7.17-7.23 (m, 6H), 7.23-7.28 (m, 12H), 7.37-7.42 (m, 12H), 7.42-7.46 (m, 1H). MS, m/z (M+H)$^+$: 841.28

Compound 39:

2-((7-bromoheptyl)(2-(tritylthio)ethyl)amino)-N-(2-(tritylthio)ethyl)acetamide

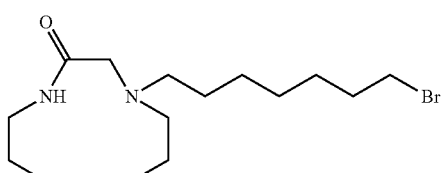

39

$^1$H NMR (CDCl$_3$) δ 1.15-1.26 (m, 4H), 1.26-1.42 (m, 4H), 1.75-1.82 (m, 2H), 2.21-2.28 (m, 4H), 2.32-2.42 (m, 4H), 2.82 (s, 1H), 2.98-3.04 (m, 2H), 3.34 (t, 2H, J=7.2 Hz), 7.16-7.23 (m, 6H), 7.23-7.27 (m, 12H), 7.36-7.41 (m, 12H), 7.42-7.46 (m, 1H). MS, m/z (M+H, 855.3017

Compound 40

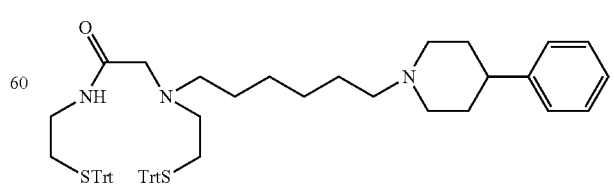

40

$^1$H NMR (CDCl$_3$) δ 1.20-1.30 (m, 4H), 1.30-1.38 (m, 2H), 1.44-1.57 (m, 2H), 1.80-1.93 (m, 4H), 2.02-2.14 (m, 2H), 2.22-2.30 (m, 4H), 2.31-2.46 (m, 6H), 2.46-2.56 (m, 1H), 2.83 (s, 2H), 3.00-3.18 (m, 4H), 7.16-7.22 (m, 6H), 7.16-7.26 (m, 14H), 7.28-7.32 (m, 3H), 7.36-7.42 (m, 12H), 7.46 (t, 1H, J=4.8 Hz). MS, m/z (M+H)+: 921.47.

Re-40:

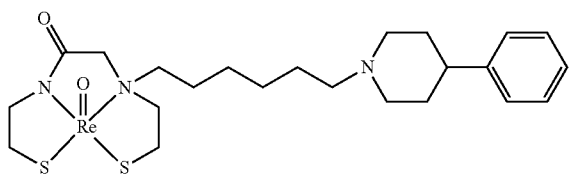

¹H NMR (CDCl₃) δ 1.38-1.46 (m, 4H), 1.54-1.63 (m, 3H), 1.73-1.90 (m, 6H), 2.02-2.10 (m, 2H), 2.36-2.43 (m, 2H), 2.48-2.54 (m, 1H), 2.83-2.88 (m, 1H), 3.04-3.12 (m, 2H), 3.12-3.20 (m, 1H), 3.32-3.39 (m, 1H), 3.46-3.53 (m, 1H), 3.92-3.98 (m, 1H), 4.04-4.08 (m, 1H), 4.10 (X of AX, 1H, J=16.2 Hz), 4.54-4.58 (m, 1H), 4.63 (A of AX, 1H, J=16.2 Hz), 7.16-7.31 (m, 5H). MS, m/z (M+H)+: 638.188

Compound 41

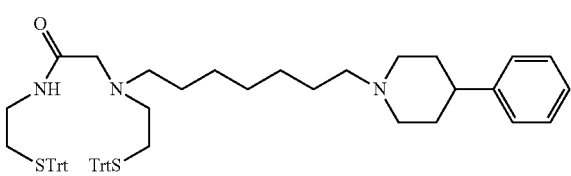

¹H NMR (CDCl₃) δ 1.20-1.30 (m, 6H), 1.30-1.38 (m, 2H), 1.44-1.57 (m, 2H), 1.80-1.93 (m, 4H), 2.02-2.14 (m, 2H), 2.22-2.30 (m, 4H), 2.31-2.46 (m, 6H), 2.46-2.56 (m, 1H), 2.83 (s, 2H), 3.00-3.18 (m, 4H), 7.16-7.22 (m, 6H), 7.16-7.26 (m, 14H), 7.28-7.32 (m, 3H), 7.36-7.42 (m, 12H), 7.46 (t, 1H, J=4.8 Hz). MS, m/z (M+H)+: 936.49.

Compound 42:

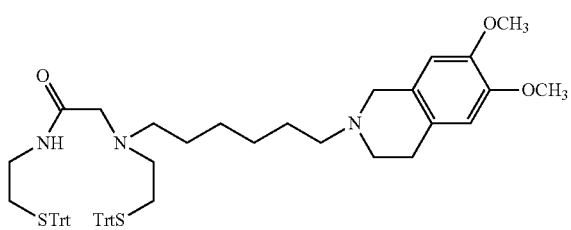

¹H NMR (CDCl₃) δ 1.10-1.41 (m, 6H), 1.41-1.63 (m, 2H), 2.18-2.55 (m, 10H), 2.62-2.73 (m, 2H), 2.73-2.80 (m, 4H), 2.95-3.08 (m, 2H), 3.53 (s, 2H), 3.80 (s, 3H), 3.83 (s, 3H), 6.49 (s, 1H), 6.59 (s, 1H), 7.10-7.43 (m, 30H), 7.43-7.52 (m, 1H). MS, m/z (M+H)+: 953.4624.

Re-42:

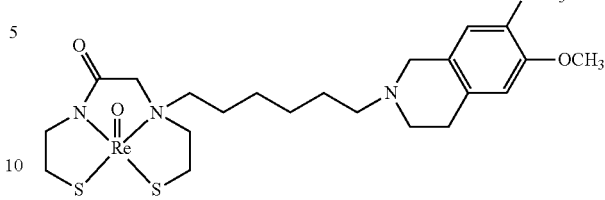

¹H NMR (CDCl₃) δ 1.40-1.51 (m, 4H), 1.51-1.60 (m, 1H), 1.60-1.72 (m, 2H), 1.72-1.88 (m, 2H), 2.53-2.58 (m, 2H), 2.74-2.88 (m, 5H), 3.10-3.18 (m, 1H), 3.18-3.26 (m, 2H), 3.30-3.36 (m, 1H), 3.45-3.52 (m, 1H), 3.62 (s, 2H), 3.84 (s, 3H), 3.85 (s, 3H), 3.90-3.97 (m, 1H), 4.02-4.07 (m, 1H), 4.09 (X of AX, 1H, J=16.2 Hz), 4.52-4.57 (m, 1H), 4.63 (A of AX, 1H, J=16.2 Hz), 6.55 (s, 1H), 6.62 (s, 1H). MS, m/z (M+H)+: 670.1776.

Compound 43:

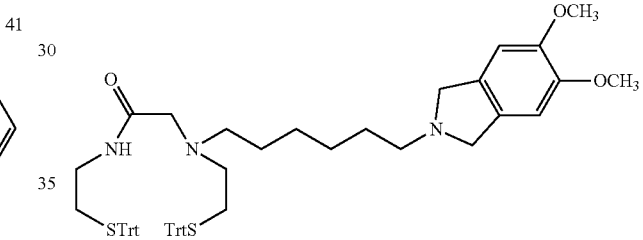

¹H NMR (CDCl₃) δ ¹H NMR (CDCl₃) δ 1.20-1.28 (m, 2H), 1.28-1.36 (m, 4H), 1.50-1.56 (m, 2H), 2.22-2.30 (m, 4H), 2.31-2.42 (m, 4H), 2.67 (t, 2H, J=7.2 Hz), 2.83 (s, 2H), 3.00-3.04 (m, 2H), 3.84 (s, 6H), 3.87 (s, 4H), 6.71 (s, 2H), 7.15-7.27 (m, 18H), 7.36-7.40 (m, 12H), 7.40-7.52 (m, 1H). MS, m/z (M+H)+: 953.462.

Compound 44:

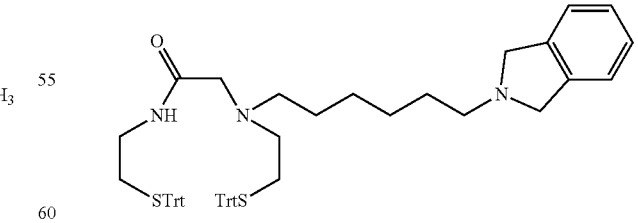

¹H NMR (CDCl₃) δ ¹H NMR (CDCl₃) δ 1.23-1.37 (m, 6H), 1.38-1.66 (m, 2H), 2.22-2.29 (m, 4H), 2.34 (t, 2H, J=6.0 Hz), 2.40 (t, 2H, J=6.0 Hz), 2.70-2.78 (m, 2H), 2.83 (s, 2H), 3.01-3.05 (m, 2H), 4.00 (s, 4H), 6.71 (s, 2H), 7.15-7.32 (m, 22H), 7.36-7.40 (m, 12H), 7.45-7.52 (m, 1H). MS, m/z (M+H)+ 880.433.

Compound 45:

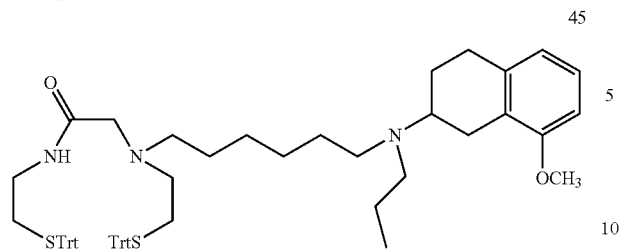

¹H NMR (CDCl₃) δ ¹H NMR (CDCl₃) δ 0.91 (t, 3H, J=7.2 Hz), 1.18-1.37 (m, 7H), 1.38-1.66 (m, 5H), 2.22-2.29 (m, 4H), 2.34 (t, 2H, J=6.0 Hz), 2.40 (t, 2H, J=6.0 Hz), 2.48-2.56 (m, 4H), 2.83 (s, 2H), 2.83-2.88 (m, 2H), 2.93-3.00 (m, 2H), 3.01-3.06 (m, 2H), 3.82 (s, 3H), 6.67 (d, 1H, J=7.2 Hz), 6.71 (d, 1H, J=7.2 Hz), 7.10 (t, 1h, J=7.2 Hz), 7.16-7.28 (m, 21H), 7.38-7.44 (m, 12H), 7.45-7.52 (m, 1H). MS, m/z (M+H)⁺: 980.522.

Compound Re-45:

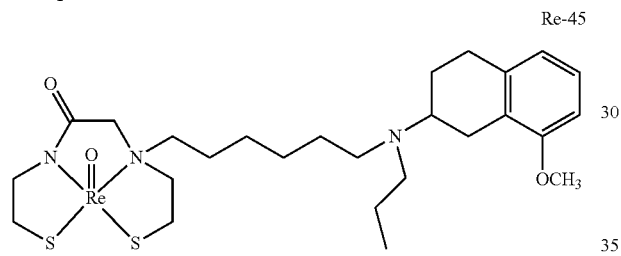

¹H NMR (CDCl₃) δ ¹H NMR (CDCl₃) δ 0.91 (t, 3H, J=7.2 Hz), 1.38-1.64 (m, 11H), 1.70-1.86 (m, 2H), 2.40-2.47 (m, 1H), 2.47-2.60 (m, 4H), 2.80-3.00 (m, 5H), 3.12-3.19 (m, 1H), 3.20-3.27 (m, 2H), 3.30-3.37 (m, 1H), 3.43-3.51 (m, 1H), 3.81 (s, 2H), 3.91-3.96 (m, 1H), 4.04-4.50 (m, 1H), 4.10 (X of AX, 1H, J=16.2 Hz), 4.52-4.59 (m, 1H), 4.62 (A of AX, 1H, J=16.2 Hz), 6.65 (d, 1H, J=7.2 Hz), 6.71 (d, 1H, J=7.2 Hz), 7.07 (t, 1H, J=7.2 Hz). MS, m/z (M+H)⁺: 696.230.

Re-45-OH

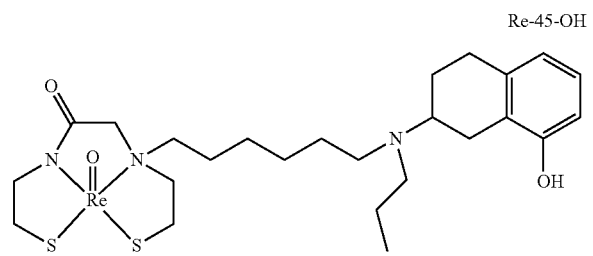

¹H NMR (CDCl₃) δ 0.92 (t, 3H, J=7.2 Hz), 1.22-1.88 (m, 12H), 2.05-2.15 (m, 1H), 2.54-2.92 (m, 8H), 2.96-3.26 (m, 6H), 2.29-3.37 (m, 1H), 3.42-3.48 (m, 1H), 3.86-3.97 (m, 1H), 4.02-4.13 (m, 2H), 4.50-4.56 (m, 1H), 4.63 (t, 1H, J=17.4 Hz), 6.60-6.65 (m, 1H), 6.60-6.71 (m, 1H), 6.95 (t, 1H, J=7.2 Hz). MS, m/z (M+H)⁺: 682.215.

Compound 46:

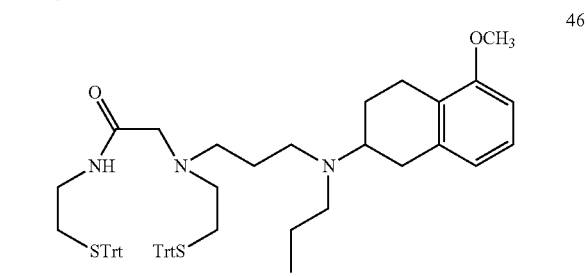

¹H NMR (CDCl₃) δ ¹H NMR (CDCl₃) δ 0.82 (t, 3H, J=7.2 Hz), 1.20-2.06 (m, 7H), 2.14-2.65 (m, 12H), 2.65-3.05 (m, 8H), 3.79 (s, 3H), 6.60-6.68 (m, 1H), 7.01-7.47 (m, 33H). MS, m/z (M+H)⁺: 938.475.

Compound Re-46:

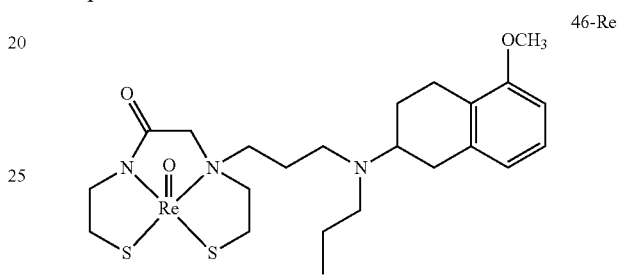

¹H NMR (CDCl₃) δ ¹H NMR (CDCl₃) δ 0.91 (t, 3H, J=7.2 Hz), 1.38-1.70 (m, 4H), 1.70-2.10 (m, 4H), 2.43-3.1 (m, 10H), 3.10-3.50 (m, 3H), 3.68-3.80 (m, 1H), 3.80 (s, 3H), 3.90-4.14 (m, 3H), 4.48-4.72 (m, 2H), 6.67 (t, 2H, J=7.8 Hz), 7.08 (t, 1H, J=7.8 Hz). MS, m/z (M+H)⁺: 654.183.

Example 53

General Procedure for Deprotection of Trityl Protected Thiol Groups (AADT Ligands)

6.0 mg of a bis-trityl-protected AADT-ligand was dissolved in 3 ml of trifluoro acetic acid and stirred at room temperature for 5 min. 1-2 drops of triethylsilyl hydride were added until the former yellowish reaction mixture became colorless.

The solvent was evaporated completely and the residue placed under high vacuum overnight.

Example 54

General Procedures for Rhenium Complexation (AADT Ligands)

The two procedures described below were generally used.
Procedure 1

A bistrityl-protected ligand (100 mg, 0.1 mmol) was dissolved in 0.25 ml anisol and 10 ml trifluoroacetic acid. The resulting yellow solution was stirred for 5 min and then titrated with triethylsilyl hydride until colorless. The solution was evaporated and placed on high vacuum till completely dry residue remained. The residue was redissolved in 5 ml 20% MeOH in water previously argon-saturated. To this solution was added an aqueous solution of NaReO₄ (30 mg, 0.1 mmol) and Na-glucoheptonate (55 mg, 0.22 mmol) and, while stirring, solid SnCl₂ (21 mg, 0.11 mmol). The solution began to turn a brownish purple color. The pH of the reaction mixture was adjusted to 7 and the reaction was heated at 75° C. for 1 hr. The solution was then cooled to room temperature and the pH was adjusted to 8, followed by extraction with $CH_2Cl_2$. The $CH_2Cl_2$ extract was concentrated and chromatographed on silica gel, eluting with 4% MeOH in $CH_2Cl_2$ to yield the desired product as a pale purple solid.

Procedure 2

The tetradentate $N_2S_2$-chelated ligand (5.0 mg) was mixed with TFA (10 mL) in a clean round bottom flask, the resulting yellow solution was stirred for 5 min, and then titrated with triethylsilylhydride until colorless. The solution was then evaporated and the residue was placed under high vacuum till complete dryness. The dry residue was later redissolved in argon-saturated methanol and distributed into 10 vials that were dried and kept under vacuum for later preparation of the technetium-99m-labeled compound.

100 µL solution of a (10 mg/ml) sodium salt of Salicylic acid solution made in argon-saturated water was mixed with generator eluted $^{99m}TcO4^-$ (25-30 mCi) in a glass test tube or vial. To this solution was added 20 µL of a $SnCl_2$ solution (1-2 mg/ml) freshly made in argon-saturated water, after gently stirring in a water bath (75° C.) for 1-2 min, this prereduced $^{99m}Tc$-Salicyclic acid.

Example 55

$5HT_{1A}$ Receptor Assays

The in vitro $5HT_{1A}$ binding affinities of rhenium coordinated complexes were determined in a competition assay using rat hippocampus and high-affinity $5HT_{1A}$-ligand [$^3H$]-8-OH-DPAT (135 Ci/mmol, NEN Life Science Inc., Cambridge, Mass.). See, *Brain Res.* 1995, 673, 217-225.

Male Sprague-Dawley rats (weighing 150-170 g) were sacrificed using anesthesia agent isoflurane. The brains were rapidly removed, and hippocampus, frontal cortex, hypothalamus, and striatum were hand-dissected on ice and stored at −70° C. Tissue was thawed at room temperature and homogenized using a Brinkmann Polytron tissue disrupter in 50 volumes (wt/vol) of ice-cold 50 mM Tris-HCl buffer (pH 7.4). The suspension was centrifuged twice at 27,000 g for 20 min at 4° C. The membrane pellets were resuspended in 50 volumes of (wt/vol) Tris-HCl buffer and incubated at 37° C. for 20 min in a water bath, before a final centrifugation step (27,000 g; 20 min; 4° C.). The final tissue pellets were stored at −70° C. until assayed.

Twelve concentrations of the nonradioactive rhenium complexes ranging from $1\times10^{-11}$ to $1\times10^{-4}$ and protein samples (0.15 mg of membrane protein) were incubated with 1.5 nM [$^3H$]-8-OH-DPAT in a total volume of 0.25 mL of Tris-HCl (50 mM, pH 7.4, 10 mM $MgSO_4$). Incubations were carried out for 60 min at 25° C. All assays were terminated by dilution with 5 mL of ice-cold Tris-HCl (10 mM), pH 7.4, and solution were filtered through glass-fiber filters (Whatman GF/F; presoaked in 0.5% polyethyleneimine for 30 min at 25° C.). Filters were then washed three times with 5 mL of ice-cold Tris-HCl (50 mM, pH 7.4), and counted in Hionic-Fluor cocktail (Packard, Groningen, the Netherlands). The corresponding $IC_{50}$ values were determined with Origin 6.0 software (OriginLab, Northampton, Mass.) and were used for the calculation of the apparent $K_i$ values with the Cheng-Prusoff equation. See, *Biochem. Pharmacol.* 1973, 22, 3099-3108.

Example 56

Alpha-1, $\alpha_1$ Receptor Assays

The in vitro $\alpha_1$ receptor binding affinities of rhenium coordinated complexes were determined in a competition assay using rat frontal cortex and high-affinity $\alpha_1$ ligand [$^3H$]-Prazosin (80 Ci/mmol, NEN Life Science Inc., Cambridge, Mass.). See, *Eur. J. Nucl. Med.* 2002, 29, 82-87.

The frontal cortex of rat brain was prepared as described above and store at −70° C. until used in the binding assays. Ten concentrations of the nonradioactive rhenium complexes ranging from $1\times10^{-1}$ to $1\times10^{-3}$ and protein samples (0.15 mg of membrane protein) were incubated with 1.5 nM [$^3H$]-Prazosin in a total volume of 0.25 mL of Tris-HCl (50 mM, pH 7.4, 10 mM $MgSO_4$). Incubations were carried out for 60 min at 25° C. All assays were terminated by dilution with 5 mL of ice-cold Tris-HCl (10 mM), pH 7.4, and solution were filtered through glass-fiber filters (Whatman GF/F; presoaked in 0.5% polyethyleneimine for 30 min at 25° C.). Filters were then washed three times with 5 mL of ice-cold Tris-HCl (50 mM, pH 7.4), and counted in Hionic-Fluor cocktail (Packard, Groningen, the Netherlands). The corresponding $IC_{50}$ values were determined with Origin 6.0 software (OriginLab, Northampton, Mass.) and were used for the calculation of the apparent $K_i$ values with the Cheng-Prusoff equation. See, *Biochem. Pharmacol.* 1973, 22, 3099-3108.

Example 57

Sigma-1, $\sigma_1$ Receptor Assays

The in vitro $\sigma_1$ receptor binding affinities of rhenium coordinated complexes were determined in a competition assay using rat frontal cortex and high-affinity $\sigma_1$ ligand [$^3H$]-(+)-pentazocine (28 Ci/mmol, NEN Life Science Inc., Cambridge, Mass.). See, *Mol. Neuropharmacol.* 1993, 3, 117-126.

The membranes were prepared from guinea pig brain (minus cerebellum) as described above and stored at −70° C. Twelve concentrations of the nonradioactive rhenium complexes ranging from $1\times10^{-11}$ to $1\times10^{-3}$ and protein samples (0.15 mg of membrane protein) were incubated with 5 nM [$^3H$]-(+)-pentazocine in a total volume of 0.25 mL of Tris-HCl (50 mM, pH 8.0). Incubations were carried out for 120 min at 25° C. All assays were terminated by dilution with 5 mL of ice-cold Tris-HCl (10 mM), pH 8.0, and solution were filtered through glass-fiber filters (Whatman GF/F; presoaked in 0.5% polyethyleneimine for 30 min at 25° C.). Filters were then washed three times with 5 mL of ice-cold Tris-HCl (50 mM, pH 8.0), and counted in Hionic-Fluor cocktail (Packard, Groningen, the Netherlands). The corresponding $IC_{50}$ values were determined with Origin 6.0 software (OriginLab, Northampton, Mass.) and were used for the calculation of the apparent $K_i$ values with the Cheng-Prusoff equation. See, *Biochem. Pharmacol.* 1973, 22, 3099-3108.

Example 58

$\sigma_2$ Receptor Binding Assays

Rat liver membranes were prepared from male Sprague-Dawley rat livers as previously described (Eur. J. Pharmacol.-Mol. Pharmacol. Sect. 1994, 268, 9-18). The in vitro $\sigma_2$ receptor binding affinities of rhenium coordinated complexes were determined in a competition assay using rat livers and [$^3H$]-DTG (31 Ci/mmol, NEN Life Science Inc., Cambridge, Mass.) as radioligand in the presence of 10 µM 1-pyrrolidinylethyl 3,4-dichlorophenylacetate oxalate (ACT915 oxalate) to mask $\sigma_1$ receptors (Bioorg. & Med. Chem. Lett. 2000, 10, 17-18). Competition assays were performed with twelve concentrations of the nonradioactive rhenium complexes ranging from $1\times10^{-1}$ to $1\times10^{-3}$ and protein samples (0.15 mg of membrane protein) in a total volume of 0.25 mL of Tris-HCl (50 mM, pH 8.0) for 120 min at 25° C. All other manipulations and data analysis were performed as described vide supra for the $\sigma_1$—receptor assays.

Example 59

In-Vivo Tumor Uptake

To study the tumor uptake of radiolabeled metal complexes, in vivo, biodistribution experiments at 1 h after their administration were carried out in C57B16 male mice with palpable B16 melanoma nodules.

Example 60

Results of Binding Assays

The results of certain binding assays for selected compounds are shown in Tables 3 and 4.

TABLE 3

| Compound | Re Complex | $\sigma$-1 (nM) | $\sigma$-2 (nM) | $5HT_{1A}$ (nM) | $D_2$ (nM) |
|---|---|---|---|---|---|
| Re-L3 | 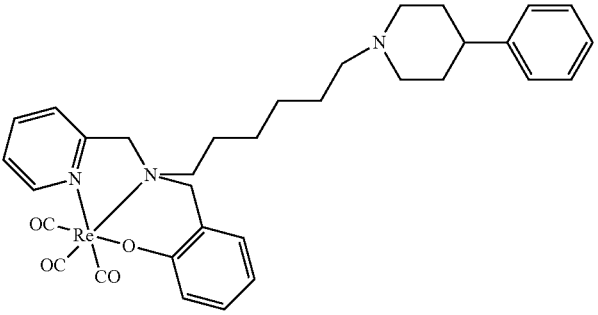 | 70.08 ± 14.3 | 27.38 ± 1.66 | 438 ± 99 | |
| Re-L4 | 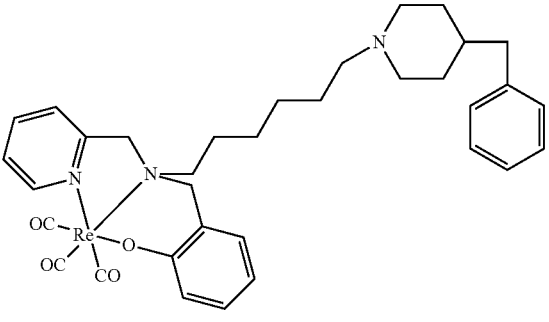 | 305.42 ± 7.64 | 61.42 ± 0.46 | 1600 ± 647 | |
| Re-L6 | 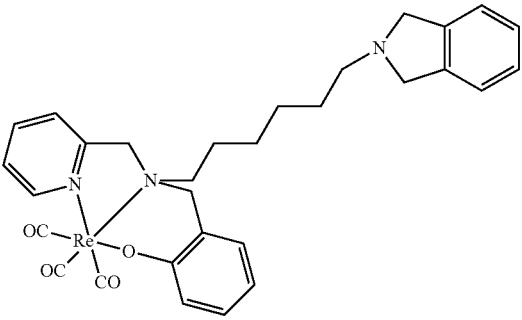 | 1600 | 70 | | |
| Re-L11 | 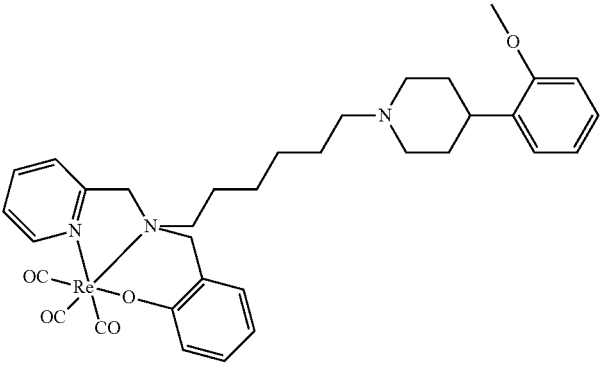 | 120 ± 21 | | | |

TABLE 3-continued
| Compound | Re Complex | σ-1 (nM) | σ-2 (nM) | 5HT$_{1A}$ (nM) | D$_2$ (nM) |
|---|---|---|---|---|---|
| Re-L12 | 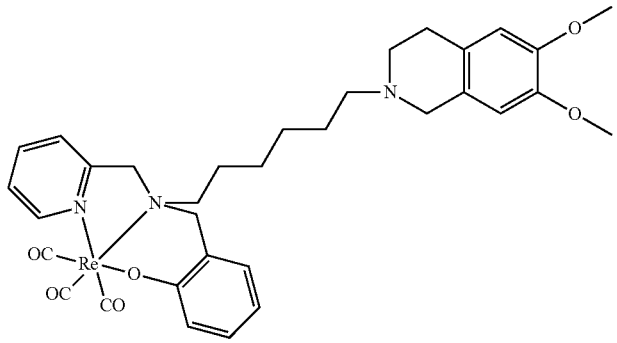 | 4397 ± 280 | 3.37 | 940 ± 216 | |
| Re-L13 | 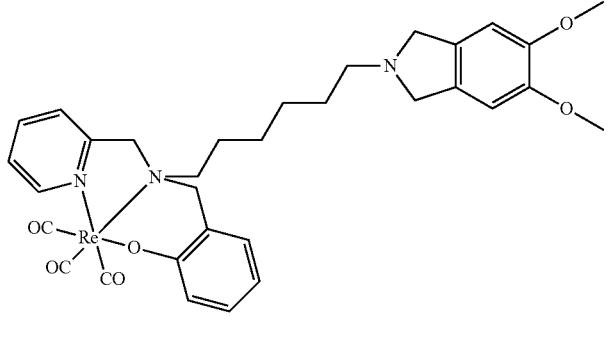 | 5311.59 ± 973 | 35.64 ± 2.83 | | |
| Re-L16a | 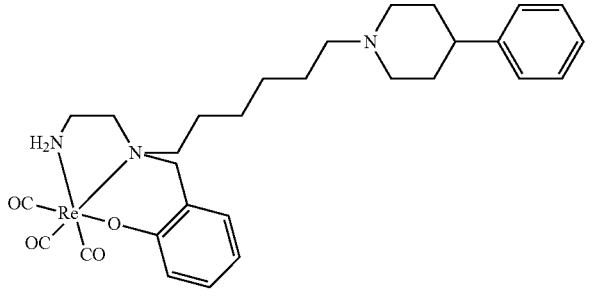 | 39.34 ± 1.43 | 222.83 ± 8.78 | 629 ± 12 | |
| Re-L16b | 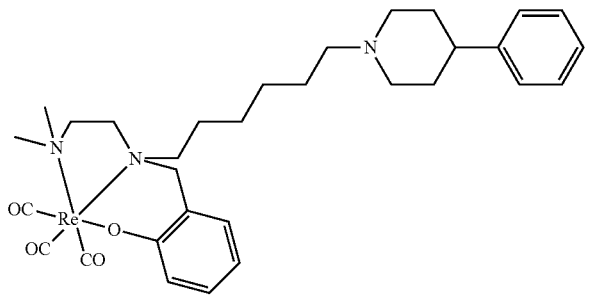 | 9.12 ± 0.14 | 6425 ± 387 | 439 ± 121 | |

TABLE 3-continued

| Compound | Re Complex | σ-1 (nM) | σ-2 (nM) | 5HT$_{1A}$ (nM) | D$_2$ (nM) |
|---|---|---|---|---|---|
| Re-L17a | | | | 48 ± 5 | |
| Re-L17b | | | | 18 ± 8 | |

TABLE 4

| Compound | Re Complex | σ-1 (nM) | σ-2 (nM) | 5HT$_{1A}$ (nM) | D$_2$ (nM) |
|---|---|---|---|---|---|
| Re-32 | | 29.68 ± 4.31 | 222.9 ± 6.54 | | |
| Re-33 | | 22.93 ± 1.78 | 188 ± 18.8 | | |
| Re-40 | | 30.02 ± 6.3 | 43.38 ± .99 | | |

TABLE 4-continued

| Compound | Re Complex | σ-1 (nM) | σ-2 (nM) | 5HT$_{1A}$ (nM) | D$_2$ (nM) |
|---|---|---|---|---|---|
| Re-41 | | 7.60 ± 0.67 | 21.25 ± 0.19 | | |
| Re-42 | | 671.95 ± 17.58 | 12.05 ± 0.61 | | |
| Re-43 | | 1484.51 ± 226.78 | 11.47 ± 0.2 | | |
| Re-44 | | 63.97 ± 5.9 | 61.0 ± 3.91 | | |
| Re-45 | | 41.05 ± 3.58 | 441.8 ± 105.6 | 1.21 ± 0.13 | 1200 |
| Re-45-HO | | | | 0.42 ± 0.08 | 4240 |
| Re-46 | | | | 91.34 ± 4.1 | 222.3 ± 15.6 |

TABLE 4-continued

| Compound | Re Complex | σ-1 (nM) | σ-2 (nM) | 5HT$_{1A}$ (nM) | D$_2$ (nM) |
|---|---|---|---|---|---|
| Re-46 HO | 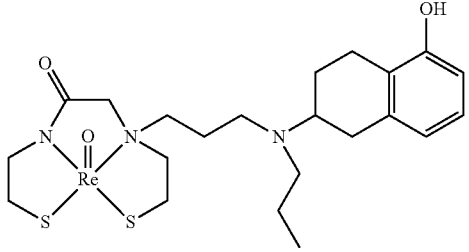 | | | 81.39 ± 5.24 | 13.4 ± 2.3 |
| Re-47 | 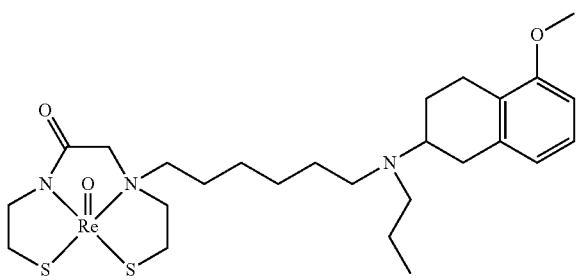 | 64.27 ± 1.27 | 243.5 ± 8.56 | 15.4 ± 4.06 | 184.27 ± 20.4 |
| Re-47 HO | 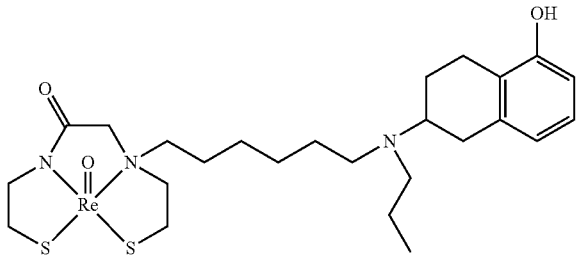 | | | 25.97 ± 2.71 | 7.37 ± 0.42 |

Example 61

Additional Compounds

The tridentate N—N—O chelate core (N-(2-methoxybenzyl)-1-(pyridin-2-yl)methanamine) was synthesized via single step reaction (Scheme 6). Chelate derivatives containing the C$_2$- and C$_3$-linked piperidine and dialkylamino substituents were introduced via alkylation of the amine using commercially available chloroalkylpiperidine (alkyl=Et,Pr) and 2-chloro-N,N-diethylethanamine. Subsequent demethylation of the phenol with BBr$_3$ afforded the final compounds.

Scheme 6

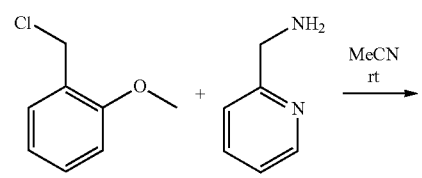

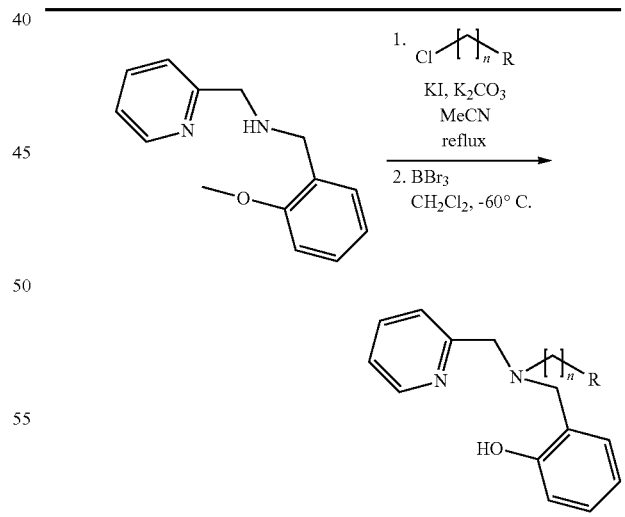

| Compound | n | R |
|---|---|---|
| 2 | 2 | diethylethanamine |
| 3 | 2 | piperidine |
| 4 | 3 | piperidine |

The C₆-linked piperidine derivative was synthesized via alkylation of (N-(2-methoxybenzyl)-1-(pyridin-2-yl)methanamine) with 1,6-dibromohexane and subsequent addition of piperidine as shown below:

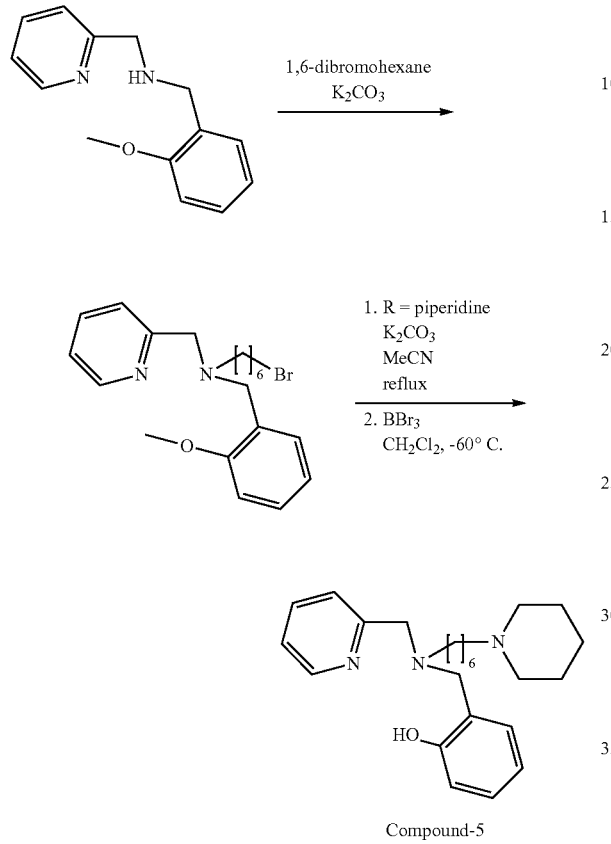

Compound-5

Compound 6 was synthesized by alkylation of (2-methoxyphenyl)methanamine with 3 equivalents of 2-bromo-N,N-diethylethanamine in acetonitrile at room temperature, as shown below:

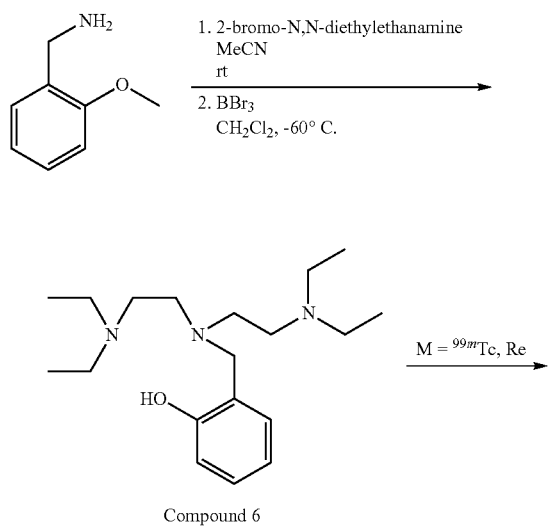

Compound 6

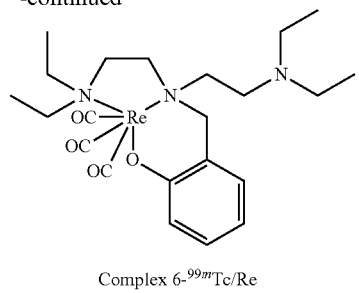

Complex 6-$^{99m}$Tc/Re

Neutral technetium-99m complexes were synthesized by reacting the tridentate ligands with the [99 mTc(CO)₃(H₂O)₃]+ precursor synthesized using Na[99 mTcO₄] and an Isolink® kit generously provided by Mallinckrodt Inc., as shown below:

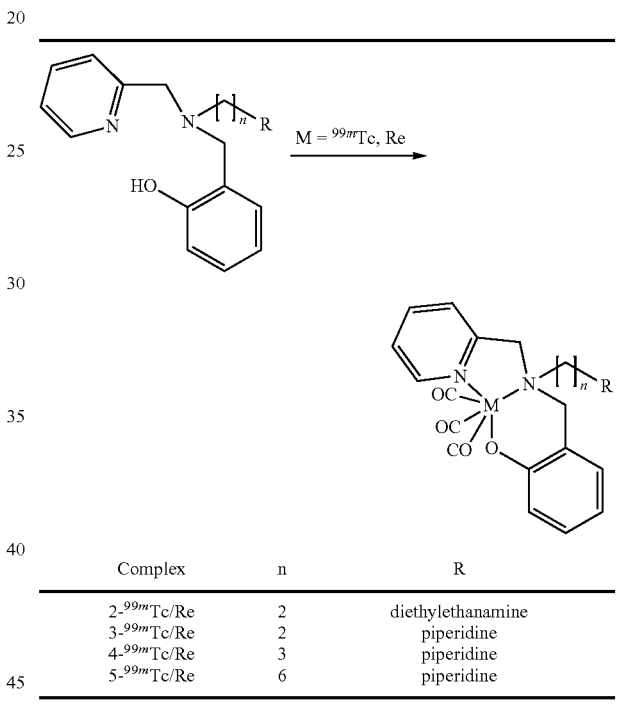

| Complex | n | R |
|---|---|---|
| 2-$^{99m}$Tc/Re | 2 | diethylethanamine |
| 3-$^{99m}$Tc/Re | 2 | piperidine |
| 4-$^{99m}$Tc/Re | 3 | piperidine |
| 5-$^{99m}$Tc/Re | 6 | piperidine |

All the complexes were obtained with a >90% radiochemical yield. The analogous neutral rhenium complexes were synthesized by the reaction of [Net₄][ReBr₃(CO)₃] with the final ligands in acetonitrile at room temperature.

Biodistribution of 99 mTc complexes in mice bearing subcutaneous B16F10 melanoma tumor was studied for complexes Tc-1-Tc-6.

Among the [Tc(CO₃)]-complexes studied, 99 mTc-2 displayed the highest tumor uptake of 3.2% ID/g at 1 h post injection. Despite the lower absolute tumor uptake compared to the 99 mTc-1 (7.62 ID/g), 99 mTc-2 displays significant tumor retention over a 6 h period (99 mTc-1=45% and for 99 mTc-2=65%). A similar behavior was observed with 99 mTc-3. Additional modifications of the pendant tertiary amine results in similar uptake and retention characteristics. The alkyl-amine analog 99 mTc-6, however, displayed poor tumor uptake and retention. This suggests that using the Tc(CO₃) core with an appropriate tridentate chelate based upon substituted tertiary amine can result in small technetium complexes that display slower washout of the complex from tumor.

117

In general, modification of the metal-chelate from the [TcON$_2$S$_2$] core to the [Tc(CO)$_3$] core may result in a lower absolute tumor uptake, an increase in tumor retention over time is observed with pyridyl-containing complexes such as Tc-3, Tc-4 and Tc-5.

This study also suggests that structural modifications of the metal chelate moiety can significantly effect the in vivo distribution characteristics of small molecules technetium complexes.

Example 62

In this example, we describe studies in evaluating the 4-(2-methoxyphenyl)piperidine as a lead structure using the fac-$^{99m}$Tc/Re(CO)$_3$, core. Several derivatives containing tridentate coordinating donor groups were used to synthesized rhenium-tricarbonyl complexes to elaborate and also elucidate the structural requirements of the ligand-metal complexes/receptor-protein interaction, distal from the 4-(2-methoxyphenyl)piperidine pharmacophore which also influence the 5-HT$_{1A}$ receptor affinity for such compounds.

Experimental

The synthetic route employed to obtain the final ligands L1-L9 is illustrated in Scheme 6. Using t-butoxybenzaldehyde reductively aminated with the corresponding amine to afforded tridentate chelates 2, 3, 4 and 5. To obtain chelate 21, 2-(Aminomethyl)pyridine was alkylated with t-But-chloroacetate. Subsequent alkylation of the chelates was achieved using commercially available dihalo reagents. The alkyl derivatives thus obtained were subsequently reacted with 2-methoxy-4-phenyl piperidine to yield the desired compounds. In the case of 19 and 20, the amide group was then reduced with LiAlH$_4$ to afford the desired amine derivatives. Final cleavage of the t-butyl ethers provided the target ligands L1-L9.

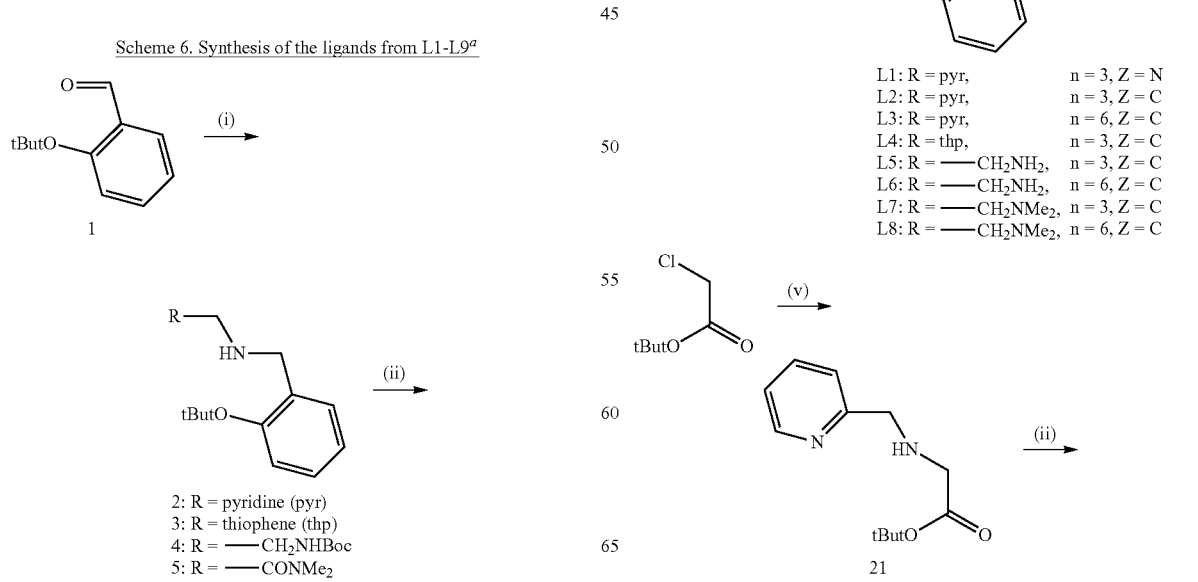

Scheme 6. Synthesis of the ligands from L1-L9$^a$

-continued

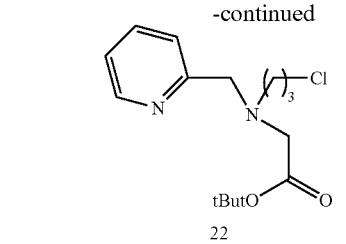
22

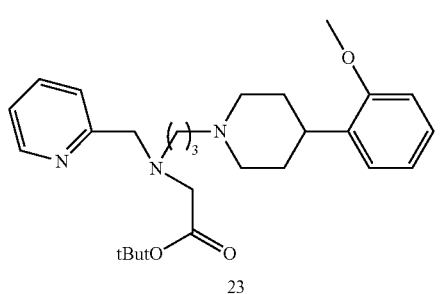
23

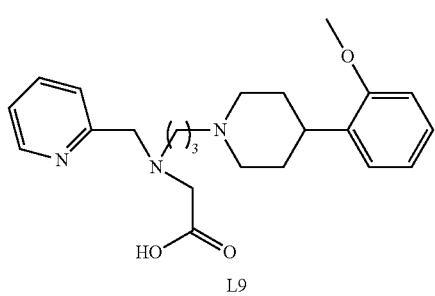
L9

$^a$(i) a) Amine: 2-(Aminomethyl)pyridine/thiophene methyl amine/
N-Boc-ethylenediamine/glycinedimethylamide, EtOH, reflux, 4 hr b) NaBH$_4$, MeOH,
rt, overnight; (ii) 1,6-dibromohexane/1,3-chlorobromopropane, K$_2$CO$_3$, CH$_3$CN, rt;
(iii) 4-(2-methoxyphenyl)piperazine/4-(2-methoxyphenyl)piperidine, CH$_3$CN, K$_2$CO$_3$,
reflux; In the case of 19 and 20: LiAlH$_4$, THF, reflux, overnight; (iv) 50%
TFA/CH$_2$Cl$_2$, 3 hr, rt (v) 2-(Aminomethyl)pyridine, CH$_2$Cl$_2$, K$_2$CO$_3$, rt, overnight.

Rhenium complexes were synthesized by the reaction of [ReBr(CO)$_3$(C$_4$H$_8$O)]$_2$ with the final ligands in acetonitrile at room temperature. The in vitro 5-HT$_{1A}$ binding affinities of complexes Re(CO)$_3$-L1-L9 were determined in competitive receptor binding assay using hippocampal homogenates that were prepared from Sprague Dawley rat hippocampus and the high-affinity [$^3$H]-8-OH-DPAT as the 5HT$_{1A}$ specific ligand.

Results and Discussion

Figure 3:
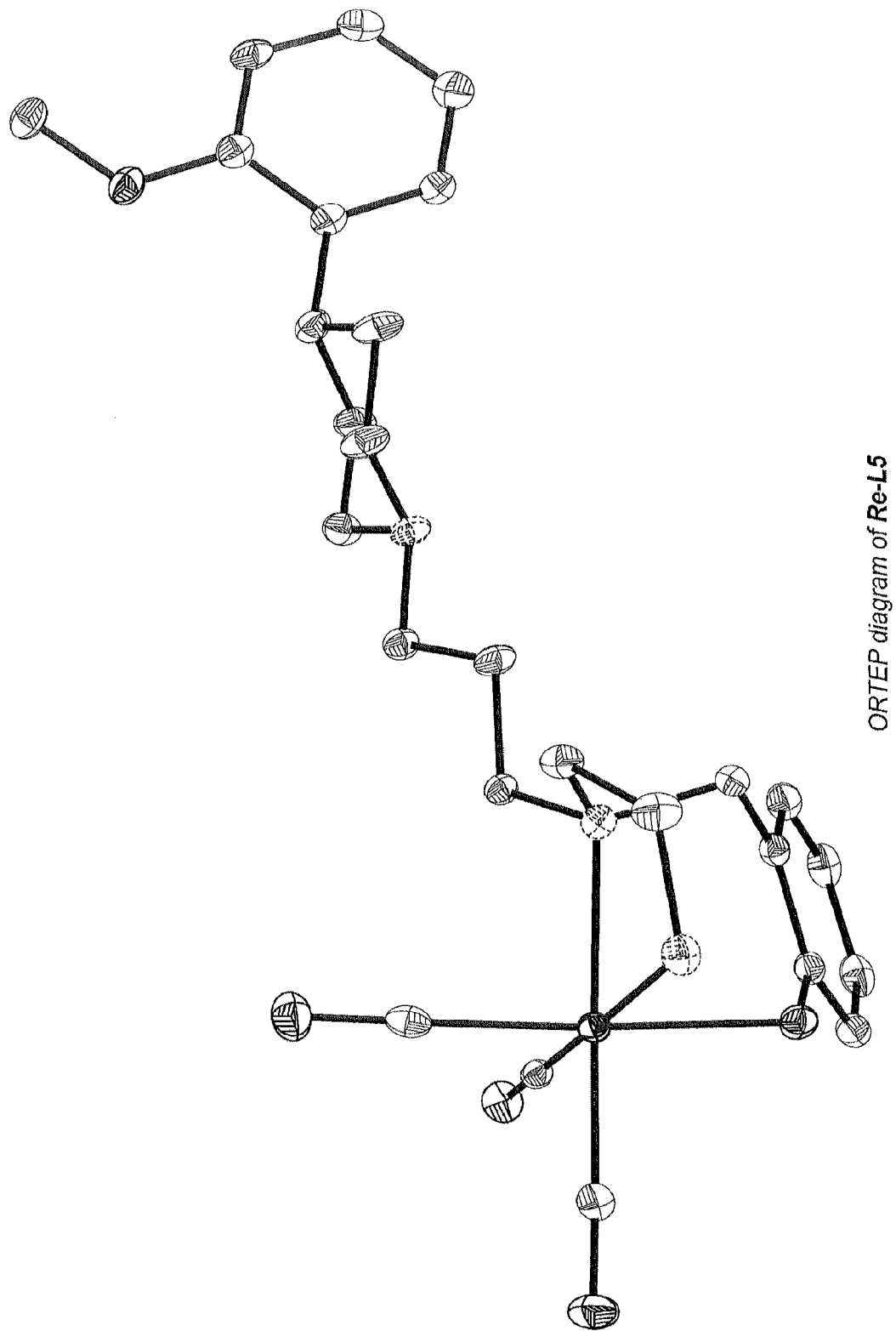
FIG. 3 is an ORTEP depiction of the X-ray crystal structure of a compound of the invention.

The ligands were synthesized using procedures outlined in Scheme 6. Rhenium complexes were synthesized with % 60-80 yield and characterized by $^1$H NMR, $^{13}$C NMR, FTIR and MS. An X-ray crystal structure of Re-L5 (FIG. 3) illustrates the fac-CO coordination, with the remaining face of the octahedron occupied by tridentate N,N,O chelate. The coordinated phenol and bridging amine forms a six-membered ring with the metal, while pendent primary-amine and the bridging tertiary amine forms a five-membered ring with the metal center.

The in vitro affinity of Re(CO)$_3$-L complexes for the 5-HT$_{1A}$ receptors were assessed by their ability to compete with the high affinity 5HT$_{1A}$ radioligand [$^3$H]-8-OH-DPAT. All Re-L complexes showed in vitro affinity for the 5-HT$_{1A}$ receptor binding sites with K$_i$ values ranging from nanomole to micromole (Table 5).

TABLE 5

Structure and K$_i$ values of the Re(CO)$_3$—L complexes.

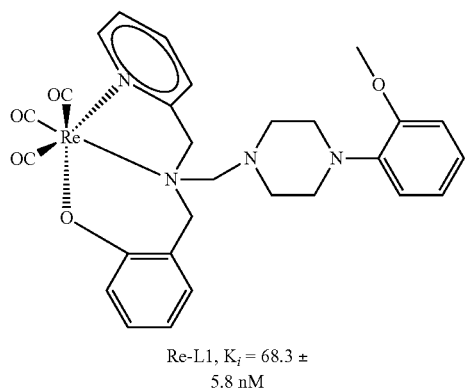

Re-L1, K$_i$ = 68.3 ± 5.8 nM

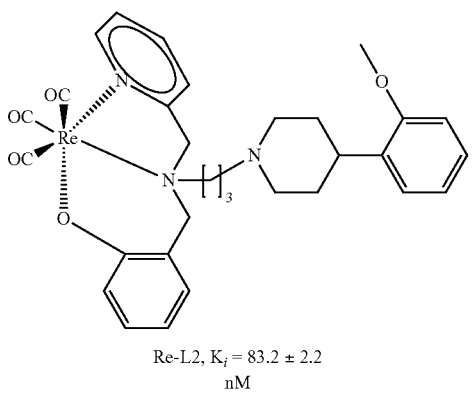

Re-L2, K$_i$ = 83.2 ± 2.2 nM

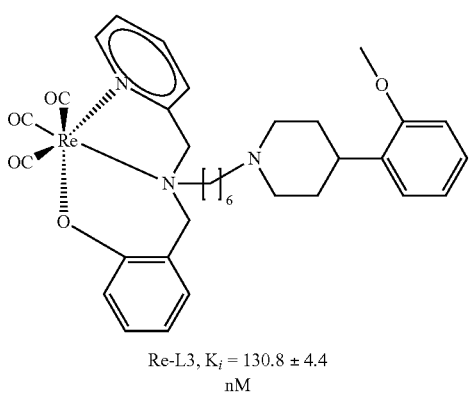

Re-L3, K$_i$ = 130.8 ± 4.4 nM

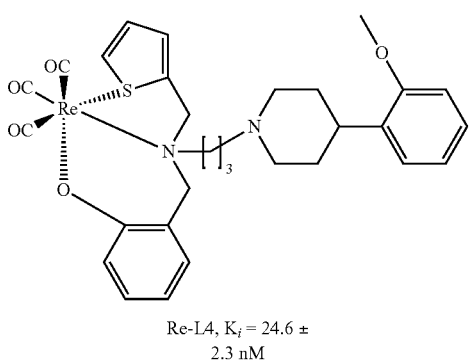

Re-L4, K$_i$ = 24.6 ± 2.3 nM

TABLE 5-continued

Structure and $K_i$ values of the $Re(CO)_3$—L complexes.

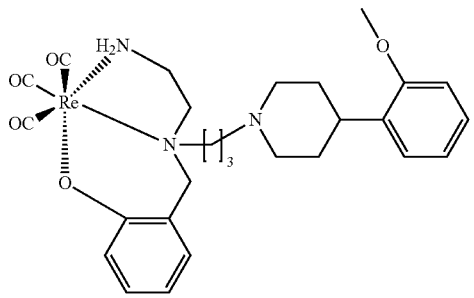

Re-L5, $K_i$ = 435.7 ± 12.7 nM

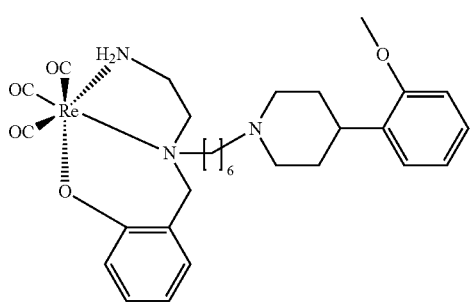

Re-L6, $K_i$ = 47.9 ± 2.5 nM

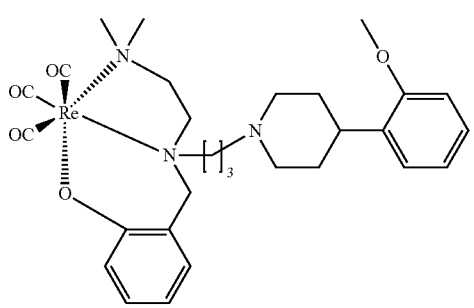

Re-L7, $K_i$ = 30.9 ± 1.2 nM

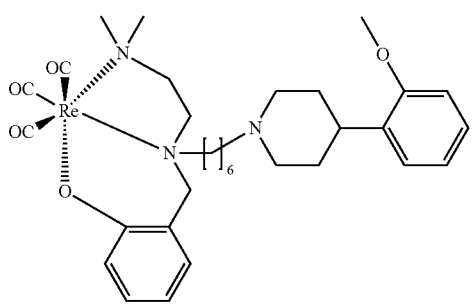

Re-L8, $K_i$ = 18.1 ± 3.6 nM

TABLE 5-continued

Structure and $K_i$ values of the $Re(CO)_3$—L complexes.

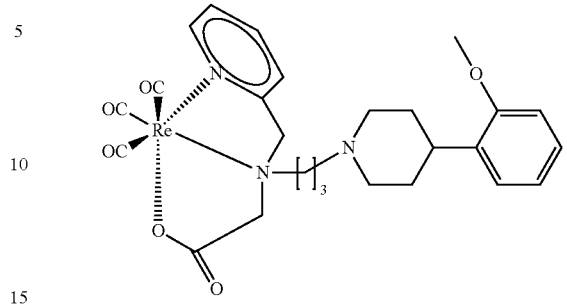

Re-L9, $K_i$ = 60.9 ± 2.8 nM

Re-L1 and Re-L2 were synthesized to investigate the effect of substitution of the anilinic nitrogen within 4-(2-methoxyphenyl)piperazine) moiety towards 5-HT$_{1A}$ receptor affinity, the in-vitro 5-HT$_{1A}$ receptor binding assay of these complexes displayed K, values 83.2±2.2 and 68.3±5.8 nM for Re-L1 and Re-L2 respectively, suggesting that 4-(2-methoxyphenyl)piperazine) and 4-(2-methoxyphenyl)piperidine) pharmacophores behave as bioisostere.

The pyridyl group in L2 was replaced with a smaller thiophene to give L4, and its respective Re(CO)$_3$ complexes, the in-vitro receptor binding studies of this Re-L4 complex displays a noticeable increase in 5-HT$_{1A}$ affinity (24.6±2.3 nM). Further decrease in the steric volume was investigated by the synthesis of complexes with a primary amine replacing the thiophene as a coordinating substituent (Re-L5). A drastic decrease in 5-HT$_{1A}$ binding affinity ($K_i$=435.7±126.4 nM) was observed for this complex suggesting a potential negative ligand/protein interaction introduced by the primary amine group in this part of the 5-HT$_{1A}$ receptor protein binding pocket. To avoid this and still attain a smaller volume, the Re-L7 complex was synthesized with a N,N-dimethyl amine group as a substitute for primary amine group. In this case, the 5-HT$_{1A}$ receptor affinity (Re-L7, $K_i$=30.9±1.2 nM) was restored to that observed for the thiophene analogue (Re-L4). Similarly, reduction of steric volume by replacing the phenol donor group in Re-L2 to a much small carboxylic acid (Re-L9) also results in an modest increase in the affinity. (Re-L9: $K_i$=60.1±2.8).

Additional ligands with the longer —C$_6$— chain lengths and their Re(CO)$_3$-complexes were also synthesized (Re-L3, Re-L6 and Re-L8). In the case of Re-L6 and Re-L8, both complexes with reduced molecular volume displayed improved 5-HT$_{1A}$ binding affinities (47.9 nM and 18.1 nM) respectively compared to their —C3-analogues.

REFERENCES

1. V. W. Pike, C. Halldin, H. Wikström, S. Marchais, J. A. McCarron, J. Sandell, B. Nowicki, C. Swahn, S. Osman, S. Hume, M. Constantinou, B. Andrée and L. Farde, Nucl. Med. Biol. 27: 449-455 (2000).
2. R. Alberto, R. Schibli, P. A. Schubiger, U. Abram, H. J. Pietzsch, Johannsen, J. Am. Chem. Soc. 121: 6076-6077 (1999).
3. A. Mahmood, J. F. Kronauge, E. Barbarics, E. Freiberg, B. K. Madras, J. Li, A. Davison, A. G. Jones. Technetium, Rhenium and other Metals in Chemistry and Nuclear Medicine 393-399. M. Nicolini, U. Mazzi, Eds. SGE Editoriali, Padova, Italy, (1999).

4. C. Bolzati, A. Mahmood, E. Malagb, L. Uccelli, A. Boschi, A. G. Jones, F. Refosco, A. Duatti, F. Tisato. *Bioconj. Chem.* 14:1231-1242 (2003).

5. O. G. Carvalho, M. M. Gonsalves, A. B. Zeraib, E. Muramoto, M. A. T. M. Almeida, Development of $^{99m}$Tc Agents for Imaging Central Neural System Receptors. IAEA Technical Reports Series. 426, 19-37 (2004).

All patents, patent applications, and published references cited herein are hereby incorporated by reference in their entirety.

While this invention has been particularly illustrated and described with reference to particular examples, it will be understood by those skilled in the art that various changes in form and details may be made therein without departing from the scope and spirit of the invention encompassed by the appended claims.

What is claimed is:

1. A compound represented by the formula:

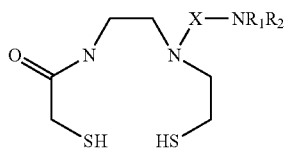

or a complex represented by the formula:

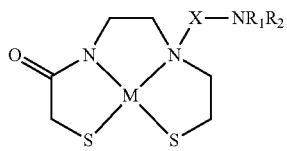

wherein:
X is a linking group comprising an aliphatic backbone chain having 1 to about 8 atoms, in which the aliphatic backbone chain optionally includes ester, amide, ether or thioether linkages in the aliphatic backbone chain; and $R_1$ and $R_2$ each are independently selected from the group consisting of hydrogen, unsubstituted alkyl groups having from 1 to about 8 carbon atoms, alkoxyalkyl group having from 2 to about 8 carbon atoms, and substituted alkyl or alkoxyalkyl groups having from 1 to about 8 carbon atoms which are substituted with one or more groups selected from optionally substituted aryl, optionally substituted cycloalkyl, optionally substituted heteroalicyclic, and optionally substituted heteroaryl; or wherein $R_1$ and $R_2$ taken together with the nitrogen atom to which they are attached form a heterocyclic ring having from 3 to 8 atoms in the ring; or one of $R_1$ or $R_2$ is alkyl and the other is a moiety selected from:

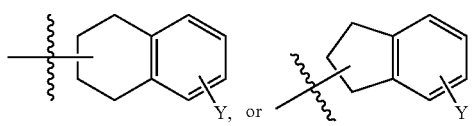

in which Y represents 0-4 substituents independently selected from halogen, alkyl, alkoxyl, or cyano;

or a salt thereof;

wherein M is a metal selected from technetium and rhenium.

2. The compound or complex of claim 1, wherein X is an optionally substituted $C_{2-8}$alkylene group, $R_1$ is an $C_{1-6}$alkyl group and $R_2$ is an optionally substituted (aryl)$C_{1-4}$alkyl or an optionally substituted (heteroaryl)$C_{1-4}$alkyl.

3. The compound or complex of claim 1, wherein X is selected from the group consisting of —(CH$_2$)$_m$—C(O)NH— and an α,ω-alkylene group, wherein the alkylene group has between about 1 and about 10 carbon atoms and between 0 and about 3 oxygen or sulfur atoms in the alkylene chain; and m is an integer of from about 1 to about 5.

4. The compound or complex of claim 1, wherein X is $C_3$-$C_6$ alkylene.

5. The compound or complex of claim 4, wherein $R_1$ and $R_2$ are each lower alkyl.

6. The compound or complex of claim 4, wherein $R_1$ and $R_2$ are taken together with the nitrogen atom to which they are attached form a heterocyclic ring having from 3 to 8 atoms in the ring.

7. The compound or complex of claim 1, wherein $R_1$ and $R_2$ are taken together with the nitrogen atom to which they are attached form a substituted or unsubstituted piperidine or morpholine ring.

8. The compound or complex of claim 1, wherein $NR_1 R_2$ is a moiety selected from:

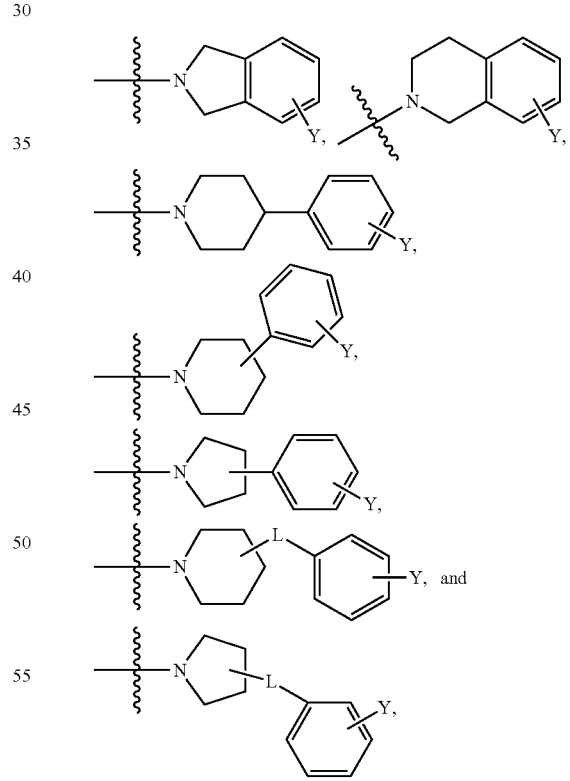

in which L represents a one or two atom linking group and Y represents 0-4 substituents independently selected from halogen, alkyl, alkoxyl, or cyano.

9. A method for in-vivo or in-vitro imaging of at least one tumor comprising the steps of:

providing a complex of claim 1, wherein the complex is a radiolabeled metal complex;

administering the radiolabeled metal complex to a subject or sample; and making a radiographic image to visualize the tumor(s).

10. The method of claim 9, wherein the metal ion M is one or more isotopes of a metal selected from the group consisting of technetium, rhenium, yttrium, copper, gallium, indium, bismuth, platinum and rhodium.

11. The method of claim 9, wherein the radiolabeled metal complex binds to, or has affinity for, one or more proteins or receptors selected from melanin, serotonin receptors, adrenergic receptors, adrenoceptors receptors, dopamine receptors, sigma receptors, emopamil binding proteins, calcium channel receptors.

12. The method of claim 11, wherein the protein or receptor(s) are selected from $5HT_{1A}$, $\sigma_1$, $\sigma_2$, $\alpha_1$, $Ca^{+2}$ channel receptors, EBP or a combination thereof.

13. A method for in-vivo or in-vitro imaging of at least one tissue expressing one or more proteins, receptors, or melanin for which radiolabeled complexes have affinity, the method comprising the steps of:

providing a complex of claim 1, wherein the complex is a radiolabeled metal complex;

administering the radiolabeled metal complex to a subject or sample; and making a radiographic image to visualize the tissue(s).

* * * * *